(12) United States Patent
Douchin et al.

(10) Patent No.: US 11,168,343 B2
(45) Date of Patent: Nov. 9, 2021

(54) PRODUCTION OF STEVIOL GLYCOSIDES IN RECOMBINANT HOSTS

(71) Applicant: Evolva SA, Reinach (CH)

(72) Inventors: Veronique Douchin, Frederiksberg (DK); Micheael Dalgaard Mikkelsen, Vaerlose (DK); Iben Møller-Hansen, Frederiksberg (DK)

(73) Assignee: EVOLVA SA, Reinach (CH)

( * ) Notice: Subject to any disclaimer, the term of this patent is extended or adjusted under 35 U.S.C. 154(b) by 0 days.

(21) Appl. No.: 16/533,295

(22) Filed: Aug. 6, 2019

(65) Prior Publication Data

US 2020/0024630 A1  Jan. 23, 2020

Related U.S. Application Data

(62) Division of application No. 15/328,365, filed as application No. PCT/EP2015/068314 on Aug. 7, 2015, now Pat. No. 10,421,983.

(60) Provisional application No. 62/035,902, filed on Aug. 11, 2014.

(51) Int. Cl.
    C12P 21/06    (2006.01)
    C12P 19/44    (2006.01)
    A23L 27/30    (2016.01)
    C07H 1/08     (2006.01)
    C12N 1/16     (2006.01)

(52) U.S. Cl.
    CPC ............... *C12P 19/44* (2013.01); *A23L 27/36* (2016.08); *C07H 1/08* (2013.01); *C12N 1/16* (2013.01)

(58) Field of Classification Search
    None
    See application file for complete search history.

(56) References Cited

U.S. PATENT DOCUMENTS

| | | | |
|---|---|---|---|
| 4,590,160 A | 5/1986 | Nishihashi et al. | |
| 5,198,360 A | 3/1993 | Ballou | |
| 5,204,253 A | 4/1993 | Sanford et al. | |
| 5,306,862 A | 4/1994 | Chappell et al. | |
| 5,460,949 A | 10/1995 | Saunders et al. | |
| 5,538,880 A | 7/1996 | Lundquist et al. | |
| 6,013,863 A | 1/2000 | Lundquist et al. | |
| 6,215,051 B1 | 4/2001 | Yu et al. | |
| 6,255,557 B1 | 7/2001 | Brandle | |
| 6,284,493 B1 | 9/2001 | Roth | |
| 6,284,506 B1 | 9/2001 | Hoshino et al. | |
| 6,329,571 B1 | 12/2001 | Hiei | |
| 6,586,202 B2 | 7/2003 | Hoshino et al. | |
| 6,660,507 B2 | 12/2003 | Cheng et al. | |
| 6,806,076 B1 | 10/2004 | Miyake et al. | |
| 6,969,595 B2 | 11/2005 | Brzostowicz et al. | |
| 7,034,140 B2 | 4/2006 | Bramucci et al. | |
| 7,056,717 B2 | 6/2006 | Cheng et al. | |
| 7,098,000 B2 | 8/2006 | Cheng et al. | |
| 7,129,392 B2 | 10/2006 | Hahn et al. | |
| 7,132,268 B2 | 11/2006 | Miyake et al. | |
| 7,172,886 B2 | 2/2007 | Keasling et al. | |
| 7,183,089 B2 | 2/2007 | Keasling et al. | |
| 7,186,891 B1 | 3/2007 | Chappell et al. | |
| 7,208,298 B2 | 4/2007 | Miyake et al. | |
| 7,335,815 B2 | 2/2008 | Boronat et al. | |
| 7,364,885 B2 | 4/2008 | Miyake et al. | |
| 7,422,884 B2 | 9/2008 | Bai et al. | |
| 7,514,597 B2 | 4/2009 | Nakamura et al. | |
| 7,569,389 B2 | 9/2009 | Feldmann et al. | |
| 7,692,065 B2 | 4/2010 | Harper et al. | |
| 7,838,287 B2 | 11/2010 | Goldsmith et al. | |
| 7,923,541 B2 | 4/2011 | Yang et al. | |
| 7,927,851 B2 | 4/2011 | Brandle et al. | |
| 7,981,647 B2 | 7/2011 | Berry et al. | |
| 9,441,233 B2 | 9/2016 | Apuya et al. | |
| 9,562,251 B2 | 2/2017 | Kishore et al. | |
| 9,957,539 B2 | 5/2018 | Ono et al. | |
| 9,957,540 B2 | 5/2018 | Mikkelsen et al. | |
| 2002/0142408 A1 | 10/2002 | DiCosimo et al. | |
| 2003/0033626 A1 | 2/2003 | Hahn et al. | |
| 2003/0148416 A1 | 8/2003 | Berry et al. | |
| 2003/0148479 A1 | 8/2003 | Keasling et al. | |
| 2003/0190734 A1 | 10/2003 | Hoshino et al. | |
| 2003/0219798 A1 | 11/2003 | Gokarn et al. | |
| 2004/0010815 A1 | 1/2004 | Lange et al. | |
| 2004/0072311 A1 | 4/2004 | DiCosimo et al. | |
| 2004/0078846 A1 | 4/2004 | Desouza et al. | |
| 2004/0176570 A1 | 9/2004 | Bacher et al. | |
| 2004/0194162 A1 | 9/2004 | Hahn et al. | |
| 2005/0003474 A1 | 1/2005 | Desouza | |
| 2005/0032169 A1 | 2/2005 | Miyake et al. | |
| 2006/0014264 A1 | 1/2006 | Sauer | |
| 2006/0079476 A1 | 4/2006 | Keasling et al. | |

(Continued)

FOREIGN PATENT DOCUMENTS

| | | |
|---|---|---|
| CN | 101314776 | 12/2008 |
| CN | 101720910 | 6/2010 |

(Continued)

OTHER PUBLICATIONS

Hebling et al (Genbank Accession #: S64499. May 17, 1996).*
Saier, "Families of transmembrane sugar transport proteins," Mol Microbiol., 35(4):699-710 (2000).
Chen et al., "Progress in the Application of Affinity Tags for the Expression and Purification of Recombinant Proteins," China Biotechnology, vol. 32, No. 12, pp. 93-103, Dec. 15, 2012 (English Abstract).
Gloster, "Advances in understanding glycosyltransferases from a structural perspective," Curr Opin Struct Biol. 28:131-41 (2014).
Guo et al., "Protein tolerance to random amino acid change", (Continued)

*Primary Examiner* — Jennifer E Graser
(74) *Attorney, Agent, or Firm* — McDonnell Boehnen Hulbert & Berghoff LLP

(57) ABSTRACT

The invention relates to recombinant microorganisms and methods for producing steviol glycosides and steviol glycoside precursors.

29 Claims, 11 Drawing Sheets

Specification includes a Sequence Listing.

(56) References Cited

U.S. PATENT DOCUMENTS

| | | |
|---|---|---|
| 2006/0083838 A1 | 4/2006 | Jackson et al. |
| 2007/0004000 A1 | 1/2007 | Miyake et al. |
| 2007/0077616 A1 | 4/2007 | Keasling et al. |
| 2007/0099261 A1 | 5/2007 | Keasling et al. |
| 2007/0118916 A1 | 5/2007 | Puzio et al. |
| 2007/0128311 A1 | 6/2007 | Prakash et al. |
| 2007/0166782 A1 | 7/2007 | Keasling et al. |
| 2007/0202579 A1 | 8/2007 | Berry et al. |
| 2007/0238157 A1 | 10/2007 | Millis et al. |
| 2007/0238159 A1 | 10/2007 | Millis et al. |
| 2007/0238160 A1 | 10/2007 | Millis et al. |
| 2007/0254354 A1 | 11/2007 | Millis et al. |
| 2007/0269857 A1 | 11/2007 | Miyake et al. |
| 2007/0286850 A1 | 12/2007 | Bai et al. |
| 2008/0064063 A1 | 3/2008 | Brandle |
| 2008/0081358 A1 | 4/2008 | Vittanen et al. |
| 2008/0131926 A1 | 6/2008 | Miyake et al. |
| 2008/0216397 A1 | 9/2008 | Busby et al. |
| 2008/0261280 A1 | 10/2008 | Hahn et al. |
| 2008/0271205 A1 | 10/2008 | Yamaguchi et al. |
| 2008/0286870 A1 | 11/2008 | Vittanen et al. |
| 2008/0292775 A1 | 11/2008 | Prakash et al. |
| 2008/0318227 A1 | 12/2008 | Bacher et al. |
| 2009/0004724 A1 | 1/2009 | Keasling et al. |
| 2009/0047718 A1 | 2/2009 | Blaschek et al. |
| 2009/0055974 A1 | 2/2009 | Tanksley et al. |
| 2009/0074935 A1 | 3/2009 | Lee |
| 2009/0143308 A1 | 6/2009 | Monk et al. |
| 2009/0286262 A1 | 11/2009 | Slack |
| 2009/0298706 A1 | 12/2009 | Lee et al. |
| 2010/0112156 A1 | 5/2010 | Abelyan et al. |
| 2010/0120096 A1 | 5/2010 | Kitaoka et al. |
| 2010/0221801 A1 | 9/2010 | Van Dyk |
| 2010/0297722 A1 | 11/2010 | Anterola et al. |
| 2010/0316782 A1 | 12/2010 | Shi et al. |
| 2011/0087011 A1 | 4/2011 | Chiang et al. |
| 2011/0092684 A1 | 4/2011 | Abelyan et al. |
| 2011/0126318 A1 | 5/2011 | Allen et al. |
| 2011/0160311 A1 | 6/2011 | Prakash et al. |
| 2012/0021111 A1 | 1/2012 | Pfister et al. |
| 2012/0083593 A1 | 4/2012 | Liu et al. |
| 2012/0164678 A1 | 6/2012 | Stephanopoulos et al. |
| 2012/0178169 A1 | 7/2012 | Voytas et al. |
| 2013/0137138 A1 | 5/2013 | Hansen |
| 2013/0171328 A1 | 7/2013 | Kishore et al. |
| 2014/0329281 A1 | 11/2014 | Houghton-Larsen et al. |
| 2015/0159188 A1 | 6/2015 | Ono et al. |
| 2015/0342234 A1 | 12/2015 | Hicks et al. |

FOREIGN PATENT DOCUMENTS

| | | |
|---|---|---|
| CN | 102559528 | 7/2012 |
| CN | 103397064 | 11/2013 |
| EP | 0955363 | 11/1999 |
| EP | 1072683 | 1/2001 |
| EP | 1171610 | 4/2007 |
| EP | 1198575 | 9/2007 |
| EP | 1383864 | 1/2008 |
| EP | 1897951 | 3/2008 |
| EP | 1947189 | 7/2008 |
| EP | 1392824 | 8/2008 |
| EP | 2575432 | 4/2013 |
| EP | 2902410 | 8/2015 |
| JP | 5910-001408 | 6/1984 |
| JP | 3-277275 | 12/1991 |
| JP | 05-115298 | 5/1993 |
| JP | 2005185101 | 7/2005 |
| JP | 2009034080 | 2/2009 |
| KR | 1020120088035 | 8/2012 |
| KR | 2015 0000258 | 1/2015 |
| WO | WO 1999/018224 | 4/1999 |
| WO | WO 2000/036081 | 6/2000 |
| WO | WO 2000/037663 | 6/2000 |
| WO | WO 2000/063400 | 10/2000 |
| WO | WO 2001/012828 | 2/2001 |
| WO | WO 2001/083769 | 11/2001 |
| WO | WO 2001/094561 | 12/2001 |
| WO | 2002/024865 | 3/2002 |
| WO | WO 2002/020728 | 3/2002 |
| WO | WO 2002/020815 | 3/2002 |
| WO | WO 2002/055709 | 7/2002 |
| WO | WO 2003/008540 | 1/2003 |
| WO | WO 2004/029255 | 4/2004 |
| WO | WO 2005/079183 | 9/2005 |
| WO | WO 2006/016395 | 2/2006 |
| WO | WO 2006069610 | 7/2006 |
| WO | WO 2006/093289 | 9/2006 |
| WO | WO 2006/096392 | 9/2006 |
| WO | WO 2007/136847 | 11/2007 |
| WO | WO 2008/008256 | 1/2008 |
| WO | WO 2008/034648 | 3/2008 |
| WO | WO 2008/039499 | 4/2008 |
| WO | WO 2008/051349 | 5/2008 |
| WO | WO 2009/005704 | 1/2009 |
| WO | WO 2009/037329 | 3/2009 |
| WO | WO 2009/071277 | 6/2009 |
| WO | WO 2009/086049 | 7/2009 |
| WO | WO 2009/105612 | 8/2009 |
| WO | WO 2009/108680 | 9/2009 |
| WO | WO 2009/111513 | 9/2009 |
| WO | 2009/140394 | 11/2009 |
| WO | WO 2009/140394 | 11/2009 |
| WO | WO 2010/021001 | 2/2010 |
| WO | WO 2010/038911 | 4/2010 |
| WO | WO 2010/044960 | 4/2010 |
| WO | 2010/142305 | 12/2010 |
| WO | WO 2010/146463 | 12/2010 |
| WO | WO 2011/028671 | 3/2011 |
| WO | WO 2011/037959 | 3/2011 |
| WO | WO 2011/046423 | 4/2011 |
| WO | WO 2011/056834 | 5/2011 |
| WO | WO 2011/060057 | 5/2011 |
| WO | WO 2011/153378 | 8/2011 |
| WO | 2011/140329 | 11/2011 |
| WO | 2011/151326 | 12/2011 |
| WO | 2011/153378 | 12/2011 |
| WO | WO 2011/151326 | 12/2011 |
| WO | WO 2011/153144 | 12/2011 |
| WO | WO 2012/075030 | 6/2012 |
| WO | 2013/022989 | 2/2013 |
| WO | WO 2013/019050 | 2/2013 |
| WO | WO 2013/022989 | 2/2013 |
| WO | WO 2013/021261 | 5/2013 |
| WO | WO 20131076577 | 5/2013 |
| WO | WO 2013/096420 | 6/2013 |
| WO | WO 2013/102793 | 7/2013 |
| WO | WO 2013/110673 | 8/2013 |
| WO | WO 2013/176738 | 11/2013 |
| WO | WO 2014/086890 | 6/2014 |
| WO | WO 2014/122227 | 8/2014 |
| WO | WO 2014/122328 | 8/2014 |
| WO | 2014/191580 | 12/2014 |
| WO | 2014/191581 | 12/2014 |
| WO | 2015/011209 | 1/2015 |
| WO | 2015/014959 | 2/2015 |
| WO | 2015/016393 | 2/2015 |
| WO | WO 2015/014969 | 2/2015 |
| WO | 2016/023844 | 2/2016 |
| WO | WO 2016/038095 | 3/2016 |
| WO | 2017/025362 | 2/2017 |
| WO | WO 2017/025362 | 2/2017 |

OTHER PUBLICATIONS

Proceedings of the National Academy of Sciences USA, vol. 101, No. 25, pp. 9205-9210 (2004).

Liu et al., "Biosynthesis of Rebaudioside A by Whole Cell of Recombinant Saccharomyces cerevisiae," Food and Fermentation Industries, 38(7) : 6-10 (2012) (Abstract translation).

Ni et al., "Outer membrane mutation effects on UDP-glucose permeability and whole-cell catalysis rate," Appl Microbiol Biotechnol. 73(2):384-93 (2006).

(56) References Cited

OTHER PUBLICATIONS

Prisic et al, "Synergistic substrate inhibition of ent-copalyl diphosphate synthase: a potential feed-forward inhibition mechanism limiting gibberellin metabolism," Plant Physiol. 144(1):445-54 (2007).
Ünligil et al., "Glycosyltransferase structure and mechanism," Curr Opin Struct Biol. 10(5):510-7 (2000).
Wanchao et al., "Advances on the Steviol Glycoside Biosynthesis and Its Key Enzymes," Biotechnology Bulletin, Feb. 2008 (English Abstract Translation).
Liu et al., "Functional and Biochemical Characteritzation of *Escherichia coli* Sugar Efflux Transporters," JBC, 274(33):22977-22984 (Aug. 1999).
Sun et al., "Regulation and Function of *Escherichia coli* Sugar Efflux Transporter A (Set A) during Glucose-Phosphate Stress," J of Bacteriology, 193(1):143-153 (Jan. 2011).
International Search Report and Written Opinion of the International Searching Authority for International Application No. PCT/EP2016/068259; dated Jan. 24, 2017, pp. 1-18.
Uniprot Accession No. P53320, dated Feb. 17, 2016 (pp. 1-10).
Uniprot Accession No. P38735, dated Feb. 17, 2016 (pp. 1-13).
Uniprot Accession No. P38734, dated Feb. 17, 2016 (pp. 1-10).
Uniprot Accession No. P38702, dated Feb. 17, 2016 (pp. 1-9).
Uniprot Accession No. P38695, dated Feb. 17, 2016 (pp. 1-11).
Uniprot Accession No. P40556, dated Feb. 17, 2016 (pp. 1-10).
Uniprot Accession No. P40475, dated Feb. 17, 2016 (pp. 1-9).
Uniprot Accession No. P40474, dated Jan. 20, 2016 (pp. 1-11).
Uniprot Accession No. P40445, dated Dec. 9, 2015 (pp. 1-9).
Uniprot Accession No. P10566, dated Feb. 17, 2016 (pp. 1-10).
Uniprot Accession No. P40885, dated Feb. 17, 2016 (pp. 1-11).
Uniprot Accession No. P30902, dated Nov. 11, 2015 (pp. 1-9).
Uniprot Accession No. P35736, dated Jan. 20, 2016 (pp. 1-8).
Uniprot Accession No. P32332, dated Feb. 17, 2016 (pp. 1-10).
Uniprot Accession No. P36062, dated Jan. 20, 2016 (pp. 1-10).
Uniprot Accession No. P12866, dated Jan. 20, 2016 (pp. 1-14).
Uniprot Accession No. P19145, dated Feb. 17, 2016 (pp. 1-12).
Uniprot Accession No. Q06686, dated Nov. 11, 2015 (pp. 1-9).
Uniprot Accession No. Q03697, dated Feb. 17, 2016 (pp. 1-10).
Uniprot Accession No. Q03829, dated Feb. 17, 2016 (pp. 1-9).
Uniprot Accession No. Q03263, dated Feb. 17, 2016 (pp. 1-10).
Uniprot Accession No. P38921, dated Feb. 17, 2016 (pp. 1-10).
Uniprot Accession No. P32487, dated Feb. 17, 2016 (pp. 1-12).
Uniprot Accession No. P53389, dated Feb. 17, 2016 (pp. 1-10).
Uniprot Accession No. Q08299, dated Feb. 17, 2016 (pp. 1-10).
Uniprot Accession No. Q12289, dated Feb. 17, 2016 (pp. 1-10).
Uniprot Accession No. P33302, dated Feb. 17, 2016 (pp. 1-23).
Uniprot Accession No. Q12029, dated Jan. 20, 2016 (pp. 1-9).
Uniprot Accession No. Q12256, dated Feb. 17, 2016 (pp. 1-12).
Uniprot Accession No. P22215, dated Feb. 17, 2016 (pp. 1-11).
Uniprot Accession No. P22203, dated Jan. 20, 2016 (pp. 1-10).
Uniprot Accession No. P15380, dated Feb. 17, 2016 (pp. 1-11).
Uniprot Accession No. P19657, dated Feb. 17, 2016 (pp. 1-12).
International Search Report issued by the International Searching Authority for International Application No. PCT/US2011/038967, dated Sep. 1, 2011 (10 pages).
Written Opinion of the International Searching Authority for International Application No. PCT/US2011/038967, dated Sep. 1, 2011 (12 pages).
International Preliminary Report on Patentability issued by the International Bureau for International Application No. PCT/US2011/038967, dated Dec. 4, 2012 (13 pages).
Third-Party Submission under 37 CFR 1.290 for U.S. Appl. No. 13/701,406, dated Mar. 7, 2014 (238 pages).
Extended European Search Report and Opinion issued by the European Patent Office for European Application No. 11790428.4, dated Dec. 20, 2013.
Search Report issued by the Intellectual Property Office of Singapore for Singaporean Application No. 201208854-8, dated Nov. 3, 2014.
Non-Final Office Action for U.S. Appl. No. 14/237,540, dated Dec. 30, 2015 (pp. 1-19).
Final Office Action issued in U.S. Appl. No. 14/237,540; dated Jul. 8, 2016, pp. 1-19.
International Search Report issued by the International Searching Authority for International Application No. PCT/US2012/050021, dated Apr. 12, 2013.
Written Opinion of the International Searching Authority for International Application No. PCT/US2012/050021, dated Apr. 12, 2013.
International Preliminary Report on Patentability issued by the International Bureau for International Application No. PCT/US2012/050021, dated Feb. 11, 2014.
Extended European Search Report issued in EP 15193074.0; dated Feb. 12, 2016, pp. 1-9.
International Search Report from the International Searching Authority for International Application No. PCT/EP2014/052363, dated Sep. 22, 2014 (12 pages).
Written Opinion of the International Searching Authority for International Application No. PCT/EP2014/052363, dated Sep. 22, 2014 (10 pages).
International Preliminary Report on Patentability issued by the International Bureau for International Application No. PCT/EP2014/052363, dated Aug. 11, 2015. (11 pages).
International Preliminary Report on Patentability issued by the International Bureau for International Application No. PCT/EP2014/052675, dated Aug. 11, 2015 (8 pages).
International Search Report of the International Searching Authority for International Application No. PCT/EP2013/075587, dated Feb. 20, 2014 (pp. 1-5).
Written Opinion of the International Searching Authority for International Application No. PCT/EP2013/075587, dated Feb. 20, 2014 (pp. 1-9).
International Preliminary Report on Patentability from the International Bureau for International Application No. PCT/EP2013/075587, dated Jun. 9, 2015 (pp. 1-10).
Third Party Submission in U.S. Appl. No. 14/648,747; dated Mar. 28, 2016, pp. 1-231.
Invitation to Pay Additional Fees and, Where Applicable, Protest Fee by the International Searching Authority for International Application No. PCT/EP2015/070620, dated Nov. 27, 2015 (pp. 1-14).
International Search Report by the International Searching Authority for International Application No. PCT/EP2015/070620; dated Mar. 29, 2016, pp. 1-10.
Written Opinion of the International Searching Authority for International Application No. PCT/EP2015/070620; dated Mar. 29, 2016, pp. 1-24.
International Search Report and Written Opinion of the International Searching Authority for International Application No. PCT/EP2015/068314, dated Jan. 20, 2016 (pp. 1-7).
Written Opinion of the International Searching Authority for International Application No. PCT/EP2015/068314, dated Jan. 20, 2016 (pp. 1-9).
International Search Report and Written Opinion of the International Searching Authority for International Application No. PCT/EP2015/052007; dated Jul. 4, 2016, pp. 1-24.
GenBank Accession No. XM_001467423, dated Jul. 16, 2015 (2 pages).
GenBank Accession No. XP_002282091, dated Dec. 7, 2011 (1 page).
GenBank Accession No. XP_002288339, dated Jul. 15, 2009 (2 pages).
GenBank Accession No. XP_002311286, dated Dec. 31, 2013 (2 pages).
GenBank Accession No. ZP_05004570, dated Jun. 8, 2010 (2 pages).
Gossen & Bujard, "Studying gene function in eukaryotes by conditional gene inactivation," Annu. Rev. Genet. 36:153-73 (Jun. 2002).
Gritz & Davies, "Plasmid-encoded hygromycin B resistance: the sequence of hygromycin B phosphotransferase gene and its expression in *Escherichia coli* and *Saccharomyces cerevisiae*," Gene 25(2-3):179-88 (Nov. 1983).

(56) References Cited

OTHER PUBLICATIONS

Hallstrom & Moye-Rowley, "Divergent transcriptional control of multidrug resistance genes in Saccharomyces cerevisiae," J. Biol. Chem. 273(4):2098-104 (Jan. 1998).

Katzmann et al., "Expression of an ATP-binding cassette transporter-encoding gene (YOR1) is required for oligomycin resistance in Saccharomyces cerevisiae," Mol. Cell Biol. 15(12):6875-83 (Dec. 1995).

Li et al., "Phylogenetic analysis of the UDP-glycosyltransferase multigene family of Arabidopsis thaliana," J. Biol. Chem. 276(6):4338-43 (Oct. 2000).

Masada et al., "An efficient chemoenzymatic production of small molecule glucosides with in situ UDP-glucose recycling," FEBS Lett. 581(13):2562-6 (May 2007).

Morita et al., "Japanese morning glory dusky mutants displaying reddish-brown or purplish-gray flowers are deficient in a novel glycosylation enzyme for anthocyanin biosynthesis, UDP-glucose:anthocyanidin 3-O-glucoside-2"-O-glucosyltransferase, due to 4-bp insertions in the gene," Plant J. 42(3):353-63 (May 2005).

Nagy et al., "Role of the yeast ABC transporter Yor1p in cadmium detoxification," Biochimie 88(11):1665-71 (Jun. 2006).

Nikaido & Takatsuk, "Mechanisms of RND multidrug efflux pumps," Biochim. Biophys. Acta. 1794(5):769-81 (May 2009).

Osmani et al., "Catalytic key amino acids and UDP-sugar donor specificity of a plant glucuronosyltransferase, UGT94B1: molecular modeling substantiated by site-specific mutagenesis and biochemical analyses," Plant Physiol. 148(3):1295-308 (Nov. 2008).

Osmani et al., "Substrate specificity of plant UDP-dependent glycosyltransferases predicted from crystal structures and homology modeling," Phytochemistry 70(3):325-47 (Feb. 2009).

Richman et al., "Functional genomics uncovers three glucosyltransferases involved in the synthesis of the major sweet glucosides of Stevia rebaudiana," Plant J. 41(1):56-67 (Jan. 2005).

Riesmeier et al., "Isolation and characterization of a sucrose carrier cDNA from spinach by functional expression in yeast," EMBO J. 11(13):4705-13 (Dec. 1992).

Rodríguez-Concepción & Boronat, "Elucidation of the methylerythritol phosphate pathway for isoprenoid biosynthesis in bacteria and plastids. A metabolic milestone achieved through genomics," Plant Physiol. 130(3):1079-89 (Nov. 2002).

Saier Jr et al., "The major facilitator superfamily," J. Mol. Microbiol. Biotechnol. 1(2):257-79 (Nov. 1999).

Saier Jr et al., "The Transporter Classification Database: recent advances," Nucleic Acids Res. 37:D274-8 (Jan. 2009).

Sauer et al., "The soluble and membrane-bound transhydrogenases UdhA and PntAB have divergent functions in NADPH metabolism of Escherichia coli," J. Biol. Chem. 279(8):6613-9 (Dec. 2003).

Sawada et al., "UDP-glucuronic acid:anthocyanin glucuronosyltransferase from red daisy (Bellis perennis) flowers. Enzymology and phylogenetics of a novel glucuronosyltransferase involved in flower pigment biosynthesis," J. Biol. Chem. 280(2):899-906 (Jan. 2005).

Shao et al., "Enhanced production of alpha-galactosyl epitopes by metabolically engineered Pichia pastoris," Appl. Environ. Microbiol. 69(9):5238-42 (Sep. 2003).

Son et al., "Production of flavonoid O-glucoside using sucrose synthase and flavonoid O-glucosyltransferase fusion protein," J. Microbiol. Biotechnol. 19(7):709-12 (Jul. 2009).

Sonnhammer et al., "Pfam: a comprehensive database of protein domain families based on seed alignments," Proteins 28(3):405-20 (Jul. 1997).

Sonnhammer et al., "Pfam: multiple sequence alignments and HMM-protiles of protein domains," Nucleic Acids Res. 26(1):320-2 (Jan. 1998).

Yadav et al., "Steviol Glycosides from Stevia: Biosynthesis Pathway Review and their Application in Foods and Medicine", Critical Reviews in Food Science and Nutrition, vol. 52, No. 11, pp. 988-998; (2012).

International Search Report by the International Searching Authority for International Application No. PCT/EP2014/052675, dated Apr. 23, 2014 (5 pages).

Written Opinion of the International Searching Authority for International Application No. PCT/EP2014/052675, dated Apr. 23, 2014 (7 pages).

Non-Final Office Action for U.S. Appl. No. 14/648,747, dated Mar. 23, 2017 (pp. 1-20).

International Preliminary Report on Patentability from the International Bureau for International Application No. PCT/EP2015/068314, dated Feb. 14, 2017 (pp. 1-10).

International Search Report and Written Opinion of the International Searching Authority for International Application No. PCT/EP2016/080516; dated Mar. 15, 2017, pp. 1-22.

Shao et al., "Crystal structures of a multifunctional triterpene/flavonoid glycosyltransferase from Medicago truncatula," Plant Cell 17(11):3141-54 (2005).

Shibata et al., "Glucosylation of Steviol and Steviol-Glucosides in Extracts from Stevia rebaudiana Bertoni" Plant Physiol. 95(1):152-56 (1991).

Singh et al., "Compendium of Transgenic Crop Plants: Transgenic Sugar, Tuber and Fiber," Ed. Kole & Hall, Blackwell Publishing Ltd. pp. 97-115 (2008).

U.S. Food and Drug Administration GRAS Notice 323, "GRAS Assessment of High Purity Steviol Glycosides; Food Usage Conditions for General Recognition of Safety for PureCircle USA, Inc.," pp. 1-262 (Feb. 2010).

U.S Food and Drug Administration GRAS Notice Notice 329, "Notice to the U.S. Food and Drug Administration that the use of RebpureTM (Rebaudioside A) derived from Stevia rebaudiana, as a Food Ingredient is Generally Recognized as Safe (GRAS)," pp. 1-275 (Mar. 2010).

Van Ooyen et al., "Heterologous protein production in the yeast Kluyveromyces lactis," FEMS Yeast Res. 6(3):381-92 (May 2006).

Vazquez De Aldana et al., "Nucleotide sequence of the exo-1,3-beta-glucanase-encoding gene, EXG1, of the yeast Saccharomyces cerevisiae," Gene 97(2):173-82 (1991).

Verwaal et al., "High-Level Production of Beta-Carotene in Saccharomyces cerevisiae by Successive Transformation with Carotenogenic Genes from Xanthophyllomyces dendrorhous," Appl Environ Microbiol. 73 (13):4342-50 (2007).

Wallin, "Steviol Glycosides," Chem. Tech Assessment—63rd JECFA, pp. 1-5 (2004).

Wallin, "Steviol Glycosides," Chem. Tech Assessment—69th JECFA, pp. 1-7 (2007).

Wallner & Elofsson, "Can correct protein models be identified?," Protein Sci. 12(5):1073-86 (May 2003).

Wang, "Structure, mechanism and engineering of plant natural product glycosyltransferases," FEBS Letters 583(20):3303-9 (2009).

Xu et al., "Generation of hepatitis B virus PreS2-S antigen in Hansenula polymorpha," Virol Sin. 29(6):403-9 (Dec. 2014).

Yadav et al., "A review on the improvement of stevia [Stevia rebaudiana (Bertoni)]," Can J Plant Sci. 91:1-27 (2011).

Yao et al., "A genetic linkage map for Stevia rebaudiana," Genome 42:657-61 (1999).

Yazaki, "ABC transporters involved in the transport of plant secondary metabolites," FEBS Lett. 580(4):1183-91 (Feb. 2006).

Yu et al., "Bioconversion of ethyl 4-chloro-3-oxobutanoate by permeabilized fresh brewer's yeast cells in the presence of allyl bromide," J Ind Microbiol Biotechnol. 34(2)151-6 (2007).

Yuan et al., "Kinetics and activation parameters for oxidations of styrene by Compounds I from the cytochrome P450 (BM-3) (CYP102A1) heme domain and from CYP119," Biochemistry 48(38):9140-6 (Sep. 2009).

Zheng et al. "An efficient one-step site-directed and site-saturation mutagenesis protocol," Nucleic Acids Res. 32(14): e115 (Aug. 2004).

Zhu et al., "A multi-omic map of the lipid-producing yeast Rhodosporidium toruloides," Nature Commun. 3:1112 (Oct. 2012).

GenBank Accession No. AAF61439.1, dated Sep. 25, 2000 (2 pages).

GenBank Accession No. AAM53963.1, dated Jun. 17, 2002 (2 pages).

(56) References Cited

OTHER PUBLICATIONS

GenBank Accession No. AAR06918.1, dated Dec. 28, 2004 (2 pages).
GenBank Accession No. AAT93110.1, dated Apr. 24, 2007 (2 pages).
GenBank Accession No. ACE87855.1, dated Jun. 24, 2008 (1 page).
GenBank Accession No. ACM47734.1, dated Feb. 7, 2009 (1 page).
GenBank Accession No. ACT33422.1, dated Jul. 17, 2009 (1 page).
GenBank Accession No. AF515727.1, dated Jun. 17, 2002 (2 pages).
GenBank Accession No. AY345974.1, dated Dec. 28, 2004 (2 pages).
GenBank Accession No. AY345978.1, dated Dec. 28, 2004 (2 pages).
Genbank Accession No. AY345980.1, dated Dec. 28, 2004 (2 pages).
GenBank Accession No. AY345982.1, dated Dec. 28, 2004 (2 pages).
GenBank Accession No. BG521726.1, dated May 13, 2000 (2 pages).
GenBank Accession No. CAA23011.1, dated Oct. 23, 2008 (2 pages).
GenBank Accession No. CAA46815.1, dated Apr. 18, 2005 (2 pages).
GenBank Accession No. DQ269454A, dated May 28, 2008 (2 pages).
GenBank Accession No. EU722415.1, dated Jun. 10, 2008 (2 pages).
GenBank Accession No. EU751291.1, dated Jun. 24, 2008 (2 pages).
EBI Accession No. AAY05902, "Jerusalem artichoke in-chain hydroxylase CYP8161" (1 page).
EBI Accession No. ABM86477, "Rice abiotic stress responsive polypeptide SEQ ID No:4723" (1 page).
UniProt Accession No. F2DG34, May 2011 (pp. 1-4).
UniProt Accession No. Q6VAA8, 2004 (pp. 1-6).
UniProt Accession No. Q7FPQ4, 2004 (pp. 1-6).
Uniprot Accession No. P07213, dated Feb. 17, 2016 (pp. 1-12).
Uniprot Accession No. P41948, dated Feb. 17, 2016 (pp. 1-12).
Uniprot Accession No. P38967, dated Feb. 17, 2016 (pp. 1-12).
Uniprot Accession No. Q08234, dated Feb. 17, 2016 (pp. 1-12).
Uniprot Accession No. P81451, dated Nov. 11, 2015 (pp. 1-8).
Uniprot Accession No. P38925, dated Jan. 20, 2016 (pp. 1-11).
Uniprot Accession No. Q12067, dated Dec. 9, 2015 (pp. 1-9).
Uniprot Accession No. Q12324, dated Jan. 20, 2016 (pp. 1-10).
Uniprot Accession No. Q99252, dated Jan. 20, 2016 (pp. 1-10).
Uniprot Accession No. Q12375, dated Feb. 17, 2016 (pp. 1-10).
Uniprot Accession No. Q99297, dated Feb. 17, 2016 (pp. 1-10).
Uniprot Accession No. Q12697, dated Feb. 17, 2016 (pp. 1-12).
Uniprot Accession No. Q08777, dated Feb. 17, 2016 (pp. 1-11).
Uniprot Accession No. P32798, dated Feb. 17, 2016 (pp. 1-11).
Uniprot Accession No. Q01926, dated Feb. 17, 2016 (pp. 1-9).
Uniprot Accession No. P05626, dated Feb. 17, 2016 (pp. 1-10).
Uniprot Accession No. P33311, dated Dec. 9, 2015 (pp. 1-11).
Uniprot Accession No. Q08986, dated Feb. 17, 2016 (pp. 1-12).
Uniprot Accession No. P53394, dated Feb. 17, 2016 (pp. 1-10).
Uniprot Accession No. Q12251, dated Feb. 17, 2016 (pp. 1-9).
Uniprot Accession No. P32331, dated Feb. 17, 2016 (pp. 1-9).
Uniprot Accession No. Q06497, dated Feb. 17, 2016 (pp. 1-10).
Uniprot Accession No. Q06598, dated Feb. 17, 2016 (pp. 1-13).
Uniprot Accession No. P38124, dated Feb. 17, 2016 (pp. 1-9).
Uniprot Accession No. P05316, dated Jan. 20, 2016 (pp. 1-10).
Uniprot Accession No. P38227, dated Feb. 17, 2016 (pp. 1-11).
Uniprot Accession No. P38355, dated Jan. 20, 2016 (pp. 1-9).
Uniprot Accession No. P38360, dated Feb. 17, 2016 (pp. 1-13).
Uniprot Accession No. P38361, dated Jan. 20, 2016 (pp. 1-10).
Uniprot Accession No. P25568, dated Jan. 20, 2016 (pp. 1-11).
Uniprot Accession No. P25371, dated Jan. 20, 2016 (pp. 1-13).
Uniprot Accession No. Q07376, dated Jan. 20, 2016 (pp. 1-10).
Uniprot Accession No. Q12154, dated Dec. 9, 2015 (pp. 1-12).
Uniprot Accession No. P54854, dated Feb. 17, 2016 (pp. 1-10).
Uniprot Accession No. P0CD99, dated Feb. 17, 2016 (pp. 1-10).
Uniprot Accession No. P32568, dated Feb. 17, 2016 (pp. 1-12).
Uniprot Accession No. P32916, dated Jan. 20, 2016 (pp. 1-10).
Uniprot Accession No. P30605, dated Feb. 17, 2016 (pp. 1-12).
Uniprot Accession No. P39953, dated Feb. 17, 2016 (pp. 1-10).
Uniprot Accession No. P25515, dated Jan. 20, 2016 (pp. 1-11).
Uniprot Accession No. P39980, dated Feb. 17, 2016 (pp. 1-10).
Uniprot Accession No. P52871, dated Nov. 11, 2015 (pp. 1-9).
Uniprot Accession No. P40035, dated Feb. 17, 2016 (pp. 1-10).
Uniprot Accession No. P40074, dated Jan. 20, 2016 (pp. 1-10).
Uniprot Accession No. P43569, dated Dec. 9, 2015 (pp. 1-9).
Uniprot Accession No. P43617, dated Feb. 17, 2016 (pp. 1-9).
Uniprot Accession No. P53154, dated Jan. 20, 2016 (pp. 1-10).
Uniprot Accession No. P53142, dated Jan. 20, 2016 (pp. 1-11).
Uniprot Accession No. P53134, dated Jan. 20, 2016 (pp. 1-9).
Uniprot Accession No. P13586, dated Feb. 17, 2016 (pp. 1-12).
Chen, "Summary on Study of Stevioside," China Pharmacist, vol. 10, No. 6, p. 598-599 (2007).
Chen et al., "Sugar transporters for intercellular exchange and nutrition of pathogens," Nature 468(7323):527-32 (2010).
Chen et al., "Fusion protein linkers: Property, design, and functionality", Advanced Drug Delivery reviews, 65(0):1257-69 (2013).
Daran et al., "Genetic and biochemical characterization of the UGP1 gene encoding the UDP-glucose pyrophosphorylase from Saccharomyces cerevisiae," Eur J Biochem. 233(2):520-30 (1995).
Garber et al., "Computational methods for transcriptome annotation and quantification using RNA-seq," Nat Methods 8(6):469-77 (2011).
Husar et al., Overexpression of the UGT73C6 alters brassinosteriod glucoside formation in *Arabidopsis thaliana*, BMC Plant Biology, 11:1-14 (2011).
Kawai et al., "Transformation of Saccharomyces cerevisiae and other fungi: methods and possible underlying mechanism," Bioeng Bugs. 1(6):395-403 (2010).
Lin et al., "Arrestin-related ubiquitin-ligase adaptors regulate endocytosis and protein turnover at the cell surface," Cell 135(4):714-25 (2008).
Nagalakshmi et al., "The transcriptional landscape of the yeast genome defined by RNA sequencing," Science 320(5881): 1344-9 (2008).
Nagatoshi et al., "UGT75L6 and UGT94E5 mediate sequential glucosylation of crocetin to crocin in Gardenia lasminoides", FEBS Letters, 586:1055-1061 (2012).
Nikko et al. "Arrestin-like proteins mediate ubiquitination and endocytosis of the yeast metal transporter Smf1," EMBO Rep. 9(12):1216-21 (2008).
Nikko & Pelham, "Arrestin-mediated endocytosis of yeast plasma membrane transporters," Traffic 10(12):1856-67 (2009).
Ohta et al., MassBank Accession No. FU000299 (May 2016).
Ohta et al., MassBank Accession No. FU000332 (May 2016).
Olsson et al., "Microbial production of next-generation stevia sweeteners," Microbial Cell Factories, 15:1-14 (2016).
Partow et al., "Characterization of different promoters for designing a new expression vector in Saccharomyces cerevisiae," Yeast 27:955-64 (2010).
Robinson & Oshlack et al., "A scaling normalization method for differential expression analysis of RNA-seq data," Genome Biol. 11(3):R25 (2010).
Saier Jr. et al., "The transporter classification database," Nucl. Acids Res., 42(1):D251-258 (2014).
Song et al., "The Aspergillus fumigatus 1-29 damage resistance protein family coordinately regulates ergosterol biosynthesis and azole susceptibility," MBIO, 7:1-13 (2016).
Wang et al., "RNA-Seq: a revolutionary tool for transcriptomics," Nat Rev Genet. 10(1):57-63 (2009).
Wang et al., "Design and construction of artificial biological systems for complex natural products biosynthesis," Chinese Journal of Biotechnology, 29(8):1146-60 (2013).
Wilhelm et al., "Defining transcribed regions using RNA-seq," Nature Protocols 5:255-66 (2010).

(56) References Cited

OTHER PUBLICATIONS

Yang Quanhua et.al., "Analysis of the Chemical constituents of Stevia rebaudiana and its sweetness," Journal of Beijing University of Chemical Technology, vol. 39, No. 2., p. 28-32 (2012) (English Abstract).
Yang et al., Base substitution mutations in uridinediphosphate-dependent glycosyltransferase 76G1 gene of Stevia rebaudiana causes the low levels of rebaudioside A: mutations in UGT76G1, a key gene of steviol glycosides synthesis, Plant Physiol Biochem. 80:220-5 (2014).
GenBank Accession No. Q08902, dated Jul. 22, 2015 (5 pages).
GenBank Accession No. Q12256, dated Jul. 22, 2015 (8 pages).
Non-Final Office Action for U.S. Appl. No. 14/764,898, dated Mar. 30, 2017 (pp. 1-17).
Non-Final Office Action for U.S. Appl. No. 14/761,629, dated Mar. 21, 2017 (pp. 1-19).
Final Office Action for U.S. Appl. No. 14/761,629, dated Aug. 11, 2017 (pp. 1-16).
Arnold, F. H. "Combinatorial and computational challenges for biocatalyst design," Nature 409(6817):253-257 (2001).
Duetz, "Microtiter plates as mini-bioreactors: miniaturization of fermentation methods," Trends Microbiol 15(10):469-75 (2007).
EBI Accession No. AAY05902, "Jerusalem artichoke in-chain hydroxylase CYP81B1" (1 page), Jun. 15, 2009.
EBI Accession No. ABM86477, "Rice abiotic stress responsive polypeptide SEQ ID No. 4723" (1 page), dated Jun. 2, 2005.
François et al., "Reserve carbohydrates metabolism in the yeast Saccharomyces cerevisiae," FEMS Microbiol Rev., 25(1):125-45 (2001).
Jones et al., "UGT73C6 and UGT78D1, Glycosyltransferases Involved in Flavonol Glycoside Biosynthesis in *Arabidopsis thaliana*," J. Biol. Chem., vol. 278, No. 45, pp. 43910-43918 (2003).
Mikayama et al., "Molecular cloning and functional expression of a cDNA encoding glycosylation-inhibiting factor," Proc Natl Acad Sci U S A. 90(21):10056-60 (1993).
Popenberger et al., Heterologous Expression of Arabidopsis UDP-Glucosyltransferases in Saccharomyces cerevisiae for Production of Zearalenone-4-0-Glucoside, Appl. Environ. Microbial., vol. 72, pp. 4404-4410 (2006).
Rudinger et al., "Characteristics of the amino acids as components of a peptide hormone sequence," Peptide Hormones. Biol. Council. pp. 5-7 (1976).
Non-Final Office Action for U.S. Appl. No. 15/328,365, dated Feb. 1, 2019 (pp. 1-18).
Jewett et al. "An integrated cell-free metabolic platform for protein production and synthetic biology," Mol Syst Biol. 4:220 (2008).
Johnstone et al., "Cloning an Aspergillus nidulans developmental gene by transformation," EMBO J. 4(5):1307-11 (1985).
Khoury et al., "Computational design of Candida boidinii xylose reductase for altered cofactor specificity," Protein Sci. 18(10):2125-38 (Oct. 2009).
Kim et al., "Hydroxylation of ent-Kaurenoic Acid to Steviol in Stevia rebaudiana Bertoni-Purification and Partial Characterization of the Enzyme," Arch Biochem Biophys. 332(2):223-30 (1996).
Kim & Shibata, "Characterization of ent-kaurenoic acid 13-hydroxylase in steviol biosynthesis of Stevia rebaudiana Bertoni," Journal of the Korean Agriculturalchemical Society 40(6):501-7 (1997).
Knowles et al., "Genetic Transformation and Plant Regeneration in Stevia rebaudiana Using Microprojectile Bombardment," In Vitro Cellular & Developmental Biology 39(abstract):23-A (2003).
Kohda et al., "New Sweet Diterpene glucoside from Stevia Rebaudiana," Phytochemistry 15(6):981-3 (1976).
Kondo et al., "Preparation of high activity whole cell biocatalyst by permeabilization of recombinant flocculent yeast with alcohol," Enzyme Microb Technol. 27(10),806-11 (2000).
Kumar et al., "A comprehensive analysis of fifteen genes of steviol glycosides biosynthesis pathway in Stevia rebaudiana (Bertoni)" Gene 492:276-84 (Epub Oct. 20, 2011).
Kusama et al., "Transglucosylation into stevioside by the enzyme system from Streptomyces sp.," Agric. Biol. Chem. 50(10):2445-51 (Oct. 1986).
Li et al., "Crystal structure of Medicago truncatula UGT85H2—insights into the structural basis of a multifunctional (iso) flavonoid glycosyltransferase," J Mol Biol. 370(5):951-63 (2007).
Li et al., "Systematic Mutational Analysis of Peptide Inhibition of the p53-MDM2/MDMX," J Mol Biol. 398(2):200-13 (2010).
Li et al., "High-density cultivation of oleaginous yeast Rhodosporidium toruloides Y4 in fed-batch culture," Enzyme and Microbial Technology 41(3):312-7 (Aug. 2007).
Liu et al., "Preparation of high-activity whole cell biocatalysts by permeabilization of recombinant yeasts with alcohol," J Biosci Bioeng. 89(6):554-8 (2000).
Ma et al., "Molecular cloning and characterization of Stevia Rebaudiana UDP-glucosyltransferase," Acta Biologiae Experimentalis Sinica 36(2):123-9 (2003).
Ma "Part 1. Molecular Cloning and Functional Analysis of UDPG Glucosyltransferase Gene. Part 2. Molecular Cloning, Sequence Analysis and Evolution of Actin and EF1a Genes in Stevia Rebaudiana." Chinese Doctor and Master Dissertations Full-Text Database, Agricultural Technology Part, vol. 2; pp. 1-74 (2004).
Madan et al., "Stevia rebaudiana (Bert.) Bertoni—A Review," Indian Journal of Natural Products and Resources 1(3)267-86 (2010).
Madhav et al., "Functional and structural variation of uridine diphosphate glycosyltransferase (UGT) gene of Stevia rebaudiana—UGTSr involved in the synthesis of rebaudioside A," Plant Physiol. Biochem. 63:245-53 (Feb. 2013).
Malonek et al., "The NADPH-cytochrome P450 Reductase Gene from Gibberalla fujikuroi is Essential for Gibberellin Biosynthesis," J Bio Chem. 279(24):25075-84 (2004).
Mantovaneli et al., "The effect of temperature and flow rate on the clarification of the aqueous stevia-extract in a fixed-bed column with zeolites," Braz J Chem Eng. 21(3):449-58 (2004).
Mattanovich et al., "Recombinant protein production in yeasts," Methods Mol Biol. 824:329-58 (2012).
Megeji et al., "Introducing Stevia rebaudiana, a natural zero-calorie sweetener," Current Science 88(5):801-4 (2005).
Mohamed et al., "UDP-dependent glycosyltransferases involved in the biosynthesis of steviol glycosides" Journal of Plant Physiology 168(10):1136-1141 (Jul. 2011; Epub Apr. 7, 2011).
Mumberg et al., "Yeast vectors for the controlled expression of heterologous proteins in different genetic backgrounds," Gene 156(1):119-22 (1995).
Naesby et al., "Yeast artificial chromosomes employed for random assembly of biosynthetic pathways and production of diverse compounds in Saccharomyces cerevisiae," Microb Cell Fact. 8:45 (2009).
Naglak & Wang, "Rapid protein release from *Escherichia coli* by chemical permeabilization under fermentation conditions," Biotechnol Bioeng. 39(7):732-40 (1991).
Nakagiri et al., "cDNA cloning, functional expression and characterization of ent-copalyl diphosphate synthase from Scoparia dulcis L.," Plant Sci. 169:760-7 (2005).
Nelson et al., "P450 superfamily: update on new sequences, gene mapping, accession numbers and nomenclature," Pharmacogenetics 6:1-42 (1996).
Newman et al., "High-level production of amorpha-4,11-diene in a two-phase partitioning bioreactor of metabolically engineered *Escherichia coli*," Biotechnol Bioeng 95(4):684-91 (2006).
Nicaud, "Yarrowia lipolytica," Yeast 29(10):409-18 (Oct. 2012).
Nielsen et al., "Efficient PCR-based gene targeting with a recyclable marker for Aspergillus nidulans," Fungal Genet Biol. 43(1):54-64 (2006).
Nour-Eldin et al., "USER cloning and USER fusion: the ideal cloning techniques for small and big laboratories," Methods Mol Biol. 643:185-200 (2010).
Ohta et al., "Characterization of Novel Steviol Glycosides from Leaves of Stevia rebaudiana Morita," J. Applied Glycosides 57(3):199-209 (Mar. 2010).
Ohta et al., MassBank Accession No. FU000341 (May 2011).
Ohta et al., MassBank Accession No. FU000342 (May 2011).

(56) References Cited

OTHER PUBLICATIONS

Ohta et al., MassBank Accession No. FU000343 (May 2011).
Ohtani et al., "Further Study on the 1,4-alpha-Transglucosylation of Rubusoside, a Sweet Steviol-Bisglucoside from Rubus suavissimus," Agric Biol Chem. 55(2):449-53 (1991).
Oka & Jigami, "Reconstruction of de novo pathway for synthesis of UDP-glucuronic acid and UDP-xylose from Intrinsic UDP-glucose in Saccharomyces cerevisiae," FEBS J. 273(12):2645-57 (2006).
Orihara et al., "Biotransformation of steviol by cultured cells of eucalyptus perriniana and Coffea Arabica," Phytochemistry 30(12):3989-92 (1991).
Paradise et al., "Redirection of flux through the FPP branch-point in Saccharomyces cerevisiae by down-regulating squalene synthase," Biotechnol Bioeng. 100(2):371-8 (2008).
Pearson & Lipman, "Improved tools for biological sequence comparison," Proc Natl Acad Sci. 85(8):2444-8 (1998).
Piirainen et al., "Glycoengineering of yeasts from the perspective of glycosylation efficiency," N Biotechnol. 31(6):532-7 (Dec. 2014).
Pompon et al., "Yeast Expression of Animal and Plant P450s in Optimized RedoxEnvironments," Methods Enzymol 272:51-64 (1996).
Prelich, "Gene overexpression: uses, mechanisms, and interpretation," Genetics 190(3):841-54 (Mar. 2012).
Presecki & Vasic-Racki, "Production of L-malic acid by permeabilized cells of commercial Saccharomyces sp. strains," Biotechnol Lett. 27(23-24):1835-9 (2005).
Ro et al., "Production of the antimalarial drug precursor artemisinic acid in engineered yeast," Nature 440(7086):940-3 (2006).
Saenge et al., "Potential use of oleaginous red yeast Rhodotorula glutinis for the bioconversion of crude glycerol from biodiesel plant to lipids and carotenoids," Process Biochemistry 46(1):210-8 (Jan. 2011).
Schwab et al., Poster, "Watchmaker®—Compound Generation by Combinatorial Genetics and Screening in Yeast," 141st Annual Conference in St. Louis, 2008, 1 page.
Sen et al., "Developments in Directed Evolution for Improving Enzyme Functions," Appl Biochem Biotechnol.143(3):212-23 (2007).
Senthilraja et al., "RNA secondary structure prediction: Analysis of Saccharomyces cerevisiae RNAs," Int. J. Pharm. Rev. Res. 25(2):287-91 (Mar.-Apr. 2014).
Abraham & Bhat,"Permeabilization of bakers yeast with N-lauroyl sarcosine," J Ind Microbial Biotechnol. 35(8):799-804 (2008).
Ageitos et al., "Oily yeasts as oleaginous cell factories," Appl Microbiol Biotechnol. 90(4):1219-27 (May 2011).
Agrawal, "NMR spectroscopy in the structural elucidation of oligosaccharides and glycosides," Phytochemistry 31(10):3307-30 (1992).
Ajikumar et al., "Terpenoids: opportunities for biosynthesis of natural product drugs using engineered microorganisms," Molecular Pharmaceuticals 5(2):167-90 (2008).
Alakomi et al., "Lactic acid permeabilizes gram-negative bacteria by disrupting the outer membrane," Appl Environ Microbiol. 66(5):2001-5 (2000).
Ali et al., "Biochemical investigation during different stages of in vitro propagation of Stevia rebaudiana," Pak J Bot. 42(4):2827-37 (2010).
Bankar et al., "Environmental and industrial applications of Yarrowia lipolytica," Appl Microbiol Biotechnol. 84(5):847-65 (Oct. 2009).
Baykov et al., "A malachite green procedure for orthophosphate determination and its use in alkaline phosphatase-based enzyme immunoassay," Anal Biochem. 171(2):266-70 (Jun. 1988).
Beopoulos et al., "Yarrowia lipolytica: A model and a tool to understand the mechanisms implicated in lipid accumulation," Biochimie 91(6):692-6 (Jun. 2009).
Brandle et al., "Leaf ESTs from Stevia rebaudiana: A Resource for Gene Discovery in Diterpene Synthesis," Plant Mol Biol. 50(4-5):613-22 (2002).
Brandle & Telmer, "Steviol glycoside biosynthesis," Phytochemistry 68(14):1855-63 (2007).
Brochado et al. "Improved vanillin production in baker's yeast through in silico design," Microb Cell Fact. 9:84-98 (2010).

Carretero-Paulet et al., "Expression and Molecular Analysis of the Arabidopsis DXR Gene Encoding 1-Deoxy-d-Xylulose 5-Phosphate Reductoisomerase, the First Committed Enzyme of the 2-C-Methyl-D-Erythritol 4-Phosphate Pathway," Plant Physiol. 129(4):1581-91 (2002).
Ceunen & Geuns, "Steviol glycosides: chemical diversity, metabolism, and function," J. Nat. Prod. 76(6):1201-28 (Jun. 2013).
Chemler et al., "Biosynthesis of isoprenoids, polyunsaturated fatty acids and flavonoids in Saccharomyces cerevisiae," Microb Cell Fact. 5:20 (2006).
Chen et al., "MolProbity: all-atom structure validation for macromolecular crystallography," Acta Crystallogr D Biol Crystallogr 66(Pt 1):12-21 (Jan. 2010).
Chica et al., "Semi-rational approaches to engineering enzyme activity: combining the benefits of directed evolution and rational design," Curr Opin Biotechnol.16(4):378-84 (2005).
Chow & Palecek, "Enzyme encapsulation in permeabilized Saccharomyces cerevisiae cells," Biotechnol Prog. 20(2):449-56 (2004).
Correa et al., "Genetic mapping of 1,3-beta-glucanase-encoding genes in Saccharomyces cerevisiae," Current Genet. 22(4):283-8 (1992).
Darise et al., "Enzymic Transglucosylation of Rubusoside and the Structure-Sweetness Relationship of Steviol-Bisglycosides," Agric. Biol. Chem. 48(10):2483-8 (Jan. 1984).
Davis et al., "MolProbity: all-atom contacts and structure validation for proteins and nucleic acids," Nucleic Acids Res. 35:W375-83 (Apr. 2007).
Del Sorbo et al., "Fungal transporters involved in efflux of natural toxic compounds and fungicides," Fungal. Genet. Biol. 30(1):1-15 (Jun. 2000).
Diener et al., "Arabidopsis ALF5, a multidrug efflux transporter gene family member, confers resistance to toxins," Plant Cell 13(7):1625-38 (Jul. 2001).
Dodhia et al., "Engineering human cytochrome P450 enzymes into catalytically self-sufficient chimeras using molecular Lego," J Biol Inorg Chem. 11(7):903-16 (Oct. 2006).
Dubey, et al., An overview of the non-mevalonate pathway for terpenoid biosynthesis in plants, J. Biosci. 28(5):637-46 (2003).
Dubois & Stephenson, "Diterpenoid sweeteners. Synthesis and sensory evaluation of stevioside analogues with improved organoleptic properties," J. Med. Chem. 28(1):93-8 (Jan. 1985).
EFSA Panel on Food Additives and Nutrient Sources added to Food (ANS), "Scientific Opinion on the safety of steviol glycosides for the proposed uses as a food additive," EFSA Journal 8(4):1537 (2010).
Eisenreich et al., "Biosynthesis of isoprenoids via the non-mevalonate pathway," Cell Mol Life Sci. 61(12):1401-6 (2004).
Emboss Needle results for Pairwise Sequence Alignment of UGT91D1 and UGT91D2; dated Apr. 4, 2016, 2 pages.
Emmerstorfer et al., "Over-expression of ICE2 stabilizes cytochrome P450 reductase in Saccharomyces cerevisiae and Pichia pastoris," Biotechnol J. 10(4):623-35 (Apr. 2015).
Estrada De Martin et al., "Ice2p is important for the distribution and structure of the cortical ER network in Saccharomyces cerevisiae," J Cell Sci. 118(Pt 1):65-77 (Oct. 2006).
Fernandez et al., "Activation of chitin synthetase in permeabilized cells of a Saccharomyces cerevisiae mutant lacking proteinase B," J Bacteriol. 152(3):1255-64 (1982).
Flores et al., "Permeabilization of yeast cells (Kluyveromyces lactis) with organic solvents," Enzyme Microb Technol. 16(4):340-6 (1994).
Fowler & Zabin, "Effects of Dimethylsulfoxide on the Lactose Operon in *Escherichia coli*," J Bacteriol. 92(2):353-7 (1966).
Freire, "Differential scanning calorimetry," Methods Mol Biol. 40:191-218 (1995).
Fukunaga et al., "Enzymatic transglucosylation products of stevioside: separation and sweetness-evaluation," Agric. Biol. Chem. 53(6):1603-7 (Jan. 1989).
Geuns, "Stevioside," Phytochemistry 64(5):913-21 (2003).
Giaever & Nislow, "The yeast deletion collection: a decade of functional genomics," Genetics 197(2):451-65 (Jun. 2014).
Getz & Schiestl, "High-efficiency yeast transformation using the LiAc/SS carrier DNA/PEG method," Nat Protoc. 2(1):31-4 (2007).

(56) References Cited

OTHER PUBLICATIONS

Girvan et al., "Flavocytochrome P450 BM3 mutant W1046A is a NADH-dependent fatty acid hydroxylase: implications for the mechanism of electron transfer in the P450 BM3 dimer," Arch Biochem Biophys. 507(1):75-85 (Mar. 2011).
Goralczyk, "Compounds from Stevia for Improving and Maintaining Mental Performance," Stevia World Forum, Feb. 24-25, 2010, 17 pages.
Guleria & Yadav, "Insights into Steviol Glycoside Biosynthesis Pathway Enzymes Through Structural Homology Modeling," Am. J. Biochem. Molec. Biol. 3(1):1-19 (2013).
Gunel et al., "Metabolic Engineering for Production of Geranylgeranyl Pyrophosphate Synthase in Non-Carotenogenic Yeast Schizosaccharomyces Pombe," Biotechnol. & Biotechnol. Eq. 20(3):76-82 (2006).
Hansen et al., "De novo biosynthesis of vanillin in fission yeast (Schizosaccharomyces pombe) and baker's yeast (Saccharomyces cerevisiae)," Appl Environ Microbiol. 75(9):2765-74 (2009).
Hansen et al., "Versatile Enzyme Expression and Characterization System for Aspergillus nidulans, with the Penicillium brevicompactum Polyketide Synthase Gene from the Mycophenolic Acid Gene Cluster as a Test Case," Appl Environ Microbiol. 77(9):3044-51 (2011).
Hellfritsch et al., "Human psychometric and taste receptor responses to steviol glycosides," J. Agric. Food Chem. 60(27):6782-93 (Jul. 2012).
Humphrey et al., "Spatial organisation of four enzymes from Stevia rebaudiana that are involved in steviol glycoside synthesis," Plant Mol Bio. 61(1-2):47-62 (2006).
Iandolino et al., "High-Quality RNA, cDNA, and Derived EST Libraries From Grapevine (Vitis vinifera L.)," Plant Mol Biol Reporter 22:269-78 (2004).
Irmler et al., "Indole alkaloid biosynthesis in Catharanthus roseus: new enzyme activities and identification of cytochrome P450 CYP72A1 as secologanin synthase," Plant J. 24(6):797-804 (2000).
Jennewein et al., "Taxol biosythesis: baxane 13 alpha-hydroxylase is a cytochrome P450-dependent monooxygenase," Proc Natl Acad Sci U S A 98(24):13595-600 (2001).
GenBank Accession No. AAA23410.1, dated Jun. 11, 1993 (2 pages).
GenBank Accession No. AAB47941.1, dated Feb. 21, 1997 (2 pages).
GenBank Accession No. AAC39443, dated Apr. 17, 1998 (2 pages).
GenBank Accession No. AAT70083, dated My 23, 2006 (2 pages).
GenBank Accession No. BAE76241.1, dated Nov. 20, 2008 (14 pages).
GenBank Accession No. BAE76318.1, dated Nov. 20, 2008 (14 pages).
GenBank Accession No. NP_192187, dated Jan. 22, 2014 (3 pages).
GenBank Accession No. POCE68, dated Jul. 22, 2015 (7 pages).
GenBank Accession No. P12383, dated Jul. 22, 2015 (7 pages).
GenBank Accession No. P12866, dated Jul. 22, 2015 (9 pages).
GenBank Accession No. P13090, dated Jul. 22, 2015 (7 pages).
GenBank Accession No. P25371, dated Jul. 22, 2015 (9 pages).
GenBank Accession No. P32568, dated Jul. 22, 2015 (8 pages).
GenBank Accession No. P33200, dated Jul. 22, 2015 (4 pages).
GenBank Accession No. P33302, dated Jul. 22, 2015 (22 pages).
GenBank Accession No. P33335, dated Jul. 22, 2015 (7 pages).
GenBank Accession No. P36173, dated Jul. 22, 2015 (5 pages).
GenBank Accession No. P38124, dated Jul. 22, 2015 (4 pages).
GenBank Accession No. P38125, dated Jul. 22, 2015 (6 pages).
GenBank Accession No. P38227, dated Jul. 22, 2015 (7 pages).
GenBank Accession No. P38724, dated Jul. 22, 2015 (4 pages).
GenBank Accession No. P38731, dated Jul. 22, 2015 (5 pages).
GenBank Accession No. P38776, dated Jul. 22, 2015 (5 pages).
GenBank Accession No. P39709, dated Jul. 22, 2015 (5 pages).
GenBank Accession No. P39980, dated Jul. 22, 2015 (5 pages).
GenBank Accession No. P40445, dated Jul. 22, 2015 (4 pages).
GenBank Accession No. P40474, dated Jul. 22, 2015 (6 pages).
GenBank Accession No. P40475, dated Jul. 22, 2015 (5 pages).
GenBank Accession No. P40550, dated Jul. 22, 2015 (7 pages).
GenBank Accession No. P41930, dated Jul. 22, 2015 (8 pages).
GenBank Accession No. P50080, dated Jul. 22, 2015 (6 pages).
GenBank Accession No. P51533, dated Jul. 22, 2015 (5 pages).
GenBank Accession No. P53049, dated Jul. 22, 2015 (8 pages).
GenBank Accession No. P53099, dated Jul. 22, 2015 (6 pages).
GenBank Accession No. P53283, dated Jul. 22, 2015 (7 pages).
GenBank Accession No. P53389, dated Jul. 22, 2015 (5 pages).
GenBank Accession No. P53756, dated Jul. 22, 2015 (6 pages).
GenBank Accession No. P53943, dated Jul. 22, 2015 (7 pages).
GenBank Accession No. P54862, dated Jul. 22, 2015 (8 pages).
GenBank Accession No. Q02785, dated Jul. 22, 2015 (10 pages).
GenBank Accession No. Q03263, dated Jul. 22, 2015 (5 pages).
GenBank Accession No. Q04182, dated Jul. 22, 2015 (7 pages).
GenBank Accession No. Q05998, dated Jul. 22, 2015 (6 pages).
GenBank Accession No. Q06149, dated Jul. 22, 2015 (3 pages).
GenBank Accession No. Q06451, dated Jul. 22, 2015 (7 pages).
GenBank Accession No. Q07824, dated Jul. 22, 2015 (10 pages).
GenBank Accession No. Q07904, dated Jul. 22, 2015 (5 pages).
GenBank Accession No. Q08234, dated Jul. 22, 2015 (8 pages).
GenBank Accession No. Q08299, dated Jul. 22, 2015 (6 pages).
GenBank Accession No. Q08409, dated Jul. 22, 2015 (5 pages).
Bateman et al., "Pfam 3.1: 1313 multiple alignments and profile HMMs match the majority of proteins," Nucleic Acids Res. 27(1)260-2 (Jan. 1999).
Bay & Turner, "Diversity and evolution of the small multidrug resistance protein family," BMC Evol. Biol. 9:140 (Jun. 2009).
Brachmann et al., "Designer deletion strains derived from Saccharomyces cerevisiae S288C: a useful set of strains and plasmids for PCR-mediated gene disruption and other applications," Yeast 14:115-32 (1998).
Chen et al., "Transferring a biosynthetic cycle into a productive *Escherichia coli* strain: large-scale synthesis of galactosides," J. Am. Chem. Soc. 123(36):8866-7 (Sep. 2001).
Chenna et al., "Multiple sequence alignment with the Clustal series of programs," Nucleic Acids Res. 31(13):3497-500 (Jul. 2003).
GenBank Accession No. AAB62280, dated Jul. 2, 1997 (2 pages).
GenBank Accession No. AAB87091, dated Mar. 22, 2000 (2 pages).
GenBank Accession No. AAC28895.1, dated Aug. 6, 1998 (2 pages).
GenBank Accession No. AAC39505, dated Jul. 26, 1998 (1 pages).
GenBank Accession No. AAD34294, dated Mar. 22, 2000 (2 pages).
GenBank Accession No. AAD34295, dated Mar. 22, 2000 (2 pages).
GenBank Accession No. AAD47596, dated Aug. 9, 1999 (2 pages).
GenBank Accession No. AAH69913, dated Jul. 15, 2006 (2 pages).
GenBank Accession No. AEE36246, dated Oct. 6, 2014 (3 pages).
GenBank Accession No. AAR06912, dated Dec. 28, 2004 (2 pages).
GenBank Accession No. AAR06916.1, dated Dec. 28, 2004 (2 pages).
GenBank Accession No. AAR06920.1, dated Dec. 28, 2004 (2 pages).
GenBank Accession No. ABA42921, dated Jun. 21, 2006 (1 page).
GenBank Accession No. ABB88839, dated May 28, 2008 (2 pages).
GenBank Accession No. ABC59076, dated Jun. 6, 2007 (1 page).
GenBank Accession No. ABC98596, dated Jan. 31, 2014 (2 pages).
GenBank Accession No. ABD60225, dated May 28, 2008 (2 pages).
GenBank Accession No. ABD92926, dated Oct. 10, 2007 (2 pages).
GenBank Accession No. AC133334, dated Jan. 31, 2004 (44 pages).
GenBank Accession No. ACD93722, dated Jun. 10, 2008 (1 page).
GenBank Accession No. AF034774, dated Apr. 17, 1998 (2 pages).
GenBank Accession No. AY562490, dated May 23, 2006 (3 pages).
GenBank Accession No. BAA43200, dated Mar. 13, 1999 (2 pages).
GenBank Accession No. BAB59027, dated Jan. 30, 2002 (1 page).
GenBank Accession No. BAF61135, dated May 9, 2007 (2 pages).
GenBank Accession No. BAG30962, dated Nov. 12, 2012 (2 pages).
GenBank Accession No. BC153262, dated Oct. 4, 2007 (3 pages).
GenBank Accession No. CAA75568, dated Nov. 14, 2006 (2 pages).
GenBank Accession No. CAA76703, dated Nov. 14, 2006 (1 page).
GenBank Accession No. CAE09055, dated Nov. 14, 2006 (2 pages).
GenBank Accession No. CAG41604, dated Feb. 6, 2015 (2 pages).
GenBank Accession No. DQ3988713, dated May 28, 2008 (2 pages).
GenBank Accession No. EDY51667, dated Sep. 2, 2008 (2 pages).

(56) References Cited

OTHER PUBLICATIONS

GenBank Accession No. EU263989, dated Jun. 11, 2008 (2 pages).
GenBank Accession No. NM_116512, dated Jan. 22, 2014 (3 pages).
GenBank Accession No. NP_001105097, dated Aug. 4, 2015 (2 pages).
GenBank Accession No. NP_013636.1 (YML075C), dated Jul. 16, 2015 (3 pages).
GenBank Accession No. NP_194183, dated Jan. 22, 2014 (4 pages).
GenBank Accession No. NP_195399, dated Jan. 22, 2014 (3 pages).
GenBank Accession No. NP_197872.1, dated Jan. 22, 2014 (2 pages).
GenBank Accession No. Q9UVY5.1, dated Apr. 1, 2015 (3 pages).
GenBank Accession No. AZF53544, dated Apr. 14, 2011 (2 pages).
UniProt Accession No. B5MEX6, Nov. 4, 2008 (1 page).
UniProt Accession No. E4MVV7, Feb. 8, 2011 (1 page).
UniProt Accession No. F6KWJ2, Jul. 27, 2011 (1 page).
UniProt Accession No. H9BYK3, May 16, 2012 (1 page).
Uniprot Accession No. P38125, dated Feb. 17, 2016 (pp. 1-11).
Uniprot Accession No. P39709, dated Jan. 20, 2016 (pp. 1-10).
Uniprot Accession No. P38176, dated Feb. 17, 2016 (pp. 1-9).
Uniprot Accession No. P07251, dated Jan. 20, 2016 (pp. 1-11).
Uniprot Accession No. P38142, dated Jan. 20, 2016 (pp. 1-11).
Uniprot Accession No. P38359, dated Feb. 17, 2016 (pp. 1-11).
Uniprot Accession No. P25594, dated Feb. 17, 2016 (pp. 1-9).
Uniprot Accession No. P25621, dated Feb. 17, 2016 (pp. 1-10).
Uniprot Accession No. P17261, dated Dec. 9, 2015 (pp. 1-10).
Uniprot Accession No. Q99385, dated Jan. 20, 2016 (pp. 1-10).
Uniprot Accession No. P17255, dated Jan. 20, 2016 (pp. 1-14).
Uniprot Accession No. P10870, dated Feb. 17, 2016 (pp. 1-12).
Uniprot Accession No. P32837, dated Feb. 17, 2016 (pp. 1-10).
Uniprot Accession No. Q12298, dated Nov. 11, 2015 (pp. 1-9).
Uniprot Accession No. Q12675, dated Feb. 17, 2016 (pp. 1-13).
Uniprot Accession No. Q05497, dated Jan. 20, 2016 (pp. 1-9).
Uniprot Accession No. Q04182, dated Feb. 17, 2016 (pp. 1-12).
Uniprot Accession No. P39932, dated Feb. 17, 2016 (pp. 1-11).
Uniprot Accession No. P39986, dated Feb. 17, 2016 (pp. 1-13).
Uniprot Accession No. P32660, dated Feb. 17, 2016 (pp. 1-13).
Uniprot Accession No. P43581, dated Feb. 17, 2016 (pp. 1-11).
Uniprot Accession No. P38929, dated Feb. 17, 2016 (pp. 1-12).
Uniprot Accession No. P12383, dated Feb. 17, 2016 (pp. 1-11).
Uniprot Accession No. P32804, dated Jan. 20, 2016 (pp. 1-10).
Uniprot Accession No. P53273, dated Feb. 17, 2016 (pp. 1-12).
Uniprot Accession No. P53299, dated Jan. 20, 2016 (pp. 1-9).
Uniprot Accession No. P50077, dated Feb. 17, 2016 (pp. 1-13).
Uniprot Accession No. P50080, dated Feb. 17, 2016 (pp. 1-10).
Uniprot Accession No. P53049, dated Feb. 17, 2016 (pp. 1-13).
Uniprot Accession No. P33413, dated Feb. 17, 2016 (pp. 1-13).
Uniprot Accession No. P40501, dated Feb. 17, 2016 (pp. 1-10).
Uniprot Accession No. P40310, dated Feb. 17, 2016 (pp. 1-11).
Uniprot Accession No. P40309, dated Jan. 20, 2016 (pp. 1-11).
Uniprot Accession No. P42946, dated Nov. 11, 2015 (pp. 1-9).
Uniprot Accession No. P40897, dated Jan. 20, 2016 (pp. 1-11).
Uniprot Accession No. P47144, dated Jan. 20, 2016 (pp. 1-9).
Uniprot Accession No. POCE00, dated Feb. 17, 2016 (pp. 1-10).
Uniprot Accession No. P35724, dated Jan. 20, 2016 (pp. 1-10).
Uniprot Accession No. P28584, dated Feb. 17, 2016 (pp. 1-10).
Uniprot Accession No. P36172, dated Feb. 17, 2016 (pp. 1-10).
Uniprot Accession No. P36173, dated Feb. 17, 2016 (pp. 1-10).
Uniprot Accession No. P32366, dated Nov. 11, 2015 (pp. 1-10).
Uniprot Accession No. P13090, dated Feb. 17, 2016 (pp. 1-12).
Uniprot Accession No. Q05131, dated Feb. 17, 2016 (pp. 1-12).
Uniprot Accession No. P04710, dated Feb. 17, 2016 (pp. 1-11).
Uniprot Accession No. Q04835, dated Jan. 20, 2016 (pp. 1-10).
Uniprot Accession No. P53943, dated Feb. 17, 2016 (pp. 1-11).
Uniprot Accession No. P53507, dated Dec. 9, 2015 (pp. 1-9).
Uniprot Accession No. D6W196, dated Feb. 17, 2016 (pp. 1-11).
Uniprot Accession No. P53932, dated Jan. 20, 2016 (pp. 1-9).
Boer, "Strain and process development for fermentative production of Rebaudiosides" Abstract of Offered Oral from 33rd International Specialised Symposium on Yeasts; Jun. 26-29, 2017 University of College Cork, Ireland; pp. 1-2.
Communication of a Notice of Opposition issued by the European Patent Office for European Application No. 12750513.9, dated Mar. 6, 2017 (pp. 1-8).
Mahe et al., "The ATP Binding Cassette Transporters Pdr5 and Snq2 of Saccharomyces cerevisiae can Mediate Transport of Steriods via in Vivo", JBC, 271(41):25167-25172. (Oct. 1996).
Starratt et al., "Rebaudioside F, a diterpene glycoside from Stevia redaudiana", Phytochemistry, 59(4):367-370. (Feb. 2002). Abstract.
Sequence alignment between the sequence of Uniprot database entry Q75183 version 31, updated Jul. 22, 2008 and SEQ ID No. 152 (from European Patent No. 2742142) as cited in Notice of Opposition against EP Application No. 12750513.9; dated Mar. 6, 2017; pp. 1-2.
Statement of fact and arguments in support of opposition, dated Feb. 28, 2017 (pp. 1-24).
Uniprot Accession No. Q75183, dated Jul. 5, 2004 (pp. 1-2).
Uniprot Accession No. Q75183, dated Jul. 22, 2008 (pp. 1-4).
Third Party Observation in EP Application No. 13801569.8; dated Apr. 26, 2017. pp. 1-5.
International Search Report and Written Opinion of International Search Authority for International Application No. PCTEP2017/059028; dated Jun. 27, 2017, pp. 1-15.
GenBank Accession No. AAS07253.1, dated Jan. 31, 2004 (3 pages).
Wang et al., "Glycosylation and Glycosyltransferase of Small Molecular Compounds of Plant," China Academic Journal, vol. 44-5, 997-1003 (2008).

\* cited by examiner

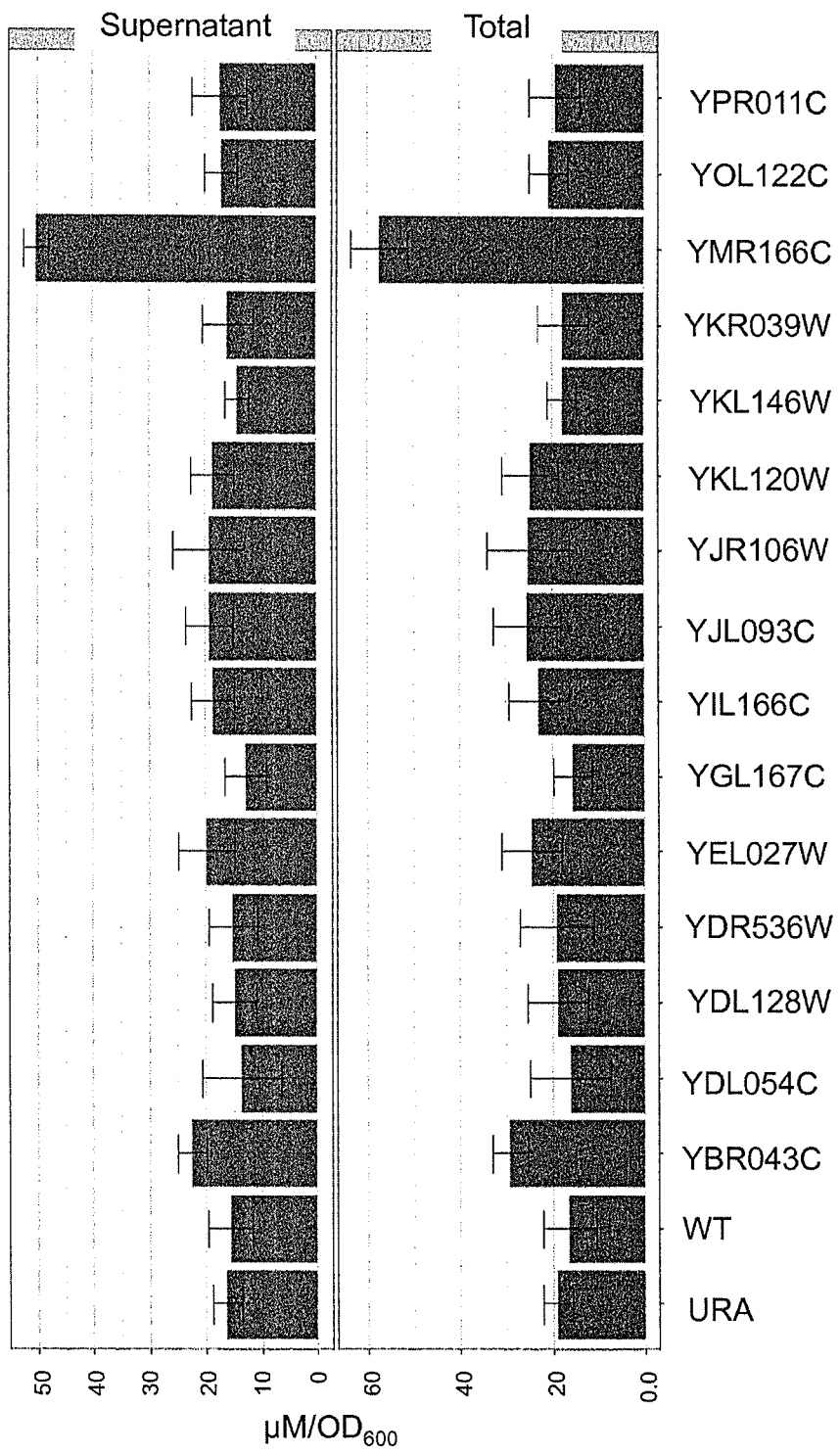

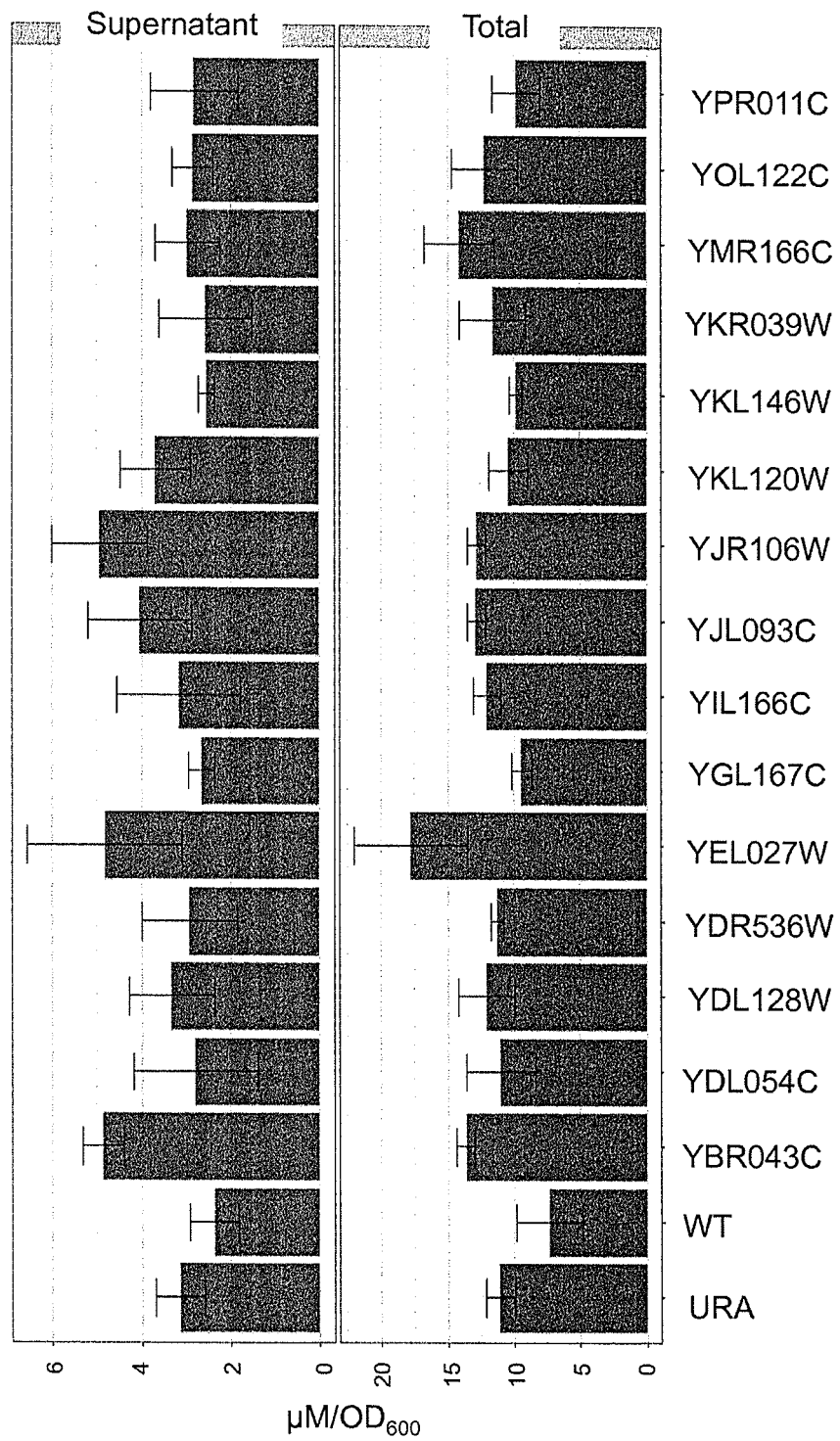

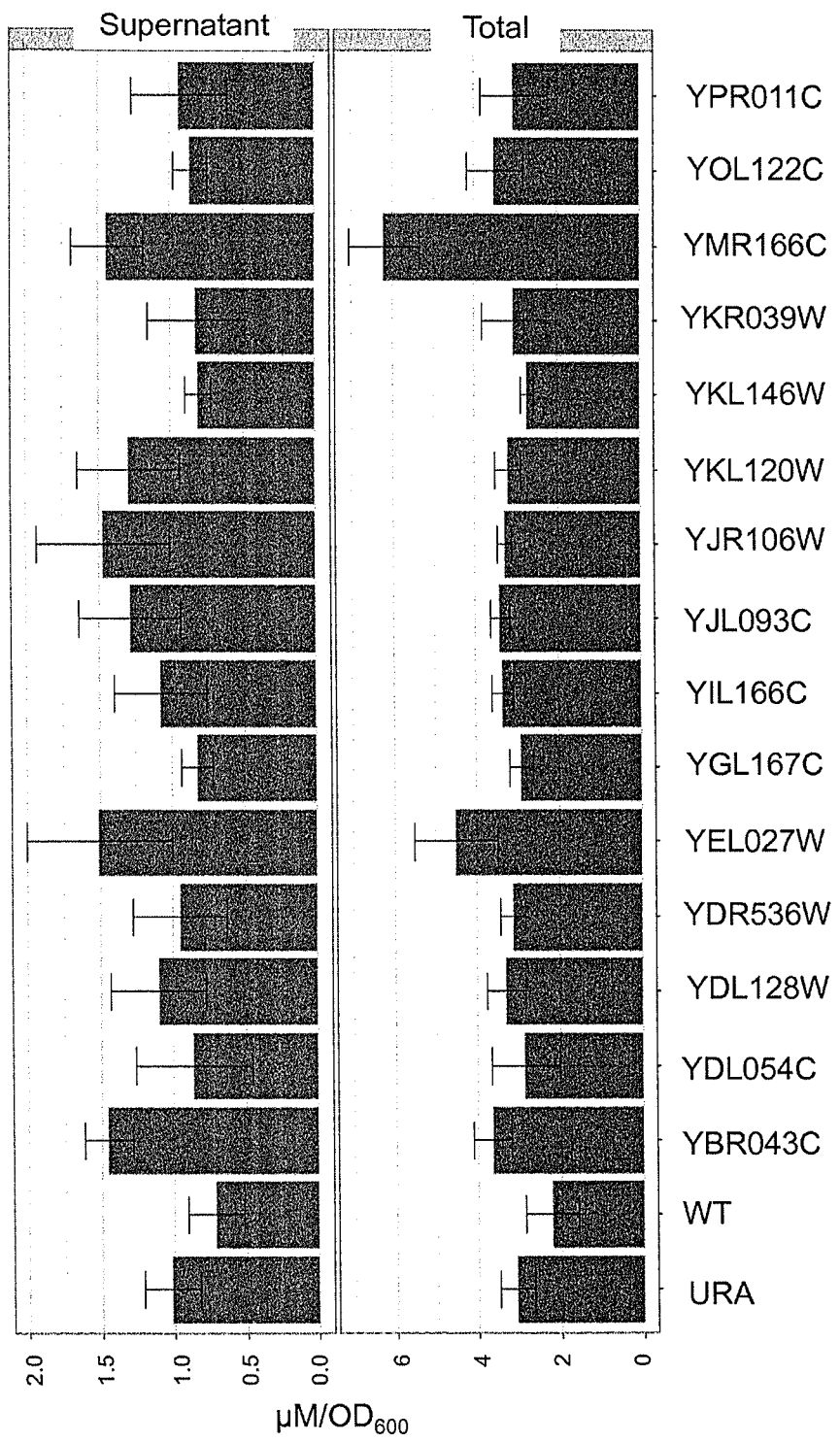

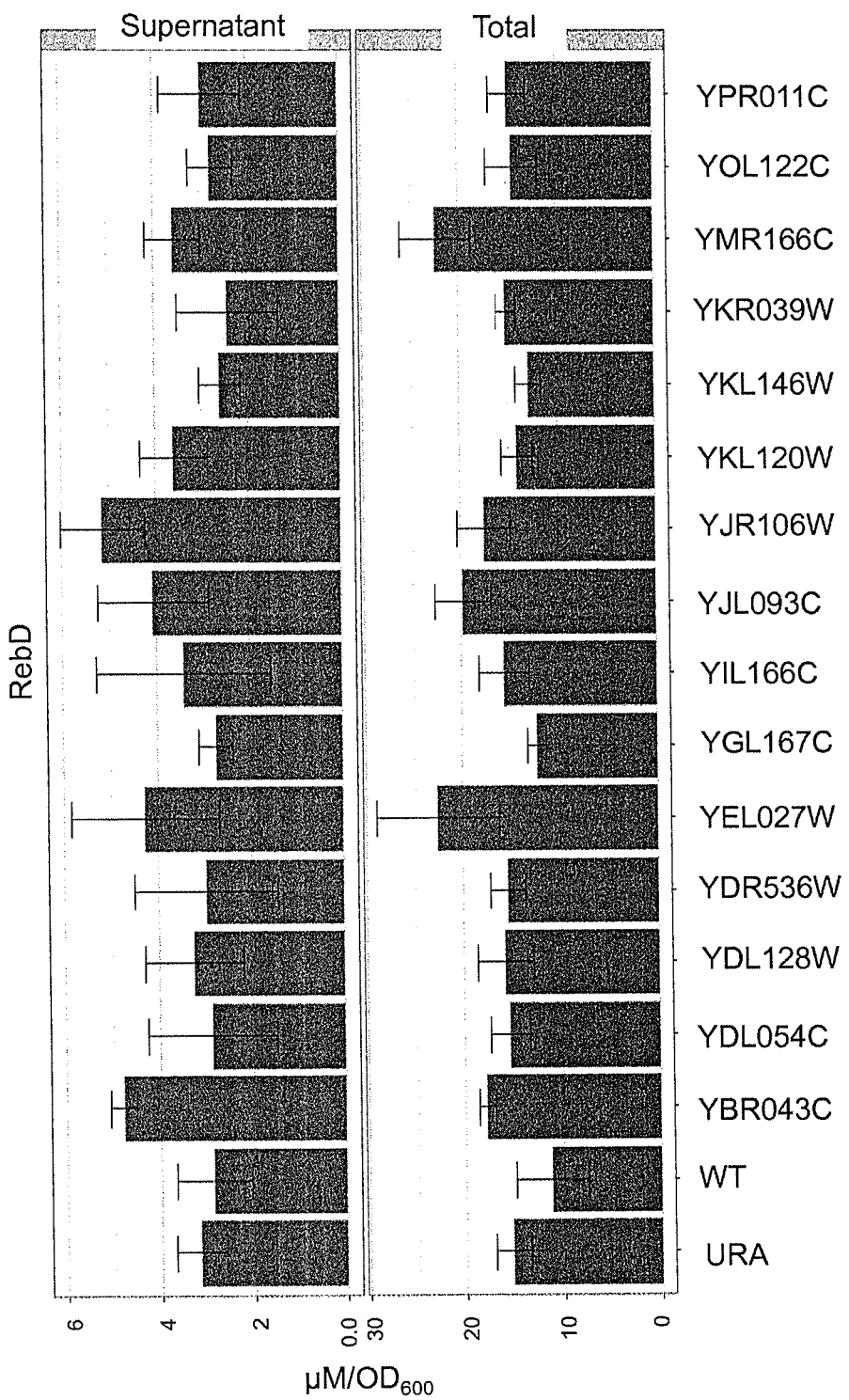

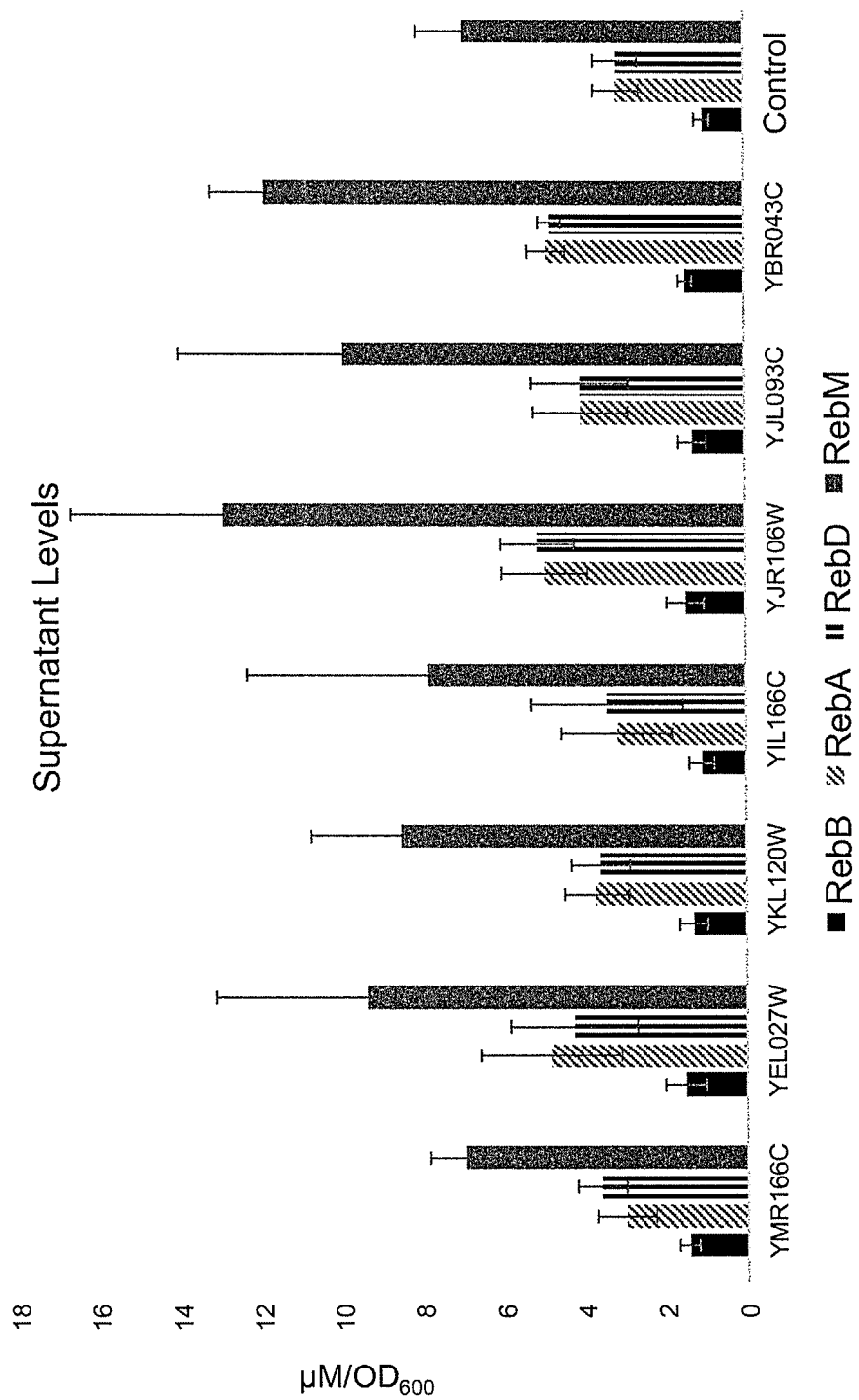

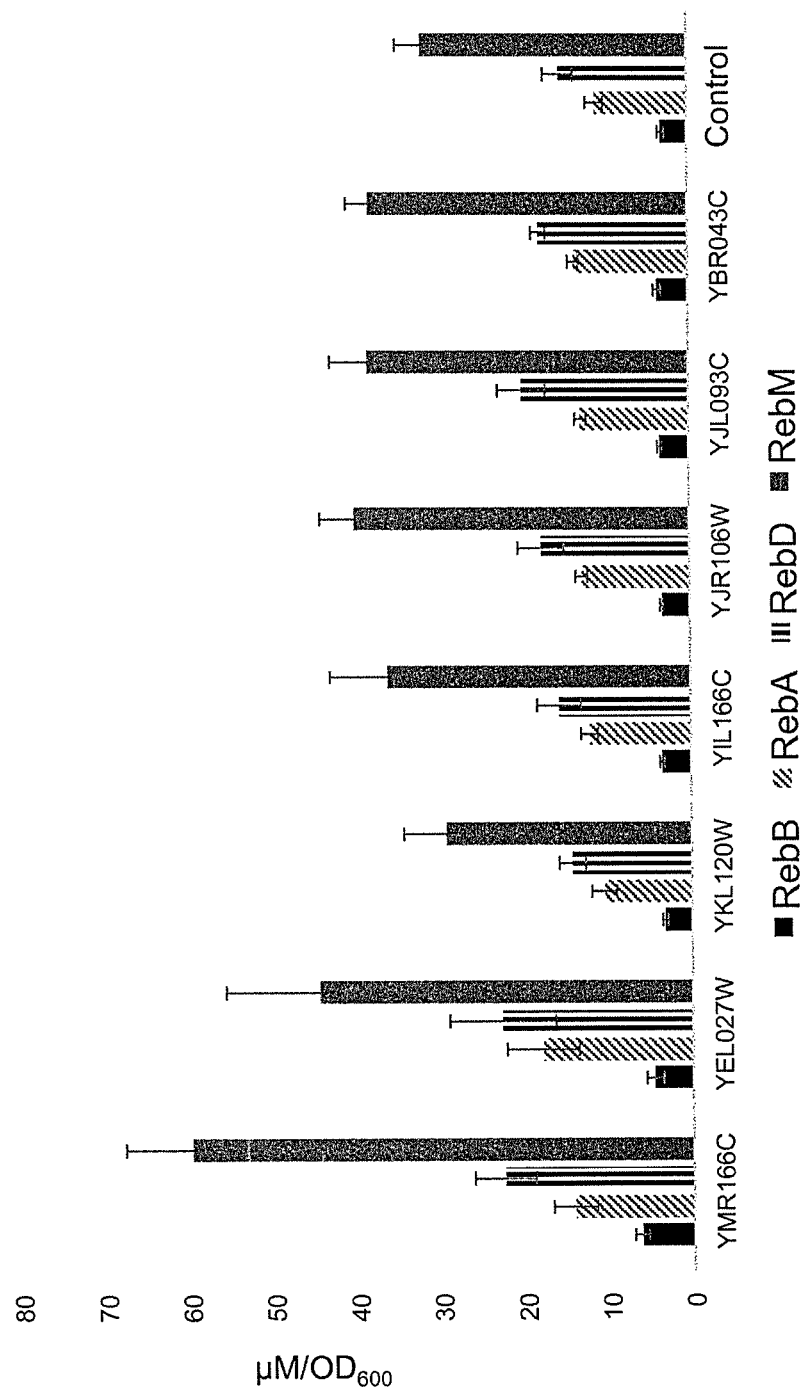

PRODUCTION OF STEVIOL GLYCOSIDES IN RECOMBINANT HOSTS

This application is a divisional of U.S. patent application Ser. No. 15/328,365, filed on Jan. 23, 2017 and issued as U.S. Pat. No. 10,421,983 on Sep. 24, 2019, which is a U.S. National Phase application under 35 U.S.C. § 371 of PCT/EP2015/068314, filed on Aug. 7, 2015, which claims priority from and the benefit of U.S. Provisional Application No. 62/035,902, filed on Aug. 11, 2014, the specifications of which are hereby incorporated by reference in their entireties.

BACKGROUND OF THE INVENTION

Field of the Invention

This disclosure relates generally to the recombinant production of steviol glycosides such as rebaudioside A (RebA), rebaudioside B (RebB), rebaudioside D (RebD), and rebaudioside M (RebM) by recombinant hosts such as recombinant microorganisms and isolation methods thereof. In particular, this disclosure relates to modifications to transport systems in a recombinant host to increase production of such steviol glycosides and/or transport of such steviol glycosides into the culture medium.

Description of Related Art

Sweeteners are well known as ingredients used most commonly in the food, beverage, or confectionary industries. The sweetener can either be incorporated into a final food product during production or for stand-alone use, when appropriately diluted, as a tabletop sweetener or an at-home replacement for sugars in baking. Sweeteners include natural sweeteners such as sucrose, high fructose corn syrup, molasses, maple syrup, and honey and artificial sweeteners such as aspartame, saccharine, and sucralose. *Stevia* extract is a natural sweetener that can be isolated and extracted from a perennial shrub, *Stevia rebaudiana*. *Stevia* is commonly grown in South America and Asia for commercial production of *stevia* extract. *Stevia* extract, purified to various degrees, is used commercially as a high intensity sweetener in foods and in blends or alone as a tabletop sweetener.

Chemical structures for several steviol glycosides are shown in FIG. 1, including the diterpene steviol and various steviol glycosides. Extracts of the *Stevia* plant generally comprise rebaudiosides and other steviol glycosides that contribute to the sweet flavor, although the amount of each steviol glycoside often varies, inter alia, among different production batches.

As recovery and purification of steviol glycosides from the *Stevia* plant have proven to be labor intensive and inefficient, there remains a need for a recombinant production system that can produce high yields of desired steviol glycosides, such as RebD and RebM.

SUMMARY OF THE INVENTION

It is against the above background that the present invention provides certain advantages and advancements over the prior art.

In particular, the invention provides a recombinant host capable of synthesizing a steviol glycoside, comprising a gene encoding a transporter polypeptide and/or a gene encoding a transcription factor polypeptide that regulates expression of at least one transporter gene; wherein expression of the gene encoding the transporter polypeptide and/or the gene encoding the transcription factor polypeptide that regulates expression of at least one transporter gene is modified and the recombinant host transports at least a portion of the synthesized steviol glycoside from the host into a culture medium.

In some aspects of the recombinant host disclosed herein, the gene encoding the transporter polypeptide is an endogenous gene.

In some aspects of the recombinant host disclosed herein, the transporter polypeptide comprises an ATP-binding cassette (ABC) transporter, a major facilitator superfamily (MFS) transporter, an amino acid/auxin permease (AAAP) family transporter, ATPase transporter, a sulfate permease (SulP) family transporter, a lysosomal cystine transporter (LCT) family transporter, a Ca2+:cation antiporter (CaCA) family transporter, an amino acid-polyamine-organocation (APC) superfamily transporter, a multidrug/oligosaccharidyl-lipid/polysaccharide (MOP) transporter, a ZRT/IRT-like protein (ZIP) metal transporter family transporter, a mitochondrial protein translocase (MPT) family transporter, a voltage-gated ion channel (VIC) family transporter, a monovalent cation:proton antiporter-2 (CPA2) family transporter, a ThrE family of putative transmembrane amino acid efflux transporter, an oligopeptide transporter (OPT) family transporter, a K$^+$ transporter (Trk) family transporter, a bile acid:Na symporter (BASS) family transporter, a drug/metabolite transporter (DMT) superfamily transporter, a mitochondrial carrier (MC) family transporter, an auxin efflux carrier (AEC) family transporter, an ammonia channel transporter (Amt) family transporter, a metal ion (Mn$^{2+}$-iron) transporter (Nramp) family transporter, a transient receptor potential Ca$^{2+}$ channel (TRP-CC) family transporter, an arsenical resistance-3 (ACR3) family transporter, a nucleobase:cation symporter-1 (NCS1) family transporter, an inorganic phosphate transporter (PIT) family transporter, an arsenite-antimonite (ArsAB) efflux family transporter, an IISP family of transporter, a glycerol uptake (GUP) family transporter, a metal ion transport (MIT) family transporter, a copper transport (Ctr) family or a cation diffusion facilitator (CDF) family transporter.

In some aspects of the recombinant host disclosed herein, the modified expression comprises modified expression comprises:
 (a) overexpressing the gene encoding the transporter polypeptide and/or the gene encoding the transcription factor polypeptide; or
 (b) deleting the gene encoding the transporter polypeptide and/or the gene encoding the transcription factor polypeptide.

In some aspects of the recombinant host disclosed herein, the gene encoding the transporter polypeptide and/or the gene encoding the transcription factor polypeptide has an activity that is increased.

In some aspects of the recombinant host disclosed herein, one or more of the genes encoding the transporter polypeptide and/or one or more of the genes encoding the transcription factor polypeptide are overexpressed.

In some aspects of the recombinant host disclosed herein, the transporter polypeptide and/or transcription polypeptide comprise YAL067C set forth in SEQ ID NO:14, YBL089W set forth in SEQ ID NO:15, YBL099W set forth in SEQ ID NO:16, YBR008C set forth in SEQ ID NO:86, YBR021W set forth in SEQ ID NO:87, YBR043C set forth in SEQ ID NO:88, YBR180W set forth in SEQ ID NO:13, YBR241C set forth in SEQ ID NO:17, YBR287W set forth in SEQ ID NO:89, YBR294W set forth in SEQ ID NO:18, YBR295W set forth in SEQ ID NO:90, YBR296C set forth in SEQ ID NO:91, YCL038C set forth in SEQ ID NO:92, YCL069W set forth in SEQ ID NO:19, YCR011C set forth in SEQ ID NO:93, YCR028C set forth in SEQ ID NO:20, YCR075C set forth in SEQ ID NO:21, YDL054C set forth in SEQ ID NO:94, YDL100C set forth in SEQ ID NO:95, YDL128W set forth in SEQ ID NO:22, YDL185W set forth in SEQ ID NO:23, YDL194W set forth in SEQ ID NO:24, YDL210W set forth in SEQ ID NO:25, YDL245C set forth in SEQ ID NO:96, YDL247W set forth in SEQ ID NO:97, YDR011W set forth in SEQ ID NO:98, YDR061W set forth in SEQ ID NO:26, YDR093W set forth in SEQ ID NO:27, YDR292C set forth in SEQ ID NO:99, YDR338C set forth in SEQ ID NO:28, YDR406W set forth in SEQ ID NO:29, YDR497C set forth in SEQ ID NO:100, YDR536W set forth in SEQ ID NO:30, YEL006W set forth in SEQ ID NO:101, YEL027W set forth in SEQ ID NO:102, YEL031W set forth in SEQ ID NO:31, YEL065W set forth in SEQ ID NO:103, YER019C-A set forth in SEQ ID NO:104, YER053C set forth in SEQ ID NO:105, YER119C set forth in SEQ ID NO:106, YER166W set forth in SEQ ID NO:32, YFL011W set forth in SEQ ID NO:33, YFL028C set forth in SEQ ID NO:107, YFR045W set forth in SEQ ID NO:108, YGL006W set forth in SEQ ID NO:34, YGL013C set forth in SEQ ID NO:35, YGL084C set forth in SEQ ID NO:109, YGL104C set forth in SEQ ID NO:110, YGL114W set forth in SEQ ID NO:111, YGL167C set forth in SEQ ID NO:112, YGL255W set forth in SEQ ID NO:36, YGR125W set forth in SEQ ID NO:37, YGR181W set forth in SEQ ID NO:38, YGR217W set forth in SEQ ID NO:39, YGR224W set forth in SEQ ID NO:40, YGR257C set forth in SEQ ID NO:113, YGR281W set forth in SEQ ID NO:41, YHL016C set forth in SEQ ID NO:42, YHL035C set forth in SEQ ID NO:114, YHL036W set forth in SEQ ID NO:115, YHR002W set forth in SEQ ID NO:116, YHR096C set forth in SEQ ID NO:117, YIL006W set forth in SEQ ID NO:118, YIL088C set forth in SEQ ID NO:43, YIL120W set forth in SEQ ID NO:119, YIL121W set forth in SEQ ID NO:120, YIL166C set forth in SEQ ID NO:121, YJL093C set forth in SEQ ID NO:44, YJL094C set forth in SEQ ID NO:45, YJL108C set forth in SEQ ID NO:46, YJL133W set forth in SEQ ID NO:122, YJL212C set forth in SEQ ID NO:47, YJL219W set forth in SEQ ID NO:123, YJR106W set forth in SEQ ID NO:48, YJR160C set forth in SEQ ID NO:49, YKL016C set forth in SEQ ID NO:124, YKL050C set forth in SEQ ID NO:125, YKL064W set forth in SEQ ID NO:50, YKL120W set forth in SEQ ID NO:126. YKL146W set forth in SEQ ID NO:127, YKL209C set forth in SEQ ID NO:128, YKR039W set forth in SEQ ID NO:129, YKR050W set forth in SEQ ID NO:51, YKR105C set forth in SEQ ID NO:52, YKR106W set forth in SEQ ID NO:53, YLR411W set forth in SEQ ID NO:130, YLR447C set forth in SEQ ID NO:54, YML038C set forth in SEQ ID NO:131, YML116W set forth in SEQ ID NO:55, YMR034C set forth in SEQ ID NO:56, YMR056C set forth in SEQ ID NO:57, YMR166C set forth in SEQ ID NO:132, YMR253C set forth in SEQ ID NO:58, YMR279C set forth in SEQ ID NO:133, YNL003C set forth in SEQ ID NO:134, YNL065W set forth in SEQ ID NO:59, YNL070W set forth in SEQ ID NO:60, YNL083W set forth in SEQ ID NO:61, YNL095C set forth in SEQ ID NO:62, YNL121C set forth in SEQ ID NO:63, YNL142W set forth in SEQ ID NO:64, YNL268W set forth in SEQ ID NO:135, YNR055C set forth in SEQ ID NO:136, YOL020W set forth in SEQ ID NO:65, YOL075C set forth in SEQ ID NO:66, YOL077W-A set forth in SEQ ID NO:67, YOL122C set forth in SEQ ID NO:68, YOL158C set forth in SEQ ID NO:137, YOR079C set forth in SEQ ID NO:69, YOR087W set forth in SEQ ID NO:70, YOR092W set forth in SEQ ID NO:71, YOR100C set forth in SEQ ID NO:138, YOR130C set forth in SEQ ID NO:72, YOR153W set forth in SEQ ID NO:139, YOR222W set forth in SEQ ID NO:73, YOR271C set forth in SEQ ID NO:140, YOR273C set forth in SEQ ID NO:141, YOR291W set forth in SEQ ID NO:74, YOR306C set forth in SEQ ID NO:75, YOR307C set forth in SEQ ID NO:142, YOR316C set forth in SEQ ID NO:76, YOR332W set forth in SEQ ID NO:143, YOR334W set forth in SEQ ID NO:77, YOR348C set forth in SEQ ID NO:144, YPL036W set forth in SEQ ID NO:145, YPL078C set forth in SEQ ID NO:78, YPL270W set forth in SEQ ID NO:79. YPL274W set forth in SEQ ID NO:80, YPR003C set forth in SEQ ID NO:81, YPR011C set forth in SEQ ID NO:82, YPR058W set forth in SEQ ID NO:83, YPR128C set forth in SEQ ID NO:84, or YPR201W set forth in SEQ ID NO:85.

In some aspects of the recombinant host disclosed herein, YBR043C set forth in SEQ ID NO:88, YDL100C set forth in SEQ ID NO:95, YDL054C set forth in SEQ ID NO:94, YDL128W set forth in SEQ ID NO:22, YDL198C set forth in SEQ ID NO:146, YDR061W set forth in SEQ ID NO:26, YDR536W set forth in SEQ ID NO:30, YEL027W set forth in SEQ ID NO:102, YFL054C set forth in SEQ ID NO:147, YGL167C set forth in SEQ ID NO:112, YGR181W set forth in SEQ ID NO:38, YHL016C set forth in SEQ ID NO:42, YIL166C set forth in SEQ ID NO:121, YJL093C set forth in SEQ ID NO:44, YJR106W set forth in SEQ ID NO:48, YKL120W set forth in SEQ ID NO:126, YKL146W set forth in SEQ ID NO:127, YKR039W set forth in SEQ ID NO:129, YMR034C set forth in SEQ ID NO:56, YMR166C set forth in SEQ ID NO:132, YOL122C set forth in SEQ ID NO:68, YOR079C set forth in SEQ ID NO:69, YPL270W set forth in SEQ ID NO:79, and/or YPR011C set forth in SEQ ID NO:82 are overexpressed.

In some aspects, the recombinant host further comprises:
(a) one or more genes encoding a sucrose transporter and a sucrose synthase;
(b) a gene encoding a geranylgeranyl diphosphate synthase (GGPPS) polypeptide;
(c) a gene encoding an ent-copalyl diphosphate synthase (CDPS) polypeptide;
(d) a gene encoding a kaurene synthase (KS) polypeptide;
(e) a gene encoding a kaurene oxidase (KO) polypeptide;
(f) a gene encoding a steviol synthase (KAH) polypeptide;
(g) a gene encoding a cytochrome P450 reductase (CPR) polypeptide;
(h) a gene encoding a UGT85C2 polypeptide;
(i) a gene encoding a UGT76G1 polypeptide;
(k) a gene encoding a UGT91D2 functional homolog; and/or
(l) a gene encoding a EUGT11 polypeptide;
wherein at least one of the genes is a recombinant gene; and
wherein the host is capable of producing one or more of RebA, RebB, RebD and/or RebM.

In some aspects of the recombinant host disclosed herein, at least one of the genes is codon optimized for expression in the host.

In some aspects of the recombinant host disclosed herein, at least one of the genes is codon optimized for expression in *Saccharomyces cerevisiae*.

In some aspects of the recombinant host disclosed herein,
(a) the GGPPS polypeptide comprises a polypeptide having at least 70% identity to an amino acid sequence set forth in SEQ ID NO:149;

(b) the CDPS polypeptide comprises a polypeptide having at least 70% identity to an amino add sequence set forth in SEQ ID NO:150;

(c) the KO polypeptide comprises a polypeptide having at least 70% identity to an amino acid sequence set forth in SEQ ID NO:152;

(d) the KS polypeptide comprises a polypeptide having at least 40% identity to an amino acid sequence set forth in SEQ ID NO:151;

(e) the KAH polypeptide comprises a polypeptide having at least 60% identity to an amino acid sequence set forth in SEQ ID NO:154;

(f) the CPR polypeptide comprises a polypeptide having at least 70% identity to an amino acid sequence set forth in SEQ ID NO:153 and/or a polypeptide having at least 65% identity to an amino acid sequence set forth in SEQ ID NO:155;

(g) the UGT85C2 polypeptide comprises a polypeptide having at least 55% identity to an amino acid sequence set forth in SEQ ID NO:156;

(h) the UGT76G1 polypeptide comprises a polypeptide having at least 50% identity to an amino acid sequence set forth in SEQ ID NO:158;

(i) the UGT74G1 polypeptide comprises a polypeptide having at least 55% identity to an amino acid sequence set forth in SEQ ID NO:157;

(j) the a UGT91D2 functional homolog comprises a UGT9D2e-b polypeptide having at least 90% identity to the amino acid sequence set forth in SEQ ID NO:159; and (k) the EUGT11 polypeptide comprises a polypeptide having at least 65% identity to an amino acid sequence set forth in SEQ ID NO:148.

In some aspects, the recombinant host disclosed herein comprises a microorganism that is a plant cell, a mammalian cell, an insect cell, a fungal cell, or a bacterial cell.

In some aspects, the bacterial cell comprises *Escherichia* bacteria cells, *Lactobacillus* bacteria cells, *Lactococcus* bacteria cells, *Cornebacterium* bacteria cells, *Acetobacter* bacteria cells, *Acinetobacter* bacteria cells, or *Pseudomonas* bacterial cells.

In some aspects, the fungal cell is a yeast cell.

In some aspects, the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeniniv- orans, Xanthophyllomyces dendrorhous*, or *Candida albicans* species.

In some aspects, the yeast cell is a *Saccharomycete*.

In some aspects, the yeast cell is a cell from the *Saccharomyces cerevisiae* species.

The invention further provides a method of producing a steviol glycoside, comprising:

(a) growing the recombinant host disclosed herein in a culture medium, under conditions in which the genes comprising recombinant host disclosed herein are expressed,
wherein the steviol glycoside is synthesized by the host; and (b) optionally isolating the steviol glycoside.

In some aspects of the methods disclosed herein, the steviol glycoside is RebA, RebB, RebD, and/or RebM, and wherein:

(a) RebA is capable of being synthesized in the recombinant host disclosed herein expressing UGT85C2, UGT76G1, UGT74G1, and UGT91D2;

(b) RebB is capable of being synthesized in the recombinant host disclosed herein expressing UGT85C2, UGT76G1, and UGT91D2;

(c) RebD is capable of being synthesized in the recombinant host disclosed herein expressing UGT85C2, UGT76G1, UGT74G1, and UGT91D2 and/or EUGT11; and (d) RebM is capable of being synthesized in the recombinant host disclosed herein expressing UGT85C2, UGT76G1, UGT74G1, and UGT91D2 and/or EUGT11.

In some aspects of the methods disclosed herein a gene encoding YBR043C set forth in SEQ ID NO:88, YDL100C set forth in SEQ ID NO:95, YDL054C set forth in SEQ ID NO:94, YDL128W set forth in SEQ ID NO:22, YDL198C set forth in SEQ ID NO:146, YDR061W set forth in SEQ ID NO:26, YDR536W set forth in SEQ ID NO:30, YEL027W set forth in SEQ ID NO:102, YFL054C set forth in SEQ ID NO:147, YGL167C set forth in SEQ ID NO:112, YGR181W set forth in SEQ ID NO:38, YHL016C set forth in SEQ ID NO:42, YIL166C set forth in SEQ ID NO:121, YJL093C set forth in SEQ ID NO:44, YJR106W set forth in SEQ ID NO:48, YKL120W set forth in SEQ ID NO:126, YKL146W set forth in SEQ ID NO:127, YKR039W set forth in SEQ ID NO:129, YMR034C set forth in SEQ ID NO:56, YMR166C set forth in SEQ ID NO:132, YOL122C set forth in SEQ ID NO:68, YOR079C set forth in SEQ ID NO:69, YPL270W set forth in SEQ ID NO:79, and/or YPR011C set forth in SEQ ID NO:82 is overexpressed.

In some aspects of the methods disclosed herein the steviol glycoside is produced at a concentration of between about 500 mg/L to about 10,000 mg/L.

The invention further provides a method of increasing production or transport of a steviol glycoside into a culture medium, comprising:

(a) growing the recombinant host disclosed herein in a culture medium, under conditions in which the genes comprising the host disclosed herein are expressed,
wherein the steviol glycoside is synthesized by the host; and (b) optionally isolating the steviol glycoside.

In some aspects of the methods disclosed herein, the steviol glycoside is RebA, RebB, RebD, and/or RebM.

The invention further provides a method increasing production of steviol or a steviol glycoside in a recombinant host, comprising modifying expression of a gene encoding a transporter polypeptide and/or a gene encoding a transcription that regulates expression of at least one transporter gene, wherein the host is capable of transporting at least a portion of the produced steviol or a steviol glycoside from the host into a culture medium.

These and other features and advantages of the present invention will be more fully understood from the following detailed description of the invention taken together with the accompanying claims. It is noted that the scope of the claims is defined by the recitations therein and not by the specific discussion of features and advantages set forth in the present description.

DESCRIPTION OF DRAWINGS

FIG. 4A shows levels of 13-SMG (total levels and supernatant levels; $\mu M/OD_{600}$), FIG. 48 shows levels of RebA (total levels and supernatant levels; $\mu M/OD_{600}$), FIG. 4C shows levels of RebB (total levels and supernatant levels; $\mu M/OD_{600}$), FIG. 4D shows levels of RebD (total levels and supernatant levels; $\mu M/OD_{600}$)

FIG. 5A shows supernatant levels of RebA, RebB, RebD, and RebM (in $\mu M/OD_{600}$) of a steviol glycoside-producing strain overexpressing YMR166C (SEQ ID NO:132), YEL027W (SEQ ID NO:102), YKL120W (SEQ ID NO:126), YIL166C (SEQ ID NO:121), YJR106W (SEQ ID NO:48), YJL093C (SEQ ID NO:44), and YBR043C (SEQ ID NO:88) by the USER cloning system. FIG. 5B shows total levels of RebA, RebB, RebD, and RebM (in $\mu M/OD_{600}$) of a steviol glycoside-producing strain overexpressing YMR166C (SEQ ID NO:132), YEL027W (SEQ ID NO:102), YKL120W (SEQ ID NO:126), YIL166C (SEQ ID NO:121), YJR106W (SEQ ID NO:48), YJL093C (SEQ ID NO:44), and YBR043C (SEQ ID NO:88) by the USER cloning system.

DETAILED DESCRIPTION

Figure 1:
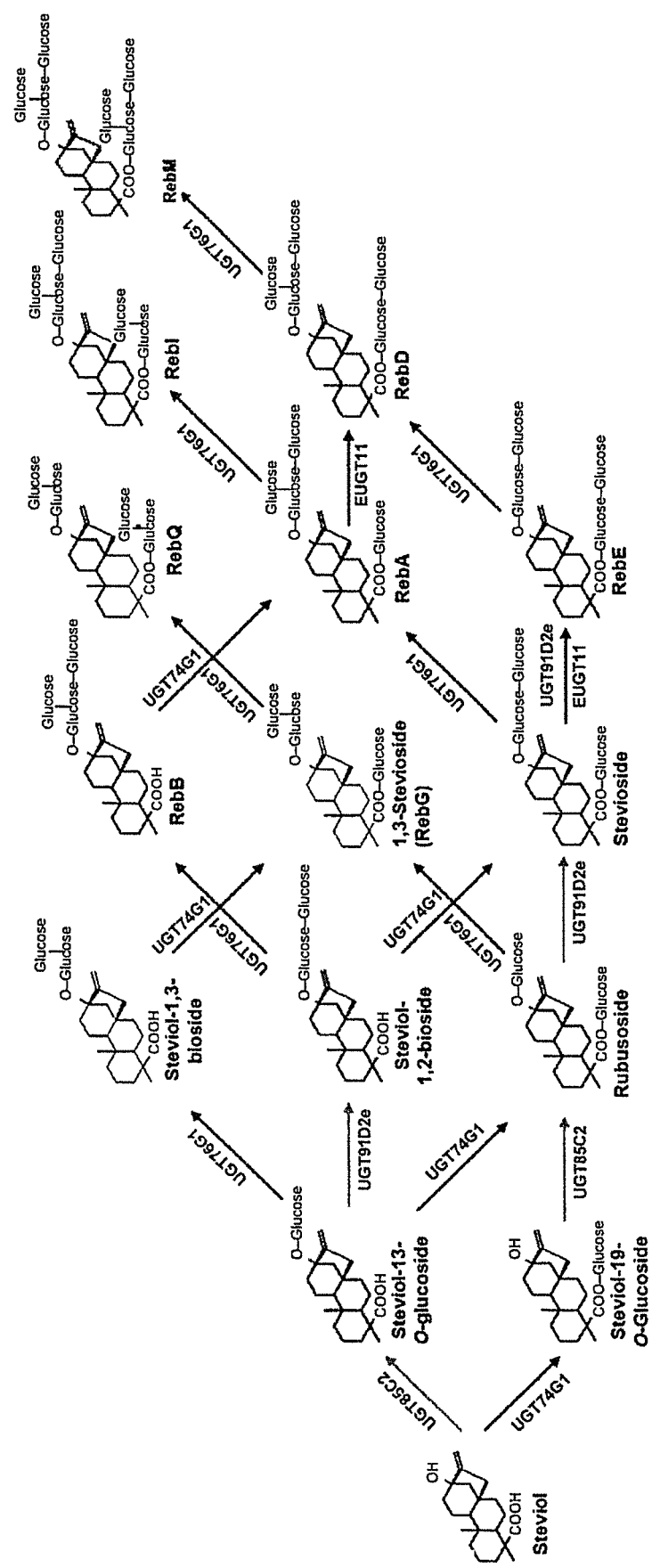
FIG. 1 shows the chemical structures and synthesis pathways for various steviol glycosides.

All publications, patents and patent applications cited herein are hereby expressly incorporated by reference in their entirety for all purposes.

Before describing the present invention in detail, a number of terms will be defined. As used herein, the singular forms "a," "an," and "the" include plural referents unless the context dearly dictates otherwise. For example, reference to "a nucleic acid" means one or more nucleic acids.

It is noted that terms like "preferably," "commonly," and "typically" are not utilized herein to limit the scope of the claimed invention or to imply that certain features are critical, essential, or even important to the structure or function of the claimed invention. Rather, these terms are merely intended to highlight alternative or additional features that can or cannot be utilized in a particular embodiment of the present invention.

For the purposes of describing and defining the present invention it is noted that the term "substantially" is utilized herein to represent the inherent degree of uncertainty that can be attributed to any quantitative comparison, value, measurement, or other representation. The term "substantially" is also utilized herein to represent the degree by which a quantitative representation can vary from a stated reference without resulting in a change in the basic function of the subject matter at issue.

Methods well known to those skilled in the art can be used to construct genetic expression constructs and recombinant cells according to this invention. These methods include in vitro recombinant DNA techniques, synthetic techniques, in vivo recombination techniques, and polymerase chain reaction (PCR) techniques. See, for example, techniques as described in Green & Sambrook, 2012, MOLECULAR CLONING: A LABORATORY MANUAL, Fourth Edition, Cold Spring Harbor Laboratory, New York; Ausubel et al., 1989, CURRENT PROTOCOLS IN MOLECULAR BIOLOGY, Greene Publishing Associates and Wiley Interscience, New York, and PCR Protocols: A Guide to Methods and Applications (Innis et al., 1990, Academic Press, San Diego, Calif.).

As used herein, the terms "polynucleotide," "nucleotide," "oligonucleotide," and "nucleic acid" can be used interchangeably to refer to nucleic acid comprising DNA, RNA, derivatives thereof, or combinations thereof.

As used herein, the terms "microorganism," "microorganism host," "microorganism host cell," "host cell," "recombinant host," "recombinant microorganism host," and "recombinant host cell" can be used interchangeably. As used herein, the term "recombinant host" is intended to refer to a host, the genome of which has been augmented by at least one DNA sequence. Such DNA sequences include but are not limited to genes that are not naturally present, DNA sequences that are not normally transcribed into RNA or translated into a protein ('expressed'), and other genes or DNA sequences which one desires to introduce into the non-recombinant host. It will be appreciated that typically the genome of a recombinant host described herein is augmented through stable introduction of one or more recombinant genes. Generally, Introduced DNA is not originally resident in the host that is the recipient of the DNA, but it is within the scope of this disclosure to isolate a DNA segment from a given host, and to subsequently introduce one or more additional copies of that DNA into the same host, e.g., to enhance production of the product of a gene or alter the expression pattern of a gene. In some instances, the introduced DNA will modify or even replace an endogenous gene or DNA sequence by, e.g., homologous recombination or site-directed mutagenesis. Suitable recombinant hosts include microorganisms.

As used herein, the term "recombinant gene" refers to a gene or DNA sequence that is introduced into a recipient host, regardless of whether the same or a similar gene or DNA sequence may already be present in such a host "Introduced," or "augmented" in this context, is known in the art to mean introduced or augmented by the hand of man. Thus, a recombinant gene can be a DNA sequence from another species or can be a DNA sequence that originated from or is present in the same species but has been incorporated into a host by recombinant methods to form a recombinant host. It will be appreciated that a recombinant gene that is introduced into a host can be identical to a DNA sequence that is normally present in the host being transformed and is introduced to provide one or more additional copies of the DNA to thereby permit overexpression or modified expression of the gene product of that DNA. Said recombinant genes are particularly encoded by cDNA.

As used herein, the term "engineered biosynthetic pathway" refers to a biosynthetic pathway that occurs in a recombinant host, as described herein, and does not naturally occur in the host.

As used herein, the term "endogenous" gene refers to a gene that originates from and is produced or synthesized within a particular organism, tissue, or cell. In some embodiments, the endogenous gene is a yeast transporter. In some embodiments, the transporter is endogenous to *S. cerevisiae*, including, but not limited to *S. cerevisiae* strain S288C. In some embodiments, an endogenous yeast transporter gene is overexpressed. As used herein, the term "overexpress" is used to refer to the expression of a gene in an organism at levels higher than the level of gene expression in a wild type organism. See, e.g., Prelich, 2012, Genetics 190:841-54. In some embodiments, an endogenous yeast transporter gene is deleted. See, e.g., Giaever & Nislow, 2014, Genetics 197 (2):451-65. As used herein, the terms "deletion," "deleted," "knockout," and "knocked out" can be used interchangeably to refer to an endogenous gene that has been manipulated to no longer be expressed in an organism, including, but not limited to, *S. cerevisiae*. In some embodiments, a deleted/knocked out gene is a transporter gene or a transcription factor gene that regulates expression of a transporter gene.

As used herein, the terms "heterologous sequence" and "heterologous coding sequence" are used to describe a sequence derived from a species other than the recombinant host. In some embodiments, the recombinant host is an *S. cerevisiae* cell, and a heterologous sequence is derived from an organism other than *S. cerevisiae*. A heterologous coding sequence, for example, can be from a prokaryotic microorganism, a eukaryotic microorganism, a plant, an animal, an insect, or a fungus different than the recombinant host expressing the heterologous sequence. In some embodiments, a coding sequence is a sequence that is native to the host.

A "selectable marker" can be one of any number of genes that complement host cell auxotrophy, provide antibiotic resistance, or result in a color change. Linearized DNA fragments of the gene replacement vector then are introduced into the cells using methods well known in the art (see below). Integration of the linear fragments into the genome and the disruption of the gene can be determined based on the selection marker and can be verified by, for example, PCR or Southern blot analysis. Subsequent to its use in selection, a selectable marker can be removed from the genome of the host cell by, e.g., Cre-LoxP systems (see, e.g., Gossen et al., 2002, Ann. Rev. Genetics 36:153-173 and U.S. 2006/0014264). Alternatively, a gene replacement vector can be constructed in such a way as to include a portion of the gene to be disrupted, where the portion is devoid of any endogenous gene promoter sequence and encodes none, or an inactive fragment of, the coding sequence of the gene.

As used herein, the terms "variant" and "mutant" are used to describe a protein sequence that has been modified at one or more amino acids, compared to the wild type sequence of a particular protein.

As used herein, the term "inactive fragment" is a fragment of the gene that encodes a protein having, e.g., less than about 10% (e.g., less than about 9%, less than about 8%, less than about 7%, less than about 6%, less than about 5%, less than about 4%, less than about 3%, less than about 2%, less than about 1%, or 0%) of the activity of the protein produced from the full-length coding sequence of the gene. Such a portion of a gene is inserted in a vector in such a way that no known promoter sequence is operably linked to the gene sequence, but that a stop codon and a transcription termination sequence are operably linked to the portion of the gene sequence. This vector can be subsequently linearized in the portion of the gene sequence and transformed into a cell. By way of single homologous recombination, this linearized vector is then integrated in the endogenous counterpart of the gene with inactivation thereof.

As used herein, the term "steviol glycoside" refers to Rebaudioside A (RebA) (CAS #58543-16-1), Rebaudioside B (RebB) (CAS #58543-17-2), Rebaudioside C (RebC) (CAS #63550-99-2), Rebaudioside D (RebD) (CAS #63279-13-0), Rebaudioside E (RebE) (CAS #63279-14-1), Rebaudioside F (RebF) (CAS #438045-89-7), Rebaudioside M (RebM) (CAS #1220616-44-3), Rubusoside (CAS #63849-39-4), Dulcoside A (CAS #64432-06-0), Rebaudioside I (RebI) (MassBank Record: FU000332), Rebaudioside Q (RebQ), 1,2-Stevioside (CAS #57817-89-7), 1,3-Stevioside (RebG), 1,2-Bioside (MassBank Record: FU000299), 1,3-Bioside, Steviol-13-O-glucoside (13-SMG), Steviol-19-O-glucoside (19-SMG), a tri-glucosylated steviol glycoside, a tetra-glycosylated steviol glycoside, a penta-glucosylated steviol glycoside, a hexa-glucosylated steviol glycoside, a hepta-glucosylated steviol glycoside, di-glucosylated kaurenoic acid, tri-glucosylated kaurenoic acid, di-glucosylated kaurenol, tri-glucosylated kaurenol, and isomers thereof.

Recombinant steviol glycoside-producing *Saccharomyces cerevisiae* (*S. cerevisiae*) strains are described in WO 2011/153378, WO 2013/022989, WO 2014/122227, and WO 2014/122328, each of which has been incorporated by reference herein in its entirety. See, also, Example 2. Methods of producing steviol glycosides in recombinant hosts, by whole cell bio-conversion, and in vitro are also described in WO 2011/153378, WO 2013/022989, WO 2014/122227, and WO 2014/122328.

In some embodiments, steviol glycosides and/or steviol glycoside precursors are produced in vivo through expression of one or more enzymes involved in the steviol glycoside biosynthetic pathway in a recombinant host. For example, a steviol-producing recombinant host expressing one or more of a gene encoding a geranylgeranyl diphosphate synthase (GGPPS) polypeptide, a gene encoding an ent-copalyl diphosphate synthase (CDPS) polypeptide, a gene encoding a kaurene synthase (KS) polypeptide, a gene encoding a kaurene oxidase polypeptide (KO), a gene encoding a steviol synthase (KAH) polypeptide, a gene encoding a cytochrome P450 reductase (CPR) polypeptide, and a gene encoding a UGT polypeptide can produce a steviol glycoside and/or steviol glycoside precursors in vivo. See Example 2.

In some embodiments, a recombinant host comprises a nucleic acid encoding a UGT85C2 polypeptide, a nucleic acid encoding a UGT76G1 polypeptide, a nucleic acid encoding a UGT74G1 polypeptide, a nucleic acid encoding a UGT91D2 polypeptide, and/or a nucleic acid encoding a EUGT11 polypeptide. The skilled worker will appreciate that expression of these genes may be necessary to produce a particular steviol glycoside but that one or more of these genes can be endogenous to the host provided that at least one (and in some embodiments, al) of these genes is a recombinant gene introduced into the microorganism. In a particular embodiment, a steviol-producing recombinant microorganism comprises exogenous nucleic acids encoding UGT85C2, UGT76G1, or UGT91D2 polypeptides. In another particular embodiment, a steviol-producing recombinant microorganism comprises exogenous nucleic acids encoding UGT85C2, UGT76G1, UGT74G1, and UGT91D2 polypeptides. In yet another particular embodiment, a steviol-producing recombinant microorganism comprises exogenous nucleic acids encoding UGT85C2, UGT76G1, UGT74G1, and EUGT11 polypeptides. In yet another particular embodiment, a steviol-producing recombinant microorganism comprises the exogenous nucleic adds encoding UGT85C2, UGT76G1, UGT74G1, UGT91D2 (including inter alia 91D2e, 91D2m, 91D2e-b, and functional homologs thereof), and EUGT11 polypeptides. See Example 2.

In certain embodiments, the steviol glycoside is RebA, RebB, RebD, and/or RebM. RebA can be synthesized in a steviol-producing recombinant microorganism expressing UGT85C2, UGT76G1, UGT74G1, and UGT91D2. RebB can be synthesized in a steviol-producing recombinant microorganism expressing UGT85C2, UGT76G1, and UGT91D2. RebD can be synthesized in a steviol-producing recombinant microorganism expressing UGT85C2, UGT76G1 UGT74G1, and UGT91D2 and/or EUGT11. RebM can be synthesized in a steviol-producing recombinant microorganism expressing UGT85C2, UGT76G1, UGT74G1, and UGT91D2 and/or EUGT11 (see FIG. 1, Example 2).

In some embodiments, steviol glycosides and/or steviol glycoside precursors are produced through contact of a steviol glycoside precursor with one or more enzymes involved in the steviol glycoside pathway in vitro. For example, contacting steviol with a UGT polypeptide can result in production of a steviol glycoside in vitro. In some embodiments, a steviol glycoside precursor is produced through contact of an upstream steviol glycoside precursor with one or more enzymes involved in the steviol glycoside pathway in vitro. For example, contacting ent-kaurenoic acid with a KAH enzyme can result in production of steviol in vitro.

In some embodiments, a steviol glycoside or steviol glycoside precursor is produced by whole cell bioconversion. For whole cell bioconversion to occur, a host cell expressing one or more enzymes involved in the steviol glycoside pathway takes up and modifies a steviol glycoside precursor in the cell; following modification in vivo, a steviol glycoside remains in the cell and/or is excreted into the culture medium. For example, a host cell expressing a gene encoding a UGT polypeptide can take up steviol and glycosylate steviol in the cell; following glycosylation in vivo, a steviol glycoside can be excreted into the culture medium. In some embodiments, the cell is permeabilized to take up a substrate to be modified or to excrete a modified product.

In some embodiments, a steviol glycoside or steviol glycoside precursor composition produced in vivo, in vitro, or by whole cell bioconversion comprises less contaminants than a *stevia* extract from, inter alia, a *stevia* plant. Contaminants include plant-derived compounds that contribute to off-flavors. Potential contaminants include pigments, lipids, proteins, phenolics, saccharides, spathulenol and other sesquiterpenes, labdane diterpenes, monoterpenes, decanoic acid, 8,11,14-eicosatrienoic acid, 2-methyloctadecane, pentacosane, octacosane, tetracosane, octadecanol, stigmasterol, β-sitosterol, α- and β-amyrin, lupeol, β-amryin acetate, pentacyclic triterpenes, centauredin, quercitin, epi-alpha-cadinol, carophyllenes and derivatives, beta-pinene, beta-sitosterol, and gibberellin.

As used herein, the terms "detectable amount," "detectable concentration," "measurable amount." and "measurable concentration" refer to a level of steviol glycosides measured in AUC, $\mu M/OD_{600}$, mg/L, $\mu M$, or mM. Steviol glycoside production (i.e., total, supernatant, and/or intracellular steviol glycoside levels) can be detected and/or analyzed by techniques generally available to one skilled in the art, for example, but not limited to, liquid chromatography-mass spectrometry (LC-MS), thin layer chromatography (TLC), high-performance liquid chromatography (HPLC), ultraviolet-visible spectroscopy/spectrophotometry (UV-Vs), mass spectrometry (MS), and nuclear magnetic resonance spectroscopy (NMR).

As used herein, the terms "or" and "and/or" is utilized to describe multiple components in combination or exclusive of one another. For example, "x, y, and/or z" can refer to "x" alone, "y" alone, "z" alone, "x, y, and z," "(x and y) or z," "x or (y and z)," or "x or y or z." In some embodiments, "and/or" is used to refer to the exogenous nucleic acids that a recombinant cell comprises, wherein a recombinant cell comprises one or more exogenous nucleic acids selected from a group. In some embodiments, "and/or" is used to refer to production of steviol glycosides and/or steviol glycoside precursors. In some embodiments, "and/or" is used to refer to production of steviol glycosides, wherein one or more steviol glycosides are produced. In some embodiments, "and/or" is used to refer to production of steviol glycosides, wherein one or more steviol glycosides are produced through one or more of the following steps: culturing a recombinant microorganism, synthesizing one or more steviol glycosides in a recombinant microorganism, and/or isolating one or more steviol glycosides.

Transporters and Transcription Factor Expression

This document describes reagents and methods that can be used to efficiently produce steviol glycoside compositions. Modification of transport systems in a recombinant host that are involved in transport of steviol glycosides into culture medium can allow more effective production of steviol glycosides in recombinant hosts.

As set forth herein, recombinant cells having modifications to cellular transport are capable of producing steviol. Recombinant hosts described herein can produce steviol and have altered expression of at least one endogenous transporter gene. Recombinant hosts described herein can produce steviol and have altered expression of a transcription factor that regulates expression of at least one endogenous transporter gene. Altering expression of endogenous transporter genes can be useful for increasing production of steviol and/or excretion of steviol into the culture medium.

As set forth herein, recombinant cells having modifications to cellular transport are capable of producing at least one steviol glycoside, including, but not limited to, RebA, RebB, RebD, and/or RebM. Recombinant hosts described herein can produce at least one steviol glycoside such as RebA, RebB, RebD, and/or RebM and have altered expression of at least one endogenous transporter gene. Recombinant hosts described herein can produce at least one steviol glycoside such as RebA, RebB, RebD, and/or RebM and have altered expression of a transcription factor that regulates expression of at least one endogenous transporter gene. Recombinant hosts described herein can produce at least one steviol glycoside such as RebA, RebB, RebD, and/or RebM and have altered expression of a plurality of endogenous transporter genes and/or of a plurality of transcription factor genes that regulate expression of a plurality of endogenous transporter genes. Altering expression of endogenous transporter genes and/or transcription factors regulating expression of at least one transporter gene can be useful for increasing production of steviol glycosides and/or excretion of steviol glycosides into the culture medium.

Recombinant hosts disclosed herein can include one or more biosynthesis genes, such as one or more genes encoding a sucrose transporter and a sucrose synthase; a gene encoding a geranylgeranyl diphosphate synthase (GGPPS) polypeptide; a gene encoding an ent-copalyl diphosphate synthase (CDPS) polypeptide; a gene encoding a kaurene synthase (KS) polypeptide; a gene encoding a kaurene oxidase (KO) polypeptide; a gene encoding a steviol synthase (KAH) polypeptide; a gene encoding a cytochrome P450 reductase (CPR) polypeptide; a gene encoding a UGT85C2 polypeptide; a gene encoding a UGT76G1 polypeptide; a gene encoding a UGT74G1 polypeptide; a gene encoding a UGT91D2 functional homolog; and/or a gene encoding a EUGT11 polypeptide; wherein expression of one or more of these genes results in production of steviol glycosides such as RebA, RebB, RebD, and/or RebM.

As used herein, the terms "transport of a steviol glycoside," "steviol glycoside transport," "excretion of a steviol glycoside," and "steviol glycoside excretion" can be used interchangeably.

As used herein, the term "transporter" (also referred to as a membrane transport protein) refers to a membrane protein involved in the movement of small molecules, macromolecules (such as carbohydrates), and ions across a biological membrane. Transporters span the membrane in which they are localized and across which they transport substances. Transporter proteins can assist in the movement (i.e., transport or excretion) of a substance from the intracellular space to the culture medium. Transporters are known to function as passive transport systems, carrying molecules down their concentration gradient, or as active transport systems, using energy to carry molecules uphill against their concentration gradient. Active transport is mediated by carriers which couple transport directly to the use of energy derived from hydrolysis of an ATP molecule or by carriers which make use of a pre-established electrochemical ion gradient to drive co-transport of the nutrient molecule and a co-transported ion. The latter category comprises symporters and antiporters, which carry the ion in the same or opposite direction, respectively, as the transported substrate.

Transport proteins have been classified according to various criteria at the Transporter Classification Database (on the world wide web at tcdb.org). See, Saier Jr. et al., Nucl. Acids Res., 42(1):D251-258 (2014). Non-limiting examples thereof include, among others, the family of Multiple Drug Resistance (MDR) plasma membrane transporters that is thought to be ubiquitous among living organisms. The MDR transporter superfamily can be further subdivided according to the mode of operation by which the substrate is transported from one side of the membrane to the other. Transporters can operate to move substances across membranes in response to chemiosmotic ion gradients or by active transport. ATP-binding cassette transporters (ABC transporters) are transmembrane proteins that utilize the energy of adenosine triphosphate (ATP) hydrolysis to carry out translocation of various substrates across membranes. They can transport a wide variety of substrates across the plasma membrane and intracellular membranes, including metabolic products, lipids and sterols, and drugs. Particular non-limiting examples of endogenous ABC transporter genes include PDR5, YDR061W, PDR15, SNQ2, YOR1, YOL075C, MDL2, ADP1, CAF16, VMR1 and STE6 (or a functional homolog thereof). In some aspects, ABC transporters transport steviol glycosides.

A second group of MDRs is further subdivided based on the nature of the chemiosmotic gradient that facilitates the transport. Saier, Jr. et al., J. Mol. Microbiol. Biotechnol. 1:257-279 (1999). In some aspects, MDR transporters transport steviol glycosides.

Another transporter family, the Major Facilitator Superfamily (MFS) transporters are monomeric polypeptides that can transport small solutes in response to proton gradients. The MFS transporter family is sometimes referred to as the uniporter-symporter-antiporter family. MFS transporters function in, inter alia, in sugar uptake and drug efflux systems. MFS transporters typically comprise conserved MFS-specific motifs. Non-limiting examples of endogenous MFS transporter genes include DTR1, SEO1, YBR241C, VBA3, FEN2, SNF3, STL1, HXT10, AZR1, MPH3, VBA5, GEX2, SNQ1, AQR1, MCH1, MCH5, ATG22, HXT15, MPH2, ITR1, SIT1, VPS73, HXT5, QDR1, QDR2, QDR3, SOA1, HXT9, YMR279C, YIL166C, HOL1, ENB1, TPO4 and FLR1 (or a functional homolog thereof). In some aspects, MFS transporters transport steviol glycosides.

Other transporter families include the SMR (small multidrug resistant) family, RND (Resistance-Nodulation-Cell Division) family, and the MATE (multidrug and toxic compound extrusion) family. The SMR family members are integral membrane proteins characterized by four alpha-helical transmembrane strands that confer resistance to a broad range of antiseptics, lipophilic quaternary ammonium compounds (QAC), and aminoglycoside resistance in bacteria. See, Bay & Turner, 2009, BMC Evol Biol., 9:140. In some aspects, SMR transporters transport steviol glycosides.

The MATE family members comprise 12 transmembrane (TM) domains. Members of the MATE family have been identified in prokaryotes, yeast such as *S. cerevisiae* and *Schizosaccharomyces pombe*, and plants. See Diener et al., 2001, Plant Cell. 13(7):1625-8. The MATE family members are sodium or proton antiporters. In some aspects, MATE transporters transport steviol glycosides.

Additional transporter families include the amino add/auxin permease (AAAP) family (for example, YKL146W/AVT3, YBL089W/AVT5, YER119C/AVT6 and YIL088C/AVT7), the ATPase family (for example, YBL099W/ATP1, YDL185W/VMA1, YLR447C/VMA6, YOL077W/ATP19, YPL078C/ATP4, YEL027W/VMA3, YKL016C/ATP7, and YOR332W/VMA4), the sulfate permease (SulP) family (for example, YBR294W/SUL1, YGR125W and YPR003C), the lysosomal cystine transporter (LCT) family (for example, YCR075C/ERS1), the Ca2+:cation antiporter (CaCA) family (for example, YDL128W/VCX1 and YJR106W/ECM27), the amino add-polyamine-organocation (APC) superfamily (for example, YDL210W/UGA4, YOL020W/TAT2, YPL274W/SAM3, YNL268W/LYP1, YHL036W/MUP3, YKR039W/GAP1 and YOR348C/PUT4), multidrug/oligosaccharidyl-lipid/polysaccharide (MOP) (for example, YDR338C), the ZRT/IRT-like protein (ZIP) metal transporter family (for example, YGL225W/ZRT1 and YOR079C/ATX2), the mitochondrial protein translocase (MPT) family (for example, YGR181W/TIM13, YNL070W/TOM7, YNL121C/TOM70, the voltage-gated ion channel (VIC) family (for example, YGR217W/CCH1 and YJL093C/TOK1), the monovalent cation:proton antiporter-2 (CPA2) family (for example, YJL094C/KHA1), the ThrE family of putative transmembrane amino acid efflux transporters (for example, YJL108C/PRM10), the oligopeptide transporter (OPT) family (for example, YJL212C/OPT1 and YGL114W), the K+ transporter (Trk) family (for example, TKR050W/TRK2), the bile acid:Na symporter (BASS) family (for example, YMR034C), the drug/metabolite transporter (DMT) superfamily (for example, YMR253C, YML038C/YMD8, and YOR307C/SLY41), the mitochondrial carrier (MC) family (for example, YMR056C/AAC1, YNL083W/SAL1, YOR130C/ORT1, YOR222W/ODC2, YPR011C, YPR058W/YMC1, YPR128C/ANT1, YEL006W/YEA6, YER053C/PIC2, YFR045W, YGR257C/MTM1, YHR002W/LEU5, YIL006W/YIA6, YJL133W/MRS3, YKL120W/OAC1, YMR166C, YNL003C/PET8 and YOR100C/CRC1), the auxin efflux carrier (AEC) family (for example, YNL095C, YOR092W/ECM3 and YBR287W), the ammonia channel transporter (Amt) family (for example, YNL142W/MEP2), the metal ion ($Mn^{2+}$-iron) transporter (Nramp) family (for example, YOL122C/SMF1), the transient receptor potential $Ca^{2+}$ channel (TRP-CC) family (for example, YOR087W/YVC1), the arsenical resistance-3 (ACR3) family (for example, YPR201W/ARR3), the nucleobase:cation symporter-1 (NCS1) family (for example, YBR021W/FUR4), the inorganic phosphate transporter (PIT) family (for example, YBR296C/PHO89), the arsenite-antimonite (ArsAB) efflux family (for example, YDL100C/GET3), the IISP family of transporters, the glycerol uptake (GUP) family (for example, YGL084C/GUP1), the metal ion transport (MIT) family (for example, YKL064W/MNR2, YKL050C and YOR334W/MRS2), the copper transport (Ctr) family (for example, YLR411W/CTR3) and the cation diffusion facilitator (CDF) family (for example, YOR316C/COT1). Particular members of any of these transporter families are included within the scope of the disclosed invention to the extent that altered expression in a cell capable of producing steviol glycoside increases production of said steviol glycoside from the cell; exemplary members are disclosed above and in Tables 5, 6, and 14.

As used herein, the term "transcription factor" refers to a DNA-binding protein that regulates gene expression. Preferably, the transcription factor regulates expression of at least one transporter gene.

Methods for identifying a gene affecting production or transport of steviol glycosides and steviol glycoside pathway intermediates are disclosed herein. Such methods can involve inactivating at least one endogenous transporter gene or modifying expression of at least one transporter gene. Typically, a library of mutant microorganisms is prepared, each mutant in the library having a different endogenous transporter gene inactivated. Methods of inactivating genes and determining their effect in a microorganisms are known to a person having ordinary skill in the art; additional methods are disclosed in WO 2014/122328, the disclosure of which is incorporated by reference in its entirety. The mutant microorganisms comprising one or more steviol glycoside pathway genes are cultured in a medium under conditions in which steviol or a steviol glycoside is synthesized, and the amount of total, supernatant, and/or intracellular steviol glycosides produced by the microorganism is measured (e.g., using LC-MS) as described herein.

The disclosure is directed to recombinant host cells in which expression of endogenous transporter or transcription factor genes is modified. In some embodiments, the transporter or transcription factor gene is endogenous to *S. cerevisiae*, including, but not limited to *S. cerevisiae* strain S288C. In some embodiments, expression of an endogenous transporter or transcription factor can be modified by replacing the endogenous promoter with a different promoter that results in increased expression of the transporter protein (e.g., at least a 5% increase in expression, such as at least a 10%, 15%, 20%, 25%, 30%, 35%, 40%, 45%, or 50%, 100%, 200% increase or more in expression). For example, an endogenous promoter can be replaced with a constitutive or inducible promoter that results in increased expression of the transporter. Homologous recombination can be used to replace the promoter of an endogenous gene with a different promoter that results in increased expression of the transporter. In other embodiments, the inducible or constitutive promoter and endogenous transporter or transcription factor can be integrated into another locus of the genome using homologous recombination. In other embodiments, the transporter or transcription factor gene can be introduced into a microorganism using exogenous plasmids with a promoter that results in overexpression of the transporter or transcription factor in the microorganism. In yet another embodiment, the exogenous plasmids may also comprise multiple copies of the transporter or transcription factor gene. In a further embodiment, the endogenous transporter or transcription factor can be induced to be overexpressed using native mechanisms to the recombinant microorganism (e.g. heat shock, stress, heavy metal, or antibiotic exposure). In yet a further embodiment, the activity of an endogenous gene product is enhanced or increased (for example, by mutation). In yet another embodiment, a homologous or orthologous gene of an endogenous yeast transporter or transcription factor gene is overexpressed.

In certain other embodiments, modified expression of a target gene in a recombinant microorganism comprises overexpressing a transporter gene and/or a transcription factor gene involved in expression of said transporter gene. In yet other embodiments, a plurality of endogenous transporter genes or transcription factor genes is overexpressed in said recombinant microorganism.

Modification of transcription factor expression can be used to increase transporter expression. For example, yeast transcriptions factor PDR1 regulates expression of the genes encoding ABC transporters PDR5, SNQ2 and YOR1. Therefore, in some embodiments, promoters for the endogenous PDR1 locus can be replaced with a different promoter that results in increased expression of the transcription factors, which can increase production of endogenous transporters.

In some embodiments, the transporter gene or transcription factor gene is (using Uniprot Ordered Locus Name for each): YAL067C, YBL089W, YBL099W, YBR008C, YBR021W, YBR043C, YBR180W, YBR241C, YBR287W, YBR294W, YBR295W, YBR296C, YCL038C, YCL069W, YCR011C, YCR028C, YCR075C, YDL054C, YDL1000, YDL128W, YDL185W, YDL194W, YDL210W, YDL245C, YDL247W, YDR011W, YDR061W, YDR093W, YDR292C, YDR338C, YDR406W, YDR497C, YDR536W, YEL006W, YEL027W, YEL031W, YEL065W, YER019C-A, YER053C, YER119C, YER166W, YFL011W, YFL028C, YFR045W, YGL006W, YGL013C, YGL084C, YGL104C, YGL114W, YGL167C, YGL255W, YGR125W, YGR181W, YGR217W, YGR224W, YGR257C, YGR281W, YHL016C0, YHL035C, YHL036W, YHR002W, YHR096C, YIL006W, YIL088C, YIL120W, YIL121W, YIL166C, YJL093C, YJL094C, YJL108C, YJL133W, YJL212C, YJL219W, YJR106W, YJR160C, YKL016C, YKL050C, YKL064W, YKL120W, YKL146W, YKL209C, YKR039W, YKR050W, YKR105C, YKR106W, YLR411W, YLR447C, YML038C, YML116W, YMR034C, YMR056C, YMR166C, YMR253C, YMR279C, YNL003C, YNL065W, YNL070W, YNL083W, YNL095C, YNL121C, YNL142W, YNL268W. YNR055C, YOL020W, YOL075C, YOL077W-A, YOL122C, YOL158C, YOR079C, YOR087W, YOR092W, YOR100C, YOR130C, YOR153W, YOR222W, YOR271C, YOR273C, YOR291W, YOR306C, YOR307C, YOR316C, YOR332W, YOR334W, YOR348C, YPL036W, YPL078C, YPL270W, YPL274W, YPR003C, YPR011C, YPR058W, YPR128C, and/or YPR201W. SEQ ID NOs, Uniprot Accession Numbers, and gene names for each Ordered Locus can be found in Tables 5, 6, and 14. In some embodiments, the above transporter genes and transcription factor genes regulate excretion of steviol glycosides.

In some embodiments, deletion in a steviol glycoside-producing strain of YDL128W (SEQ ID NO:22), YDL194W (SEQ ID NO:24), YDL210W (SEQ ID NO:25), YDR536W (SEQ ID NO:30), YFL011W (SEQ ID NO:33), YGL006W (SEQ ID NO:34), YGL013C (SEQ ID NO:35), YGL255W (SEQ ID NO:36), YGR181W (SEQ ID NO:38), YGR217W (SEQ ID NO:39), YHL016C (SEQ ID NO:42), YIL088C (SEQ ID NO:43), YJL094C (SEQ ID NO:45), YJR106W (SEQ ID NO:48), YKR050W (SEQ ID NO:51), YNL065W (SEQ ID NO:59), YNL083W (SEQ ID NO:61), YNL121C (SEQ ID NO:63), YNL142W (SEQ ID NO:64), YOR291W (SEQ ID NO:74), YOR306C (SEQ ID NO:75), YOR334W (SEQ ID NO:77), YPL270W (SEQ ID NO:79), YPR011C (SEQ ID NO:82), YPR128C (SEQ ID NO:84) results in a measurable decrease of RebD excreted into the culture medium, indicating that each plays a role in RebD excretion. See Example 3 and Tables 7-10.

In some embodiments, deletion in a steviol glycoside-producing strain of YBR180W (SEQ ID NO:13), YAL067C (SEQ ID NO:14), YBR241C (SEQ ID NO:17), YCL069W (SEQ ID NO:19), YCR075C (SEQ ID NO:21), YDL128W (SEQ ID NO:22), YDL194W (SEQ ID NO:24), YDR093W (SEQ ID NO:27), YDR338C (SEQ ID NO:28), YDR406W (SEQ ID NO:29), YER166W (SEQ ID NO:32), YFL011W (SEQ ID NO:33), YGL006W (SEQ ID NO:34), YGL013C (SEQ ID NO:35), YGL255W (SEQ ID NO:36), YGR217W (SEQ ID NO:39), YHL016C (SEQ ID NO:42), YJL094C (SEQ ID NO:45), YJL212C (SEQ ID NO:47), YJR106W (SEQ ID NO:48), YJR160C (SEQ ID NO:49), YKR050W (SEQ ID NO:51), YKR106W (SEQ ID NO:53), YML116W (SEQ ID NO:55), YMR034C (SEQ ID NO:56), YMR056C (SEQ ID NO:57), YMR253C (SEQ ID NO:58), YNL070W (SEQ ID NO:60), YNL083W (SEQ ID NO:61), YNL095C (SEQ ID NO:62), YNL121C (SEQ ID NO:63), YOL075C (SEQ ID NO:66), YOL122C (SEQ ID NO:68), YOR087W (SEQ ID NO:70), YOR222W (SEQ ID NO:73), YOR291W (SEQ ID NO:74), YOR306C (SEQ ID NO:75), YPL274W (SEQ ID NO:80), YPR003C (SEQ ID NO:81), YPR011C (SEQ ID NO:82), or YPR201W (SEQ ID NO:85) results in a measurable decrease of RebM, indicating that each plays a role in RebM excretion. See Example 3 and Tables 7-10.

Figure 2:
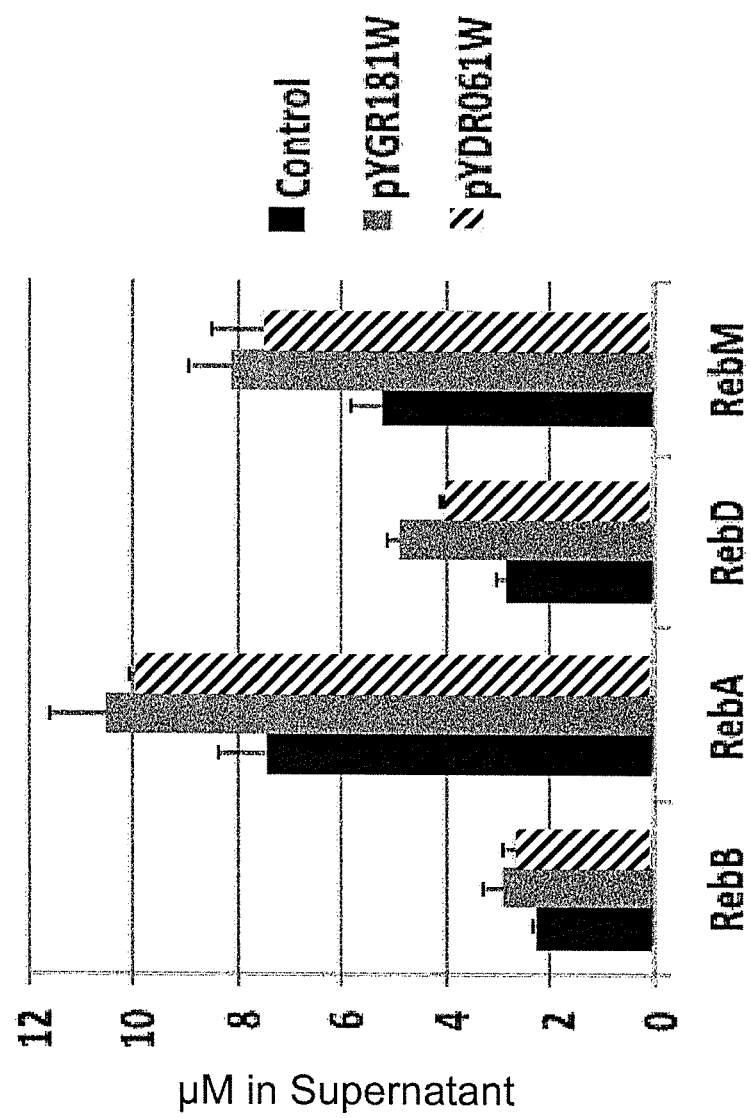
FIG. 2 is a bar graph of the amount (µM) of RebA, RebB. RebD, or RebM in the supernatant of a steviol glycoside- producing strain overexpressing transporter genes YGR181W (SEQ ID NO:38) or YDR061W (SEQ ID NO:26), compared to a control steviol glycoside-producing strain. See Example 4.

In some embodiments, overexpression of YGR181W (SEQ ID NO:38) or YDR061W (SEQ ID NO:26) improves RebD and RebM transport into the culture medium by approximately 2-fold (~400-500 mg/L of supernatant RebD and RebM in YGR181W (SEQ ID NO:38) and YDR061W (SEQ ID NO:26) overexpression strains versus ~250 mg/L of supernatant RebD and RebM in a control steviol glycoside-producing strain). See Example 4, FIG. 2, and FIG. 3.

In some embodiments, overexpression of a transporter of Table 11 Increases excretion of RebA, RebB, RebD, and/or RebM by at least 20%. In some embodiments, overexpression of a transporter of Table 12 increases production of RebA, RebB, RebD, and/or RebM by at least 40%. See Example 5.

In some embodiments, a transporter gene is integrated Into the genome of a steviol glycoside-producing host. In some embodiments, the integrated transporter is YBR043C (SEQ ID NO:88), YEL027W (SEQ ID NO:102), YJL093C (SEQ ID NO:44), YJR106W (SEQ ID NO:48), YMR166C (SEQ ID NO:132), YIL166C (SEQ ID NO:121), YKL120W (SEQ ID NO:126), YDL054C (SEQ ID NO:94), YDL128W (SEQ ID NO:22), YDR536W (SEQ ID NO:30), YGL167C (SEQ ID NO:112), YKL146W (SEQ ID NO:127), YKR039W (SEQ ID NO:129), YOL122C (SEQ ID NO:68), or YPR011C (SEQ ID NO:82). In some embodiments, Integration of YBR043C (SEQ ID NO:88), YEL027W (SEQ ID NO:102), YJL093C (SEQ ID NO:44), YJR106W (SEQ ID NO:48), YKL120W (SEQ ID NO:126), or YMR166C (SEQ ID NO:132) improves excretion and/or total production of 13-SMG. In some embodiments, integration of YBR043C (SEQ ID NO:88), YEL027W (SEQ ID NO:102), or YMR166C (SEQ ID NO:132) improves excretion and/or total production of RebA. In some embodiments, Integration of YBR043C (SEQ ID NO:88), YEL027W (SEQ ID NO:102), or YMR166C (SEQ ID NO:132) improves excretion and/or total production of RebB. In some embodiments, integration of YBR043C of SEQ ID NO:88, YEL027W of SEQ ID NO:102, YJL093C of SEQ ID NO:44, YJR106W of SEQ ID NO:48, and YMR166C of SEQ ID NO:132 improves excretion and/or total production of RebD, and YBR043C of SEQ ID NO:88, YEL027W of SEQ ID NO:102, YIL166C (SEQ ID NO:121), YJL093C of SEQ ID NO:44, YJR106W of SEQ ID NO:48, and YMR166C of SEQ ID NO:132 improves excretion end/or total production of RebM, as measured by an increase in RebD and RebM levels in the supernatant compared to a control steviol glycoside-producing strain. See Example 6.

In some embodiments, steviol glycoside-producing *S. cerevisiae* strains overexpressing YJL093C (SEQ ID NO:44) or YBR043C (SEQ ID NO:88) produce higher levels of RebD+RebM, compared to a steviol glycoside-producing *S. cerevisiae* strain that does not overexpress YJL093C or YBR043C. See Example 7.

In some embodiments, a transporter that is knocked out can also have specificity for transport of larger molecular weight steviol glycosides (for example, RebD and the knockout of YGR181W of SEQ ID NO:38 or YOR291W of SEQ ID NO:74), and therefore, can be useful to overexpress in strains where transport of RebD into the culture medium is desired. With appropriate balancing of the rate of glycosylation activity through expression of pathway UGTs, smaller molecular weight steviol glycosides are further glycosylated before they are transported into the culture medium. For example, higher expression levels of a UGT76G1 and UGT91D2e and/or EUGT11, as compared to the UGT74G1 and UGT85C2 enzymes, can prevent accumulation of the steviol monoglucosides that are transported more readily. If the UGT activity level is higher (so the glycosylation rate is faster) than the rate of transport, then greater amounts of larger molecular weight steviol glycosides will be produced.

Steviol and Steviol Glycoside Biosynthesis Nucleic Acids

A recombinant gene encoding a polypeptide described herein comprises the coding sequence for that polypeptide, operably linked in sense orientation to one or more regulatory regions suitable for expressing the polypeptide. Because many microorganisms are capable of expressing multiple gene products from a polycistronic mRNA, multiple polypeptides can be expressed under the control of a single regulatory region for those microorganisms, if desired. A coding sequence and a regulatory region are considered to be operably linked when the regulatory region and coding sequence are positioned so that the regulatory region is effective for regulating transcription or translation of the sequence. Typically, the translation initiation site of the translational reading frame of the coding sequence is positioned between one and about fifty nucleotides downstream of the regulatory region for a monocistronic gene.

In many cases, the coding sequence for a polypeptide described herein is identified in a species other than the recombinant host, i.e., is a heterologous nucleic acid. Thus, if the recombinant host is a microorganism, the coding sequence can be from other prokaryotic or eukaryotic microorganisms, from plants or from animals. In some case, however, the coding sequence is a sequence that is native to the host and is being reintroduced into that organism. A native sequence can often be distinguished from the naturally occurring sequence by the presence of non-natural sequences linked to the exogenous nucleic acid, e.g., non-native regulatory sequences flanking a native sequence in a recombinant nucleic acid construct. In addition, stably transformed exogenous nucleic acids typically are integrated at positions other than the position where the native sequence is found. "Regulatory region" refers to a nucleic acid having nucleotide sequences that influence transcription or translation initiation and rate, and stability and/or mobility of a transcription or translation product. Regulatory regions include, without limitation, promoter sequences, enhancer sequences, response elements, protein recognition sites, inducible elements, protein binding sequences, 5' and 3' untranslated regions (UTRs), transcriptional start sites, termination sequences, polyadenylation sequences, Introns, and combinations thereof. A regulatory region typically comprises at least a core (basal) promoter. A regulatory region also may include at least one control element, such as an enhancer sequence, an upstream element or an upstream activation region (UAR). A regulatory region is operably linked to a coding sequence by positioning the regulatory region and the coding sequence so that the regulatory region is effective for regulating transcription or translation of the sequence. For example, to operably link a coding sequence and a promoter sequence, the translation initiation site of the translational reading frame of the coding sequence is typically positioned between one and about fifty nucleotides downstream of the promoter. A regulatory region can, however, be positioned as much as about 5,000 nucleotides upstream of the translation initiation site, or about 2,000 nucleotides upstream of the transcription start site.

The choice of regulatory regions to be included depends upon several factors, including, but not limited to, efficiency, selectability, inducibility, desired expression level, and preferential expression during certain culture stages. It is a routine matter for one of skill in the art to modulate the expression of a coding sequence by appropriately selecting and positioning regulatory regions relative to the coding sequence. It will be understood that more than one regulatory region may be present, e.g., Introns, enhancers, upstream activation regions, transcription terminators, and inducible elements.

One or more genes can be combined in a recombinant nucleic acid construct in "modules" useful for a discrete aspect of steviol and/or steviol glycoside production. Combining a plurality of genes in a module, particularly a polycistronic module, facilitates the use of the module in a variety of species. For example, a steviol biosynthesis gene duster, or a UGT gene duster, can be combined in a polycistronic module such that, after insertion of a suitable regulatory region, the module can be introduced into a wide variety of species. As another example, a UGT gene duster can be combined such that each UGT coding sequence is operably linked to a separate regulatory region, to form a UGT module. Such a module can be used in those species for which monocistronic expression is necessary or desirable. In addition to genes useful for steviol or steviol glycoside production, a recombinant construct typically also comprises an origin of replication, and one or more selectable markers for maintenance of the construct in appropriate species.

It will be appreciated that because of the degeneracy of the genetic code, a number of nucleic acids can encode a particular polypeptide; i.e., for many amino acids, there is more than one nucleotide triplet that serves as the codon for the amino acid. Thus, codons in the coding sequence for a given polypeptide can be modified such that optimal expression in a particular host is obtained, using appropriate codon bias tables for that host (e.g., microorganism). As isolated nucleic acids, these modified sequences can exist as purified molecules and can be incorporated into a vector or a virus for use in constructing modules for recombinant nucleic acid constructs.

In some cases, it is desirable to inhibit one or more functions of an endogenous polypeptide in order to divert metabolic intermediates towards steviol or steviol glycoside biosynthesis. For example, it may be desirable to downregulate synthesis of sterols in a strain in order to further increase steviol or steviol glycoside production, e.g., by downregulating squalene epoxidase. As another example, it may be desirable to inhibit degradative functions of certain endogenous gene products, e.g., glycohydrolases that remove glucose moieties from secondary metabolites or phosphatases as discussed herein. As another example, expression of membrane transporters involved in transport of steviol glycosides can be activated, such that transportation of steviol glycosides is increased. Such regulation can be beneficial in that transportation of steviol glycosides can be increased for a desired period of time during culture of the microorganism, thereby increasing the yield of glycoside product(s) at harvest. In such cases, a nucleic add that overexpresses the polypeptide or gene product may be included in a recombinant construct that is transformed into the strain. Alternatively, mutagenesis can be used to generate mutants in genes for which it is desired to increase or enhance function.

Recombinant Hosts

Recombinant hosts can be used to express polypeptides for the producing steviol glycosides, including mammalian, insect, plant, and algal cells. A number of prokaryotes and eukaryotes are also suitable for use in constructing the recombinant microorganisms described herein, e.g., gram-negative bacteria, yeast, and fungi. A species and strain selected for use as a steviol glycoside production strain is first analyzed to determine which production genes are endogenous to the strain and which genes are not present. Genes for which an endogenous counterpart is not present in the strain are advantageously assembled in one or more recombinant constructs, which are then transformed into the strain in order to supply the missing function(s).

Typically, the recombinant microorganism is grown in a fermenter at a defined temperature(s) for a desired period of time. The constructed and genetically engineered microorganisms provided by the invention can be cultivated using conventional fermentation processes, including, inter alia, chemostat, batch, fed-batch cultivations, semi-continuous fermentations such as draw and fill, continuous perfusion fermentation, and continuous perfusion cell culture. Depending on the particular microorganism used in the method, other recombinant genes such as isopentenyl biosynthesis genes and terpene synthase and cyclase genes may also be present and expressed. Levels of substrates and intermediates, e.g., isopentenyl diphosphate, dimethylallyl diphosphate, GGPP, kaurene and kaurenoic acid, can be determined by extracting samples from culture media for analysis according to published methods.

Carbon sources of use in the instant method include any molecule that can be metabolized by the recombinant host cell to facilitate growth and/or production of the steviol glycosides. Examples of suitable carbon sources include, but are not limited to, sucrose (e.g., as found in molasses), fructose, xylose, ethanol, glycerol, glucose, cellulose, starch, cellobiose or other glucose-comprising polymer. In embodiments employing yeast as a host, for example, carbon sources such as sucrose, fructose, xylose, ethanol, glycerol, and glucose are suitable. The carbon source can be provided to the host organism throughout the cultivation period or alternatively, the organism can be grown for a period of time in the presence of another energy source, e.g., protein, and then provided with a source of carbon only during the fed-batch phase.

After the recombinant microorganism has been grown in culture for the desired period of time, steviol and/or one or more steviol glycosides can then be recovered from the culture using various techniques known in the art. In some embodiments, a permeabilizing agent can be added to aid the feedstock entering into the host and product getting out. For example, a crude lysate of the cultured microorganism can be centrifuged to obtain a supernatant. The resulting supernatant can then be applied to a chromatography column, e.g., a C-18 column, and washed with water to remove hydrophilic compounds, followed by elution of the compound(s) of interest with a solvent such as methanol. The compound (s) can then be further purified by preparative HPLC. See also, WO 2009/140394.

It will be appreciated that the various genes and modules discussed herein can be present in two or more recombinant hosts rather than a single host. When a plurality of recombinant hosts is used, they can be grown in a mixed culture to produce steviol and/or steviol glycosides.

Alternatively, the two or more hosts each can be grown in a separate culture medium and the product of the first culture medium, e.g., steviol, can be introduced into second culture medium to be converted into a subsequent intermediate, or into an end product such as, for example, RebA. The product produced by the second, or final host is then recovered. It will also be appreciated that in some embodiments, a recombinant host is grown using nutrient sources other than a culture medium and utilizing a system other than a fermenter.

Exemplary prokaryotic and eukaryotic species are described in more detail below. However, it will be appreciated that other species can be suitable. For example, suitable species can be in a genus such as *Agaricus, Aspergillus, Bacillus, Candida, Corynebacterium, Eremothecium, Escherichia, Fusarium/Gibberella, Kluyveromyces, Laetiporus, Lentinus, Phaffia, Phanerochaete, Pichia, Physcomitrella, Rhodoturula, Saccharomyces, Schizosaccharomyces, Sphaceloma, Xanthophyllomyces* or *Yarrowia*. Exemplary species from such genera include *Lentinus tigrinus, Laetiporus sulphureus, Phanerochaete chrysosporium, Pichia pastoris, Cyberlindnera jadinii, Physcomitrella patens, Rhodoturula glutinis, Rhodoturula mucilaginosa, Phaffia rhodozyma, Xanthophyllomyces dendrorhous, Fusarium fujikuroi/Gibberella fujikuroi, Candida utilis, Candida glabrata, Candida albicans*, and *Yarrowia lipolytica*.

In some embodiments, a microorganism can be a prokaryote such as *Escherichia coli*.

In some embodiments, a microorganism can be an Ascomycete such as *Gibberella fujikuroi, Kluyveromyces lactis, Schizosaccharomyces pombe, Aspergillus niger, Yarrowia lipolytica, Ashbya gossypii*, or *S. cerevisiae*.

In some embodiments, a microorganism can be an algal cell such as *Blakeslea trispora, Dunaliella salina, Haematococcus pluvialis, Chlorella sp., Undaria pinnatifida, Sargassum, Laminaria japonica, Scenedesmus almeriensis* species.

In some embodiments, a microorganism can be a cyanobacterial cell such as *Blakeslea trispora, Dunaliella salina, Haematococcus pluvialis, Chlorella sp., Undaria pinnatifida, Sargassum, Laminaria japonica, Scenedesmus almeriensis.*

*Saccharomyces* spp.

*Saccharomyces* is a widely used chassis organism in synthetic biology, and can be used as the recombinant microorganism platform. For example, there are libraries of mutants, plasmids, detailed computer models of metabolism and other information available for *S. cerevisiae*, allowing for rational design of various modules to enhance product yield. Methods are known for making recombinant microorganisms.

*Aspergillus* spp.

*Aspergillus* species such as *A. oryzae, A. niger* and *A. sojae* are widely used microorganisms in food production and can also be used as the recombinant microorganism platform. Nucleotide sequences are available for genomes of *A. nidulans, A. fumigatus, A. oryzae, A. clavatus, A. flavus, A. niger*, and *A. terreus*, allowing rational design and modification of endogenous pathways to enhance flux and increase product yield. Metabolic models have been developed for *Aspergillus*, as well as transcriptomic studies and proteomics studies. *A. niger* is cultured for the industrial production of a number of food ingredients such as citric acid and gluconic acid, and thus species such as *A. niger* are generally suitable for producing steviol glycosides.

*E. coli*

*E. coli*, another widely used platform organism in synthetic biology, can also be used as the recombinant microorganism platform. Similar to *Saccharomyces*, there are libraries of mutants, plasmids, detailed computer models of metabolism and other information available for *E. coli*, allowing for rational design of various modules to enhance product yield. Methods similar to those described above for *Saccharomyces* can be used to make recombinant *E. coli* microorganisms.

*Agaricus, Gibberella*, and *Phanerochaete* spp.

*Agaricus, Gibberella*, and *Phanerochaete* spp. can be useful because they are known to produce large amounts of isoprenoids in culture. Thus, the terpene precursors for producing large amounts of steviol glycosides are already produced by endogenous genes. Thus, modules comprising recombinant genes for steviol glycoside biosynthesis polypeptides can be introduced into species from such genera without the necessity of introducing mevalonate or MEP pathway genes.

*Arxula adeninivorans (Blastobotrys adeninivorans)*

*Arxula adeninivorans* is dimorphic yeast (it grows as budding yeast like the baker's yeast up to a temperature of 42'C, above this threshold it grows in a filamentous form) with unusual biochemical characteristics. It can grow on a wide range of substrates and can assimilate nitrate. It has successfully been applied to the generation of strains that can produce natural plastics or the development of a biosensor for estrogens in environmental samples.

*Yarrowia lipolytica*

*Yarrowia lipolytica* is dimorphic yeast (see *Arxula adeninivorans*) and belongs to the family Hemiascomycetes. The entire genome of *Yarrowia lipolytica* is known. *Yarrowia* species is aerobic and considered to be non-pathogenic. *Yarrowia* is efficient in using hydrophobic substrates (e.g. alkanes, fatty acids, oils) and can grow on sugars. It has a high potential for industrial applications and is an oleaginous microorganism. *Yarrowia lipolytica* can accumulate lipid content to approximately 40% of its dry cell weight and is a model organism for lipid accumulation and remobilization. See e.g., Nicaud, 2012, *Yeast* 29(10):409-18; Beopoulos et al., 2009, *Biohimie* 91(6):692-6; Banker at al., 2009, *Appl Microbiol Biotechnol.* 84(5):847-65.

*Rhodotorula* sp.

*Rhodotorula* is unicellular, pigmented yeast. The oleaginous red yeast, *Rhodotorula glutinis*, has been shown to produce lipids and carotenoids from crude glycerol (Saenge at al., 2011, *Process Biochemistry* 46(1):210-8). *Rhodotorula toruloides* strains have been shown to be an efficient fed-batch fermentation system for improved biomass and lipid productivity (Li et al., 2007, *Enzyme and Microbial Technology* 41:312-7).

*Rhodosporidium toruloides*

*Rhodosporidium toruloides* is oleaginous yeast and useful for engineering lipid-production pathways (See e.g. Zhu et al., 2013, *Nature Commun.* 3:1112; Ageitos et al., 2011, *Applied Microbiology and Biotechnology* 90(4):1219-27).

*Candida boidinii*

*Candida boidinii* is methylotrophic yeast (it can grow on methanol). Like other methylotrophic species such as *Hansenula polymorpha* and *Pichia pastoris*, it provides an excellent platform for producing heterologous proteins. Yields in a multigram range of a secreted foreign protein have been reported. A computational method, IPRO, recently predicted mutations that experimentally switched the cofactor specificity of *Candida boidinii* xylose reductase from NADPH to NADH. See, e.g., Mattanovich et al., 2012, *Methods Mol Biol.* 824:329-58; Khoury et al., 2009, *Protein Sci.* 18(10):2125-38.

*Hansenula polymorpha* (*Pichia angusta*)

*Hansenula polymorpha* is methylotrophic yeast (see *Candida boidinii*). It can furthermore grow on a wide range of other substrates; it is thermo-tolerant and can assimilate nitrate (see also *Kluyveromyces lactis*). It has been applied to producing hepatitis B vaccines, insulin and interferon alpha-2a for the treatment of hepatitis C, furthermore to a range of technical enzymes. See, e.g., Xu et al., 2014, *Virol Sin.* 29(6):403-9.

*Kluyveromyces lactis*

*Kluyveromyces lactis* is yeast regularly applied to the production of kefir. It can grow on several sugars, most importantly on lactose which is present in milk and whey. It has successfully been applied among others for producing chymosin (an enzyme that is usually present in the stomach of calves) for producing cheese. Production takes place in fermenters on a 40,000 L scale. See, e.g., van Ooyen et al., 2006, *FEMS Yeast Res.* 6(3):381-92.

*Pichia pastoris*

*Pichia pastoris* is methylotrophic yeast (see *Candida boidinii* and *Hansenula polymorpha*). It provides an efficient platform for producing foreign proteins. Platform elements are available as a kit and it is worldwide used in academia for producing proteins. Strains have been engineered that can produce complex human N-glycan (yeast glycans are similar but not identical to those found in humans). See, e.g., Piirainen et al., 2014, *N Biotechnol.* 31(6):532-7.

*Physcomitrella* spp.

*Physcomitrella mosses*, when grown in suspension culture, have characteristics similar to yeast or other fungal cultures. This genera can be used for producing plant secondary metabolites, which can be difficult to produce in other types of cells.

Steviol Glycoside Compositions

Steviol glycosides do not necessarily have equivalent performance in different food systems. It is therefore desirable to have the ability to direct the synthesis to steviol glycoside compositions of choice. Recombinant hosts described herein can produce compositions that are selectively enriched for specific steviol glycosides (e.g., RebD) and have a consistent taste profile. Thus, the recombinant hosts described herein can facilitate the production of compositions that are tailored to meet the sweetening profile desired for a given food product and that have a proportion of each steviol glycoside that is consistent from batch to batch. Hosts described herein do not produce the undesired plant by-products found in *Stevia* extracts. Thus, steviol glycoside compositions produced by the recombinant hosts described herein are distinguishable from compositions derived from *Stevia* plants.

The amount of an individual steviol glycoside (e.g., RebA, RebB, RebD, or RebM) produced can be from about 1 mg/i to about 2,800 mg/L, e.g., about 1 to about 10 mg/L, about 3 to about 10 mg/L, about 5 to about 20 mg/L, about 10 to about 50 mg/L, about 10 to about 100 mg/L, about 25 to about 500 mg/L, about 100 to about 1,500 mg/L, or about 200 to about 1,000 mg/L, at least about 1,000 mg/L, at least about 1,200 mg/L, at least about at least 1,400 mg/L, at least about 1,600 mg/L, at least about 1,800 mg/L, or at least about 2,800 mg/L. In some aspects, the amount of an individual steviol glycoside can exceed 2,800 mg/L. The amount of a combination of steviol glycosides (e.g., RebA, RebB, RebD, or RebM) produced can be from about 1 mg/L to about 6,000 mg/L, e.g., about 200 to about 1,500, at least about 2,000 mg/L, at least about 3,000 mg/L, at least about 4,000 mg/L, at least about 5,000 mg/L, or at least about 6,000 mg/l. In some aspects, the amount of a combination of steviol glycosides can exceed 6,000 mg/L. In general, longer culture times will lead to greater amounts of product. Thus, the recombinant microorganism can be cultured for from 1 day to 7 days, from 1 day to 5 days, from 3 days to 5 days, about 3 days, about 4 days, or about 5 days.

It will be appreciated that the various genes and modules discussed herein can be present in two or more recombinant microorganisms rather than a single microorganism. When a plurality of recombinant microorganisms is used, they can be grown in a mixed culture to produce steviol and/or steviol glycosides. For example, a first microorganism can comprise one or more biosynthesis genes for producing steviol and null mutations in a first group of endogenous transporters, while a second microorganism comprises steviol glycoside biosynthesis genes and null mutations in a second group of endogenous transporters. The product produced by the second, or final microorganism is then recovered. It will also be appreciated that in some embodiments, a recombinant microorganism is grown using nutrient sources other than a culture medium and utilizing a system other than a fermenter.

Alternatively, the two or more microorganisms each can be grown in a separate culture medium and the product of the first culture medium, e.g., steviol, can be introduced into second culture medium to be converted into a subsequent intermediate, or into an end product such as RebA. The product produced by the second, or final microorganism is then recovered. The microorganisms can have the same or a different group of mutations in endogenous transporters. It will also be appreciated that in some embodiments, a recombinant microorganism is grown using nutrient sources other than a culture medium and utilizing a system other than a fermenter.

Steviol glycosides do not necessarily have equivalent performance in different food systems. It is therefore desirable to have the ability to direct the synthesis to steviol glycoside compositions of choice. Recombinant hosts described herein can produce compositions that are selectively enriched for specific steviol glycosides (e.g., RebD)

and have a consistent taste profile. Thus, the recombinant microorganisms described herein can facilitate the production of compositions that are tailored to meet the sweetening profile desired for a given food product and that have a proportion of each steviol glycoside that is consistent from batch to batch. Microorganisms described herein do not produce the undesired plant byproducts found in *Stevia* extracts. Thus, steviol glycoside compositions produced by the recombinant microorganisms described herein are distinguishable from compositions derived from *Stevia* plants.

Steviol glycosides and compositions obtained by the methods disclosed herein can be used to make food products, dietary supplements and sweetener compositions. See, e.g., WO 2011/153378, WO 2013/022989, WO 2014/122227, and WO 2014/122328, each of which has been incorporated by reference in its entirety.

For example, substantially pure steviol or steviol glycoside such as RebM or RebD can be included in food products such as ice cream, carbonated beverages, fruit juices, yogurts, baked goods, chewing gums, hard and soft candies, and sauces. Substantially pure steviol or steviol glycoside can also be included in non-food products such as pharmaceutical products, medicinal products, dietary supplements and nutritional supplements. Substantially pure steviol or steviol glycosides may also be included in animal feed products for both the agriculture industry and the companion animal industry. Alternatively, a mixture of steviol and/or steviol glycosides can be made by culturing recombinant microorganisms separately, each producing a specific steviol or steviol glycoside, recovering the steviol or steviol glycoside in substantially pure form from each microorganism and then combining the compounds to obtain a mixture comprising each compound in the desired proportion. The recombinant microorganisms described herein permit more precise and consistent mixtures to be obtained compared to current *Stevia* products. For example, recombinant microorganisms described herein can express transporters specific for transport of a particular rebaudioside into the culture medium. When a transporter is specific for a particular rebaudioside it will enrich the concentration of that compound in the fermentation broth, preventing it from being further reacted to a different compound, and by selectively transporting the rebaudioside into the fermentation broth it will make it easier to recover from the other rebaudiosides and therefore making the process more efficient.

In another alternative, a substantially pure steviol or steviol glycoside can be incorporated into a food product along with other sweeteners, e.g. saccharin, dextrose, sucrose, fructose, erythritol, aspartame, sucralose, monatin, or acesulfame potassium. The weight ratio of steviol or steviol glycoside relative to other sweeteners can be varied as desired to achieve a satisfactory taste in the final food product. See, e.g., U.S. 2007/0128311. In some embodiments, the steviol or steviol glycoside may be provided with a flavor (e.g., citrus) as a flavor modulator.

Compositions produced by a recombinant microorganism described herein can be incorporated into food products. For example, a steviol glycoside composition produced by a recombinant microorganism can be incorporated into a food product in an amount ranging from about 20 mg steviol glycoside/kg food product to about 1800 mg steviol glycoside/kg food product on a dry weight basis, depending on the type of steviol glycoside and food product. For example, a steviol glycoside composition produced by a recombinant microorganism can be incorporated into a dessert, cold confectionary (e.g., ice cream), dairy product (e.g., yogurt), or beverage (e.g., a carbonated beverage) such that the food product has a maximum of 500 mg steviol glycoside/kg food on a dry weight basis. A steviol glycoside composition produced by a recombinant microorganism can be incorporated into a baked good (e.g., a biscuit) such that the food product has a maximum of 300 mg steviol glycoside/kg food on a dry weight basis. A steviol glycoside composition produced by a recombinant microorganism can be incorporated into a sauce (e.g., chocolate syrup) or vegetable product (e.g., pickles) such that the food product has a maximum of 1000 mg steviol glycoside/kg food on a dry weight basis. A steviol glycoside composition produced by a recombinant microorganism can be incorporated into a bread such that the food product has a maximum of 160 mg steviol glycoside/kg food on a dry weight basis. A steviol glycoside composition produced by a recombinant microorganism, plant, or plant cell can be incorporated into a hard or soft candy such that the food product has a maximum of 1600 mg steviol glycoside/kg food on a dry weight basis. A steviol glycoside composition produced by a recombinant microorganism, plant, or plant cell can be incorporated into a processed fruit product (e.g., fruit juices, fruit filling, jams, and jellies) such that the food product has a maximum of 1000 mg steviol glycoside/kg food on a dry weight basis.

For example, such a steviol glycoside composition can have from 90-99% RebA and an undetectable amount of *stevia* plant-derived contaminants, and be incorporated into a food product at from 25-1600 mg/kg, e.g., 100-500 mg/kg, 25-100 mg/kg, 250-1000 mg/kg, 50-500 mg/kg or 500-1000 mg/kg on a dry weight basis.

Such a steviol glycoside composition can be a RebB-enriched composition having greater than 3% RebB and be incorporated into the food product such that the amount of RebB in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebB-enriched composition has an undetectable amount of *stevia* plant-derived contaminants.

Such a steviol glycoside composition can be a RebD-enriched composition having greater than 3% RebD and be incorporated into the food product such that the amount of RebD in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebD-enriched composition has an undetectable amount of *stevia* plant-derived contaminants.

Such a steviol glycoside composition can be a RebE-enriched composition having greater than 3% RebE and be incorporated into the food product such that the amount of RebE in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebE-enriched composition has an undetectable amount of *stevia* plant-derived contaminants.

Such a steviol glycoside composition can be a RebM-enriched composition having greater than 3% RebM and be incorporated into the food product such that the amount of RebM in the product is from 25-1600 mg/kg, e.g., 100-500 mg/kg, 25-100 mg/kg, 250-1000 mg/kg, 50-500 mg/kg or 500-1000 mg/kg on a dry weight basis. Typically, the RebM-enriched composition has an undetectable amount of *stevia* plant-derived contaminants.

In some embodiments, a substantially pure steviol or steviol glycoside is incorporated into a tabletop sweetener or "cup-for-cup" product. Such products typically are diluted to the appropriate sweetness level with one or more bulking agents, e.g., maltodextrins, known to those skilled in the art. Steviol glycoside compositions enriched for RebA, RebB, RebD, RebE, or RebM, can be package in a sachet, for example, at from 10,000 to 30,000 mg steviol glycoside/kg product on a dry weight basis, for tabletop use.

The invention will be further described in the following examples, which do not limit the scope of the invention described in the claims.

EXAMPLES

The Examples that follow are illustrative of specific embodiments of the invention, and various uses thereof. They are set forth for explanatory purposes only, and are not to be taken as limiting the invention.

Example 1. LC-MS Analytical Procedures

The LC-MS methods described here are oriented towards the separation, general detection and potential identification of chemicals of particular masses (i.e. steviol glycosides) in the presence of a mixture (i.e. culture media). LC-MS analyses were performed on: (A) an UltiMate® 3000-TSQ (Thermo Fisher Scientific); (B) a 1290 Infitity-6130SQ (Agilent); or (C) an Acquity-XevoTQD (Waters) system. Specific methods used for each system are described below.

Method A:

LC-MS analyses were performed using an UltiMate® 3000 UPLC system (Dionex) fitted with a waters ACQUITY UPLC® BEH shield RP18 column (2.1×50 mm, 1.7 μm particles, 130 Å pore size) connected to a TSQ Quantum® Access (ThermoFisher Scientific) triple quadropole mass spectrometer with a heated electrospray ion (HESI) source, unless otherwise indicated. Elution was carried out using a mobile phase of eluent B (MeCN with 0.1% Formic acid) and eluent A (water with 0.1% Formic acid) by increasing the gradient from 25% to 47% B from min. 0.0 to 4.0, increasing 47% to 100% B in min. 4.0 to 5.0, holding 100% B from min. 5.0 to 6.5 re-equilibration. The flow rate was 0.4 mL/min and the column temperature 35° C. The steviol glycosides were detected using SIM (Single Ion Monitoring) with the following m/z-traces.

TABLE 1

MS analytical information for Steviol Glycosides

| Description | Exact Mass | m/z trace | compound (typical $t_R$ in min) |
|---|---|---|---|
| Steviol + 1 Glucose | $[M + H]^+$ 481.2796 $[M + Na]^+$ 503.2615 | 481.2 ± 0.5 503.1 ± 0.5 | 19-SMG (2.29), 13-SMG (3.5) |
| Steviol + 2 Glucose | $[M + Na]^+$ 665.3149 | 665 ± 0.5 | Rubusoside (2.52) Steviol-1,2-bioside (2.92) Steviol-1,3-bioside (2.28) |
| Steviol + 3 Glucose | $[M + Na]^+$ 827.3677 | 827.4 ± 0.5 | 1,2-Stevioside (2.01) 1,3-Stevioside (2.39) RebB (2.88) |
| Steviol + 4 Glucose | $[M + Na]^+$ 989.4200 | 989.4 ± 0.5 | RebA (2.0) |
| Steviol + 5 Glucose | $[M + Na]^+$ 1151.4728 | 1151.4 ± 0.5 | RebD (1.1) |
| Steviol + 6 Glucose | $[M + Na]^+$ 1313.5257 | 1313.5 ± 0.5 | RebM (1.3) |

The levels of steviol glycosides were quantified by comparing with calibration curves obtained with authentic standards from LGC Standards. For example, standard solutions of 0.5 to 100 μM RebA were typically utilized to construct a calibration curve.

Method B:

A second analytical method was performed on the Agilent system 1290 Infinity fitted with a waters ACQUITY UPLC® BEH shield RP18 column (2.1×50 mm, 1.7 μm particles, 130 Å pore size, Waters) was connected to a 6130 single quadrupol mass detector (Agilent) with a APCI ion source. Elution was carried out using a mobile phase of eluent B (MeCN with 0.1% Formic acid) and eluent A (water with 0.1% Formic acid) by increasing the gradient from 23% to 47% B from min. 0.0 to 4.0, increasing 47% to 100% B in min. 4.0 to 5.0, holding 100% B from min. 5.0 to 6.5 re-equilibration. The flow rate was 0.6 mL/min and the column temperature 50° C. The steviol glycosides were detected using SIM (Single Ion Monitoring) with the following m/z-traces.

TABLE 2

MS analytical information for Steviol Glycosides

| SIM trace No | time window | m/z trace | Exact Mass | Description | compound (typical $t_R$ in min) |
|---|---|---|---|---|---|
| 1 | 0.0-1.51 min | 1289.5 | $[M - H]^-$ 1289.5281 | Steviol + 6 Glucose | RebM (0.91) |
|  | 1.51-1.90 min | 687.3 | $[M + HCOOH - H]^-$ 687.3217 | Steviol + 2 Glucose | Rubusoside |
|  | 1.90-5.0 min | 641.0 | $[M - H]^-$ 641.3168 | Steviol + 2 Glucose | 1,2-Stevioside (1.44) 1,3-stevioside (1.74) |
| 2 | 0.0-1.0 min | 1127.4 | $[M - H]^-$ 1127.4752 | Steviol + 5 Glucose | RebD (0.81) |
|  | 1.0-5.0 min | 525.3 | $[M - HCOOH - H]^-$ 525.2689 | Steviol + 1 Glucose | 19SMG (2.49) 13SMG (2.65) |
| 3 | 0.0-2.8 min | 965.4 | $[M - H]^-$ 965.4224 | Steviol + 4 Glucose | RebA (1.42) |
| 4 | 0.0-3.2 min | 803.4 | $[M - H]^-$ 803.3696 | Steviol + 2 Glucose | 1,2-Stevioside (2.16) 1,3-Stevioside (2.34) RebB (2.13) |

The levels of steviol glycosides were quantified by comparing with calibration curves obtained with authentic standards from LGC Standards. For example, standard solutions of 0.3 to 25 µM RebA were typically utilized to construct a calibration curve.

Method C:

A third analytical method used was LC-MS analyses performed using a Waters ACQUITY UPLC (Waters Corporation, Milford, Mass.) with Waters ACQUITY UPLC® BEH C18 column (2.1×50 mm, 1.7 µm particles, 130 Å pore size) coupled to a Waters ACQUITY TQD triple quadropole mass spectrometer with electrospray ionization (ESI) in negative mode. Compound separation was achieved by a gradient of the two mobile phases A (water with 0.1% formic acid) and B (MeCN with 0.1% formic acid) by increasing from 20% to 50% B between 0.3 to 2.0 min, increasing to 100% B at 2.01 min, holding 100% B for 0.6 min and re-equilibrate for another 0.6 min. The flow rate was 0.6 mL/min and the column temperature 55'C. RebD (m/z 1127.5), RebM (m/z 1289.5), redaudioside A (m/z 965.4) and RebB (m/z 803.4) were monitored using SIM (Single Ion Monitoring) and quantified by comparing with authentic standards.

Example 2. Construction of a Steviol Glycoside-Producing Yeast Strain

Steviol glycoside-producing *S. cerevisiae* strains were constructed as described in WO 2011/153378, WO 2013/022989, WO 2014/122227, and WO 2014/122328, each of which is incorporated by reference in its entirety. For example, a yeast strain comprising a recombinant gene encoding a *Synechococcus* sp. GGPPS polypeptide (SEQ ID NO:1, SEQ ID NO:149), a recombinant gene encoding a truncated *Zea mays* CDPS polypeptide (SEQ ID NO:2, SEQ ID NO:150), a recombinant gene encoding an *A. thaliana* KS polypeptide (SEQ ID NO:3, SEQ ID NO:151), a recombinant gene encoding a recombinant *S. rebaudiana* KO1 polypeptide (SEQ ID NO:4, SEQ ID NO:152), a recombinant gene encoding an *A. thaliana* ATR2 polypeptide (SEQ ID NO:5, SEQ ID NO:153), a recombinant gene encoding an *O. sativa* EUGT11 polypeptide (SEQ ID NO:12; SEQ ID NO:148), a recombinant gene encoding an SrKAHe1 polypeptide (SEQ ID NO:6, SEQ ID NO:154), a recombinant gene encoding an *S. rebaudiana* CPR8 polypeptide (SEQ ID NO:7, SEQ ID NO:155), a recombinant gene encoding an *S. rebaudiana* UGT85C2 polypeptide (SEQ ID NO:8, SEQ ID NO:156), a recombinant gene encoding an *S. rebaudiana* UGT74G1 polypeptide (SEQ ID NO:9, SEQ ID NO:157), a recombinant gene encoding an *S. rebaudiana* UGT76G1 polypeptide (SEQ ID NO:10, SEQ ID NO:158), and a recombinant gene encoding an *S. rebaudiana* UGT91D2 variant (or functional homolog), UGT91D2e-b (SEQ ID NO:11, SEQ ID NO:159) polypeptide produced steviol glycosides. As analyzed by LC-MS (Method C) following DMSO-extraction of total steviol glycosides from the whole cell and broth mixture (total production), the strain produced between 18-21 µg/mL or 1-1.5 µg/mL/OD$_{600}$ RebM after growth for five days in 1 mL SC (Synthetic Complete) media at 30° C. with 400 rpm shaking in deep-well plates. See Table 3.

TABLE 3

Steviol glycoside production in a representative *S. cerevisiae* strain comprising genes encoding GGPPS, truncated CDPS, KS, KO, ATR2, EUGT11, SrKAHe1, CPR8, UGT85C2, UGT74G1, UGT76G1, and EUGT11 polypeptides.

| RebB (µg/mL/ OD$_{600}$) | RebA (µg/mL/ OD$_{600}$) | RebD (µg/mL/ OD$_{600}$) | RebM (µg/mL/ OD$_{600}$) | Normalized by OD$_{600}$ |
|---|---|---|---|---|
| 0.21 | 0.33 | 0.33 | 1.3 | Average |
| 0.028 | 0.054 | 0.032 | 0.14 | Std Deviation |

| RebB (µg/mL) | RebA (µg/mL) | RebD (µg/mL) | RebM (µg/mL) | |
|---|---|---|---|---|
| 3.1 | 4.9 | 5.0 | 19.0 | Average |
| 0.42 | 0.81 | 0.48 | 2.1 | Std Deviation |

A second strain, which comprised additional copies of the genes of the first strain, was analyzed for steviol glycoside production. The second strain produced RebD and RebM as primary steviol glycosides, although at higher levels than the first strain.

As analyzed by LC-MS (Method C) following DMSO-extraction of total steviol glycosides from the whole cell and broth mixture (total production), the second strain produced between 60-80 µg/mL or 4-6 µg/mL/OD$_{600}$ RebM, after growth for five days in 1 mL SC media at 30° C. with 400 rpm shaking in deep-well plates. Production of RebA, RebB, RebD and RebM by the second strain is shown in Table 4.

TABLE 4

Steviol glycoside production in an *S. cerevisiae* strain comprising additional copies of genes encoding GGPPS, truncated CDPS, KS, KO, ATR2, EUGT11, SrKAHe1, CPR8, UGT85C2, UGT74G1, UGT76G1, and EUGT11 polypeptides.

| RebA (µg/mL/ OD$_{600}$) | RebB (µg/mL/ OD$_{600}$) | RebD (µg/mL/ OD$_{600}$) | RebM (µg/mL/ OD$_{600}$) | Normalized by OD$_{600}$ |
|---|---|---|---|---|
| 2.1 | 0.67 | 1.6 | 4.8 | Average |
| 0.66 | 0.21 | 0.75 | 2.3 | Std Deviation |

| RebA (µg/mL) | RebB (µg/mL) | RebD (µg/mL) | RebM (µg/mL) | |
|---|---|---|---|---|
| 31.0 | 10.1 | 23.7 | 72.5 | Average |
| 9.9 | 3.1 | 11.3 | 34.4 | Std Deviation |

Example 3. Knockout of Yeast Endogenous Transport Genes and Transport-Related Genes Observations from deep-well studies of Example 2 and similar strains indicated that the fraction of RebA, RebB, RebD or RebM in the supernatant changes with time, and the effect was determined not to be the result of cell lysis. To determine the effect of various transporters on steviol glycoside excretion in *S. cerevisiae*, deletion cassettes for homologous recombination were obtained by designing primers annealing approximately 200 bp upstream and downstream of the open reading frame (ORF) and then amplifying the ORF-specific deletion cassette from the *S. cerevisiae* deletion collection. The candidate genes selected include identified ORFs with relation to transport or comprising membrane spanning domains, regardless of subcellular localization. In the resulting colonies, the presence of the deletion cassette at the correct locus was verified by colony PCR. A maximum of 6 clones of each deletion was frozen down as freezer stock. All samples for analysis were initiated from the freezer stock and grown in SC medium for 5 days (30° C., shaking 400 rpm) prior to harvest and extraction of samples for LC-MS. Samples were analyzed for the presence of RebA, RebB, RebD and RebM in the culture broth lacking cells (Supernatant) as well as in the whole cell and broth mixture (Total production).

Concentrations of total and supernatant RebA, RebB, RebD and RebM were compared to the levels in a control steviol glycoside-producing strain. The amounts of RebA, RebB, RebD and RebM in each sample were normalized to the control strain by dividing the value of a particular steviol glycoside with the corresponding value for the control strain, thereby calculating a percentage to the control strain, where 1 equals 100 percent. The "ideal candidate" would exhibit a decrease in RebA, RebB, RebD and/or RebM levels in the supernatant, as compared to the control steviol glycoside-producing strain, without decreasing RebA, RebB, RebD, and/or RebM total production.

The effect of yeast gene knockouts on transport of higher molecular weight steviol glycosides into the culture medium was tested in a strain that produces steviol glycosides, such as the strains described in Example 2. Disruption of each specific transporter gene was performed by homologous recombination. After 5 days of growth in 1 mL SC medium at 30° C. and 400 rpm, cells were harvested. A 50 µL aliquot of the culture was mixed with an equal volume of 100% DMSO, vortexed, and heated to 80'C for 10 min. The suspension was then centrifuged to remove cell debris. 60 µL of the mixture were analyzed by LC-MS as the "Total" sample. The remaining culture was then centrifuged to pellet cells. An aliquot of 50 µL was removed from the supernatant (i.e., the culture medium) and mixed with an equal volume of 100% DMSO. The suspension was heated to 80'C for 10 min and centrifuged. 60 µL of the mixture were analysed by LC-MS as the "Supernatant" sample. The amounts of higher molecular weight steviol glycosides (including RebA, RebB, RebD, RebM) were measured by LC-MS (Method C), as described in Example 1.

The data demonstrate that disruption of a single endogenous yeast transporter gene in a steviol glycoside-producing strain resulted in a decrease in the level of various steviol glycosides in the supernatant of the culture media, as evaluated by the normalized amount transported into the supernatant (see Tables 5-10). Tables 5-10 comprise lists of transport related genes that were knocked out in a steviol glycoside-producing strain. More specifically, Table 5 comprises a compiled list of genes by ordered locus name found to affect steviol glycoside excretion in steviol glycoside-producing strains and are therefore identified as having a role in steviol glycoside excretion. When the specified genes were knocked out, a more than 40% decrease in either the supernatant alone or in the ratio of supernatant/total production of RebA, RebB, RebD, and/or RebM was observed. This corresponded approximately to more than 2 standard deviations removed from the mean of a control steviol glycoside-producing strain (a value of 1 equals 100 percent of the control strain, whereas a value of 0.5 Indicates a 50% decrease).

Table 6 comprises a compiled list of genes by ordered locus name found to affect steviol glycoside excretion in steviol glycoside-producing strains and are therefore identified as having a role in steviol glycoside excretion. When knocked out, these genes caused a mean of between 20-40% decrease in either the supernatant alone or in the ratio of supernatant/total production. This corresponded to approximately between 1 and 2 standard deviations removed from the mean of the control strain (a value of 1 equals 100 percent of the control strain, whereas a value of 0.5 indicates a 50% decrease).

TABLE 5A

Transport related genes with over a 40% decrease in Reb A, RebB, RebD or RebM levels compared to a control steviol glycoside-producing strain.

| SEQ ID No. | Ordered Locus Name | Family | Description | Gene name | Uniprot Accession No. |
|---|---|---|---|---|---|
| 13 | YBR180W | MFS | Secondary Transporter | DTR1 | P38125 |
| 14 | YAL067C | MFS | Secondary Transporter | SEO1 | P39709 |
| 15 | YBL089W | AAAP | Secondary Transporter | AVT5 | P38176 |
| 16 | YBL099W | F-ATPase | ATP-Dependent | ATP1 | P07251 |
| 17 | YBR241C | MFS | Secondary Transporter | | P38142 |
| 18 | YBR294W | SulP | Secondary Transporter | SUL1 | P38359 |
| 19 | YCL069W | MFS | Secondary Transporter | VBA3 | P25594 |
| 20 | YCR028C | MFS | Secondary Transporter | FEN2 | P25621 |
| 21 | YCR075C | LCT | Secondary Transporter | ERS1 | P17261 |
| 22 | YDL128W | CaCA | Secondary Transporter | VCX1 | Q99385 |
| 23 | YDL185W | F-ATPase | ATP-Dependent | VMA1 | P17255 |
| 24 | YDL194W | MFS | Secondary Transporter | SNF3 | P10870 |
| 25 | YDL210W | APC | Secondary Transporter | UGA4 | P32837 |
| 26 | YDR061W | ABC | ATP-Dependent | | Q12298 |
| 27 | YDR093W | P-ATPase | ATP-Dependent | DNF2 | Q12675 |
| 28 | YDR338C | MOP/MATE | Secondary Transporter | | Q05497 |
| 29 | YDR406W | ABC | ATP-Dependent | PDR15 | Q04182 |
| 30 | YDR536W | MFS | Secondary Transporter | STL1 | P39932 |
| 31 | YEL031W | P-ATPas | ATP-Dependent | SPF1 | P39986 |
| 32 | YER166W | P-ATPase | ATP-Dependent | DNF1 | P32660 |
| 33 | YFL011W | MFS | Secondary Transporter | HXT10 | P43581 |
| 34 | YGL006W | P-ATPase | ATP-Dependent | PMC1 | P38929 |
| 35 | YGL013C | | Transcription factor | PDR1 | P12383 |
| 36 | YGL255W | ZIP | Secondary Transporter | ZRT1 | P32804 |
| 37 | YGR125W | SulP | Secondary Transporter | | P53273 |
| 38 | YGR181W | MPT | ATP-Dependent | TIM13 | P53299 |
| 39 | YGR217W | VIC | Ion Channels | CCH1 | P50077 |
| 40 | YGR224W | MFS | Secondary Transporter | AZR1 | P50080 |

TABLE 5A-continued

Transport related genes with over a 40% decrease in Reb A, RebB, RebD or RebM levels compared to a control steviol glycoside-producing strain.

| SEQ ID No. | Ordered Locus Name | Family | Description | Gene name | Uniprot Accession No. |
|---|---|---|---|---|---|
| 41 | YGR281W | ABC | ATP-Dependent | YOR1 | P53049 |
| 42 | YHL016C | SSS | Secondary Transporter | DUR3 | P33413 |
| 43 | YIL088C | AAAP | Secondary Transporter | AVT7 | P40501 |
| 44 | YJL093C | VIC | Ion Channels | TOK1 | P40310 |
| 45 | YJL094C | CPA2 | Secondary Transporter | KHA1 | P40309 |
| 46 | YJL108C | ThrE | Secondary Transporter | PRM10 | P42946 |
| 47 | YJL212C | OPT | Secondary Transporter | OPT1 | P40897 |
| 48 | YJR106W | CaCA | Secondary Transporter | ECM27 | P47144 |

TABLE 5B

Continued list of Transport related genes with over a 40% decrease in Reb A, RebB, RebD or RebM levels compared to a control steviol glycoside-producing strain.

| No. | Ordered Locus Name | Family | Description | Gene name | Uniprot Accession No. |
|---|---|---|---|---|---|
| 49 | YJR160C | MFS | Secondary Transporter | MPH3 | P0CE00 |
| 50 | YKL064W | MIT | Ion Channels | MNR2 | P35724 |
| 51 | YKR050W | Trk | Secondary Transporter | TRK2 | P28584 |
| 52 | YKR105C | MFS | Secondary Transporter | VBA5 | P36172 |
| 53 | YKR106W | MFS | Secondary Transporter | GEX2 | P36173 |
| 54 | YLR447C | F-ATPase | ATP-Dependent | VMA6 | P32366 |
| 55 | YML116W | MFS | Secondary Transporter | SNQ1/ATR1 | P13090 |
| 56 | YMR034C | BASS | Secondary Transporter | | Q05131 |
| 57 | YMR056C | MC | Secondary Transporter | AAC1 | P04710 |
| 58 | YMR253C | DMT | Secondary Transporter | | Q04835 |
| 59 | YNL065W | MFS | Secondary Transporter | AQR1 | P53943 |
| 60 | YNL070W | MPT | ATP-Dependent | TOM7 | P53507 |
| 61 | YNL083W | MC | Secondary Transporter | SAL1 | D6W196 |
| 62 | YNL095C | AEC | Secondary Transporter | | P53932 |
| 63 | YNL121C | MPT | ATP-Dependent | TOM70 | P07213 |
| 64 | YNL142W | Amt | Ion Channels | MEP2 | P41948 |
| 65 | YOL020W | APC | Secondary Transporter | TAT2 | P38967 |
| 66 | YOL075C | ABC | ATP-Dependent | | Q08234 |
| 67 | YOL077W-A | F-ATPase | ATP-Dependent | ATP19 | P81451 |
| 68 | YOL122C | Nramp | Secondary Transporter | SMF1 | P38925 |
| 69 | YOR079C | ZIP | Secondary Transporter | ATX2 | Q12067 |
| 70 | YOR087W | TRP-CC | Ion Channels | YVC1 | Q12324 |
| 71 | YOR092W | AEC | Secondary Transporter | ECM3 | Q99252 |
| 72 | YOR130C | MC | Secondary Transporter | ORT1 | Q12375 |
| 73 | YOR222W | MC | Secondary Transporter | ODC2 | Q99297 |
| 74 | YOR291W | P-ATPase | ATP-Dependent | YPK9 | Q12697 |
| 75 | YOR306C | MFS | Secondary Transporter | MCH5 | Q08777 |
| 76 | YOR316C | CDF | Secondary Transporter | COT1 | P32798 |
| 77 | YOR334W | MIT | Ion Channels | MRS2 | Q01926 |
| 78 | YPL078C | F-ATPase | ATP-Dependent | ATP4 | P05626 |
| 79 | YPL270W | ABC | ATP-Dependent | MDL2 | P33311 |
| 80 | YPL274W | APC | Secondary Transporter | SAM3 | Q08986 |
| 81 | YPR003C | SulP | Secondary Transporter | | P53394 |
| 82 | YPR011C | MC | Secondary Transporter | | Q12251 |
| 83 | YPR058W | MC | Secondary Transporter | YMC1 | P32331 |
| 84 | YPR128C | MC | Secondary Transporter | ANT1 | Q06497 |
| 85 | YPR201W | ACR3 | Secondary Transporter | ARR3 | Q06598 |

TABLE 6A

Transport related genes with a 20-40% decrease in Reb A, RebB, RebD or RebM levels compared to a control steviol glycoside-producing strain.

| SEQ ID No. | Ordered Locus Name | Family | Description | Gene name | Uniprot Accession No. |
|---|---|---|---|---|---|
| 86 | YBR008C | MFS | Secondary Transporter | FLR1 | P38124 |
| 87 | YBR021W | NCS1 | Secondary Transporter | FUR4 | P05316 |
| 88 | YBR043C | MFS | Secondary Transporter | QDR3 | P38227 |
| 89 | YBR287W | AEC | Secondary Transporter | | P38355 |
| 90 | YBR295W | P-ATPase | ATP-Dependent | PCA1 | P38360 |
| 91 | YBR296C | PiT | Secondary Transporter | PHO89 | P38361 |
| 92 | YCL038C | MFS | Secondary Transporter | ATG22 | P25568 |
| 93 | YCR011C | ABC | ATP-Dependent | ADP1 | P25371 |
| 94 | YDL054C | MFS | Secondary Transporter | MCH1 | Q07376 |
| 95 | YDL100C | ArsAB | ATP-Dependent | GET3 | Q12154 |
| 96 | YDL245C | MFS | Secondary Transporter | HXT15 | P54854 |
| 97 | YDL247W | MFS | Secondary Transporter | MPH2 | P0CD99 |
| 98 | YDR011W | ABC | ATP-Dependent | SNQ2 | P32568 |
| 99 | YDR292C | IISP | ATP-Dependent | SRP101 | P32916 |
| 100 | YDR497C | MFS | Secondary Transporter | ITR1 | P30605 |
| 101 | YEL006W | MC | Secondary Transporter | YEA6 | P39953 |
| 102 | YEL027W | F-ATPase | ATP-Dependent | VMA3 | P25515 |
| 103 | YEL065W | MFS | Secondary Transporter | SIT1 | P39980 |
| 104 | YER019C-A | IISP | ATP-Dependent | SBH2 | P52871 |
| 105 | YER053C | MC | Secondary Transporter | PIC2 | P40035 |
| 106 | YER119C | AAAP | Secondary Transporter | AVT6 | P40074 |
| 107 | YFL028C | ABC | ATP-Dependent | CAF16 | P43569 |
| 108 | YFR045W | MC | Secondary Transporter | | P43617 |
| 109 | YGL084C | GUP | Secondary Transporter | GUP1 | P53154 |
| 110 | YGL104C | MFS | Secondary Transporter | VPS73 | P53142 |
| 111 | YGL114W | OPT | Secondary Transporter | | P53134 |
| 112 | YGL167C | P-ATPase | ATP-Dependent | PMR1 | P13586 |
| 113 | YGR257C | MC | Secondary Transporter | MTM1 | P53320 |
| 114 | YHL035C | ABC | ATP-Dependent | VMR1 | P38735 |
| 115 | YHL036W | APC | Secondary Transporter | MUP3 | P38734 |

TABLE 6B

Continued list of Transport related genes with a 20-40% decrease in Reb A, RebB, RebD or RebM levels compared to a control steviol glycoside-producing strain.

| No. | Ordered Locus Name | Family | Description | Gene name | Accession No. |
|---|---|---|---|---|---|
| 116 | YHR002W | MC | Secondary Transporter | LEU5 | P38702 |
| 117 | YHR096C | MFS | Secondary Transporter | HXT5 | P38695 |
| 118 | YIL006W | MC | Secondary Transporter | YIA6 | P40556 |
| 119 | YIL120W | MFS | Secondary Transporter | QDR1 | P40475 |
| 120 | YIL121W | MFS | Secondary Transporter | QDR2 | P40474 |
| 121 | YIL166C | MFS | Secondary Transporter | SOA1 | P40445 |
| 122 | YJL133W | MC | Secondary Transporter | MRS3 | P10566 |
| 123 | YJL219W | MFS | Secondary Transporter | HXT9 | P40885 |
| 124 | YKL016C | F-ATPase | ATP-Dependent | ATP7 | P30902 |
| 125 | YKL050C | MIT | Ion Channels | | P35736 |
| 126 | YKL120W | MC | Secondary Transporter | OAC1 | P32332 |
| 127 | YKL146W | AAAP | Secondary Transporter | AVT3 | P36062 |
| 128 | YKL209C | ABC | ATP-Dependent | STE6 | P12866 |
| 129 | YKR039W | APC | Secondary Transporter | GAP1 | P19145 |
| 130 | YLR411W | Ctr | Ion Channels | CTR3 | Q06686 |
| 131 | YML038C | DMT | Secondary Transporter | YMD8 | Q03697 |
| 132 | YMR166C | MC | Secondary Transporter | | Q03829 |
| 133 | YMR279C | MFS | Secondary Transporter | | Q03263 |
| 134 | YNL003C | MC | Secondary Transporter | PET8 | P38921 |
| 135 | YNL268W | APC | Secondary Transporter | LYP1 | P32487 |
| 136 | YNR055C | MFS | Secondary Transporter | HOL1 | P53389 |
| 137 | YOL158C | MFS | Secondary Transporter | ENB1 | Q08299 |
| 138 | YOR100C | MC | Secondary Transporter | CRC1 | Q12289 |
| 139 | YOR153W | ABC | ATP-Dependent | PDR5 | P33302 |
| 140 | YOR271C | MTC | Secondary Transporter | FSF1 | Q12029 |
| 141 | YOR273C | MFS | Secondary Transporter | TPO4 | Q12256 |

TABLE 6B-continued

Continued list of Transport related genes with a 20-40% decrease in Reb A, RebB, RebD or RebM levels compared to a control steviol glycoside-producing strain.

| No. | Ordered Locus Name | Family | Description | Gene name | Accession No. |
|---|---|---|---|---|---|
| 142 | YOR307C | DMT | Secondary Transporter | SLY41 | P22215 |
| 143 | YOR332W | F-ATPase | ATP-Dependent | VMA4 | P22203 |
| 144 | YOR348C | APC | Secondary Transporter | PUT4 | P15380 |
| 145 | YPL036W | P-ATPase | ATP-Dependent | PMA2 | P19657 |

Steviol glycoside exporter candidates were selected from the data based on two selection criteria for each steviol glycoside measured (i.e., two methods of normalizing expression).

Transporter selection criterion 1 corresponded to selection based on the level of high molecular weight steviol glycosides (RebA, RebB, RebD, or RebM) available in the supernatant, as well as the total production of the said steviol glycoside. Both values were normalized to the value of the corresponding steviol glycoside-producing control strain. The control level was set to 1, and the corresponding steviol glycoside level was calculated as a percentage of the control. For Ordered Locus Names (i.e., genes) of interest, the steviol glycoside available in the supernatant should be below 0.6 (below 60% of the control) or between 0.8-0.6 (80-60% of the control). To avoid false positives or a bias towards transporters that decrease the production in general, the calculation had an additional requirement that the total production had to be similar to the control. In the current calculation, production was set to be between 0.85 and 1.15 of the control, when the control is set to 1. In this regard, steviol glycoside production levels did not affect results. Table 7 shows the supernatant/total ratio for each candidate that fulfills the selection criteria.

Transporter selection criterion 2 corresponded to selection based on the ratio of high molecular weight steviol glycosides (RebA, RebB, RebD, or RebM) in the supernatant relative to total production of the said steviol glycoside. The supernatant-to-total production ratio was normalized to the ratio of the corresponding steviol glycoside-producing strain control. The control level was set to 1, and the corresponding steviol glycoside ratio was calculated as a percentage of the control. For Ordered Locus Names (i.e., genes) of interest, the supernatant-to-total production ratio for a given steviol glycoside should be below 0.6 (below 60% of the control) or between 0.8-0.6 (80-60% of the control). To avoid false positives or a bias towards transporters that decrease the production in general, the calculation had an additional requirement that the total production had to be similar to the control. In the current calculation, production was set to be between 0.85 and 1.15 of the control, when the control is set to 1. In this regard, steviol glycoside production levels did not affect results. Table 8 shows the supernatant/total ratio for each candidate that fulfills the selection criteria.

The data demonstrate that disruption of a single endogenous yeast transporter gene in a steviol glycoside-producing strain resulted in a decrease in the level of various steviol glycosides in the supernatant of the culture media, as evaluated by the normalized amount transported into the supernatant (see Tables 5-10), and are therefore identified as having a role in steviol glycoside excretion.

For example, deletion in a steviol glycoside-producing strain of YDL128W (SEQ ID NO:22), YDL194W (SEQ ID NO:24), YDL210W (SEQ ID NO:25), YFL011W (SEQ ID NO:33), YGL006W (SEQ ID NO:34), YGL013C (SEQ ID NO:35), YGL255W (SEQ ID NO:36), YGR181W (SEQ ID NO:38), YGR217W (SEQ ID NO:39), YIL088C (SEQ ID NO:43), YJL094C (SEQ ID NO:45), YJR106W (SEQ ID NO:48), YNL065W (SEQ ID NO:59), YNL083W (SEQ ID NO:61), YNL121C (SEQ ID NO:63), YNL142W (SEQ ID NO:64), YOR306C (SEQ ID NO:75), or YPR011C (SEQ ID NO:82) led to a measurable decrease of RebD excreted into the culture medium, indicating that each plays a role in RebD excretion. This was confirmed by transporter selection criteria 1 and 2 (see Tables 7 and 8, RebD column).

Furthermore, for example, deletion in a steviol glycoside-producing strain of YBR180W (SEQ ID NO:13), YBR241C (SEQ ID NO:17), YCL069W (SEQ ID NO:19), YCR075C (SEQ ID NO:21), YDL128W (SEQ ID NO:22), YDL194W (SEQ ID NO:24), YDR093W (SEQ ID NO:27), YDR338C (SEQ ID NO:28), YER166W (SEQ ID NO:32), YFL011W (SEQ ID NO:33), YGL006W (SEQ ID NO:34), YGL013C (SEQ ID NO:35), YGL255W (SEQ ID NO:36), YGR217W (SEQ ID NO:39), YJL094C (SEQ ID NO:45), YJR106W (SEQ ID NO:48), YJR160C (SEQ ID NO:49), YKR106W (SEQ ID NO:53), YML116W (SEQ ID NO:55), YMR056C (SEQ ID NO:57), YNL070W (SEQ ID NO:60), YNL083W (SEQ ID NO:61), YNL095C (SEQ ID NO:62), YNL121C (SEQ ID NO:63), YOR087W (SEQ ID NO:70), YOR291W (SEQ ID NO:74), YOR306C (SEQ ID NO:75), YPL274W (SEQ ID NO:80), or YPR011C (SEQ ID NO:82) led to a measurable decrease of RebM, indicating that each plays a role in RebM excretion. This was confirmed by transporter selection criteria 1 and 2 (see Tables 7 and 8, RebM column).

Table 7 represents the calculated ratio, normalized to a steviol glycoside-producing strain comprising genes encoding GGPPS, truncated CDPS, KS, KO, ATR2, EUGT11, SrKAHe1, CPR8, UGT85C2, UGT74G1, UGT76G1, and EUGT11 polypeptides, of supernatant/total production for each gene (by ordered locus name) deleted in the steviol glycoside-producing strain. The supernatant or supernatant/total ratio of less than 0.6 represented a more than 40% decrease in either the supernatant alone or In the ratio of supernatant/total production of RebA, RebB, RebD, or RebM, which corresponded approximately to more than 2 standard deviations removed from the mean of the control steviol glycoside-producing strain and indicates the gene as having a role in steviol glycoside transportation (Table 7). The supernatant or ratio supernatant/total of between 0.6 and 0.8 represents a 40-20% decrease in either the supernatant alone or in the ratio of supernatant/total production of RebA, RebB, RebD, or RebM, which corresponds to approximately between 1 and 2 standard deviations removed from the mean of the control steviol glycoside-producing strain, and indicates the gene as having a role in steviol glycoside transportation and/or production (Table 8). Total production of each steviol glycoside was between 0.85 and 1.15 compared to the steviol glycoside-producing strain. Table 8 shows the supernatant/total ratio for each candidate that fulfills the selection criteria.

TABLE 7

Transport related genes with over a 40% decrease in RebA, RebB, RebD or RebM compared to a control steviol glycoside-producing strain comprising genes encoding GGPPS, truncated CDPS, KS, KO, ATR2, EUGT11, SrKAHe1, CPR8, UGT85C2, UGT74G1, UGT76G1, and EUGT11 polypeptides.

| | Transporter selection criterion 1 Total vs. Supernatant | | | | Transporter selection criterion 2 Ratio Sup/Total vs. Total | | | |
|---|---|---|---|---|---|---|---|---|
| | RebA | RebB | RebD | RebM | RebA | RebB | RebD | RebM |
| YBR180W | | | | 0.486 | | | | 0.486 |
| YBR241C | | | | 0.529 | | | | 0.529 |
| YCL069W | | | | 0.519 | | | | 0.519 |
| YCR075C | | | | 0.448 | | | | 0.448 |
| YDL128W | | | 0.459 | 0.405 | | | 0.459 | 0.405 |
| YDL194W | | | 0.652 | 0.482 | | | | 0.482 |
| YDL210W | | | 0.000 | | | | 0.000 | |
| YDR093W | | | | 0.569 | | | | 0.569 |
| YDR338C | | | | 0.451 | | | | 0.451 |
| YEL031W | | 0.488 | | | | 0.488 | | |
| YER166W | | | | 0.495 | | | | 0.495 |
| YFL011W | | | 0.581 | 0.547 | | | 0.581 | 0.547 |
| YGL006W | | | | | | | 0.410 | 0.424 |
| YGL013C | | | 0.673 | 0.507 | | | | 0.507 |
| YGL255W | | | 0.669 | 0.632 | | | | |
| YGR181W | | | 0.419 | | | | 0.419 | |
| YGR217W | | | 0.598 | 0.429 | | | 0.598 | 0.429 |
| YIL088C | | | 0.135 | | | | 0.135 | |
| YJL094C | | | 0.568 | 0.525 | | | 0.568 | 0.525 |
| YJR106W | | | 0.470 | 0.432 | | | 0.470 | 0.432 |
| YJR160C | | | | 0.689 | | | | |
| YKL064W | | 0.337 | | | | 0.337 | | |
| YKR106W | | | | 0.509 | | | | 0.509 |
| YML116W | | | | 0.706 | | | | |
| YMR056C | | | | | | | | 0.591 |
| YNL065W | | | | | | | 0.571 | |
| YNL070W | | | 0.633 | | | | | |
| YNL083W | | | | 0.481 | | | 0.592 | 0.481 |
| YNL095C | | | | 0.610 | | | | |
| YNL121C | | | 0.620 | 0.456 | | | | 0.456 |
| YNL142W | 0.561 | | 0.369 | | 0.561 | | 0.369 | |
| YOR087W | | | | 0.611 | | | | |
| YOR291W | | | | 0.681 | | | | |
| YOR306C | | | 0.596 | 0.559 | | | 0.596 | 0.559 |
| YOR334W | | 0.520 | | | | 0.520 | | |
| YPL078C | | 0.590 | | | | 0.590 | | |
| YPL270W | | 0.665 | | | | | | |
| YPL274W | | | | 0.561 | | | | 0.561 |
| YPR011C | | | 0.542 | 0.611 | | | 0.542 | |

TABLE 8

Transport related genes with a 20-40% decrease in Reb A, RebB, RebD or RebM compared to a control steviol glycoside-producing strain comprising genes encoding GGPPS, truncated CDPS, KS, KO, ATR2, EUGT11, SrKAHe1, CPR8, UGT85C2, UGT74G1, UGT76G1, and EUGT11 polypeptides.

| | Transports cal 1; total vs sup | | | | Transports cal 2; ratio sup/ total vs total | | | |
|---|---|---|---|---|---|---|---|---|
| | RebA | RebB | RebD | RebM | RebA | RebB | RebD | RebM |
| YBL089W | | | | 0.739 | | | | 0.739 |
| YBR008C | 0.784 | | | 0.640 | 0.784 | | | 0.640 |
| YBR021W | | 0.731 | | | | 0.731 | | |
| YBR043C | 0.755 | | | 0.796 | 0.755 | | | 0.796 |
| YBR180W | 0.747 | | | | 0.747 | | | |
| YBR241C | | | 0.688 | | 0.798 | | 0.688 | |
| YBR287W | 0.781 | 0.823 | 0.768 | | 0.781 | | 0.768 | |
| YBR295W | | | 0.885 | 0.876 | | | | |
| YBR296C | | 0.724 | 0.799 | 0.790 | | 0.724 | 0.799 | 0.790 |
| YCL038C | | 0.709 | | 0.752 | | 0.709 | | 0.752 |
| YCL069W | | | 0.785 | | | | 0.785 | |
| YCR075C | | | 0.634 | | | | 0.634 | |
| YDL054C | | | 0.920 | | | | | |
| YDL100C | | | 0.867 | | | | | |

TABLE 8-continued

Transport related genes with a 20-40% decrease in Reb A, RebB, RebD or RebM compared to a control steviol glycoside-producing strain comprising genes encoding GGPPS, truncated CDPS, KS, KO, ATR2, EUGT11, SrKAHe1, CPR8, UGT85C2, UGT74G1, UGT76G1, and EUGT11 polypeptides.

| | Transports cal 1; total vs sup | | | | Transports cal 2; ratio sup/ total vs total | | | |
|---|---|---|---|---|---|---|---|---|
| | RebA | RebB | RebD | RebM | RebA | RebB | RebD | RebM |
| YDL194W | | | | | | | 0.652 | |
| YDL210W | | | | 0.834 | | | | |
| YDL245C | 0.852 | | | | | | | |
| YDL247W | | | | 0.682 | | | | 0.682 |
| YDR011W | | | 0.852 | | | | | |
| YDR093W | 0.792 | 0.775 | 0.704 | | 0.792 | 0.775 | 0.704 | |
| YDR338C | 0.711 | 0.695 | 0.680 | | 0.711 | 0.695 | 0.680 | |
| YDR497C | | | | 0.694 | | | | 0.694 |
| YEL006W | | | | 0.657 | | | 0.774 | 0.657 |
| YEL065W | | | 0.635 | | | | 0.635 | |
| YER119C | | | | 0.872 | | | | |
| YER166W | 0.771 | 0.843 | 0.687 | | 0.771 | | 0.687 | |
| YFL011W | | 0.787 | | | | 0.787 | | |
| YFL028C | | | 0.641 | | | | 0.641 | |
| YFR045W | | | 0.779 | | | | 0.779 | |
| YGL006W | | | 0.410 | 0.424 | | | | |
| YGL013C | | | | | | | 0.673 | |
| YGL084C | 0.804 | | | | | | | |
| YGL104C | 0.628 | 0.731 | | 0.683 | 0.628 | 0.731 | | 0.683 |
| YGL114W | | | | | | 0.796 | | |
| YGL167C | 0.829 | | | | | | | |
| YGL255W | | | | | | | 0.669 | 0.632 |
| YGR217W | | 0.801 | | | | | | |
| YGR257C | 0.842 | | | | | | | |
| YHL035C | | | 0.900 | 0.792 | | | | 0.792 |
| YHL036W | | | | 0.798 | | | | 0.798 |
| YHR096C | | | 0.879 | 0.798 | | | | 0.798 |
| YIL006W | 0.763 | | | 0.689 | 0.763 | | 0.791 | 0.689 |
| YIL120W | | | | 0.814 | | | | |
| YIL121W | | | 0.903 | | | | | |
| YIL166C | | | 0.844 | | | | | |
| YJL212C | | | 0.817 | 0.682 | | | | 0.682 |
| YJR106W | 0.719 | | | | 0.719 | | | |
| YJR160C | | 0.781 | 0.985 | | | 0.781 | | 0.689 |
| YKL050C | | | | 0.896 | | | | |
| YKL120W | | | | 0.706 | | | | 0.706 |
| YKL146W | | 0.890 | | | | | | |
| YKR039W | 0.763 | | | | 0.763 | | | |
| YKR106W | | 0.785 | 0.738 | | | 0.785 | 0.738 | |
| YLR411W | 0.852 | | 0.782 | | | | 0.782 | |
| YML038C | | | 0.724 | | | | 0.724 | |
| YML116W | | | 0.898 | | | | | 0.706 |
| YMR056C | | | 0.675 | 0.591 | | 0.786 | 0.675 | |
| YMR279C | | | | 0.885 | | | | |
| YNL065W | 0.710 | 0.792 | 0.571 | | 0.710 | 0.792 | | |
| YNL070W | 0.893 | | 0.892 | | | | | 0.633 |
| YNL083W | | | 0.592 | | | | | |
| YNL095C | | | 0.726 | | | | 0.726 | 0.610 |
| YNL121C | | | | | | | 0.620 | |
| YNL268W | | 0.920 | | | | | | |
| YNR055C | | | 0.643 | | | | 0.643 | |
| YOL122C | | | | 0.935 | | | | |
| YOL158C | | | 0.848 | 0.728 | | | | 0.728 |
| YOR087W | | | | | | | | 0.611 |
| YOR100C | | 0.916 | | | | | | |
| YOR271C | | 0.889 | 0.758 | 0.608 | | | 0.758 | 0.608 |
| YOR273C | 0.726 | 0.916 | 0.635 | | 0.726 | | 0.635 | |
| YOR291W | | | | | | | | 0.681 |
| YOR307C | | | | | | | | 0.765 |
| YOR348C | | | | 0.644 | | | | 0.644 |
| YPL036W | 0.763 | | 0.698 | | 0.763 | | 0.698 | |
| YPL078C | | | 0.798 | | | | 0.798 | |
| YPL270W | | | 0.746 | | | 0.665 | 0.746 | |
| YPL274W | 0.817 | 0.807 | 0.721 | | | | 0.721 | |
| YPR011C | 0.763 | | | | 0.763 | | | 0.611 |

The effect of yeast gene knockouts on transport of higher molecular weight steviol glycosides into the culture medium (i.e., supernatant) also was tested in a steviol glycoside-producing strain comprising additional copies of genes encoding GGPPS, truncated CDPS, KS, KO, ATR2, EUGT11, SrKAHe1, CPR8, UGT85C2, UGT74G1, UGT76G1, and EUGT11 polypeptides, which was described in Example 2. The data demonstrated that disruption of a single endogenous yeast transporter gene in the steviol glycoside-producing strain resulted in a decrease in the level of various steviol glycosides in the supernatant of the culture media, as evaluated by the normalized amount transported or by the supernatant-to-total-production ratio (see Tables 9 and 10, RebD column). For example, deletion in the steviol glycoside-producing strain of YDR536W (SEQ ID NO:30), YHL016C (SEQ ID NO:42), YKR05W (SEQ ID NO:51), YOR291W (SEQ ID NO:74), YOR334W (SEQ ID NO:77), YPL270W (SEQ ID NO:79), YPR058W (SEQ ID NO:83), or YPR128C (SEQ ID NO:84) led to a measurable decrease of RebD transported into the supernatant, indicating that they play a role in RebD excretion. This was confirmed by transporter selection criteria 1 and 2 (see Tables 9 and 10, RebD column).

Furthermore, for example, deletion of YAL067C (SEQ ID NO:14), YDR406W (SEQ ID NO:29), YHL016C (SEQ ID NO:42), YJL212C (SEQ ID NO:47), YKR050W (SEQ ID NO:51), YMR034C (SEQ ID NO:56), YMR253C (SEQ ID NO:58), YOL075C (SEQ ID NO:66), YOL122C (SEQ ID NO:68), YOR222W (SEQ ID NO:73), YPR003C (SEQ ID NO:81), or YPR201W (SEQ ID NO:85) led to a measurable decrease of RebM transported into the supernatant, indicating that they play a role in RebM excretion. This was confirmed by transporter selection criteria 1 and 2 (see Tables 9 and 10, RebM column).

Table 9 represents the calculated ratio, normalized to a steviol glycoside-producing strain comprising additional copies of genes encoding GGPPS, truncated CDPS, KS, KO, ATR2, EUGT11, SrKAHe1, CPR8, UGT85C2, UGT74G1, UGT76G1, and EUGT11 polypeptides, of supernatant/total production for each gene (by ordered locus name) deleted in the steviol glycoside-producing strain. The supernatant or ratio supernatant/total of less than 0.6 represents a more than 40% decrease in either the supernatant alone or in the ratio of supernatant/total production of RebA, RebB, RebD, or RebM, which corresponds approximately to more than 2 standard deviations removed from the mean of a control steviol glycoside-producing strain, and indicates the gene as having a role in steviol glycoside transportation and/or production (Table 9). The supernatant or ratio supernatant/total of between 0.6 and 0.8 represents a 40-20% decrease in either the supernatant alone or In the ratio of supernatant/total production of RebA, RebB, RebD, or RebM, which corresponds to approximately between 1 and 2 standard deviations removed from the mean of the control strain, and indicates the gene as having a role in steviol glycoside transportation and/or production, and indicates the gene as having a role in steviol glycoside transportation and/or production (Table 10). Total production of each steviol glycoside was between 0.85 and 1.15 compared to the control steviol glycoside-producing strain. Table 10 shows the supernatant/total ratio for each candidate that fulfills the selection criteria.

TABLE 9

Transport related genes with over a 40% decrease in Reb A, RebB, RebD or RebM compared to a control steviol glycoside-producing strain comprising additional copies of genes encoding GGPPS, truncated CDPS, KS, KO, ATR2, EUGT11, SrKAHe1, CPR8, UGT85C2, UGT74G1, UGT76G1, and EUGT11 polypeptides.

| | Transporter selection criterion 1 total vs sup | | | | Transporter selection criterion 2 ratio sup/total vs total | | | |
|---|---|---|---|---|---|---|---|---|
| | RebA | RebB | RebD | RebM | RebA | RebB | RebD | RebM |
| YAL067C | | | | 0.541 | | | | 0.541 |
| YBL089W | 0.433 | 0.416 | | | 0.433 | 0.416 | | |
| YBL099W | 0.523 | | | | 0.523 | | | |
| YBR294W | 0.495 | | | | 0.495 | | | |
| YCR028C | | 0.419 | | | | 0.419 | | |
| YDL185W | 0.551 | | | | 0.551 | | | |
| YDL210W | 0.626 | 0.469 | | | | 0.469 | | |
| YDR061W | 0.482 | | 0.471 | | 0.482 | | 0.471 | |
| YDR406W | | | | 0.288 | | | | 0.288 |
| YDR536W | 0.715 | | 0.365 | | | | 0.365 | |
| YFL011W | | 0.444 | | | | 0.444 | | |
| YGR125W | | 0.400 | | | | 0.400 | | |
| YGR224W | | 0.361 | | | | 0.361 | | |
| YGR281W | | 0.596 | | | | 0.596 | | |
| YHL016C | | | 0.427 | 0.296 | | | 0.427 | 0.296 |
| YJL093C | | 0.449 | | | | 0.449 | | |
| YJL108C | 0.589 | | | | 0.589 | | | |
| YJL212C | 0.442 | | | 0.461 | 0.442 | | | 0.461 |
| YKR050W | 0.554 | | 0.378 | 0.304 | 0.554 | | 0.378 | 0.304 |
| YLR447C | 0.512 | | | | 0.512 | | | |
| YMR034C | 0.331 | | | 0.316 | 0.331 | | | 0.316 |
| YMR253C | 0.389 | | | 0.375 | 0.389 | | | 0.375 |
| YOL020W | 0.371 | | | | 0.371 | | | |
| YOL075C | 0.494 | | | 0.471 | 0.494 | | | 0.471 |
| YOL077W-A | 0.531 | | | | 0.531 | | | |
| YOL122C | | | | 0.457 | | | | 0.457 |
| YOR079C | 0.552 | | | | 0.552 | | | |
| YOR092W | 0.407 | | | | 0.407 | | | |
| YOR130C | 0.588 | | | | 0.588 | | | |

TABLE 9-continued

Transport related genes with over a 40% decrease in Reb A, RebB, RebD or RebM compared to a control steviol glycoside-producing strain comprising additional copies of genes encoding GGPPS, truncated CDPS, KS, KO, ATR2, EUGT11, SrKAHe1, CPR8, UGT85C2, UGT74G1, UGT76G1, and EUGT11 polypeptides.

| | Transporter selection criterion 1 total vs sup | | | | Transporter selection criterion 2 ratio sup/total vs total | | | |
|---|---|---|---|---|---|---|---|---|
| | RebA | RebB | RebD | RebM | RebA | RebB | RebD | RebM |
| YOR222W | 0.469 | | | 0.457 | 0.469 | | | 0.457 |
| YOR291W | | | 0.428 | | | | 0.428 | |
| YOR334W | | | 0.327 | | | | 0.327 | |
| YPL270W | | | 0.375 | | | | 0.375 | |
| YPR003C | 0.400 | | | 0.418 | 0.400 | | | 0.418 |
| YPR058W | | | 0.461 | | | | 0.461 | |
| YPR128C | | | 0.342 | | | | 0.342 | |
| YPR201W | 0.376 | | | 0.353 | 0.376 | | | 0.353 |

TABLE 10

Transport related genes with a 20-40% decrease in Reb A, RebB, RebD or RebM compared to a control steviol glycoside-producing strain comprising additional copies of genes encoding GGPPS, truncated CDPS, KS, KO, ATR2, EUGT11, SrKAHe1, CPR8, UGT85C2, UGT74G1, UGT76G1, and EUGT11 polypeptides.

| | Transports cal 1; total vs sup | | | | Transports cal 2; ratio sup/ total vs total | | | |
|---|---|---|---|---|---|---|---|---|
| | RebA | RebB | RebD | RebM | RebA | RebB | RebD | RebM |
| YCR011C | | | | 0.654 | | | | 0.654 |
| YDL210W | | | 0.729 | 0.626 | | | 0.729 | |
| YDR292C | 0.724 | | | | 0.724 | | | |
| YDR536W | | | | 0.715 | | | | |
| YEL027W | | 0.799 | | | | 0.799 | | |
| YER019C-A | 0.789 | | | | 0.789 | | | |
| YER053C | 0.651 | | | | 0.651 | | | |
| YGR256W | 0.744 | | | | 0.744 | | | |
| YHR002W | 0.795 | | | | 0.795 | | | |
| YJL133W | 0.691 | | | | 0.691 | | | |
| YJL219W | 0.674 | | | | 0.674 | | | |
| YKL016C | 0.627 | | | | 0.627 | | | |
| YKL209C | 0.721 | | | | 0.721 | | | |
| YKR105C | | | | 0.646 | | | | |
| YMR166C | | 0.924 | | | | | | |
| YNL003C | | 0.814 | | | | | | |
| YOR153W | 0.801 | | | | | | | |
| YOR316C | | | | 0.640 | | | | |
| YOR332W | 0.700 | | | | 0.700 | | | |

Knockouts of YDL210W (SEQ ID NO:25) and YPL270W (SEQ ID NO:79) resulted in decreased RebD excretion in the steviol glycoside-producing strain comprising genes encoding GGPPS, truncated CDPS, KS, KO, ATR2, EUGT11, SrKAHe1, CPR8, UGT85C2, UGT74G1, UGT76G1, and EUGT11 polypeptides and the steviol glycoside-producing strain comprising additional copies of genes encoding GGPPS, truncated CDPS, KS, KO, ATR2, EUGT11, SrKAHe1, CPR8, UGT85C2, UGT74G1, UGT76G1, and EUGT11 polypeptides. As well, knockouts of YJL212C (SEQ ID NO:47) and YOL122C (SEQ ID NO:68) resulted in decreased RebM transport in both strains.

Example 4. Confirmation of Knockout of Yeast Endogenous Transport Genes by Overexpression in a RebD/M-Producing Strain Overexpression of a subset of the initial candidate transporters from Example 3 was performed using both plasmid-based expression and an integration cassette. First, deep-well microtiter plate culture experiments were carried out. Two transport genes were overexpressed using a plasmid in a RebD/M-prodding strain in order to confirm the results from the knockout experiments. YGR181W (SEQ ID NO:38), a TIM complex, helper protein for insertion of mitochondrial inner membrane proteins, and YDR061W (SEQ ID NO:26) an ABC-like transporter ware overexpressed. The data shown in FIG. 2 demonstrate that the phenotype based on the knockout studies was confirmed with a plasmid based overexpression phenotype for YGR181W (SEQ ID NO:38) and YDR061W (SEQ ID NO:26) in deep-well plates.

Figure 3A:
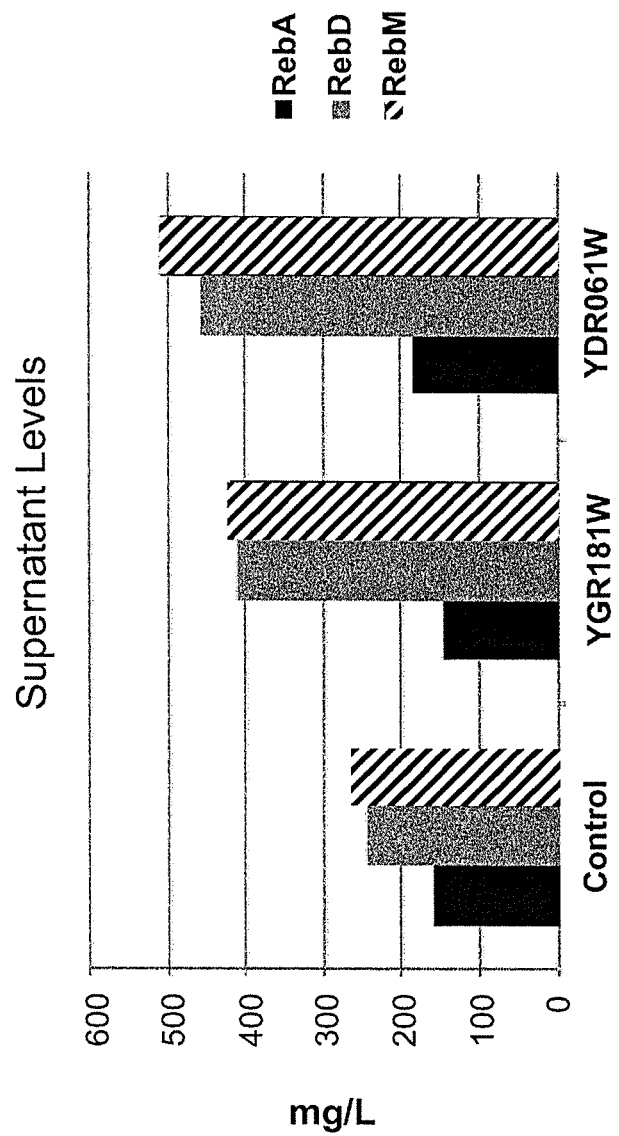
FIG. 3A and FIG. 3B are bar graphs of the amount (mg/L) of RebA, RebD, or RebM in the supernatant (FIG. 3A) or total culture (FIG. 3B) of a YGR181W (SEQ ID NO:38) or YDR061W (SEQ ID NO:26) overexpressing strain, compared to a control steviol glycoside-producing strain. See Example 4.
Figure 3B:
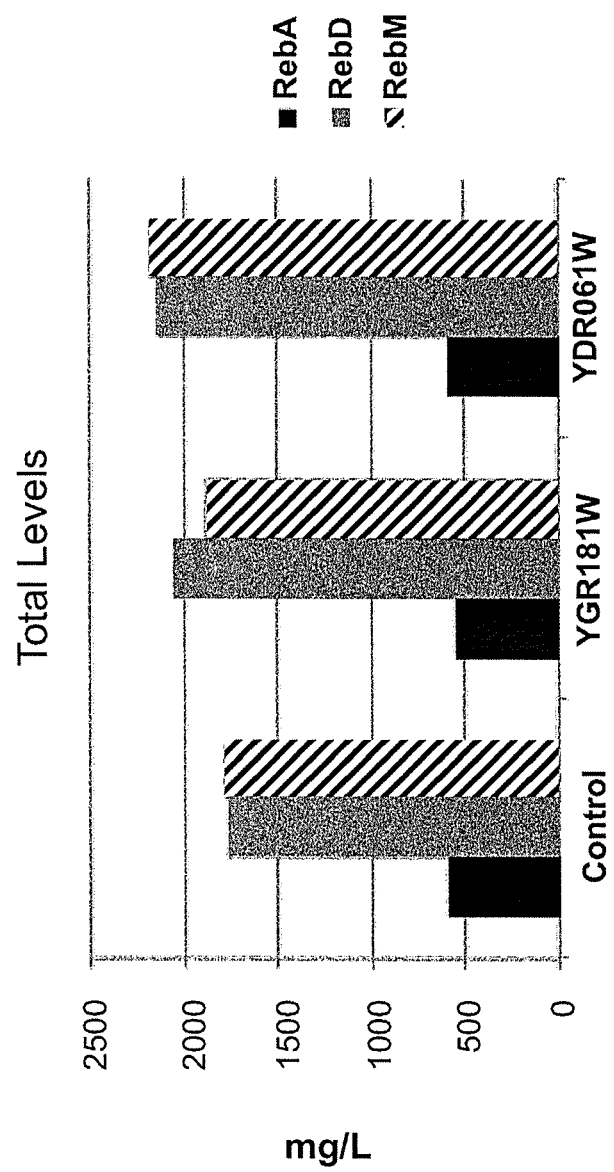

Next, confirmation of the phenotype in fermenters was performed in additional steviol glycoside-producing strains, which were characterized by intergration of YGR181W (SEQ ID NO:38) or YDR061W (SEQ ID NO:26) on chromosome XII. The steviol glycoside-producing strains were grown on defined media at 30° C. in a fed-batch fermentation for about 5 days under glucose-limited conditions, and the levels of RebA, RebB, RebD, and RebM were measured using LC-MS (Method B, Example 1). The graphs shown in FIG. 3 illustrate an approximate 2-fold increase in RebD and RebM transported in the culture medium for the new integration constructs, and little change n RebA and RebB transport. Overexpression of YGR181W (SEQ ID NO:38) or YDR061W (SEQ ID NO:26) resulted in improved (~2-fold) RebD and RebM transport into the culture medium (~400-500 mg/L of supernatant RebD and RebM in YGR181W (SEQ ID NO:38) and YDR061W (SEQ ID NO:26) overexpression strains versus ~250 mg/L of supernatant RebD and RebM in a control steviol glycoside-producing strain). See FIG. 3A. The ratio of transported RebD as compared to the total RebD increased from 0.158 in the control strain to 0.21-0.25 with the candidate genes overexpressed. RebM transport into the culture medium was also simultaneously improved. See FIG. 3.

Example 5. Overexpression of Selected Yeast Endogenous Transport Genes

Overexpression in a steviol glycoside-producing strain (as described in Example 2) using a plasmid with a constitutive promoter of the transporter genes shown in Table 11 resulted in greater than a 20% increase in excretion of RebA, RebB, RebD, and/or RebM. Results were analyzed using criterion 2 described in Example 3. Additionally, overexpression of the transporter genes shown in Table 12 resulted in greater than a 40% improvement in production of RebA, RebB, RebD, and/or RebM. Table 11 shows the supernatant/total ratio for each candidate that fulfills the selection criteria.

TABLE 11

Transport related genes with over a 20% increase in RebA, RebB, RebD or RebM excretion, compared to a control steviol glycoside-producing strain.

| | Ratio Supernatant/Total | | | |
|---|---|---|---|---|
| | RebB | RebA | RebD | RebM |
| YOR079C | | | 1.21 | |
| YMR166C | | 1.36 | 1.53 | 1.38 |
| YEL027W | | 1.62 | 1.82 | 1.52 |
| YDL054C | | 1.45 | 1.38 | 1.31 |
| YKL120W | | 1.83 | 1.89 | 1.93 |
| YDR536W | | 1.79 | 1.80 | 1.76 |
| YBL099W | | | | 1.22 |
| YML116W | | 1.32 | 1.31 | 1.42 |
| YIL166C | | | 1.27 | 1.22 |
| YKR039W | | | 1.26 | 1.41 |
| YOR307C | | | | 1.23 |
| YKL146W | | 1.36 | 1.47 | 1.66 |
| YGL167C | | | | 1.33 |
| YJL093C | | | | 1.29 |
| YOR306C | 1.67 | | | |
| YDL128W | 1.85 | | 1.29 | |
| YOR153W | 1.42 | | 1.21 | |
| YKL050C | 1.59 | 1.22 | | |
| YJL094C | 1.71 | 1.24 | 1.24 | |
| YCL069W | 1.59 | | | |
| YOL158C | 1.52 | | | |
| YFL011W | 1.44 | | | |
| YJR106W | | | 1.38 | 1.33 |
| YBR043C | | | | 1.20 |
| YPR011C | | | | 1.27 |

TABLE 12

Transport related genes with over a 40% increase in RebA, RebB, RebD or RebM production, compared to a control steviol glycoside-producing strain.

| | Increases in Production | | | |
|---|---|---|---|---|
| | RebB | RebA | RebD | RebM |
| YMR166C | | | | 1.52 |
| YIL166C | | 1.41 | 1.50 | 1.55 |
| YKR039W | | | 1.48 | 1.52 |
| YKL146W | | | | 1.42 |
| YJL093C | | | 1.46 | 1.43 |
| YOR306C | | | | 1.59 |
| YDL128W | | | | 1.49 |
| YOL122C | | 1.41 | | 1.59 |
| YIL006W | | 1.64 | | 2.03 |
| YFL028C | | | | 1.55 |
| YBR021W | | | 1.51 | 1.87 |
| YHR002W | | | 1.51 | 1.73 |
| YEL031W | | | 1.45 | 1.66 |
| YCL069W | | | | 1.53 |
| YOL158C | | | 1.42 | 1.63 |
| YKL064W | | | 1.40 | 1.44 |
| YHR096C | | | | 1.42 |
| YOR332W | | | | 1.44 |
| YDR338C | | | 1.50 | 1.55 |
| YJR106W | | | 1.41 | 1.44 |
| YBR043C | | | 1.55 | 1.49 |
| YPR011C | | | | 1.43 |
| YFR045W | | 1.44 | | |

Example 6. Genomic Integration of Transporter Genes

Figure 4E:
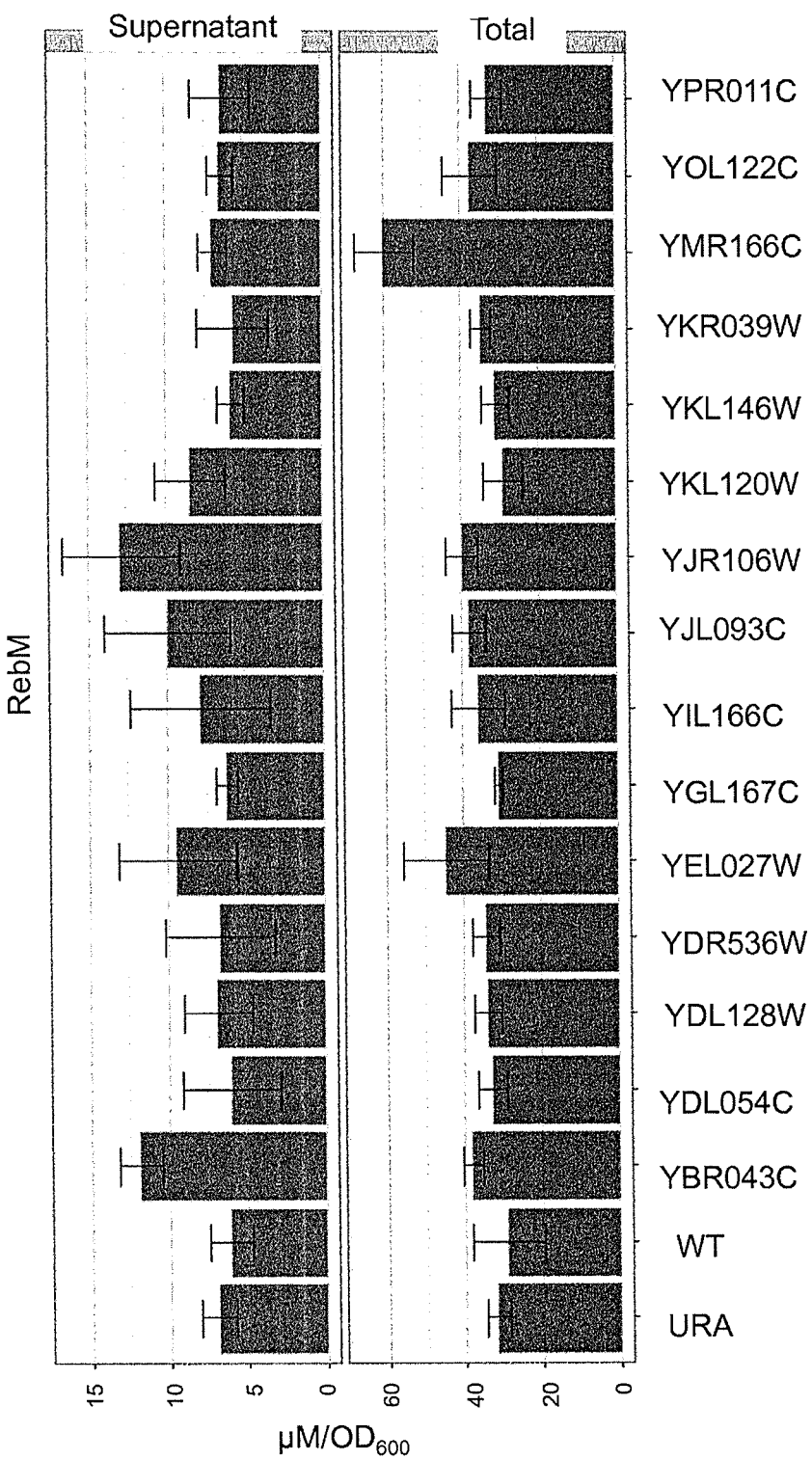
FIG. 4E shows levels of RebM (total levels and supernatant levels; $\mu M/OD_{600}$) in a steviol glycoside-producing *S. cerevisiae* strain with a genomically integrated transporter gene. The genomically integrated transporter genes of FIGS. 4A-E are YBR043C (SEQ ID NO:88), YEL027W (SEQ ID NO:102), YJL093C (SEQ ID NO:44), YJR106W (SEQ ID NO:48), YMR166C (SEQ ID NO:132), YIL166C (SEQ ID NO:121), YKL120W (SEQ ID NO:126), YDL054C (SEQ ID NO:94), YDL128W (SEQ ID NO:22), YDR536W (SEQ ID NO:30), YGL167C (SEQ ID NO:112), YKL146W (SEQ ID NO:127), YKR039W (SEQ ID NO:129), YOL122C (SEQ ID NO:68), and YPR011C (SEQ ID NO:82). See Example 6.

DNA of the transporter genes selected for integration into the genome of a RebD/M-producing *S. cerevisiae* strain (see Example 2) was amplified from an S288C background by PCR and cloned into a plasmid with homology regions for the integration site and a PGK1 promoter for overexpression, using the USER cloning system. See, e.g., Nour-Eldin et al., 2010, Methods Mol Biol. 643:185-200. The USER cloning construct including the homology regions and the transporter was cut out from the plasmid using restriction enzymes, and the linear piece of DNA was integrated into the genome of the receiving RebD/M-producing strain by standard LiAc method. The genomically integrated transporters were tested in plates that release glucose from a polymer after addition of a growth medium. A polymer that releases 20 g/L glucose over 3 days was used to mimic the feed profile during fermentation. Steviol glycoside levels were measured by LC-MS (see Example 1), and $OD_{600}$ was measured on a Perkin Elmer 2104 Multilabel reader. YBR043C (SEQ ID NO:88), YEL027W (SEQ ID NO:102), YJL093C (SEQ ID NO:44), YJR106W (SEQ ID NO:48), YKL120W (SEQ ID NO:126), and YMR166C (SEQ ID NO:132) showed improved excretion of 13-SMG. (FIG. 4A). YBR043C (SEQ ID NO:88), YEL027W (SEQ ID NO:102), and YMR166C (SEQ ID NO:132) showed improved excretion of RebA (FIG. 4B). YBR043C (SEQ ID NO:88), YEL027W (SEQ ID NO:102), and YMR166C (SEQ ID NO:132) showed improved excretion of RebB (FIG. 4C). YBR043C of SEQ ID NO:88, YEL027W of SEQ ID NO:102, YJL093C of SEQ ID NO:44, YJR106W of SEQ ID NO:48, and YMR166C of SEQ ID NO:132 showed improved production of RebD, and YBR043C of SEQ ID NO:88, YEL027W of SEQ ID NO:102, YIL166C (SEQ ID NO:121), YJL093C of SEQ ID NO:44, YJR106W of SEQ ID NO:48, and YMR166C of SEQ ID NO:132 showed improved production of RebM, as measured by an increase in RebD and RebM levels in the supernatant compared to a control steviol glycoside-producing strain. See FIGS. 40 and 4E. Controls with a URA marker are also shown in FIG. 4.

FIG. 5A shows supernatant levels of RebA, RebB, RebD, and RebM of an additional steviol glycoside-producing strain overexpressing YMR166C (SEQ ID NO:132), YEL027W (SEQ ID NO:102), YKL120W (SEQ ID NO:126), YJR106W (SEQ ID NO:48), YJL093C (SEQ ID NO:44), and YBR043C (SEQ ID NO:88) by the USER cloning system. The strain of FIG. 5 comprised a recombinant gene encoding a *Synechococcus* sp. GGPPS polypeptide (SEQ ID NO:1, SEQ ID NO:149), a recombinant gene encoding a truncated *Zea mays* COPS polypeptide (SEQ ID NO:2, SEQ ID NO:150), a recombinant gene encoding an *A. thaliana* KS polypeptide (SEQ ID NO:3, SEQ ID NO:151), a recombinant gene encoding a recombinant *S. rebaudiana* KO1 polypeptide (SEQ ID NO:4, SEQ ID NO:152), a recombinant gene encoding a KO polypeptide (SEQ ID NO:XX, SEQ ID NO:XX), a recombinant gene encoding an *A. thaliana* ATR2 polypeptide (SEQ ID NO:5, SEQ ID NO:153), a recombinant gene encoding an *O. sativa* EUGT11 polypeptide (SEQ ID NO:12; SEQ ID NO:148), a recombinant gene encoding an SrKAHe1 polypeptide (SEQ ID NO:6, SEQ ID NO:154), a recombinant gene encoding an *S. rebaudiana* CPR8 polypeptide (SEQ ID NO:7, SEQ ID NO:155), a recombinant gene encoding an *S. rebaudiana* UGT85C2 polypeptide (SEQ ID NO:8, SEQ ID NO:156), a recombinant gene encoding an *S. rebaudiana* UGT74G1 polypeptide (SEQ ID NO:9, SEQ ID NO:157), a recombinant gene encoding an *S. rebaudiana* UGT76G1 polypeptide (SEQ ID NO:10, SEQ ID NO:158), and a recombinant gene encoding an *S. rebaudiana* UGT91D2 variant (or functional homolog), UGT91D2e-b (SEQ ID NO: 1, SEQ ID NO:159) polypeptide. FIG. 5B shows total levels of RebA, RebB, RebD, and RebM of the above described steviol glycoside-producing strain overexpressing YMR166C (SEQ ID NO:132), YEL027W (SEQ ID NO:102), YKL120W (SEQ ID NO:126), YIL166C (SEQ ID NO:132), YJR106W (SEQ ID NO:48), YJL093C (SEQ ID NO:44), and YBR043C (SEQ ID NO:88) by the USER cloning system.

Example 7. Production of RebD and RebM by Fermentation of Steviol Glycoside-Producing *S. cerevisiae* Strains Overexpressing YJL093C or YBR043C YJL093C (SEQ ID NO:44) and YBR043C (SEQ ID NO:88) were individually overexpressed in the steviol glycoside-producing strain described in Example 3. The strains were cultivated by fermentation (fed-batch, minimum medium, glucose-limiting) for approximately 130 h. Production of RebD and RebM was measured by LC-MS. As shown in Table 13, the strains overexpressing YJL093C or YBR043C produced higher levels of RebD and RebD+ RebM, as compared to a control steviol glycoside-producing strain.

TABLE 13

Production of RebD and RebM in *S. cerevisiae* strains overexpressing YJL093C and YBR043C.

| Strain | Ferm. Length (h) | Final Cell Dry Weight | RebD Titer (g/L) | RebM Titer (g/L) | RebD + RebM | RebD/ RebM Ratio (g/g) |
|---|---|---|---|---|---|---|
| Control | 126.83 | 104.53 | 1.38 | 4.47 | 5.85 | 0.31 |
| YJL093C | 130.10 | 114.40 | 3.42 | 2.80 | 6.22 | 1.22 |
| YBR043C | 129.17 | 112.00 | 3.56 | 2.72 | 6.28 | 1.31 |

TABLE 14

Sequences disclosed herein.

*Synechococcus* sp. GGPPS (GenBank ABC98596.1)

SEQ ID NO: 1

```
atggtcgcac aaactttcaa cctggatacc tacttatccc aaagacaaca acaagttgaa      60
gaggccctaa gtgctgctct tgtgccagct tatcctgaga gaatatacga agctatgaga     120
tactccctcc tggcaggtgg caaaagatta agacctatct tatgtttagc tgcttgcgaa     180
ttggcaggtg gttctgttga acaagccatg ccaactgcgt gtgcacttga aatgatccat     240
acaatgtcac taattcatga tgacctgcca gccatggata acgatgattt cagaagagga     300
aagccaacta atcacaaggt gttcggggaa gatatagcca tcttagcggg tgatgcgctt     360
ttagcttacg cttttgaaca tattgcttct caaacaagag gagtaccacc tcaattggtg     420
ctacaagtta ttgctagaat cggacacgcc gttgctgcaa caggcctcgt tggaggccaa     480
gtcgtagacc ttgaatctga aggtaaagct atttccttag aaacattgga gtatattcac     540
tcacataaga ctggagcctt gctggaagca tcagttgtct caggcggtat tctcgcaggg     600
gcagatgaag agcttttggc cagattgtct cattacgcta gagatatagg cttggctttt     660
caaatcgtcg atgatatcct ggatgttact gctacatctg aacagttggg gaaaaccgct     720
ggtaaagacc aggcagccgc aaaggcaact tatccaagtc tattgggttt agaagcctct     780
agacagaaag cggaagagtt gattcaatct gctaaggaag ccttaagacc ttacggttca     840
caagcagagc cactcctagc gctggcagac ttcatcacac gtcgtcagca ttaa     894
```

TABLE 14-continued

Sequences disclosed herein.

Zea mays truncated CDPS

SEQ ID NO: 2

```
atggcacagcaca catcagaatc cgcagctgtc gcaaagggca gcagtttgac ccctatagtg   60
agaactgacg ctgagtcaag gagaacaaga tggccaaccg atgacgatga cgccgaacct   120
ttagtggatg agatcagggc aatgcttact tccatgtctg atggtgacat ttccgtgagc   180
gcatacgata cagcctgggt cggattggtt ccaagattag acggcggtga aggtcctcaa   240
tttccagcag ctgtgagatg gataagaaat aaccagttgc ctgacggaag ttggggcgat   300
gccgcattat tctctgccta tgacaggctt atcaataccc ttgcctgcgt tgtaactttg   360
acaaggtggt ccctagaacc agagatgaga ggtagaggac tatcttttt gggtaggaac   420
atgtggaaat tagcaactga agatgaagag tcaatgccta ttggcttcga attagcattt   480
ccatctttga tagagcttgc taagagccta ggtgtccatg acttcccta tgatcaccag   540
gccctacaag gaatctactc ttcaagagag atcaaaatga gaggattcc aaaagaagtg   600
atgcataccg ttcdaacatc aatattgcac agtttggagg gtatgcctgg cctagattgg   660
gctaaactac ttaaactaca gagcagcgac ggaagttttt tgttctcacc agctgccact   720
gcatatgctt taatgaatac cggagatgac aggtgtttta gctacatcga tagaacagta   780
aagaaattca acggcggcgt ccctaatgtt tatccagtgg atctatttga acatatttgg   840
gccgttgata gacttgaaag attaggaatc tccaggtact tccaaaagga gatcgaacaa   900
tgcatggatt atgtaaacag gcattggact gaggacggta tttgttgggc aaggaactct   960
gatgtcaaag aggtggacga cacagctatg gcctttagac ttcttaggtt gcacggctac  1020
agcgtcagtc ctgatgtgtt taaaaacttc gaaaaggacg tgaattttt cgcatttgtc  1080
ggacagtcta atcaagctgt taccggtatg tacaacttaa acagagcaag ccagatatcc  1140
ttcccaggcg aggatgtgct tcatagagct ggtgccttct catatgagtt cttgaggaga  1200
aaagaagcag agggagcttt gagggacaag tggatcattt ctaaagatct acctggtgaa  1260
gttgtgtata ctttggattt tccatggtac ggcaacttac ctagagtcga ggccagagac  1320
tacctagagc aatacggagg tggtgatgac gtttggattg caagacatt gtataggatg  1380
ccacttgtaa acaatgatgt atatttggaa ttggcaagaa tggatttcaa ccactgccag  1440
gctttgcatc agttagagtg gcaaggacta aaaagatggt atactgaaaa taggttgatg  1500
gactttggtg tcgcccaaga agatgcccctt agagcttatt tcttgcagc cgcatctgtt  1560
tacgagcctt gtagagctgc cgagaggctt gcatgggcta gagccgcaat actagctaac  1620
gccgtgagca cccacttaag aaatagccca tcattcagag aaaggttaga gcattctctt  1680
aggtgtagac ctagtgaaga gacagatggc tcctggttta actcctcaag tggctctgat  1740
gcagttttag taaaggctgt cttaagactt actgattcat tagccaggga agcacagcca  1800
atccatggag gtgacccaga agatattata cacaagttat taagatctgc ttgggccgag  1860
tgggttaggg aaaaggcaga cgctgccgat agcgtgtgca atggtagttc tgcagtagaa  1920
caagagggat caagaatggt ccatgataaa cagacctgtc tattattggc tagaatgatc  1980
gaaatttctg ccggtagggc agctggtgaa gcagccagtg aggacggcga tagaagaata  2040
attcaattaa caggctccat ctgcgacagt cttaagcaaa aatgctagt ttcacaggac  2100
cctgaaaaaa atgaagagat gatgtctcac gtggatgacg aattgaagtt gaggattaga  2160
gagttcgttc aatatttgct tagactaggt gaaaaaaaga ctggatctag cgaaaccagg  2220
caaacatttt taagtatagt gaaatcatgt tactatgctg ctcattgccc acctcatgcc  2280
```

TABLE 14-continued

Sequences disclosed herein.

```
gttgatagac acattagtag agtgattttc gagccagtaa gtgccgcaaa gtaaccgcgg    2340
```

*Arabidopsis thaliana* KS (similar to GenBank AEE36246.1)

SEQ ID NO: 3

```
atgtctatta atttgagatc ttccggttgt agctccccaa taagcgcaac tttggaaagg      60
ggtctagact ctgaagttca aacaagagca aacaatgtat cttttgagca gaccaaagag     120
aagatcagga aaatgcttga gaaggtcgag ttgagcgtga gtgcctatga cactagttgg     180
gtagctatgg tcccatcacc atccagtcaa aacgcacctc ttttcccaca gtgcgtcaaa     240
tggctacttg ataatcaaca tgaggacggc tcttggggat tggataacca cgaccatcag     300
agcttaaaga aagatgtgtt gtcatccaca ttagcctcta tcctagctct taagaaatgg     360
ggaataggcg aaagacagat caataagggt ctacagttca ttgaattaaa ctctgcacta     420
gttaccgatg aaactataca aaaacctaca ggtttcgaca tcattttttcc aggaatgatt     480
aagtacgcca gggaccttaa tttgaccata cctcttggct cagaagtagt cgacgatatg     540
atcaggaaaa gagatctaga cttaaagtgt gatagcgaga aattcagcaa aggtagagag     600
gcttatcttg cctatgttct tgaaggaact aggaacttga aggactggga cttaattgtg     660
aaatatcaga gaaagaacgg tagtctattt gatagtccag ctacaaccgc cgcagctttc     720
actcaatttg gcaatgacgg ttgcttgagg tacttatgtt cacttttaca gaaattcgag     780
gccgcagtgc ctagtgtata tccatttgat caatacgcta gattaagcat aatcgtcact     840
ttagaatcat tgggaattga cagagatttc aagactgaga taaaaagcat attggatgag     900
acctataggt actggcttag aggtgacgaa gaaatttgcc tagatttggc cacatgtgca     960
cttgctttta ggttgctttt agcccacggc tatgacgtgt catacgatcc tctaaagcca    1020
tttgcagagg aatctggttt cagcgatacc cttgagggat atgttaaaaa caccttttcc    1080
gtattagagc ttttcaaggc tgcccaaagt taccctcatg agagtgcttt gaaaaagcag    1140
tgttgctgga caaaacaata tctagaaatg gaactaagtt catgggttaa aacaagcgtt    1200
agggacaagt acttgaaaaa ggaagtggag gatgcttttgg catttccatc atatgcctct    1260
ttagaaagaa gtgaccacag aaggaaaatt cttaatggct cagcagttga aaacacaaga    1320
gtaaccaaga cctcttacag gttgcataat atatgtacat cagatatctt aaaacttgct    1380
gtcgacgatt tcaactttg ccaatctatt catagagagg aaatggaaag attggataga    1440
tggatagtgg agaatagact acaggaatta aagttcgcca gacaaaaatt ggcttactgt    1500
tactttagtg gcgctgccac actattctct ccagaattgt ctgacgcaag gatctcatgg    1560
gctaagggag gtgttctaac cacagtagtc gatgactttt ttgatgttgg cggtagtaaa    1620
gaagagcttg agaacttaat tcacttggtg gaaaagtggg atcttaatgg agttcctgaa    1680
tactcttcag agcatgtaga aataattttc tctgtcctaa gagacactat cttagaaacc    1740
ggtgataaag cctttacata tcagggcaga aacgttactc accatattgt gaaaatatgg    1800
ttggacttac ttaagagcat gctaagggag gctgaatggt ccagtgacaa atcaacccca    1860
tctttggaag attacatgga gaatgcctat atcagcttcg cattaggtcc tattgtattg    1920
ccagctacat accttatagg acctccacta cctgaaaaga ctgtcgactc ccaccaatat    1980
aatcaattat acaaattggt tagtaccatg ggtagactat taaacgatat ccagggcttt    2040
aagagggaat cagccgaggg aaaacttaat gcagtgtctc tacatatgaa gcatgaaaga    2100
gacaacagaa gcaagaggt tattatagaa tccatgaaag gattggctga aggaaaaga     2160
gaggaattac acaaacttgt actagaagag aaaggtagtg tcgttccaag agaatgcaag    2220
```

TABLE 14-continued

Sequences disclosed herein.

| | |
|---|---|
| gaaggcttct taaaaatgtc aaaagtgttg aacctttttt ataggaagga tgatggcttc | 2280 |
| acatctaacg acttgatgag ccttgtgaaa tccgtcatct acgagcctgt ttcacttcaa | 2340 |
| aaggagagtc taacttga | 2358 |

S. rebaudiana KO1 (codon optimized)

SEQ ID NO: 4

| | |
|---|---|
| atggatgctg tgacgggttt gttaactgtc ccagcaaccg ctataactat tggtggaact | 60 |
| gctgtagcat tggaggtagc gctaatcttt tggtacctga atcctacac atcagctaga | 120 |
| agatcccaat caaatcatct tccaagagtg cctgaagtcc caggtgttcc attgttagga | 180 |
| aatctgttac aattgaagga gaaaaagcca tacatgactt ttacgagatg ggcagcgaca | 240 |
| tatggaccta tctatagtat caaaactggg gctacaagta tggttgtggt atcatctaat | 300 |
| gagatagcca aggaggcatt ggtgaccaga ttccaatcca tatctacaag gaacttatct | 360 |
| aaagccctga agtacttac agcagataag acaatggtcg caatgtcaga ttatgatgat | 420 |
| tatcataaaa cagttaagag acacatactg accgccgtct gggtcctaa tgcacagaaa | 480 |
| aagcatagaa ttcacagaga tatcatgatg ataacatat ctactcaact tcatgaattc | 540 |
| gtgaaaaaca acccagaaca ggaagaggta gaccttagaa aaatctttca atctgagtta | 600 |
| ttcggcttag ctatgagaca agccttagga aaggatgttg aaagtttgta cgttgaagac | 660 |
| ctgaaaatca ctatgaatag agacgaaatc tttcaagtcc ttgttgttga tccaatgatg | 720 |
| ggagcaatcg atgttgattg gagagacttc tttccatacc taaagtgggt cccaaacaaa | 780 |
| aagttcgaaa atactattca acaaatgtac atcagaagag aagctgttat gaaatcttta | 840 |
| atcaaagagc acaaaaagag aatagcgtca ggcgaaaagc taaatagtta tcgattac | 900 |
| cttttatctg aagctcaaac tttaaccgat cagcaactat tgatgtcctt gtgggaacca | 960 |
| atcattgaat cttcagatac aacaatggtc acaacagaat gggcaatgta cgaattagct | 1020 |
| aaaaaccta aattgcaaga taggttgtac agagacatta gtccgtctg tggatctgaa | 1080 |
| aagataaccg aagagcatct atcacagctg ccttacatta cagctatttt ccacgaaaca | 1140 |
| ctgagaagac actcaccagt tcctatcatt cctctaagac atgtacatga agataccgtt | 1200 |
| ctaggcggct accatgttcc tgctggcaca gaacttgccg ttaacatcta cggttgcaac | 1260 |
| atggacaaaa acgtttggga aaatccagag gaatggaacc cagaaagatt catgaaagag | 1320 |
| aatgagacaa ttgattttca aaagacgatg gccttcggtg gtggtaagag agtttgtgct | 1380 |
| ggttccttgc aagccatttt aactgcatct attgggattg ggagaatggt tcaagagttc | 1440 |
| gaatggaaac tgaaggatat gactcaagag gaagtgaaca cgataggcct aactacacaa | 1500 |
| atgttaagac cattgagagc tattatcaaa cctaggatct aa | 1542 |

A. thaliana ATR2 (codon optimized)

SEQ ID NO: 5

| | |
|---|---|
| atgtcttcct cttcctcttc cagtacctct atgattgatt tgatggctgc tattattaaa | 60 |
| ggtgaaccag ttatcgtctc cgacccagca aatgcctctg cttatgaatc agttgctgca | 120 |
| gaattgtctt caatgttgat cgaaacagaa caattcgcca tgatcgtaac tacatcaatc | 180 |
| gctgttttga tcggttgtat tgtcatattg tatggagaa gatccggtag tggtaattct | 240 |
| aaaagagtcg aacctttgaa accattagta attaagccaa gaagaagaa atagatgac | 300 |
| ggtagaaaga aagttacaat attttttcggt acccaaactg gtacagctga aggttttgca | 360 |
| aaagccttag gtgaagaagc taaggcaaga tacgaaaaga ctagattcaa gatagtcgat | 420 |
| ttggatgact atgccgctga tgacgatgaa tacgaagaaa agttgaagaa agaagatgtt | 480 |

TABLE 14-continued

Sequences disclosed herein.

```
gcatttttct ttttggcaac ctatggtgac ggtgaaccaa ctgacaatgc agccagattc    540
tacaaatggt ttacagaggg taatgatcgt ggtgaatggt tgaaaaactt aaagtacggt    600
gttttcggtt tgggtaacag acaatacgaa catttcaaca aagttgcaaa ggttgtcgac    660
gatattttgg tcgaacaagg tgctcaaaaa ttagtccaag taggtttggg tgacgatgac    720
caatgtatag aagatgactt tactgcctgg agagaagctt tgtggcctga attagacaca    780
atcttgagag aagaaggtga caccgccgtt gctacccat atactgctgc agtattagaa    840
tacagagttt ccatccatga tagtgaagac gcaaagttta atgatatcac tttggccaat    900
ggtaacggtt atacagtttt cgatgcacaa caccttaca aagctaacgt tgcagtcaag    960
agagaattac ataccagat atccgacaga agttgtatac acttggaatt tgatatcgct   1020
ggttccggtt taaccatgaa gttgggtgac catgtaggtg ttttatgcga caatttgtct   1080
gaaactgttg atgaagcatt gagattgttg gatatgtccc ctgacactta ttttagtttg   1140
cacgctgaaa aagaagatgg tacaccaatt tccagttctt taccacctcc attccctcca   1200
tgtaacttaa gaacagcctt gaccagatac gcttgattgt tatcatcccc taaaaagtcc   1260
gccttgattg ctttagccgc tcatgctagt gatcctactg aagcagaaag attgaaacac   1320
ttagcatctc cagccggtaa agatgaatat tcaaagtggg tagttgaatc tcaaagatca   1380
ttgttagaag ttatggcaga atttccatct gccaagcctc cattaggtgt cttctttgct   1440
ggtgtagcac ctagattgca accaagattc tactcaatca gttcttcacc taagatcgct   1500
gaaactagaa ttcatgttac atgtgcatta gtctacgaaa agatgccaac cggtagaatt   1560
cacaagggtg tatgctctac ttggatgaaa aatgctgttc cttacgaaaa atcagaaaag   1620
ttgttcttag gtagaccaat cttcgtaaga caatcaaact tcaagttgcc ttctgattca   1680
aaggttccaa taatcatgat aggtcctggt acaggtttag ccccattcag aggtttcttg   1740
caagaaagat tggctttagt tgaatctggt gtcgaattag gtccttcagt tttgttcttt   1800
ggttgtagaa acagaagaat ggatttcatc tatgaagaag aattgcaaag attcgtcgaa   1860
tctggtgcat tggccgaatt atctgtagct tttttcaagag aaggtccaac taaggaatac   1920
gttcaacata agatgatgga taaggcatcc gacatatgga acatgatcag tcaaggtgct   1980
tatttgtacg tttgcggtga cgcaaagggt atggccagag atgtccatag atctttgcac   2040
acaattgctc aagaacaagg ttccatggat agtaccaaag ctgaaggttt cgtaaagaac   2100
ttacaaactt ccggtagata cttgagagat gtctggtga                          2139
```

*Stevia rebaudiana* KAHe1 (codon-optimized)

SEQ ID NO: 6

```
atggaagcct cttacctata catttctatt ttgcttttac tggcatcata cctgttcacc     60
actcaactta aaggaagag cgctaatcta ccaccaaccg tgtttccatc aataccaatc    120 attgacact tatacttact caaaaagcct ctttatagaa ctttagcaaa aattgccgct    180
aagtacggac caatactgca attacaactc ggctacagac gtgttctggt gatttcctca    240
ccatcagcag cagaagagtg ctttaccaat aacgatgtaa tcttcgcaaa tagacctaag    300
acattgtttg gcaaaatagt gggtggaaca tcccttggca gtttatccta cggcgatcaa    360
tggcgtaatc taaggagagt agcttctatc gaaatcctat cagttcatag gttgaacgaa    420
tttcatgata tcagagtgga tgagaacaga ttgttaatta gaaaacttag aagttcatct    480
tctcctgtta ctcttataac agtctttttat gctctaacat tgaacgtcat tatgagaatg    540
atctctggca aaagatattt cgacagtggg gatagagaat tggaggagga aggtaagaga    600
```

TABLE 14-continued

Sequences disclosed herein.

```
tttcgagaaa tcttagacga aacgttgctt ctagccggtg cttctaatgt tggcgactac    660
ttaccaatat tgaactggtt gggagttaag tctcttgaaa agaaattgat cgctttgcag    720
aaaaagagag atgactttt ccagggtttg attgaacagg ttagaaaatc tcgtggtgct    780
aaagtaggca aagtagaaa aacgatgatc gaactcttat tatctttgca agagtcagaa    840
cctgagtact atacagatgc tatgataaga tcttttgtcc taggtctgct ggctgcaggt    900
agtgatactt cagcgggcac tatggaatgg gccatgagct tactggtcaa tcacccacat    960
gtattgaaga aagctcaagc tgaaatcgat agagttatcg gtaataacag attgattgac   1020
gagtcagaca ttggaaatat cccttacatc qggtgtatta tcaatgaaac tctaagactc   1080
tatccagcag ggccattgtt gttcccacat gaaagttctg ccgactgcgt tatttccggt   1140
tacaatatac ctagaggtac aatgttaatc gtaaaccaat gggcgattca tcacgatcct   1200
aaagtctggg atgatcctga aacctttaaa cctgaaagat ttcaaggatt agaaggaact   1260
agagatggtt tcaaactat gccattcggt tctgggagaa gaggatgtcc aggtgaaggt   1320
ttggcaataa ggctgttagg gatgacacta ggctcagtga tccaatgttt tgattgggag   1380
agagtaggag atgagatggt tgacatgaca gaaggtttgg gtgtcacact tcctaaggcc   1440
gttccattag ttgccaaatg taagccacgt tccgaaatga ctaatctcct atccgaactt   1500
taa                                                                 1503
```

*Stevia rebaudiana* CPR8

SEQ ID NO: 7

```
ATGCAATCTAACTCCGTGAAGATTTCGCCGCTTGATCTGGTAACTGCGCTGTTTAGCGGCAAGGTTTT
GGACACATCGAACGCATCGGAATCGGGAGAATCTGCTATGCTGCCGACTATAGCGATGATTATGGAGA
ATCGTGAGCTGTTGATGATACTCACAACGTCGGTTGCTGTATTGATCGGATGCGTTGTCGTTTTGGTG
TGGCGGAGATCGTCTACGAAGAAGTCGGCGTTGGAGCCACCGGTGATTGTGGTTCCGAAGAGAGTGCA
AGAGGAGGAAGTTGATGATGGTAAGAAGAAAGTTACGGTTTTCTTCGGCACCCAAACTGGAACAGCTG
AAGGCTTCGCTAAGGCACTTGTTGAGGAAGCTAAAGCTCGATATGAAAAGGCTGTCTTTAAAGTAATT
GATTTGGATGATTATGCTGCTGATGACGATGAGTATGAGGAGAAACTAAAGAAAGAATCTTTGGCCTT
TTTCTTTTTGGCTACGTATGGAGATGGTGAGCCAACAGATAATGCTGCCAGATTTTATAAATGGTTTA
CTGAGGGAGATGCGAAAGGAGAATGGCTTAATAAGCTTCAATATGGAGTATTTGGTTTGGGTAACAGA
CAATATGAACATTTTAACAAGATCGCAAAGTGGTTGATGATGGTCTTGTAGAACAGGGTGCAAAGCG
TCTTGTTCCTGTTGGACTTGGAGATGATGATCAATGTATTGAAGATGACTTCACCGCATGGAAAGAGT
TAGTATGGCCGGAGTTGGATCAATTACTTCGTGATGAGGATGACACAACTGTTGCTACTCCATACACA
GCTGCTGTTGCAGAATATCGCGTTGTTTTTCATGAAAAACCAGACGCGCTTTCTGAAGATTATAGTTA
TACAAATGGCCATGCTGTTCATGATGCTCAACATCCATGCAGATCCAACGTGGCTGTCAAAAAGGAAC
TTCATAGTCCTGAATCTGACCGGTCTTGCACTCATCTTGAATTTGACATCTCGAACACCGGACTATCA
TATGAAACTGGGGACCATGTTGGAGTTTACTGTGAAAACTTGAGTGAAGTTGTGAATGATGCTGAAAG
ATTAGTAGGATTACCACCAGACACTTACTCCTCCATCCACACTGATAGTGAAGACGGGTCGCCACTTG
GCGGAGCCTCATTGCCGCCTCCTTTCCCGCCATGCACTTTAAGGAAAGCATTGACGTGTTATGCTGAT
GTTTTGAGTTCTCCCAAGAAGTCGGCTTTGCTTGCACTAGCTGCTCATGCCACCGATCCCAGTGAAGC
TGATAGATTGAAATTTCTTGCATCCCCCGCCGGAAAGGATGAATATTCTCAATGGATAGTTGCAAGCC
AAAGAAGTCTCCTTGAAGTCATGGAAGCATTCCCGTCAGCTAAGCCTTCACTTGGTGTTTTCTTTGCA
TCTGTTGCCCCGCGCTTACAACCAAGATACTACTCTATTTCTTCCTCACCCAAGATGGCACCGGATAG
```

TABLE 14-continued

Sequences disclosed herein.

```
GATTCATGTTACATGTGCATTAGTCTATGAGAAAACACCTGCAGGCCGCATCCACAAAGGAGTTTGTT

CAACTTGGATGAAGAACGCAGTGCCTATGACCGAGAGTCAAGATTGCAGTTGGGCCCCAATATACGTC

CGAACATCCAATTTCAGACTACCATCTGACCCTAAGGTCCCGGTTATCATGATTGGACCTGGCACTGG

TTTGGCTCCTTTTAGAGGTTTCCTTCAAGAGCGGTTAGCTTTAAAGGAAGCCGGAACTGACCTCGGTT

TATCCATTTTATTCTTCGGATGTAGGAATCGCAAAGTGGATTTCATATATGAAAACGAGCTTAACAAC

TTTGTGGAGACTGGTGCTCTTTCTGAGCTTATTGTTGCTTTCTCCCGTGAAGGCCCGACTAAGGAATA

TGTGCAACACAAGATGAGTGAGAAGGCTTCGGATATCTGGAACTTGCTTTCTGAAGGAGCATATTTAT

ACGTATGTGGTGATGCCAAAGGCATGGCCAAAGATGTACATCGAACCCTCCACACAATTGTGCAAGAA

CAGGGATCTCTTGACTCGTCAAAGGCAGAACTCTACGTGAAGAATCTACAAATGTCAGGAAGATACCT

CCGTGACGTTTGGTAA
```

Stevia rebaudiana UGT85C2 (codon optimized)
SEQ ID NO: 8

```
atggatgcaa tggcaactac tgagaaaaag cctcatgtga tcttcattcc atttcctgca    60
caatctcaca taaaggcaat gctaaagtta gcacaactat tacaccataa gggattacag    120
ataactttcg tgaataccga cttcatccat aatcaatttc tggaatctag tggccctcat    180
tgtttggacg gagccccagg gtttagattc gaaacaattc ctgacggtgt ttcacattcc    240
ccagaggcct ccatcccaat aagagagagt ttactgaggt caatagaaac caacttttg    300 gatcgtttca ttgacttggt cacaaaactt ccagacccac caacttgcat aatctctgat    360
ggctttctgt cagtgtttac tatcgacgct gccaaaaagt tgggtatccc agttatgatg    420
tactggactc ttgctgcatg cggtttcatg ggtttctatc acatccattc tcttatcgaa    480
aagggttttg ctccactgaa agatgcatca tacttaacca acggctacct ggatactgtt    540
attgactggg taccaggtat ggaaggtata agacttaaag attttccttt ggattggtct    600
acagacctta atgataaagt attgatgttt actacagaag ctccacaaag atctcataag    660
gtttcacatc atatctttca cccttgat gaattggaac atcaatcat caaaaccttg    720 tctctaagat acaatcatat ctacactatt ggtccattac aattacttct agatcaaatt    780
cctgaagaga aaagcaaac tggtattaca tccttacacg ctactctttt agtgaaagag    840
gaaccagaat gttttcaatg gctacaaagt aaagagccta attctgtggt ctacgtcaac    900
ttcggaagta acacagtcat gtccttggaa gatatgactg aatttggttg ggcccttgct    960
aattcaaatc attactttct atggattatc aggtccaatt tggtaatagg ggaaaacgcc   1020
gtattacctc cagaattgga ggaacacatc aaaagagag gtttcattgc ttcctggtgt   1080
tctcaggaaa aggtattgaa acatccttct gttggtggtt tccttactca ttgcggttgg   1140
ggctctacaa tcgaatcact aagtgcagga gttccaatga tttgttggcc atattcatgg   1200
gaccaactta caaattgtag gtatatctgt aaagagtggg aagttggatt agaaatggga   1260
acaaaggtta acgtgatga agtgaaaaga ttggttcagg agttgatggg ggaaggtggc   1320
cacaagatga gaaacaaggc caaagattgg aaggaaaaag ccagaattgc tattgctcct   1380
aacgggtcat cctctctaaa cattgataag atggtcaaag agattacagt cttagccaga   1440
aactaa                                                               1446
```

S. rebaudiana UGT74G1 (GenBank AAR06920.1)
SEQ ID NO: 9

```
atggcggaac aacaaaagat caagaaatca ccacacgttc tactcatccc attcccttta    60
caaggccata taaacccttt catccagttt ggcaaacgat taatctccaa aggtgtcaaa    120
```

TABLE 14-continued

Sequences disclosed herein.

```
acaacacttg ttaccaccat ccacacctta aactcaaccc taaaccacag taacaccacc    180
accacctcca tcgaaatcca agcaatttcc gatggttgtg atgaaggcgg ttttatgagt    240
gcaggagaat catatttgga aacattcaaa caagttgggt ctaaatcact agctgactta    300
atcaagaagc ttcaaagtga aggaaccaca attgatgcaa tcatttatga ttctatgact    360
gaatgggttt tagatgttgc aattgagttt ggaatcgatg gtggttcgtt tttcactcaa    420
gcttgtgttg taaacagctt atattatcat gttcataagg gtttgatttc tttgccattg    480
ggtgaaactg tttcggttcc tggatttcca gtgcltcaac ggtgggagao accgttaatt    540 ttgcagaatc atgagcaaat acagagccct tggtctcaga tgttgtttgg tcagtttgct    600
aatattgatc aagcacgttg ggtcttcaca aatagttttt acaagctcga ggaagaggta    660
atagagtgga cgagaaagat atggaacttg aaggtaatcg ggccaacact tccatccatg    720
taccttgaca aacgacttga tgatgataaa gataacggga ttaatctcta caaagcaaac    780
catcatgagt gcatgaactg gttagacgat aagccaaagg aatcagttgt ttacgtagca    840
tttggtagcc tggtgaaaca tggacccgaa caagtggaag aaatcacacg ggctttaata    900
gatagtgatg tcaacttctt gtgggttatc aaacataaag aagagggaaa gctcccagaa    960
aatctttcgg aagtaataaa aaccggaaag ggtttgattg tagcatggtg caaacaattg   1020
gatgtgttag cacacgaatc agtaggatgc tttgttacac attgtgggtt caactcaact   1080
cttgaagcaa taagtcttgg agtccccgtt gttgcaatgc ctcaattttc ggatcaaact   1140
acaaatgcca agcttctaga tgaaattttg ggtgttggag ttagagttaa ggctgatgag   1200
aatgggatag tgagaagagg aaatcttgcg tcatgtatta agatgattat ggaggaggaa   1260
agaggagtaa taatccgaaa gaatgcggta aaatggaagg atttggctaa agtagccgtt   1320
catgaaggtg gtagctcaga caatgatatt gtcgaatttg taagtgagct aattaaggct   1380 taaattttg ttgctttgta ttttatgtgt tatggttttt tgatttagat gtattcaatt   1440
aatattgaat cataactaaa ttcaagatta ttgtttgtaa tattctttgt cctaaaattt   1500
tgcgacttaa aacctttagt ttataaaaag aaattagaaa atactattgc acgga         1555
```

*S. rebaudiana* UGT76G1 (codon optimized)

SEQ ID NO: 10

```
atggaaaaca agaccgaaac aacagttaga cgtaggcgta gaatcattct gtttccagta     60
ccttttcaag ggcacatcaa tccaatacta caactagcca acgttttgta ctctaaaggt    120
ttttctatta caatctttca caccaatttc aacaaaccaa aaacatccaa ttacccacat    180
ttcacattca gattcatact tgataatgat ccacaagatg aacgtatttc aaacttacct    240
acccacggtc ctttagctgg aatgagaatt ccaatcatca tgaacatggt gccgatgag    300 cttagaagag aattagagtt acttatgttg gcatccgaag aggacgagga agtctcttgt    360
ctgattactg acgctctatg gtactttgcc caatctgtgg ctgatagttt gaatttgagg    420
agattggtac taatgacatc cagtctgttt aactttcacg ctcatgttag tttaccacaa    480
tttgacgaat gggatacttt ggaccctgat gacaagacta ggttagagga caggcctct    540 ggttttccta tgttgaaagt caaagatatc aagtctgcct attctaattg gcaaatcttg    600
aaagagatct taggaaagat gatcaaacag acaaaggctt catctggagt gatttggaac    660
agtttcaaag agttagaaga gtctgaattg gagactgtaa tcagagaaat tccagcacct    720
tcattcctga taccattacc aaaacatttg actgcttcct cttcctcttt gttggatcat    780
gacagaacag tttttcaatg gttggaccaa caaccaccta gttctgtttt gtacgtgtca    840
```

TABLE 14-continued

Sequences disclosed herein.

```
tttggtagta cttctgaagt cgatgaaaag gacttccttg aaatcgcaag aggcttagtc    900
gatagtaagc agtcattcct ttgggtcgtg cgtccaggtt tcgtgaaagg ctcaacatgg    960
gtcgaaccac ttccagatgg ttttctaggc gaaagaggta gaatagtcaa atggggttcct  1020
caacaggaag ttttagctca tggcgctatt ggggcattct ggactcattc cggatggaat   1080
tcaactttag aatcagtatg cgaaggggta cctatgatct tttcagattt tggtcttgat   1140
caaccactga acgcaagata catgtctgat gttttgaaag tgggtgtata tctagaaaat   1200
ggctgggaaa ggggtgaaat agctaatgca ataagacgtg ttatggttaa tgaagagggg   1260
gagtatatca gacaaaacgc aagagtgctg aagcaaaagg ccgacgtttc tctaatgaag   1320
ggaggctctt catacgaatc cttagaatct cttgtttcct acatttcatc actgtaa     1377
```

*S. rebaudiana* UGT91D2e-b (codon optimized)

SEQ ID NO: 11
```
atggctactt ctgattccat cgttgacgat agaaagcaat gcatgttgc tacttttcca     60
tggttggctt tcggtcatat tttgccatac ttgcaattgt ccaagttgat tgctgaaaag   120
ggtcacaagg tttcattctt gtctaccacc agaaacatcc aaagattgtc ctctcatatc   180
tccccattga tcaacgttgt tcaattgact ttgccaagag tccaagaatt gccagaagat   240
gctgaagcta ctactgatgt tcatccagaa gatatccctt acttgaaaaa ggcttccgat   300
ggtttacaac cagaagttac tagattcttg gaacaacatt ccccagattg gatcatctac   360
gattatactc attactggtt gcatccatt gctgcttcat ggggtatttc tagagcccat   420
ttctctgtta ctactccatg ggctattgct tatatgggtc catctgctga tgctatgatt   480
aacggttctg atggtagaac taccgttgaa gatttgacta ctccaccaaa gtggtttcca   540
tttccaacaa aagtctgttg gagaaaacac gatttggcta gattggttcc atacaaagct   600
ccaggtattt ctgatggtta cagaatgggg atggttttga aaggttccga ttgcttgttg   660
tctaagtgct atcatgaatt cggtactcaa tggttgcctt tgttggaaac attgcatcaa   720
gttccagttg ttccagtagg tttgttgcca ccagaaattc caggtgacga aaaagacgaa   780
acttgggttt ccatcaaaaa gtggttggat ggtaagcaaa agggttctgt tgtttatgtt   840
gctttgggtt ccgaagcttt ggtttctcaa accgaagttg ttgaattggc tttgggtttg   900
gaattgtctg gtttgccatt tgtttgggct acagaaaaac ctaaaggtcc agctaagtct   960
gattctgttg aattgccaga tggtttcgtt gaaagaacta gaaatagagg tttggtttgg  1020
acttcttggg ctccacaatt gagaatttg tctcatgaat ccgtctgtgg tttcttgact  1080
cattgtggtt ctggttctat cgttgaaggt ttgatgtttg gtcacccatt gattatgttg  1140
ccaatctttg gtgaccaacc attgaacgct agattattgg aagataagca agtcggtatc  1200
gaaatcccaa gaaatgaaga agatggttgc ttgaccaaag aatctgttgc tagatctttg  1260
agatccgttg tcgttgaaaa agaaggtgaa atctacaagg ctaacgctag agaattgtcc  1320
aagatctaca acgataccaa ggtcgaaaaa gaataggttt cccaattcgt tgactacttg  1380
gaaaagaatg ctagagctgt tgccattgat catgaatctt ga                     1422
```

*Oryza sativa* sequence encoding EUGT11 (codon optimized)

SEQ ID NO: 12
```
atggatagtg ctactcctc atcttatgct gctgccgctg gtatgcacgt tgtgatctgc     60
ccttggttgg cctttggtca cctgttacca tgtctggatt tagcccaaag actggcctca   120
agaggccata gagtatcatt tgtgtctact cctagaaata tctctcgttt accaccagtc   180
agacctgctc tagctcctct agttgcattc gttgctcttc cacttccaag agtagaagga   240
```

TABLE 14-continued

Sequences disclosed herein.

```
ttgccagacg gcgctgaatc tactaatgac gtaccacatg atagacctga catggtcgaa    300
ttgcatagaa gagcctttga tggattggca gctccatttt ctgagttcct gggcacagca    360
tgtgcagact gggttatagt cgatgtattt catcactggg ctgctgcagc cgcattggaa    420
cataaggtgc cttgtgctat gatgttgtta gggtcagcac acatgatcgc atccatagct    480
gatagaagat tggaaagagc tgaaacagaa tccccagccg cagcaggaca aggtaggcca    540
gctgccgccc caacctttga agtggctaga atgaaattga ttcgtactaa aggtagttca    600
gggatgagtc ttgctgaaag gttttctctg acattatcta gatcatcatt agttgtaggt    660
agatcctgcg tcgagttcga acctgaaaca gtacctttac tatctacttt gagaggcaaa    720
cctattactt tccttggtct aatgcctcca ttacatgaag aaggagaga agatggtgaa    780 gatgctactg ttaggtggtt agatgcccaa cctgctaagt ctgttgttta cgttgcattg    840
ggttctgagg taccactagg ggtggaaaag gtgcatgaat tagcattagg acttgagctg    900
gccggaacaa gattcctttg ggctttgaga aaaccaaccg tgtttctga cgccgacttg    960 ctaccagctg ggtcgaaga gagaacaaga ggccgtggtg tcgttgctac tagatgggtc   1020
ccacaaatga gtattctagc tcatgcagct gtaggggcct ttctaaccca ttgcggttgg   1080
aactcaacaa tagaaggact gatgtttggt catccactta ttatgttacc aatctttggc   1140
gatcagggac craacgcaag attgattgag gcaagaacg caggtctgca ggttgcacgt   1200
aatgatggtg atggttcctt tgatagaaa ggcgttgcag ctgccatcag agcagtcgcc   1260
gttgaggaag agtcatctaa agttttccaa gctaaggcca aaaaattaca agagattgtg   1320
gctgacatgg cttgtcacga aagatacatc gatggtttca tccaacaatt gagaagttat   1380
aaagactaa                                                           1389
```

YBR180W
>sp|P38125|DTR1_YEAST Dityrosine transporter 1 OS = Saccharomyces
cerevisiae (strain ATCC 204508/S288c) GN = DTR1 PE = 1 SV = 1
SEQ ID NO: 13

MGSEPFQKKNLGLQINSQESGTTRSTFHSLEDLGDDVINESWDQVNQKRANIDHDVFHEH

PDSSPSLSAQKAKTKEEEVAVKSSNSQSRDPSPDTQAHIPYTYFSKDQRLIIFGIIIFIG

FLGPMSGNIYIPALPLLQREYDVSATTINATVSVFMAVFSVGPLFWGALADFGGRKFLYM

VSLSLMLIVNILLAAVPVNIAALFVLRIFQAFASSSVISLGAGTVIDVVPPKHRGKAIAY

FMMGPNMGPIIAPIVAGLILMKGNYWRWLFGFTSIMTGIALILVTALLPETLRCIVGNGD

PKWGDKKDERENNESPFFEGNKISHRRLFPDIGIRKPVNNDAFFQENFPKPPKAGLTLYW

KMIKCPPIIITSVSTALLFSSYYAFSVTFSYYLEHDYRFTMLEIGAAYVCPGVAMLLGSQ

SGGHLSDYLRSRWIKSHPKKKFPAEFRLLLNLIGILLTICGTIGYGWAIFFHYHFVVLLV

FSALTAFGMTWCSNISMTYLTELFPKRAAGTVAVSSFFRNVGAAISSAIILQLCNAMGIG

WCFTGLGLCSSISLIGILYLLIFQRKYTAKEF

YAL067C
>sp|P39709|SEO1_YEAST Probable transporter SEO1 OS = Saccharomyces
cerevisiae (strain ATCC 204508/S288c) GN = SEO1 PE = 1 SV = 1
SEQ ID NO: 14

MYSIVKEIIVDPYKRLKWGFIPVKRQVEDLPDDLNSTEIVTISNSIQSHETAENFITTTS

EKDQLHFETSSYSEHKDNVNVTRSYEYRDEADRPWWRFFDEQEYRINEKERSHNKWYSWF

KQGTSFKEKKLLIKLDVLLAFYSCIAYWVKYLDTVNINNAYVSGMKEDLGFQGNDLVHTQ

VMYTVGNIIFQLPFLIYLNKLPLNYVLPSLDLCWSLLTVGAAYVNSVPHLKAIRFFIGAF

EAPSYLAYQYLFGSFYKHDEMVRRSAFYYLGQYIGILSAGGIQSAVYSSLNGVNGLEGWR

TABLE 14-continued

Sequences disclosed herein.

WNFIIDAIVSVVVGLIGFYSLPGDPYNCYSIFLTDDEIRLARKRLKENQTGKSDFETKVF

DIKLWKTIFSDWKIYILTLWNIFCWNDSNVSSGAYLLWLKSLKRYSIPKLNQLSMITPGL

GMVYLMLTGIIADKLHSRWFAIIFTQVFNIIGNSILAAWDVAEGAKWFAFMLQCFGWAMA

PVLYSWQNDICRRDAQTRAITLVTMNIMAQSSTAWISVLVWKTEEAPRYLKGFTFTACSA

FCLSIWTFVVLYFYKRDERNNAKKNGIVLYNSKHGVEKPISKDVETLSVSDEK

YBL089W
>sp|P38176|AVT5_YEAST Vacuolar amino acid transporter 5
OS = Saccharomyces cerevisiae (strain ATCC 204508/S288c) GN = AVT5
PE = 3 SV = 2
SEQ ID NO: 15

MPSNVRSGVLTLLHTACGAGVLAMPFAFKPFGLMPGLITLTFCGICSLCGLLLQTRIAKY

VPKSENASFAKLTQLINPSISVVFDFAIAVKCFGVGVSYLIIVGDLVPQIVQSIFYRNDD

NMSGSQEHHMFLDRRLYITLIIVFVISPLCFKRSLNSLRYASMIAIVSVAYLSGLIIYHF

VNRHQLERGQVYFMVPHGDSQSHSPLTTLPIFVFAYTCHHNMFSVINEQVDKSFKVIRRI

PIFAIVLAYFLYIIIGGTGYMTFGENIVGNILTLYPNSISTTIGRLAMLLLVMLAFPLQC

HPCRSSVKNIIIFIENFRKGKLYDNRASFIPLDNFNSEDPQEAPTQQNNEEPNLRSESLR

HINIITLCILLFSYLLAISITSLAKVLAIVGAIGSTSISFILPGLEGYKLIGSEFTGINE

RVPTSIKIFKYLSLSLFIWGIAVMVASLSAIVFLGTSSH

YBL099W
>sp|P07251|ATPA_YEAST ATP synthase subunit alpha, mitochondrial
OS = Saccharomyces cerevisiae (strain ATCC 204508/S288c) GN = ATP1
PE = 1 SV = 5
SEQ ID NO: 16

MLARTAAIRSLSRTLINSTKAARPAAAALASTRRLASTKAQPTEVSSILEERIKGVSDEA

NLNETGRVLAVGDGIARVFGLNNIQAEELVEFSSGVKGMALNLEPGQVGIVLEGSDRLVK

EGELVKRTGNIVDVEWGPGLLGRVVDALGNPIDGKGPIDAAGRSRAQVKAPGILPRRSVH

EPVQTGLKAVDALVPIGRGQRELIIGDRQTGKTAVALDTILNQKRWNNGSDESKKLYCVY

VAVGQKRSTVAQLVQTLEQHDAMKYSIIVAATASEAAPLQYLAPFTAASIGEWERDNGKH

ALIVYDDLSKQAVAYRQLSLLLRRPPGREAYPGDVFYLHSRLLERAAKLSEKEGSGSLTA

LPVIETQGGDVSAYIPTNVISITDGQIFLEAELFYKGIRPAINVGLSVSRVGSAAQVKAL

KQVAGSLKLFLAQYREVAAFAQFGSDLDASTKQTLVRGERLTQLLKQNQYSPLATEEQVP

LIYAGVNGHLDGIELSRIGEFESSFLSYLKSNHNELLTEIREKGELSKELLASLKSATES

FVATF

YBR241C
>sp|P38142|YB91_YEAST Probable metabolite transport protein YBR241C
OS = Saccharomyces cerevisiae (strain ATCC 204508/S288c) GN = YBR241C
PE = 1 SV = 1
SEQ ID NO: 17

MAETERLMPNGGSRETKPLITGHLILGTIVACLGSIQYGYHIAELNAPQEFLSCSRFEAP

DENISYDDTWVGQHGLKQCIALTDSQYGAITSIFSIGGLFGSYYAGNWANRYGRKYVSMG

ASAMCMVSSLLLFFSNSYLQLLFGRFLVGMSCGTAIVITPLFINEIAPVEWRGAMGSMNQ

VSINLGILLTQTLALKYADSYNWRWLLFSGSVIAVANILAWLKVDESPRWLVSHGFVSEA

ETALFKLRPGTYQQAKQEIQDWQRSHGHNRDPESSEETHSGPTLWQYVTDPSYKKPRTVI

LAILSCQQFCGINSIIFYGVKVIGKILPDYSIQVNFAISILNVVVILAASAIIDHVGRRP

LLLASTTVMTAMSLLISVGLTLSVSFLLVTATEVYIAAFAIGLGPIPFLIIGELSYPQDA

ATAQSFGTVCNWLATFIVGYLFPIGHGLMGGYVFAIFAAIAAMFATYVYKRVPETKGKIT

TABLE 14-continued

Sequences disclosed herein.

YSEVWAGY

YBR294W
>sp|P38359|SUL1_YEAST Sulfate permease 1 OS = *Saccharomyces cerevisiae*
(strain ATCC 204508/S288c) GN = SUL1 PE = 1 SV = 2

SEQ ID NO: 18

MSRKSSTEYVHNQEDADIEVFESEYRTYRESEAAENRDGLHNGDEENWKVNSSKQKFGVT

KNELSDVLYDSIPAYEESTVTLKEYYDHSIKNNLTAKSAGSYLVSLFPIIKWFPHYNFTW

GYADLVAGITVGCVLVPQSMSYAQIASLSPEYGLYSSFIGAFIYSLFATSKDVCIGPVAV

MSLQTAKVIAEVLKKYPEDQTEVTAPIIATTLCLLCGIVATGLGILRLGELVELISLNAV

AGFMTGSAFNIIWGQIPALMGYNSLVNTREATYKVVINTLKHLPNIKLDAVFGLIPLVIL

YVWKWWCGTFGITLADRYYRNQPKVANRLKSFYFYAQAMRNAVVIVVFTAISWSITRNKS

SKDRPISILGTVPSGLNEVGVMKIPDGLLSNMSSEIPASIIVLVLEHIAISKSFGRINDY

KVVPDQELIAIGVTNLIGIFFHSYTATGSFSRSALKAKCNVRTPFSGVFTGGCVLLALYC

LTDAFFFIPKATLSAVIIHAVSDLLTSYKTTWITWKTNPLDCISFIVIVFITVFSSIENG

IYFAMCWSCAMLLLKQAFPAGKFLGRVEVAEVLNPTVQEDIDAVISSNELPNELNKQVKS

TVEVLPAPEYKFSVKWVPFDRGYSRELNINTIVRPPPPGVIVYRLGDSFTYVNCSRHYDI

IFDRIKEETRRGQLITLRKKSDRPWNDPGEWKMPDSLKSLFKFKRHSATTNSDLPISNGS

SNGETYEKPLLKVVCLDFSQVAQVDSTAVQSLVDLRKAVNRYADRQVEFHFAGIISPWIK

RSLLSVKFGTTNEEYSDDSIIAGHSSFEVAKVLKDDVDYTDEDSRISTSYSNYETLCAAT

GTNLPFFHIDIPDFSKWDV

YCL069W
>sp|P25594|VBA3_YEAST Vacuolar basic amino acid transporter 3
OS = *Saccharomyces cerevisiae* (strain ATCC 204508/S288c) GN = VBA3
PE = 1 SV = 1

SEQ ID NO: 19

MNMLIVGRVVASVGGSGLQTLCFVIGCTMVGERSRPLVISILSCAFAVAAIVGPIIGGAF

TTHVTWRWCFYINLPIGGLAIIMFLLTYKAENKGILQQIKDAIGTISSFIFSKFRHQVNF

KRLMNGIIFKFDFFGFALCSAGLVLFLLGLTFGGNKYSWNSGQVIAYLVLGVLLFIFSLV

YDFFLFDKFNPEPDNISYRPLLLRRLVAKPAIIIINMVTFLLCTGYNGQMIYSVQFFQLI

FASSAWKAGLHLIPIVITNVIAAIASGVITKKLGLVKPLLIFGGVLGVIGAGLMTLMTNT

STKSTQIGVLLLPGFSLGFALQASLMSAQLQITKDRPEAAMDFIEVTAFNTFMKSLGTTL

GGVLSTTVFSASFHNKVSRAHLEPYEGKTVDDMILYRLQNYDGSHSTIGNILSDSIKNVF

WMDLGFYALGFLFCSFSSNKKLIIPKKDETPEDNLEDK

YCR028C
>sp|P25621|FEN2_YEAST Pantothenate transporter FEN2 OS = *Saccharomyces
cerevisiae* (strain ATCC 204508/S288c) GN = FEN2 PE = 1 SV = 1

SEQ ID NO: 20

MMKESKSITQHEVERESVSSKRAIKKRLLLFKIDLFVLSFVCLQYWINYVDRVGFTNAYI

SGMKEDLKMVGNDLTVSNTVFMIGYIVGMVPNNLMLLCVPPRIWLSFCTFAWGLLTLGMY

KVTSFKHICAIRFFQALFESCTFSGTHFVLGSWYKEDELPIRSAIFTGSGLVGSMFSGFM

QTSIFTHLNGRNGLAGWRWLFIIDFCITLPIAIYGFIFFPGLPDQTSAVSKFSMTRYIFN

EQELHYARRALPARDESTRLDWSTIPRVLKRWHWWMFSLVWVLGGENLGFASNSTFALWL

QNQKYTLAQRNNYTSGIFAVGIVSTLCSAVYMSKIPRARHWHVSVFISLVMVIVAVLIRA

DPLNPKVVFSAQYLGGVAYAGQAVFFSWANIICHADLQERAIVLASMNMFSGAVNAWWSI

LFFASDMVPKFERGCYALLATAISSGIVSVVIRSLQIKENLSKKQVPYIDANDMPGEDDD

DDNQDNENDGDDESMEVELHNEEMAEISNPFR

TABLE 14-continued

Sequences disclosed herein.

YCR075C
>sp|P17261|ERS1_YEAST Cystine transporter OS = Saccharomyces
cerevisiae (strain ATCC 204508/S288c) GN = ERS1 PE = 1 SV = 1

SEQ ID NO: 21

MVSLDDILGIVYVTSWSISKYPPIITNWRHKSASAISMDFVMLNTAGYSYLVISIFLQLY

CWKMTGDESDLGRPKLTQFDFWYCLHGCLMNVVLLTQVVAGARIWRFPGKGHRKMNPWYL

RILLASLAIFSLLTVQFMYSNYWYDWHNSRTLAYCNNLFLLKISMSLIKYIPQVTHNSTR

KSMDCFPIQGVFLDVTGGIASLLQLIWQLSNDQGFSLDTFVTNFGKVGLSMVTLIFNFIF

IMQWFVYRSRGHDLASEYPL

YDL128W
>sp|Q99385|VCX1_YEAST Vacuolar calcium ion transporter
OS = Saccharomyces cerevisiae (strain ATCC 204508/S288c) GN = VCX1
PE = 1 SV = 1

SEQ ID NO: 22

MDATTPLLTVANSHPARNPKHTAWRAAVYDLQYILKASPLNFLLVFVPLGLIWGHFQLSH

TLTFLFNFLAIIPLAAILANATEELADKAGNTIGGLLNATFGNAVELIVSIIALKKGQVR

IVQASMLGSLLSNLLLVLGLCFIFGGYNRVQQTFNQTAAQTMSSLLAIACASLLIPAAFR

ATLPHGKEDHFIDGKILELSRGTSIVILIVYVLFLYFQLGSHHALFEQQEEETDEVMSTI

SRNPHHSLSVKSSLVILLGTTVIISFCADFLVGTIDNVVESTGLSKTFIGLIVIPIVGNA

AEHVTSVLVAMKDKMDLALGVAIGSSLQVALFVTPFMVLVGWMIDVPMTLNFSTFETATL

FIAVFLSNYLILDGESNWLEGVMSLAKYILIAMAFFYYPDEKTLDSIGNSL

YDL185W
>sp|P17255|VATA_YEAST V-type proton ATPase catalytic subunit A
OS = Saccharomyces cerevisiae (strain ATCC 204508/S288c) GN = VMA1
PE = 1 SV = 3

SEQ ID NO: 23

MAGAIENARKEIKRISLEDHAESEYGAIYSVSGPVVIAENMIGCAMYELVKVGHDNLVGE

VIRIDGDKATIQVTEETAGLTVGDPVLRTGKPLSVELGPGLMETIYDGIQRPLKAIKEES

QSIYIPRGIDTPALDRTIKWQFTPGKFQVGDHISGGDIYGSVFENSLISSHKILLPPRSR

GTITWIAPAGEYTLDEKILEVEFDGKKSDFTLYHTWPVRVPRPVTEKLSADYPLLTGQRV

LDALFPCVQGGTTCIPGAFGCGKTVISQSLSKYSNSDAITYVGCFAKGTNVLMADGSIEC

IENIEVGNKVMGKDGRPREVIKLPRGRETMYSVVQKSQHRAHKSDSSREVPELLKFTCNA

THELVVRTPRSVRRLSRTIKGVEYFEVITFEMGQKKAPDGRIVELVKEVSKSYPISEGPE

RANELVESYRKASNKAYFEWTIEARDLSLLGSHVRKATYQTYAPILYENDHFFDYMQKSK

FHLTIEGPKVLAYLLGLWIGDGLSDRATFSVDSRDTSLMERVTEYAEKLNLCAEYKDRKE

PQVAKTVNLYSKVVRGNGIRNNLNTENPLWDAIVGLGFLKDGVKNIPSFLSTDNIGTRET

FLAGLIDSDGYVTDEHGIKATIKTIHTSVRDGLVSLARSLGLVVSVNAEPAKVDMNGTKH

KISYAIYMSGGDVLLNVLSKCAGSKKFRPAPAAAFARECRGFYFELQELKEDDYYGITLS

DDSDHQFLLANQVVVHNCGERGNEMAEVLMEFFELYTEMSGTKEPIMKRTTLVANTSNMP

VAAREASIYTGITLAEYFRDQGKNVSMIADSSSRWAEALREISGRLGEMPADQGFPAYLG

AKLASFYERAGKAVALGSPDRTGSVSIVAAVSRAGGDFSDPVTTATLGITQVFWGLDKKL

AQRKHFPSINTSVSYSKYTNVLNKFYDSNYPEFPVLRDRMKEILSNAEELEQVVQLVGKS

ALSDSDKITLDVATLIKEDFLQQNGYSTYDAFCPIWKTFDMMRAFISYHDEAQKAVANGA

NWSKLADSTGDVKHAVSSSKFFEPSRGEKEVHGEFEKLLSTMQERFAESTD

TABLE 14-continued

Sequences disclosed herein.

YDL194W
>sp|P10870|SNF3_YEAST High-affinity glucose transporter SNF3
OS = *Saccharomyces cerevisiae* (strain ATCC 204508/S288c) GN = SNF3
PE = 1 SV = 3

SEQ ID NO: 24

MDPNSNSSSETLRQEKQGFLDKALQRVKGIALRRNNSNKDHTTDDTTGSIRTPTSLQRQN

SDRQSNMTSVFTDDISTIDDNSILFSEPPQKQSMMMSICVGVETAVGGFLFGYDTGLINS

ITSMNYVKSHVAPNHDSFTAQQMSILVSFLSLGTFFGALTAFFISDSYGRKPTIIFSTIF

IFSIGNSLQVGAGGITLLIVGRVISGIGIGAISAVVPLYQAEATHKSLRGAIISTYQWAI

TWGLLVSSAVSQGTHARNDASSYRIPIGLQYVWSSFLAIGMFFLPESPRYYVLKDKLDEA

AKSLSFLRGVPVHDSGLLEELVEIKATYDYEASFGSSNFIDCFISSKSRPKQTLRMFTGI

ALQAFQQFSGINFIFYYGVNFFNKTGVSNSYLVSFITYAVNVVFNVPGLFFVEFFGRRKV

LVVGGVIMTIANFIVAIVGCSLKTVAAAKVMIAFICLFIAAFSATWGGVVWVISAELYPL

GVRSKCTAICAAANWLVNFICALITPYIVDTGSHTSSLGAKIFFIWGSLNAMGVIVVYLT

VYETKGLTLEEIDELYIKSSTGVVSPKFNKDIRERALKFQYDPLQRLEDGKNTFVAKRNN

FDDETPRNDFRNTISGEIDHSPNQKEVHSIPERVDIPTSTEILESPNKSSGMTVPVSPSL

QDVPIPQTTEPAEIRTKYVDLGNGLGLNTYNRGPPSLSSDSSEDYTEDEIGGPSSQGDQS

NRSTMNDINDYMARLIHSTSTASNTTDKFSGNQSTLRYHTASSHSDTTEEDSNLMDLGNG

LALNAYNRGPPSILMNSSDEEANGGETSDNLNTAQDLAGMKERMAQFAQSYIDKRGGLEP

ETQSNILSTSLSVMADTNEHNNEILHSSEENATNQFVNENNDLK

YDL210W
>sp|P32837|UGA4_YEAST GABA-specific permease OS = *Saccharomyces cerevisiae* (strain ATCC 204508/S288c) GN = UGA4 PE = 1 SV = 1

SEQ ID NO: 25

MSMSSKNENKISVEQRISTDIGQAYQLQGLGSNLRSIRSKTGAGEVNYIDAAKSVNDNQL

LAEIGYKQELKRQFSTLQVFGIAFSIMGLLPSIASVMGGGLGGGPATLVWGWFVAAFFIL

LVGITMAEHASSIPTAGGLYYWTYYYAPEGYKEIISFIIGCSNSLALAAGVCSIDYGLAE

EIAAAVTLIKDGNFEVTSGKLYGIFAGAVVVMCICTCVASGAIARLQTLSIFANLFIIVL

LFIALPIGTKHRMGGENDGDFIEGKYENLSDWNNGWQFCLAGEMPAVWTIGSFDSCVHQS

EEAKDAKKSVPIGIISSIAVCWILGWLIIICLMACINPDIDSVLDSKYGFALAQIIYDSL

GKKWAIAFMSLIAFCQFLMGASITTAVSRQVWAFSRDNGLPLSKYIKRVDSKYSVPFFAI

LAACVGSLILGLLCLIDDAATDALFSLAVAGNNLAWSTPTVERLTSGRDLFRPGPFYLGK

IWSPIVAWTGVAFQLFIIILVMFPSQQHGITKSTMNYACVIGPGIWILAGIYYKVYKKKY

YHGPATNLSDDDYTEAVGADVIDTIMSKQEP

YDR061W
>sp|Q12298|YD061_YEAST Uncharacterized ABC transporter ATP-binding
protein YDR061W OS = *Saccharomyces cerevisiae* (strain ATCC 204508/S288c) GN = YDR061W PE = 1 SV = 2

SEQ ID NO: 26

MSTNKFVVRITNALEKSSLASNSPPVY2KRIRHFEILPNEKWVIWGPGKGKFLDVLNNKY

ICEPPLSLREGFLKESSNILPRIEQVAFKGVMPTAHLSARYEYEKDDYDQTCKQFIFDKA

SGSNAVSYKVETNNRQINMELYNALVENLNLSSLQDRWVMGLSNGQMRRARLARSILKEP

DLLLIDDPFLGLDPAAIATISQFLAKYDSIEVSGGCPIVIGLRYQDTIPAWCTHICCVDE

KNGILFEGPIEKLQSKMDETRSRALKELEQLKKASNSKEDISINDLICIHPMYGKKEHEI

IKMPHLIELDGLSVSYKGEAVLENLHWKVQPGSKWHIRGDNGSGKSILLSLLTAEHPQSW

NSRVIDNGVPRRIGKINYFDLNSKIGMSSPELHAIFLKNAGGRLNIRESVATGYHEASSN

TABLE 14-continued

Sequences disclosed herein.

NYLPIWKRLDKNSQEIVNMYLKYTGLDKDADSVLFEQLSVSDQKLVLEVRSLIKMPQILI

LDEAFSGMEVEPMMRCHEFLEEWPGTVLVVAHVAEETPKCAHYLRLISPGEYEIGDMEN

YDR093W
>sp|Q12675|ATC4_YEAST Phospholipid-transporting ATPase DNF2
OS = Saccharomyces cerevisiae (strain ATCC 204508/S288c) GN = DNF2
PE = 1 SV = 1

SEQ ID NO: 27

MSSPSKPTSPFVDDIEHESGSASNGLSSMSPFDDSFQFEKPSSAHGNIEVAKTGGSVLKR

QSKPMKDISTPDLSKVIFDGIDDYSNDNDINDDDELNGKKTEIHEHENEVDDDLHSFQAT

PMPNTGGFEDVELDNNEGSNNDSQADHKLKRVREGTRRNKSGRIDINRSKILKWAKKNFH

NAIDEFSTKEDSLENSALQNRSDELRTVYYNLPLPEDMLDEDGLPLAVYPRNKIRTIKYT

PLTFFPKNILFQFHNFANIYFLILLILGAFQIFGVTNPGFASVPLIVIVIITAIKDGIED

SRRTVLDLEVNNTRTHILSGVKNENVAVDNVSLWRRFKKANTRALIKIFEYFSENLTAAG

REKKLQKKREELRRKRNSRSFGPRGSLDSIGSYRMSADFGRPSLDYENLNQTMSQANRYN

DGENLVDRTLQPNPECRFAKDYWKNVKVGDIVRVHNNDEIPADMILLSTSDVDGACYVET

KNLDGETNLKVRQSLKCSKIIKSSRDITRTKFWVESEGPHANLYSYQGNEKWQDTQNGNI

RNEPVNINNLLLRGCTLRNTKWAMGMVIFTGDDTKIMINAGVIPTKKSRISRELNESVIL

NFVLLFILCFTAGIVNGVYYKQKPRSRDYFEFGTIGGSASTNGFVSFWVAVILYQSLVPI

SLYISVEIIKTAQAIFIYTDVLLYNAKLDYPCIPKSWNISDDLGQIEYIFSDKTGTLTQN

VMEFKKCTINGVSYGRAYTEALAGLRKRQGVDVESEGRREKEEIAKDRETMIDELRSMSD

NTQFCPEDLTFVSKEIVEDLKGSSGDHQQKCCEHFLLALALCHSVLVEPNKDDPKKLDIK

AQSPDESALVSTARQLGYSFVGSSKSGLIVEIQGVQKEFQVLNVLEFNSSRKRMSCIIKI

PGSTPKDEPKALLICKGADSVIYSRLDRIQNDAILLEKTALHLEEYATEGLRTLCLAQRE

LTWSEYERWVKTYDVAAASVTNREEELDKVIDVIERELILLGGTAIEDRLQDGVPDSIAL

LAEAGIKLWVLTGDKVETAINIGESCNVLNNDMELLVVKASGEDVEEFGSDPIQVVNNLV

TKYLREKEGMSGSEEELKEAKREHGLPQGNFAVIIDGDALKVALNGEEMRRKELLLCKNC

KAVLCCRVSPAQKAAVVKLVKKTLDVMTLAIGDGSNDVAMIQSADVGVGIAGEEGRQAVM

CSDYAIGQFRYVTRLVLVHGKWCYKRLAEMIPQFFYKNVIFTLSLFWYGIYNNFDGSYLF

EYTYLTFYNLAFTSVPVILLAVLDQDVSDTVSMLVPQLYRVGILRKEWNQTKFLWYMLDG

VYQSVICEFFPYLAYRKNMVVTENGLGLDHRYFVGVEVTAIAVTSCNEYVFMEQYRWDWF

CGLFICLSLAVFYGWTGIWTSSSSSNEFYKGAARVFAQPAYWAVLFVGVLFCLLPRFTID

CIRKIFYPKDIEIVREMWLRGDFDLYPQGYDPTDPSRPRINEIRPLTDEKEPISLDTHED

GVSHSQETIVTEEIPMSILNGEQGSRKGYRVSTTLERRDQLSPVTTTNNLPRRSMASARG

NKLRTSLDRTREEMLANHQLDTRYSVERARASLDLPGINHAETLLSQRSRDR

YDR338C
>sp|Q05497|YD338_YEAST Uncharacterized transporter YDR338C
OS = Saccharomyces cerevisiae (strain ATCC 204508/S288c) GN = YDR338C
PE = 1 SV = 1

SEQ ID NO: 28

MAGILSKTLSEVHPSLRTNGMGIGNTHRRISLGELPPNKKNPLVRKFRARTRNIDQRSFR

SLTDDEGSNVHEPNPYIGNIDEEPDLYYHDEEDGELSRTISLPSRVSETPELSPQDVDWI

LHEHERRYSSVCNSDNEEASQSNTPDRIQEYSGRELEYDEFMNRLQAQKQKLTRSAVTDA

KGTSHHRRPSFVSVTSRGSVPTIYQEIDENDSEALAELAHSHVTFKSEARVLASYSFPLI

FTELLEQIFPMVCSLTVGHLGKNELAAVSLASMTSNITLAIFEGIATSLDTLCPQAYGSG

TABLE 14-continued

Sequences disclosed herein.

REYSVGVHLQRCIAFSLVIYIETAVMWWYSEPLLSYIIPEKELINLTSRFLRVLILGAPA

YIFFENLKRFLQAQGIFDAGIYVLTICAPLNVLVSYTLVWNKYIGVGFIGAAIAVVLNEW

LMFELLLFYALYIDGRKCWGGESRKAFTHWNDLGHLAFSGIIMLEAEELSYELLTLFSAY

YGVSYLAAQSAVSTMAALLYMIFFAIGISTSTRIANFIGAKRTDFAHISSQVGLSFSFIA

GFINCCILVFGRNLIANIYSKDPEVIKLIAQVLPLVGIVQNFDSLNAVAGSCLRGQGMQS

LGSIVNLMAYYLEGIPLALILSWEEDMKLYGLWIGIGSAMLLIGLVEAYYVLEPDWDKIM

TYAEILKETEDDEVDSDEYITDSDDPDENTALLGA

YDR406W
>sp|Q04182|PDR15_YEAST ATP-dependent permease PDR15 OS = *Saccharomyces cerevisiae* (strain ATCC 204508/S288c) GN = PDR15 PE = 1 SV = 1
SEQ ID NO: 29

MSSDIRDVEERNSRSSSSSSSSNSAAQSIGQHPYRGEDSEAAERVHELARTLTSQSLLYT

ANSNNSSSSNHNAHNADSRSVESTDMEGVNPVETNPDTPGYNPKLDPNSDQFSSTAWVQN

MANICTSDPDFYKPYSLGCVWKNLSASGDSADVSYQSTFANIVPKLLTKGLRLLKPSKEE

DTFQILKPMDGCLNPGELLVVLGRPGSGCTTLLKSISSNSHGFKIAKDSIVSYNGLSSSD

IRKHYRGEVVYNAESDIHLPHLTVYQTLFTVARMKTPQNRIKGVDREAYANHVTEVAMAT

YGLSHTRDTKVGNDLVRGVSGGERKRVSIAEVAICGARFQCWDNATRGLDSATALEFIRA

LKTQADIGKTAATVAIYQCSQDAYDLEDKVCVLDDGYQLYFGPAKDAKKYFQDMGYYCPP

RQTTADFLTSITSPTERIISKEFIEKGTRVPQTPKDMAEYWLQSESYKNLIKDIDSTLEK

NTDEARNIIRDAHHAKQAKRAETSSPYVVNYGMQVKYLLIRNEWRMKQSASVTLWQVIGN

SVMAFILGSMFYKVMKKNDTSTFITRGAAMFFAILFNAFSCLLEIFSLYETRPITEKHRT

YSLYHPSADAFASVLSEMPFKLITAVCFNIIPYFLVDERRNGGVFFEYFLINVIATFTLS

HLFRCVGSLTKTLQEAMVPASMLLLAISMYTGFAIPKTKILGWSIWIWYINPLAYLFESL

MINEFHDRRFPCAQYIPAGPAYQNITGTQRVCSAVGAYPGNDYVLGDDFLKESYDYEHKH

KWRGEGIGMAYVVEFFEVYLILCEYNEGAKQKGEMVVFLRSKIKQLKKEGKLQEKHRPGD

IENNAGSSPDSATTEKKILDDSSEGSDSSSDNAGLGLSKSEAIFHWRDLCYDVPIKGGQR

RILNNVDGWVKPGTLTALMGASGAGKTTILDCLAERVTMGVITGNIFVDGRLRDESFPRS

IGYCQQQDLHLKTATVRESLRFSAYLRQPSSVSIEEKNRYVEEVIKILEMQQYSDAVVGV

AGEGLNVEQRKRLTIGVELAARPKLLVFLDEPTSGLDSQTAWDTCQLMRKLATHGQAILC

TIHQPSAILMQQFDRLLFLQKGGQTVYTGDLGEGCKTMIDYFESKGAHKCPPDANPAEWM

LEVVGAAPGSHATQDYNEVWRNSDEYKAVQEELDWMEKNLPGRSKEPTAEEHKPFAASLY

YQFKMVTIRLFQQYWRSPDYLWSKFILTIFNQVFIGFTFFKADRSLQGLQNQMLSIFMYT

VIFNPILQQYLPSFVQQRDLYEARERPSRTFSWLAFFLSQIIVEIPWNILAGTIAYCIYY

YAVGFYANASAAGQLHERGALFWLFSIAFYVYIGSMGLLMISFNEVAETAAHMGTLLFTM

ALSFCGVMATPKVMPRFWIFMYRVSPLTYMIDALLALGVANVDVKCSNYEMVKFTPPSGT

TCGDYMASYIKLAGTGYLSDPSATDICSFCAVSTTNAFLATFSSHYYRRWRNYGIFICYI

AFDYIAATFLYWLSRVPKKNGKISEKPKK

YDR536W
>sp|P39932|STL1_YEAST Sugar transporter STL1 OS = *Saccharomyces cerevisiae* (strain ATCC 204508/S288c) GN = STL1 PE = 1 SV = 2
SEQ ID NO: 30

MKDLKLSNFKGKFISRTSHWGLIGKKLRYFITIASMTGFSLFGYDQGLMASLITGKQFNY

EFPATKENGDHDRHATVVQGATTSCYELGCFAGSLFVMFCGERIGRKPLILMGSVITIIG

TABLE 14-continued

Sequences disclosed herein.

AVISTCAFRGYWALGQFIIGRVVTGVGIGLNTSTIPVWQSEMSKAENRGLLVNLEGSTIA

FGTMIAYWIDFGLSYTNSSVQWRFPVSMQIVFALFLLAFMIKLPESPRWLISQSRTEEAR

YLVGTLDDADPNDEEVITEVAMLHDAVNRTKHEKHSLSSLFSRGRSQNLQRALIAASTQF

FQQFTGCNAAIYYSTVLFNKTIKLDYRLSMIIGGVFATIYALSTIGSFFLIEKLGRRKLF

LLGATGQAVSFTITFACLVKENKENARGAAVGLFLFITFFGLSLLSLPWIYPPEIASMKV

RASTNAFSTCTNWLCNFAVVMFTPIFIGQSGWGCYLFFAVMNYLYIPVIFFFYPETAGRS

LEEIDIIFAKAYEDGTQPWRVANHLPKLSLQEVEDHANALGSYDDEMEKEDFGEDRVEDT

YNQINGDNSSSSSNIKNEDTVNDKANFEG

YEL031W
>sp|P39986|ATC6_YEAST Manganese-transporting ATPase 1
OS = Saccharomyces cerevisiae (strain ATCC 204508/S288c) GN = SPF1
PE = 1 SV = 1

SEQ ID NO: 31

MTKKSFVSSPIVRDSTLLVPKSLIAKPYVLPFFPLYATFAQLYFQQYDRYIKGPEWTFVY

LGTLVSLNILVMLMPAWNVKIKAKFNYSTIKNVNEATHILIYTTPNNGSDGIVEIQRVTE

AGSLQTFFQFQKKRFLWHENEQVFSSPKFLVDESPKIGDFQKCKGHSGDLTHLKRLYGEN

SFDIPIPTFMELFKEHAVAPLFVFQVFCVALWLLDEFWYYSLFNLFMIISMEAAAVFQRL

TALKEFRTMGIKPYTINVFRNKKWVALQTNELLPMDLVSITRTAEESAIPCDLILLDGSA

IVNEAMLSGESTPLLKESIKLRPSEDNLQLDGVDKIAVLHGGTKALQVTPPERKSDIPPP

PDGGALAIVIKTGFETSQGSLVRVMIYSAERVSVDNKEALMFILFLLIFAVIASWYVWVE

GTKMGRIQSKLILDCILIITSVVPPELPMELTMAVNSSLAALAKFYVYCTEPFRIPFAGR

IDVCCFDKTGILTGEDLVFEGLAGISADSENIRHLYSAAEAPESTILVIGAAHALVKLED

GDIVGDPMEKATLKAVGWAVERKNSNYREGIGKLDIIRRFQFSSALKRSASIASHNDALF

AAVKGAPETIRERLSDIPKNYDEIYKSFTRSGSRVLALASKSLPKMSQSKIDDLNRDDVE

SELTFNGFLIFHCPLKDDAIETIKMLNESSHRSIMITGDNPLTAVHVAKEVGIVFGETLI

LDRAGKSDDNQLLFRDVEETVSIPFDPSKDIFDHSKLFDRYDIAVTGYALNALEGHSQLR

DLLRHTWVYARVSPSQKEFLLNTLKDMGYQTLMCGDGINDVGALKQAHVGIALLNGTEEG

LKKLGEQRRLEGMKMMYIKQTEFMARWNQPQPPVPEPIAHLFPPGPKNPHYLKALESKGT

VITPEIRKAVEEANSKETEVIKPNGLSEKKPADLASLLLNSAGDAQGDEAPALKLGDASC

AAPFTSKLANVSAVINIIRQGRCALVNTIQMYKILALNCLISAYSLSIIYMAGVKFGDGQ

ATVSGLLLSVCFLSISRGKPLEKLSKQRPQSGIFNVYIMGSILSQFAVHIATLVYITTEI

YKLEPREPQVDLEKEFAPSLLNTGIFIIQLVQQVSTFAVNYQGEPFRENIRSNKGMYYGL

LGVTGLALASATEFLPELNEAMKFVPMTDDFKIKLTLILLLDFFGSWGVEHFFKFFFMDD

KPSDISVQQVKIASK

YER166W
>sp|P32660|ATC5_YEAST Phospholipid-transporting ATPase DNF1
OS = Saccharomyces cerevisiae (strain ATCC 204508/S288c) GN = DNF1
PE = 1 SV = 2

SEQ ID NO: 32

MSGTFHGDGHAPMSPFEDTFQFEDNSSNEDTHIAPTHFDDGATSNKYSRPQVSFNDETPK

NKREDAEEFTENDDTEYDNHSFQPTPKLNNGSGTFDDVELDNDSGEPHTNYDGMKRFRMG

TKRNKKGNPIMGRSKTLKWARKNIPNPFEDFTKDDIDPGAINRAQELRTVYYNMPLPKDM

IDEEGNPIMQYPRNKIRTTKYTPLTFLPKNILFQFHNFANVYFLVLIILGAFQIFGVTNP

GLSAVPLVVIVIITAIKDAIEDSRRTVLDLEVNNTKTHILEGVENENVSTDNISLWRREK

TABLE 14-continued

Sequences disclosed herein.

KANSRLLFKFIQYCKEHLTEEGKKKRMQRKRHELRVQKTVGTSGPRSSLDSIDSYRVSAD

YGRPSLOYDNLEQGAGEANIVDRSLPPRTDCKFAKNYWKGVKVGDIVRIHNNDEIPADII

LLSTSDTDGACYVETKNLDGETNLKVRQSLKCTNTIRTSKDIARTKFWIESEGPHSNLYT

YQGNMKWRNLADGEIRNEPITINNVLLRGCTLRNTKWAMGVVMFTGGDTKIMLNSGITPT

KKSRISRELNESVVINFVLLFILCFVSGIANGVYYDKKGRSRFSYEFGTIAGSAATNGFV

SFWVAVILYQSLVPISLYISVEIIKTAQAAFIYGDVLLYNAKLDYPCTPKSWNISDDLGQ

VEYIFSDKTGTLTQNVMEFKKCTINGVSYGRAYTEALAGLRKRQGIDVETEGRREKAEIA

KDRDTMIDELRALSGNSQFYPEEVTFVSKEFVRDLKGASGEVQQRCCEHEMLALALCHSV

LVEANPDNPKKLDLKAQSPDEAALVATARDVGFSFVGKTKKGLIIEMQGIQKEFEILNIL

EFNSSRKRMSCIVKIPGLNPGDEPRALLICKGADSIIYSRLSRQSGSNSEAILEKTALHL

EQYATEGLRTLCIAQRELSWSEYEKWNEKYDIAAASLANREDELEVVADSIERELILLGG

TAIEDRLQDGVPDCIELLAEAGIKLWVLTGDKVETAINIGFSCNLLNNEMELLVIKTTGD

DVKEFGSEPSEIVDALLSKYLKEYFNLTGSEEEIFEAKKDHEFPKGNYAIVIDGDALKLA

LYGEDIRRKFLLLCKNCRAVLCCRVSPSQKAAVVKLVKDSLDVMTLAIGDGSNDVAMIQS

ADVGIGIAGEEGRQAVMCSDYAIGQFRYLARLVLVHGRWSYKRLAEMIPEFFYKNMIFAL

ALFWYGIYNDEDGSYLYEYTYMMFYNLAFTSLPVIFLGILDQDVNDTISLVVPQLYRVGI

LRKEWNQRKFLWYMLDGLYQSIICFFFPYLVYHKNMIVTSNGLGLDHRYFVGVYVTTIAV

ISCNTYVLLHQYRWDWFSGLFIALSCLVVFAWTGIWSSAIASREFFKAAARIYGAPSFWA

VFFVAVLFCLLPRFTYDSFQKFFYPTDVEIVREMWQHGHEDHYPPGYDPTDPNRPKVTKA

GQHGEKIIEGIALSDNLGGSNYSRDSVVTEEIPMTFMHGEDGSPSGYQKQETWMTSPKET

QDLLQSPQFQQAQTFGRGPSTNVRSSLDRTREQMIATNQLDNRYSVERARTSLDLPGVTN

AASLIGTQQNN

YFL011W
>sp|P43581|HXT10_YEAST Hexose transporter HXT10 OS = Saccharomyces
cerevisiae (strain ATCC 204508/S288c) GN = HXT10 PE = 1 SV = 1
SEQ ID NO: 33

MVSSSVSILGTSAKASTSLSRKDEIKLTPETREASLDIPYKPIIAYWTVMGLCLMIAFGG

FIFGWDTGTISGFINQTDFKRRFGELQRDGSFQLSDVRTGLIVGIFNIGCALGGLTLGRL

GDIYGRKIGLMCVILVYVVGIVIQIASSDKWYQYFIGRIVSGMGVGGVAVLSPTLISEIS

PKHLRGTCVSFYQLMITLGIFLGYCTNYGTKKYSNSIQWRVPLGLCFAWAIFMVIGMVMV

PESPRYLVEKGKYEEARRSLAKSNKVTVTDPGVVFEFDTIVANMELERAVGNASWHELFS

NKGAILPRVIMGIVIQSLQQLTGCNYFFYYGTTIFNAVGMQDSFETSIVLGAVNFASTEV

ALYIVDKFGRRKCLLWGSASMAICFVIFATVGVTRLWPQGKDQPSSQSAGNVMIVETCFF

IFSFAITWAPIAYVIVAETYPLRVKNRAMAIAVGANWMWGFLIGFFTPFITRSIGFSYGY

VFMGCLIFSYFYVFFEVCETKGLTLEEVNEMYEERIKPWKSGGWIPSSRRTPQPTSSTPL

VIVDSK

YGL006W
>sp|P38929|ATC2_YEAST Calcium-transporting ATPase 2 OS = Saccharomyces
cerevisiae (strain ATCC 204508/S288c) GN = PMC1 PE = 1 SV = 1
SEQ ID NO: 34

MSRQDENSALLANNENNKPSYTGNENGVYDNFKLSKSQLSDLHNPKSIRSEVRLFGYESN

SLFKYLKTDKNAGISLPEISNYRKTNRYKNYGDNSLPERIPKSFLQLVWAAFNDKTMQLL

TVAAVVSFVLGLYELWMQPPQYDPEGNKIKQVDWIEGVAIMIAVFVVVLVSAANDYQKEL

TABLE 14-continued

Sequences disclosed herein.

QFAKLNKKKENRKIIVIRNDQEILISIHHVLVGDVISLQTGDVVPADCVMISGKCEADES
SITGESNTIQKFPVDNSLRDFKKFNSIDSHNHSKPLDIGDVNEDGNKIADCMLISGSRIL
SGLGRGVITSVGINSVYGQTMTSLNAEPESTPLQLHLSQLADNISVYGCVSAIILFLVLF
TRYLFYIIPEDGRFHDLDPAQKGSKFMNIFITSITVIVVAVPEGLPLAVTLALAFATTRM
TKDGNLVRVLRSCETMGSATAVCSDKTGILTENVMTVVRGFPGNSKFDDSKSLPVSEQRK
LNSKKVFEENCSSSLRNDLLANIVLNSTAFENRDYKKNDKNTGSKNMSKNLSFLDKCKS
RLSFFKKGNREDDEDQLFKNVNKGRQEPFIGSKTETALLSLARLSLGLQPGELQYLRDQP
MEKFNIEKVVQTIETESSRKWAGLVVKYKEGKNKKPFYRFFIKGAAEIVSKNCSYKRNSD
DTLEEINEDNKKETDDEIKNLASDALRAISVAHKDFCECDSWPPEQLRDKDSPNIAALDL
LFNSQKGLILDGLLGIQDPLRAGVRESVQQCQRAGVIVRMVTGDNILTAKAIARNCAILS
TDISSEAYSAMEGTEFRKLTKNERIRILPNLRVLARSSPEDKRLLVETLKGMGDVVAVTG
DGTNDAPALKLADVGFSMGISGTEVAREASDIILMTDDFSAIVNAIKWGRCVSVSIKKFI
QFQLIVNITAVILTFVSSVASSDETSVLTAVQLLWINLIMDTLAALALATDKPDPNIMDR
KPRGRSTSLISVSTWKMILSQATLQLIVTFILHFYGPELFFKKHEDEITSHQQQQLNAMT
FNIFVWLQFFTMLVSRKLDEGDGISNWRGRISAANLNFFQDLGRNYYFLTIMAIIGSCQV
LIMFFGGAPFSIARQTKSMWITAVLCGMLSLIMGVLVRICPDEVAVKVFPAAFVQRFKYV
FGLEFLRKNHTGKHDDEEALLEESDSPESTAFY

YGL013C
>sp|P12383|PDR1_YEAST Transcription factor PDR1 OS = Saccharomyces
cerevisiae (strain ATCC 204508/S288c) GN = PDR1 PE = 1 SV = 2
SEQ ID NO: 35
MRGLTPKNGVHIETGPTTESSADSSNFSTGFSGKIRKPRSKVSKACDNCRKRKIKCNGKF
PCASCEIYSCECTFSTRQGGARIKNLHKISLEGTIVQVKEETDSSSTSFSNPQRCTDGPC
AVEQPTKFFENFKLGGRSSGDNSGSDGKNDDDVNRNGFYEDDSESQATLTSLQTTLKNLK
EMAHLGTHVTSAIESIELQISDLLKRWEPKVRTKELATTKFYPNKSIETQLMKNKYCDVV
HLTRYAAWSNNKKDQDTSSQPLIDEIFGLYSPFQFLSLQGIGKCFQNYRSKSKCEIFPRT
AKETIYIMLRFFDVCFHHINQGCVSIANPLENYLQKMNLLPSTPSSISSAGSPNTAHTKS
HVALVINHLPQPFVRNITGISNSELLSEMNNDISMFGILLKMLDMHKNSYQNFLMEITSN
PSVAKNTQSIDVLQEFIHYCQAGEALIALCYSYYNSTLYNYVDFTCDITHLEQLLYFLDL
LFWLSEIYGFEKVLNVAVHFVSRVGLSRWEFYVGLDENFAERRRNLWWKAFYFEKTLASK
LGYPSNIDDSKINCLLPKNFRDVGFLDNRDFIENVHLVRRSEAFDNMCISDLKYYGELAV
LQIVSHFSSSVLFNEKFTSIRNTSKPSVVREKLLFEVLEIFNETEMKYDAIKEQTGKLFD
IAFSKDSTELKVSREDKIMASKFVLFYEHHFCRMVNESDNIVARLCVHRRPSILIENLKI
YLHKIYKSWIDMNKILLDFDNDYSVYRSFAHYSISCIILVSQAFSVAEFIKVNDVVNMIR
VFKRFLDIKIFSENETNEHVFNSQSFKDYTRAFSFLTIVTRIMLLAYGESSSINLDVISK
YIDENAPDLKGIIELVLDINSCAYRFLLEPVQKSGFHLTVSQMLKNRKFQEPLMSNEDNK
QMKHNSGKNLNPDLPSLKIGTSCLLNGIESPQLPFNGRSAPSPVRNNSLPEFAQLPSFRS
LSVSDMINPDYAQPTNGQNNTQVQSNKPINAQQQIPTSVQVPFMNINEINNNNNNNNNK
NNINNINNNNSNNFSATSFNLGTLDEFVNNGDLEDLYSILWSDVYPDS TABLE 14-continued Sequences disclosed herein.

YGL255W
>sp|P32804|ZRT1_YEAST Zinc-regulated transporter 1 OS = *Saccharomyces cerevisiae* (strain ATCC 204508/S288c) GN = ZRT1 PE = 1 SV = 1

SEQ ID NO: 36

MSNVITPWWKQWDPSEVTLADKTETDVWKTCVLQGVYFGGNEYNGNLGARISSVFVILFV

SIFFTMFPLISTKVKRLRIPLYVYLFAKYFGSGVIVATAFIHLMDPAYGAIGGTTCVGQI

GNWGLYSWCPAIMLISLTFTFLTDLFSSVWVERKYGLSHDHTHDEIKDTVVRNTAAVSSE

NDNENGTANGSHDTKNGVEYYEDSDATSMDVVQSFQAQFYAFLILEFGVIFHSVMIGLNL

GSVGDEFSSLYPVLVFHQSFEGLGIGARLSAIEFPRSKRWWPWALCVAYGLITPICVAIG

LGVRTRYVSGSYTALVISGVLDAISAGILLYTGLVELLARDFIFNPQRTKDLRELSFNVI

CTLFGAGIMALIGKWA

YGR125W
>sp|P53273|YG35_YEAST Uncharacterized vacuolar membrane protein YGR125W OS = *Saccharomyces cerevisiae* (strain ATCC 204508/S288c) GN = YGR125W PE = 1 SV = 1

SEQ ID NO: 37

MGRTIRRRSNSSLSEAISVSLGINQDSSVNKMHRASVSAMSPPLCRSYMSGFFIGGNSP

MINNLSDSKLPISNKQHPKVIRGSENLHRQTAQLSNEFCSSSVEENSPTIKDYMDIIGNG

DRKDDQSMRTIEENIDEEYSDEYSRLLLSPASSNVDDDRNRGLQNSSLPELEDGYAGGYQ

SLRPSHNLRFRPRNLWHMCTSFPSKFAHYLPAAVLGLLLNILDALSYGMIIFPITEPVFS

HLGPTGISMFYISTIISQAVYSGGWSSFPSGIGSEMIEITPFYHTMALAIKEALAGNDDE

IITTTIFCYVISSMLIGVVFYALGKLRLGKIVGFFPRHILIGCIGGVGYFLIITGIEVTT

RVAKFEYSWPFFSGLFTDYDTLAKWLLPVLLTVVLIGTQRYFKNSLVLPSFYILTLVLFH

FIVAIIPTLSLDALRQAGWIFPIANSDSKWYDHYRLFNVHKVHWSLVLQQIPTMMALTFF

GILHVPINVPALAMSLQMDKYDVDRELIAHGYSNFFSGLLGSVQNYLVYINSVLFIRAGA

DSPFAGFLLIALTICIMIIGPVIISFIPICIVGSLIFLLGYELLVEALVDTWNKLNRFEY

LTVVIIVFTMGIFDFVLGIIVGILIACFSFLVDSTKLQTINGEYNGNVARSTVYRDYVQT

KFLDGIGEQIYVLKLQNLLFFGTIISIEEKIERLLQISNKDATKRRIKYLILDFKNINAD

NIDYSAAEGFNRIKRFTETKRIKLIISSIKERDRIYNAFNNVGLLNDVELFADLNSALEW

CENEFLFQYKQLRKKAKERLEEGKQNNVVSAVIAATKNKKIDTIGNGLNRGSNGDTARNL

MSLPTNTPRNYQILSVAQNVFVNDEQAVKNFKKEYKDDEPVLPILLFALKQYRPDIISEV

QKVREKEIKFWAQLCPYFIRRRLASQSHLLHADNIFFLVEIGMLKATYELPQGTLYEIFS

NGTCFGKIIAPGNAMPREQKLTIETETDSVLWVIDSSSLNKLKEDNLALYVEVALMVMCI

KDTRFKELLGYTLVSA

YGR181W
>sp|P53299|TIM13_YEAST Mitochondrial import inner membrane translocase subunit TIM13 OS = *Saccharomyces cerevisiae* (strain ATCC 204508/S288c) GN = TIM13 PE = 1 SV = 1

SEQ ID NO: 38

MGLSSIFGGGAPSQQKEAATTAKTTPNPIAKELKNQIAQELAVANATELVNKISENCFEK

CLISPYATRNDACIDQCLAKYMRSWNVISKAYISRIQNASASGEI

YGR217W
>sp|P50077|CCH1_YEAST Calcium-channel protein CCH1 OS = *Saccharomyces cerevisiae* (strain ATCC 204508/S288c) GN = CCH1 PE = 1 SV = 1

SEQ ID NO: 39

MQGRKRTLTEPFEPNTNPFGDNAAVMTENVEDNSETDGNRLESKPQALVPPALNIVPPES

SIHSTEEKKGDEYNGNDKDSSLISNIFRTRVGRSSHENLSRPKLSLKTASFGAAESSRRN

VSPSTKSAKSSSQYIDLNDERLRRRSFSSYSRSSSRRVSNSPSSTDRPPRSAKVLSLIAA

TABLE 14-continued

Sequences disclosed herein.

DDMDDFEDLQKGFKSAIDEEGLTWLPQLKSEKSRPVSDVGEDRGEGEQESIPDVHTPNVG

ASATPGSIHLTPEPAQNGSVSEGLEGSINNSRKKPSPKFFHHLSPQKEDKDQTEVIEYAE

DILDFETLQRKLESRPFVLYGHSLGVESPINPLRIKIARFLLHRRYSLLYNTLLIFYAIL

LAIRTYNPHNVVFLYRFSNWIDYFIFILSACFIGNDIAKIIAFGFWDDSEMFKAYGREYK

SILQRSGIMKLYIYLREKYGRKLIDFIIPFRIISPGEETKYQRSSLSTSLIKPYGAKENQ

RPFGTPRAFARSSWNRIDLVSSVSFWLGMFLSIKSYDTKIGIRIFKPLAILRILRLVNVD

TGMPSILRGLKYGIPQLVNVSSMLVYFWIFFGILGVQIFQGSFRRQCVWFNPEDPTDTYQ

YDMQFCGGYLDPVTKRKQNYIYEDGSEGSVSKGFLCPQYSKCVSNANPYNGRISFDNIVN

SMELVFVIMSANTFTDLMYYTMDSDEMAACLFFIVCIFVLTIWLLNLLIAVLVSSFEIAN

EEYKKKKFIYGSRKTGYVARIVTGYWKYFKLKANQTKFPNWSQKGLAIYSHVEFIFVILI

ICDIGMRASVKVSTSANCNNILLKTDRGISIVLFIESLARLVLYLPNMWKFLTKPSYVYD

FIISIITLVISCLAVEGVLGHMYAWLSIFHISRFYRVIISFNLTKKLWKQILSNGVMIWN

LSSFYFFFTFLVAIIMAVYTEGVIPPEEMADQPFGMYSLPNSFLSLFIIGSTENWTDILY

ALQKHSPNISSTFFCSVFFIIWFLLSNSVILNIFIALISESMEVKEEEKRPQQIKHYLKF

VYPQKIQEYTHASLVARIRKKFFGGHRNEDIRDFKQFLMRGTAIMNIAQNMGELADEFKE

PPSENLFKKGLSKLTIGVPSLKRLRMFANNPFYKNSDVVFTETNDINGRTYILELNEYED

EKLDYLKKYPLFNYSYYFFSPQHRFRRFCQRLVPPSTGKRTDGSRFFEDSTDLYNKRSYF

HHIERDVFVFIFALATILLIVCSCYVTPLYRMHHKMGTWNWSSALDCAFIGAFSIEFIVK

TVADGFIYSPNAYLRNPWNFIDFCVLISMWINLIAYLKNNGNLSRIFKGLTALRALRCLT

ISNTARQTFNLVMFDGLNKIFEAGLISLSLLFPFTVWGLSIFKGRLGTCNDGSLGRADCY

NEYSNSVFQWDIMSPRVYQQPYLHLDSFASAFSSLYQIISLEGWVDLLENMMNSSGIGTP

ATVMGSAGNALFLVLFNFLSMVFILNLFVSFIVNNQARTTGSAYFTIEEKAWLESQKLLS

QAKPKAIPNLIELSRVRQFFYQLAVEKKNFYYASFLQVVLYLHIIMLLSRSYNPGNLIGY

QGVYFMFSTSVFLIQEALHMCGEGPRLYFRQKWNSIRLSIIIIAFIMNAVAFHVPASHYW

FHNIKGFFLLVIFLFIIPQNDTLTELLETAMASLPPILSLTYTWGVLFLVYAIALNQIFG

LTRLGSNTTDNINFRTVIKSMIVLFRCSFGEGWNYIMADLTVSEPYCSSDDNSTYTDCGS

ETYAYLLLMSWNIISMYIFVNMFVSLIIGNFSYVYRSGGSRSGINRSEIKKYIEAWSKFD

TDGTGELELSYLPRIMHSFDGPLSFKIWEGRLTIKSLVENYMEVNPDDPYDVKIDLIGLN

KELNTIDKAKIIQRKLQYRRFVQSIHYTNAYNGCIRFSDLLLQIPLYTAYSARECLGIDQ

YVHHLYILGKVDKYLENQRNFDVLEMVVTRWKFHCRMKRTIEPEWDVKDPTVSSHISNIN

VNLEPAPGILEREPIATPRMDYGVNNFMWSPRMNQDSTMEPPEEPIDNNDDSANDLIDR

YGR224W
>sp|P50080|AZR1_YEAST Azole resistance protein 1 OS = *Saccharomyces cerevisiae* (strain ATCC 204508/S288c) GN = AZR1 PE = 1 SV = 1

SEQ ID NO: 40

MKGEPKTYSMSDLSYYGEKAQQQNEKQQKQYVVRRNSTQSTSKQNVSVVLEDNASESNEL

PKGFILYASLIALALSLFLAALDIMIVSTIIEEVAKQFGSYSEIGWLFTGYSLPNALLAL

IWGRIATPIGFKETMLFAIVIFEIGSLISALANSMSMLIGGRVIAGVGGCGIQSLSFVIG

STLVEESQRGILIAVLSCSFAIASVVGPFLGGVFTSSVTWRWCFYVNLPIGGLAFFLFLF

FYNPGLSTFQETMDNIRKFPSQFIEIVRNVAYHLLKIKGFSKLNGWRKPFMELIFMYDII

EFVFCSAGFTCILLAFTFGGNRYAWNSASIIILFIIGIVLVVLAGIYDFLVFAKFNIVKA

TABLE 14-continued

Sequences disclosed herein.

TPHYQPLMSWTNIKKPGIFTVNIALFLTCAGYISQFTYIVQYFQLIYNDSAWRAAVHLVA

CIISTVVTAILCGAITDKTRQIKPIIVISSIFGVVGAGILTLLNNNANNSAHIGLLILPG

VAFGGLAQSSMLASQIQLDKKSPTFRSDFVSITTFNTFCKNLGQALGGVISNTVFSAAAI

KKLTKANIQLPDGTTVDNLVIYRQTNFDGSHSKLGNIISESLTDVFYMALGFYALSLIFA

VFASNKKVTASLR

YGR281W
>sp|P53049|YOR1_YEAST Oligomycin resistance ATP-dependent permease
YOR1 OS = Saccharomyces cerevisiae (strain ATCC 204508/S288c)
GN = YOR1 PE = 1 SV = 1
SEQ ID NO: 41

MTITVGDAVSETELENKSQNVVLSPKASASSDISTDVDKDTSSSWDDKSLLPTGEYIVDR

NKPQTYLNSDDIEKVTESDIFPQKRLFSFLHSKKIPEVPQTDDERKIYPLFHTNIISNMF

FWWVLPILRVGYKRTIQPNDLFKMDPRMSIETLYZDFEKNMIYYFEKTRKKYRKRHPEAT

EEEVMENAKLPKHTVLRALLFTFKKQYFMSIVFAILANCTSGFNPMITKRLIEFVEEKAI

FHSMHVNKGIGYAIGACLMMFVNGLTFNHFFHTSQLTGVQAKSILTKAAMKKMFNASNYA

RHCFPNGKVTSFVTTDLARIEFALSFQPFLAGFPAILAICIVLLIVNLGPIALVGIGIFF

GGFFISLFAFKLILGFRIAANIFTDARVTMMREVLNNIKMIKYYTWEDAYEKNIQDIRTK

EISKVRKMQLSRNFLIAMAMSLPSIASLVTFLAMYKVNKGGRQPGNIFASLSLFQVLSLQ

MFFLPIAIGTGIDMIIGLGRLQSLLEAPEDDPNQMIEMKPSPGFDPKLALKMTHCSFEWE

DYELNDAIEEAKGEAKDEGKKNKKKRKDTWGRPSASTNKAKRLDNMLKDRDGPEDLEKTS

FRGFKDLNFDIKKGEFIMITGPIGTGKSSLLNAMAGSMRKTDGKVEVNGDLLMCGYPWIQ

NASVRDNIIFGSPFNKEKYDEVVRVCSLKADLDILPAGDMTEIGERGITLSGGQKARINL

ARSVYKKKDIYLFDDVLSAVDSRVGKHIMDECLIGMLANKTRILATHQLSLIERASRVIV

LGTDGQVDIGTVDELKARNQTLINLLQFSSQNSEKEDEEQEAVVAGELGQLKYESEVKEL

TELKKKATEMSQTANSGKIVADGHTSSKEERAVNSISLKIYREYIKAAVGKWGFIALPLY

AILVVGTTFCSLFSSVWLSYNTENKFKNRPPSFYMGLYSFFVFAAFIFMNGQFTILCAMG

IMASKWLNLRAVKRILHTPMSYIDTTPLGRILNRFTKDTDSLDNELTESLRLMTSQFANI

VGVCVMCIVYLPWFAIAIPFLLVIFVLIADHYQSSGREIKRLEAVQRSFVYNNLNEVLGG

MDTIKAYRSQERFLAKSDFLINKMNEAGYLVVVLQRWVGIFLDMVAIAFALIITLLCVTR

AFPISAASVGVLLTYVLQLPGLLNTILRAMTQTENDMNSAERLVIYATELPLEASYRKPE

MTPPESWPSMGEIIFENVDFAYRPGLPIVLKNLNLNIKSGEKIGICGRTGAGKSTIMSAL

YRLNELTAGKILIDNVDISQLGLFDLRRKLAIIPQDPVLFRGTIRKNLDPFNERTDDELW

DALVRGGAIAKDDLPEVKLQKPDENGTHGKMHKFHLDQAVEEEGSNFSLGERQLLALTRA

LVRQSKILILDEATSSVDYETDGKIQTRIVEEFGDCTILCIAHRLKTIVNYDRILVLEKG

EVAEFDTPWTLFSQEDSIFRSMCSRSGIVENDFENRS

YHL016C
>sp|P33413|DUR3_YEAST Urea active transporter OS = Saccharomyces
cerevisiae (strain ATCC 204508/S288c) GN = DUR3 PE = 1 SV = 2
SEQ ID NO: 42

MGEFKPPLPQGAGYAIVLGLGAVFAGMMVLTTYLLKRYQKEIITAEEFTTAGRSVKTGLV

AAAVSSSWIWCSTLLTSSTKEYADGIFGGYAYAAGACFQIIAFAILAIKTKQMAPNAHTY

LELVRTRYGKIGHGCYLFYAIATNILVTSMLLTSGSAVFSDLTGMNTIASCFLLPVGVVV

YTLFGGIKATFLTDYMHTCVIIIIVLVFAFKVYATSDVLGSPGKVYDLVREAAKRHPVDG

TABLE 14-continued

Sequences disclosed herein.

NYQGEYMTMTSKSAGILLIINLIGNFGTVFLDNGYWNKAISASPAASLKAYAIGGLAWFA

VPSLISLTMGLACLAVETSPNFTTYPDPLISFQANSGLVLPAAAIAIMGKGGAVASLLMI

FMAVTSAMSAELIAVSSVFTYDIYREYIDPRASGKKLIYTSHVACIFFGLAMSGFSVGLY

YGGISMGYIYEMMGIIISSAVLPVVLTLCSKDMNLVAAVVSPILGTGLAIMSWLVCTKSL

YKELTVDTTFMDYPMLTGNLVALLSPAIFIPILTYVFKPQNFDWEKMKDITRVDETAELV

QADPDIQLYDAEANDKEQEEETNSLVSDSEKNDVRVNNEKLIEPNLGVVISNAIFQEDDT

QLQNELDEEQRELARGLKIAYFLCVFFALAFLVVWPMPMYGSKYIFSKKFFTGWVVMII

WLFFSAFAVCIYPLWEGRHGIYTTLRGLYWDLSGQTYKLREWQNSNPQDLHVVTSQISAR

AHRQSSHFGQVDEII

YIL088C
>sp|P40501|AVT7_YEAST Vacuolar amino acid transporter 7
OS = Saccharomyces cerevisiae (strain ATCC 204508/S288c) GN = AVT7
PE = 1 SV = 1
SEQ ID NO: 43

MEATSSALSSTANLVKTIVGAGTLAIPYSFKSDGVLVGVILTLLAAVTSGLGLFVLSKCS

KTLINPRNSSFFTLCMLTYPTLAPIFDLAMIVQCFGVGLSYLVLIGDLFPGLFGGERNYW

IIASAVIIPLCLVKKLDQLKYSSILGLFALAYISILVFSHFVFELGKGELTNILRNDIC

WWKIHDFKGLLSTFSIIIFAFTGSMNLFPMINELKDNSMENITFVINNSISLSTALFLIV

GLSGYLTFGNETLGNLMLNYDPTSIWIVIGKFCLGSMLILSFPLLFHPLRIAVNNVIIWI

EITYGGANPEEDPQVSEYTRASNLRPISMTVEDPAQPSDALDATSYNEQECLLPNGNFDN

GSIESQENNNDERGTMAVAGDNEHHAPFVKSRFYWITALLLISMYTLALSVQSFALVLSF

VGAIGSTSISFTLPGLLGYKLIGLDSLAIGKMIPPKDRFYKRCSLLLVFYGLSVMFLSLY

VTVFNRSDEA

YJL093C
>sp|P40310|TOK1_YEAST Outward-rectifier potassium channel TOK1
OS = Saccharomyces cerevisiae (strain ATCC 204508/S288c) GN = TOK1
PE = 1 SV = 1
SEQ ID NO: 44

MTRFMNSFAKQTLGYGNMATVEQESSAQAVDSHSNNTPKQAKGVLAEELKDALRFRDERV

SIINAEPSSTLFVFWFVVSCYFPVITACLGPVANTISIACVVEKWRSLKNNSVVINPRSN

DTDVLMNQVKIVFDPPGIFAVNIISLVLGFTSNIILMLHFSKKLTYLKSQLINITGWTIA

GGMLLVDVIVCSLNDMPSIYSKTIGFWFACISSGLYLVCTIILTIHFIGYKLGKYPPTFN

LLPNERSIMAYTVLLSLWLIWGAGMFSGLLHITYGNALYFCTVSLLTVGLGDILPKSVGA

KIMVLIFSLSGVVLMGLIVFMTRSIIQKSSGPIFFFHRVEKGRSKSWKHYMDSSKNLSER

EAFDLMKCIRQTASRKQHWFSLSVTIAIFMAFWLLGALVFKFAENWSYFNCIYFCFLCLL

TIGYGDYAPRTGAGRAFFVIWALGAVPLMGAILSTVGDLLFDISTSLDIKIGESFNNKVK

SIVFNGRQRALSFMVNTGEIFEESDTADGDLEENTISSQSSQISEFNDNNSEENDSGVTS

PPASLQESFSSLSKASSPEGILPLEYVSSAEYALQDSGICNLRNLQELLKAVKKLHRICL

ADKDYTLSFSDWSYIHKLHLRNITDIEEYTRGPEFWISPDTPLKFPLNEPHFAFMMLFKN

IEELVGNLVEDEELYKVISKRKFLGEHRKTL

YJL094C
>sp|P40309|KHA1_YEAST K(+)/H(+) antiporter 1 OS = Saccharomyces
cerevisiae (strain ATCC 204508/S288c) GN = KHA1 PE = 1 SV = 1
SEQ ID NO: 45

MANTVGGILSGVNPFHYNSSSPLTLFLFQACLILLVCNLIHIPFSMMRQPKVISEVISGV

ILGPTIFGQIPNYINTIFPTSSIPGLNLVANLGIILFMFFLGLEVDIAFIKKHLKKALVI

TABLE 14-continued

Sequences disclosed herein.

GIVTLAVPFGFGCLLAIPLFHTYANKTEGERHIKFSVFMVFIAVSISVTAFPVLCRILNE

LRLIKDRAGIVVLAAGIINDIMGWILLALSIILSSAEGSPVNIVYILLITFAWFLIYFFP

LKYLLRWVLIRTHELDRSKPSPLATMCILFIMFISAYFTDIIGVHPIFGAFIAGLVVPRD

DHYVVKLTERMEDIPNIVFIPIYFAVAGLNVDLTLLNEGRDWGYVFATIGIAIFTKIISG

TLTAKLTGLFWREATAAGVLMSCKGIVEIVVLTVGLNAGIISRKIFGMFVLMALVSTFVT

TPLTQLVYPDSYRDGVRKSLSTPAEDDGAADGLDSEGVDKTEINTQLNSLADVSKYRIGE

LTTVINTTEAISPSLKLLNYISLGVSPKPKNNKHKNETSLSRMITATDSTLKSNIFKIKK

MVHIWSKSVDDVDTNLSVIDEKLIPFEGVGALRAIHLRLLTERTTDLLQSSSLYNDDPHF

TANTDSLLQIFDIFSNLSKIPFSSEVIFSTMREKAANIATMKMDSTDLILLPLKGASYEY

RGSPVFIDEKYANFDHIYSHLLGLNELSSITFKSIFQSLKANFAVQISNTYGRLNADRFK

RKRFNLLLPKPYLTQSDYLGLYLLLLICYRDGYNNDNASCSIFINSKNIDFAKDLSTAFA

EHDWLNESTIKIVDIPFETKVPEEAIEKPSFIETVLDVGLSDIALADIEETTFIIGEDLP

DESEPFSEEVRTVIFEGSNRRFDTLIVHHFSSE

YJL108C
>sp|P42946|PRM10_YEAST Pheromone-regulated membrane protein 10
OS = Saccharomyces cerevisiae (strain ATCC 204508/S288c) GN = PRM10
PE = 1 SV = 1
SEQ ID NO: 46

MIVSFGDATTRTSEVQLVRCTQGLNLWKLHQVHAVYKRVVHDTLGADEGNALLDQILADT

NLYPPWMCVLLYAFCSAMVTPYAFGGDWVNLAISFFMGLCVGSLQFILSQKSYMYSNVFE

ISASIVVSFCGRAFGSIPRSHICFGAVTQGSLALILPGYIILCGALELQSRSLVAGAVRM

FYAITYSLFLGFGITLGSALFGWMYRNATNEISCPQLISPWFRFLFVPAFTISISLLNQA

HISQLPVMVFISCTGYVVTYMAGKHFANSTEFTAALAAFVIGVLGNLYSRIWKGLAVSAM

LPAIFVQVPSGIASQNSLLSGLQSANTIVNANETITTSTSDPSSSMSFGMTMIQVCVGIS

VGLFASSLFVYPFGKKKTGLFSL

YJL212C
>sp|P40897|OPT1_YEAST Oligopeptide transporter 1 OS = Saccharomyces
cerevisiae (strain ATCC 204508/S288c) GN = OPT1 PE = 1 SV = 1
SEQ ID NO: 47

MSTIYRESDSLESEPSPTPTTIPIQINMEEEKKDAFVKNIDEDVNNLTATTDEEDRDPES

QKFDRHSIQEEGLVWKGDPTYLPNSPYPEVRSAVSIEDDPTIRLNHWRTWFLTIVFVVVF

AGVNQFFSLRYPSLEINFLVAQVVCYPIGRILALLETWKCSKVPFFDLNPGPFTKKEHAV

VTIAVALTSSTAYAMYILNAQGSFYNMKLNVGYQFLLVWTSQMIGYGAAGLTRRWVVNPA

SSIWPQTLISVSLFDSLHSRKVEKTVANGWTMPRYRFFLIVLIGSFIWYWVPGFLFTGLS

YFNVILWGSKTRHNFIANTIFGTQSGLGALPITFDYTQVSQAMSGSVFATPFYVSANTYA

SVLIFFVIVLPCLYFTNTWYAKYMPVISGSTYDNTQNKYNVIKILNEDYSINLEKYKEYS

PVFVPFSYLLSYALNFAAVIAVFVHCILYHGKDIVAKFKDRKNGGTDIHMRIYSKNYKDC

PDWWYLLLQIVMIGLGFVAVCCFDTKFPAWAFVIAILISLVNFIPQGILEAMTNQHVGLN

IITELICGYMLPLRPMANLLFKLYGFIVMRQGLNLSRDLKLAMYNKVSPRLIFAVQIYAT

IISGMVNVGVQEWMMHNIDGLCTTDQPNGFTCANGRTVFNASIIWSLPKYLFSSGRIYNP

LMWFFLIGLLFPLAVYAVQWKFPKFKFAKHIHTETFFTGPGNIPPSTPYNYSLFFAMSFC

LNLIRKRWRAWFNKYNFVMGAGVEAGVAISVVIIFLCVQYPGGKLSWWGNNVWKRTYDND

YKKFYTLKKGETFGYDKWW

YJR106W

TABLE 14-continued

Sequences disclosed herein.

>sp|P47144|ECM27_YEAST Protein ECM27 OS = Saccharomyces cerevisiae
(strain ATCC 204508/S288c) GN = ECM27 PE = 1 SV = 2

SEQ ID NO: 48

MDWAINVAHPRLLYKDPKLSVTFIVPSLFHIIIAFVLLGICASDFLCPNVAHISDPNSLR

SNGSLVSKTASHASHTGALMAVLLSWCNSSETLFSNLMSWATSTRETRSTSVSLSIGEVL

GACGIILCIVEGSIFIIMSRTHIEISQIQKLSIMRDLLFSLAAMCVMSYVSLMNQVTVLN

CLLMAFLYAFYLVVKLTFKLNHSAETETETAADTSLRENSVSPFLDDSLMASGLLETIQP

GFDISNSITHGIKPSLLSAMDFNSFLSMLENSSLEEDDSRNEMAELNTLRSMTPGQHWSA

SATVAGEATSAGRPFSEPTNAFTEYRDSERAINSSPAVFAPYRDNPDDEESQEQVLLETT

THGHFGAQEMRRFSKRSLGWIIKIFIFHLSNFSQKSISDAIFSIITVETFIIFKLSCPQP

PSDILSYDPILNRYSLTTLPIILLFIQSITAPFLLCSILSVLLTYHLGYIVYLFPLILAM

ALILLLTAFITKVNLHNKFTLSLDSSNILQEKLQKRKLLERLNTSIQIIFLAIGIINII

WISLLANSLIEMMEIYQKILGLSKAILGLTIFAWGNSVGDLISNISMCRLYKTQTHYQDR

VRLATKFFMISCASCLGGVMLNSMGGIGFSGLVSMLFIGAFNDNEWWFLRKVKLQETSQL

DNILNYKFIVSCVFIILQIILLLLFFGGPNNIKRRLTKEMKLVGISMCGLWALATLINIL

LELFS

YJR160C
>sp|P0CE00|MPH3_YEAST Alpha-glucosides permease MPH3
OS = Saccharomyces cerevisiae (strain ATCC 204508/S288c) GN = MPH3
PE = 1 SV = 1

SEQ ID NO: 49

MKNLSFLINRRKENTSDSNVYPGKAKSHEPSWIEMDDQTKKDGLDIVHVEFSPDTRAPSD

SNKVITEIFDATEDAKEADESERGMPLATALNTYPKAAAWSLLVSTTLIMEGYDTAILGA

FYALPIFQRKFGSQNDKTGEWEISASWQIGLTLCYMAGEIVGLQLTGPSVDLVGNRYTLI

IALFFLAAFTFILYFCNSLGMIAVGQALCGMPWGCFQCLTVSYASEICPLALRYYLTTYS

NLCWLFGQLFAAGIMKNSQKKYADSELGYKLPFALQWILPVPLALGIFFAPESPWWLVKK

GREDEARRSLRRTLSGKGPEKEILVTLEVDKIKVTIDKEKRLTSKEGSYSDCFEDKINRR

RTRITCLCWAGQATCGSILIGYSTYFYEKAGVSTEMSFTESIIQYCLGICATFLSWWASK

YFGRYDLYAFGLAFQTIVFFIIGGLGCSSTHGSKMGSGSLLMAVAFFYNLGIAPVVECLV

SEMPSSRLRTKTIILARNTYNVVSIICSVLILYQLNSKKWNWGAKSGFFWGVLCFCTLIW

AVVDLPETAGKTFVEINELFKLGVSARKFKSTKVDPFVVKTPPKDVSHNDPKGDIEASIA

EE

YKL064W
>sp|P35724|MNR2_YEAST Manganese resistance protein MNR2
OS = Saccharomyces cerevisiae (strain ATCC 204508/S288c) GN = MNR2
PE = 1 SV = 1

SEQ ID NO: 50

MSTDNSQKDEGVPLLSPYSSSPQLRKKKRNQKRRKDKFVGHLKSDSRRPTQLLHDNLQHN

HGQITDFDQIDSWGMLHESDSTSNDIIKSEDPSLKGAFIDHRPSMSQPREGPQSVSSTVQ

PQPIMKFSTPSYKKPAGLRPSDQNRSLVSDLSPSELESWLKRRKSVHKSFVDENSPTDRR

QSNANNDVVIDVDALMNHVNNNASTGVNDNSKARKKKRGSDDSSNKNSKSTSSDSNDEED

EYNSRPSSSLSSNNSSLDDVCLVLDDEGSEVPKAWPDCTVLEEFSKEETERLRSQAIQDA

EAFHFQYDEDEEDGTSNEDGILFSKPIVTNIDVPELGNRRVNETENLKNGRLRPKRIAPW

HLIQRPMVLGSNSTKDSKSRIQSGLQDNLLVGRNIQYPPHIISNNPEHERFTYFRVDLDS

TVHSPTISGLLQPGQKFQDLFVASIYSQDNSAGHIKTHPNSPTPGIKAETVSQLQGLTAK

NPSTLSSMSVANIEDVFPPFWLDVSNPTEEEMKILSKAFGIMPLTTEDIFLGEVREKVELF

TABLE 14-continued

Sequences disclosed herein.

RDYYLICFRSEDIVAEKHVRRRRKEKQESATLDHESISRRKSQAYGATMSNESNANNNNS

TSNASRSKWLPSILRARRRSSANRTTNTSSSSYKRRVKSEKKKMEENEKFKRKSGDRHKP

REGELEPLNVYTIVERTGVLTFHFAPTPHPINVRRRARLLKDYLNVTSDWIAYALIDDIT

DAFAPMIELIEDEVYEIEDAILKMHQSDDSSDSDSSDSDSDSGASDEDAFPFDVYSKKTS

YSSAKSSVSSRSMSTSEASFNANLIGWKRKGDMLRRIGECRKRVMSILRLLGSKADVIKG

FAKRYNEQWEASPQSEIAKYLGDIQDHIVTMVSSLNHYEKLLSRSHSNYLAQINIDMTKV

NNDMNDVLGKITILGTIVLPMNVITGLWGMNVIVPGQYRDSLTWFIGIVLFMCMLACSAY

MYTKRRFGF

YKR050W
>sp|P28584|TRK2_YEAST Low-affinity potassium transport protein
OS = *Saccharomyces cerevisiae* (strain ATCC 204508/S288c) GN = TRK2
PE = 1 SV = 1
SEQ ID NO: 51

MPTAKRTSSRASLALPFQLRLVHKKSWGHRLRDFISGELKSCRPIAKYVFPNFIVVHYTY

LITLSIIGSILLYPCKNTAFIDVLFLAAGASTQGGLATKSTNDFNLYQQIVVYVITLLST

PILIHGFLAFVRLYNFERYTDNIRDISKINFKLRRTMTLQQRELSGSSGNAARSRSEKDN

LFRGKFVSREDPRQSASDVFMDSPDTSALSSISPLNVSSSKEESSDTQSSPPNFSSKRQP

SDVDPRDIYKSIMMLQKQQEKSNANSTDSFSSETNGPAFIVQERHERRAPHCSLKRHSVL

PSSQELNKLAQTKSFQKLLGLRRDEGDHDYFDGAPHKYMVTKKKKISRTQSCNIPTYTAS

PSPKTSGQVVENHRNLAKSAPSSFVDEEMSFSPQESLNLQFQAHPPKPKRREGDIGHPFT

RTMSTNYLSWQPTFGRNSVFIGLTKQQKEELGGVEYRALRLLCCILMVYYIGFNILAFVT

IVPWACTRHHYSEIIRRNGVSFTWWGFETAMSAFSNLGLSLTADSMVSFDTAPYPLIFMM

FFIIIGNTGFPIMLRFIIWIMEKTSRDLSQFKESLGELLDHPRRCFTLLEPSGPTWWLFT

TLVVLNATDWILFIILDFNSAVVRQVAKGYRALMGLFQSVCTRTAGFNVVDLSKLHPSIQ

VSYMLMMYVSVLPLAISIRRTNVYEEQSLGLYDSGQDDENITHEDDIKETDHDGESEERD

TVSTKSKPKKQSPKSFVGAHLRRQLSFDLVYLFLGLFIICICEGRKIEDVNKPDFNVFAI

LFEVVSAYGTVGLSLGYTNTNTSLSAQFTVLSKLVIIAMLIRGRNRGLPYTLDRAIMLPS

DKLEQIDRLQDMKAKGKLLAKVGEDPMTTYVKKRSHKLKKIATKFWGKH

YKR105C
>sp|P36172|VBA5_YEAST Vacuolar basic amino acid transporter 5
OS = *Saccharomyces cerevisiae* (strain ATCC 204508/S288c) GN = VBA5
PE = 3 SV = 1
SEQ ID NO: 52

MEETKYSSQQEIEGACGSDASLNARGSNDSPMGLSLYLCLASLILVLFITALDILIVGTI

IDVVAEQFGNYSKTGWLVTGYSLPNAILSLIWGRFASIIGFQHSLILAILIFEAGSLIAA

LASSMNMLIFGRVVAGVGGSGLQTLCFVIGCTMVGERSRPLVISILSCAFAVAAIVGPII

GGAFTTHVTWRWCFYINLPIGGLAIIMFLLTYKAENKGILQQIKDAIGTISSFTFSKFRH

QVNFKRLMNGIIFKFDFFGFALCSAGLVLFLLGLTFGGNKYSWNSGQVITYLVLGVLLFI

FSLVYDFFLFDKFNPEPDNISYRPLLLRRLVAKPAIIIVNMVTFLLCTGYNGQMIYSVQF

FQLIFASSAWKAGLHLIPIVITNVIAAIASGVITKKLGLVKPLLIFGGVLGVIGAGLMTL

MINTSIKSTQIGVLLLPGFSLGFALQASLMSAQLQIIKDRPEAAMDFIEVTAFNIFMKSL

GITLGGVLSTTVFSASFHNKVSRAHLEPYEGKTVDDMILYRLQNYDGSHSTIGNILSDSI

KNVFWMDLGFYALGFLFCSFSSNKKLIIPKKDDTPEDNLEDK

YKR106W

TABLE 14-continued

Sequences disclosed herein.

>sp|P36173|GEX2_YEAST Glutathione exchanger 2 OS = *Saccharomyces cerevisiae* (strain ATCC 204508/S288c) GN = GEX2 PE = 1 SV = 1

SEQ ID NO: 53

MSSSVVGASSNKKSGIRQSCEIIERERHSNDDTYSMISTFFKLKENEIMSAQFDSLKYKI

LLISTAFVCGFGISLDYTLRSTYTGYATNSYSEHSLLSTVQVINAVVSVGSQVVYSRLSD

HFGRLRLFLVATIFYIMGTTIQSQATRLTMYAAGSVFYNCGYVGTNLLLTLILSDFSSLK

WRMFYQYASYWPYIIIPWISGNIITAANPQKNWSWNIAMWAFIYPLSTLPIIFLILYMKY

KSSKTAEWRSLKEQARKERTGGLFENLVFLFWKLDIVGILLITVSLGCILVPLTLANETS

QKWHNSKIIATLVSGGCLFFIFLYMEAKFAKSPLLPFKLLSDRGIWAPLGVTFFNFFTFF

ISCDYLYPVLLVSMKESSTSAARIVNLPDFVAATASETYSLLVAKTRKLKLSVIGGCAAW

MVCMGLFYKYRGGSGSHEGVIAASVIMGLSGLLCSNSVIVILQAMITHSRMAVITGIQYT

FSKLGAAIGASVSGAIWTQTMPNQLYKNLGNDTLAEIAYASPYTFISDYPWGSPERDAVV

ESYRYVQRIIMTVGLACTVPFFTFTMFMRNFELIDKATHEEFTEDGLVVLPDEENIFSQI

KALFRHNRSNKKSGC

YLR447C
>sp|P32366|VA0D_YEAST V-type proton ATPase subunit d
OS = *Saccharomyces cerevisiae* (strain ATCC 204508/S288c) GN = VMA6
PE = 1 SV = 2

SEQ ID NO: 54

MEGVYFNIDNGFIEGVVRGYRNGLLSNNQYINLTQCDTLEDLKLQLSSIDYGNFLSSVSS

ESLITSLIQEYASSKLYHEFNYIRDQSSGSTRKFMDYITYGYMIDNVALMITGTIHDRDK

GEILQRCHPLGWFDTLPILSVATDLESLYETVLVDTPLAPYFKNCFDTAEELDDMNIEII

RNKLYKAYLEDFYNFVTEEIPEPAKECMQTLLGFEADRRSINIALNSLQSSDIDPDLKSD

LLPNIGKLYPLATFHLAQAQDFEGVRAALANVYEYRGFLETGNLEDHFYQLEMELCRDAF

TQQFAISTVWAWMKSKEQEVRNITWIAECIAQNQRERINNYISVY

YML116W
>sp|P13090|ATR1_YEAST Aminotriazole resistance protein
OS = *Saccharomyces cerevisiae* (strain ATCC 204508/S288c) GN = ATR1
PE = 1 SV = 2

SEQ ID NO: 55

MGNQSLVVLTESKGEYENETELPVKKSSRDNNIGESLTATAFTQSEDEMVDSNQKWQNPN

YFKYAWQEYLFIFTCMISQLLNQAGTTQTLSIMNILSDSFGSEGNSKSWLMASFPLVSGS

FILISGRLGDIYGLKKMLLVGYVLVIIWSLICGITKYSGSDTFFIISRAFQGLGIAFVLP

NVLGIIGNIYVGGTFRKNIVISFVGAMAPIGATLGCLFAGLIGTEDPKQWPWAFYAYSIA

AFINFVLSIYAIPSTIPTNIHHFSMDWIGSVLGVIGLILLNFVWNQAPISGWNQAYIIVI

LIISVIFLVVFIIYEIRFAKTPLLPRAVIKDRHMIQIMLALFFGWGSFGIFTFYYFQFQL

NIRQYTALWAGGTYFMFLIWGIIAALLVGFTIKNVSPSVFLFFSMVAFNVGSIMASVTPV

HETYFRTQLGTMIILSFGMDLSFPASSIIFSDNLPMEYQGMAGSLVNTVVNYSMSLCLGM

GATVETQVNSDGKHLLKGYRGAQYLGIGLASLACMISGLYMVESFIKGRRARAAAEYDCT

VA

YMR034C
>sp|Q05131|YMS4_YEAST Uncharacterized membrane protein YMR034C
OS = *Saccharomyces cerevisiae* (strain ATCC 204508/S288c) GN = YMR034C
PE = 1 SV = 1

SEQ ID NO: 56

MKTQYSLIRKIWAHSVTEFLKSQWFFICLAILIVIARFAPNFARDGGLIKGQYSIGYGCV

AWIFLQSGLGMKSRSLMANMLNWRAHATILVLSFLITSSIVYGFCCAVKAANDPKIDDWV

LIGLILTATCPTTVASNVIMTTNAGGNSLLCVCEVFIGNLLGAFITPALVQMFTNRAPFA

TABLE 14-continued

Sequences disclosed herein.

YGNPATGNGIGALYGRVMKQVGLSVFVPLFVGQVIQNCFPKGTAYYLGFLKKYHIKIGSY

MLLLIMFSSFSTAFYQDAFTSVSHVCIIFLCFFNLGIYIFFTGLSYLCARPWFILKLFPH

EPIEGKSTRLYRYSYNIFRPFYYSKEDAICIMFCGPAKTAALGVSLITSQYGDKKEHLGK

LLVPLVLYQVEQVMTANFFVSLFKRWIQKDAQADGSESSCANENEEVDLEKIISIGTGEN

QSVLSNNVPYTQPR

YMR056C
>sp|P04710|ADT1_YEAST ADP,ATP carrier protein 1 OS = Saccharomyces
cerevisiae (strain ATCC 204508/S288c) GN = AAC1 PE = 1 SV = 1
SEQ ID NO: 57

MSHTETQTQQSHFGVDFLMGGVSAAIAKTGAAPIERVKLLMQNQEEMLKQGSLDTRYKGI

LDCFKRTATHEGIVSFWRGNTANVLRYFPTQALNFAFKDKIKSLLSYDRERDGYAKWFAG

NLFSGGAAGGLSLLFVYSLDYARTRLAADARGSKSTSQRQFNGLLDVYKKTLKTDGLLGL

YRGFVPSVLGIIVYRGLYFGLYDSFKEWLLTGALEGSFVASFLLGWVITMGASTASYPLD

TVRRRMMMTSGQTIKYDGALDCLRKIVQKEGAYSLFKGCGANIFRGVAAAGVISLYDQLQ

LIMFGKKFK

YMR253C
>sp|Q04835|YM87_YEAST Uncharacterized membrane protein YMR253C
OS = Saccharomyces cerevisiae (strain ATCC 204508/S288c) GN = YMR253C
PE = 1 SV = 1
SEQ ID NO: 58

MNPSVPKVMKRENNTHLLVSKEMNDTSLQLPSTTRSLSPKESNSNEDFNVDGNETTLQRI

SKDYLKPNIGLVLLTVSYFFNSAMVVSTKVLENDPDDIANDRQIKPLQILLVRMVITYIG

TLIYMYINKSTISDVPFGKPEVRKWLVLRGCTGFFGVFGMYYSLMYLTISDAVLITFLAP

SLTIFLSWVILRERFTKVEALGSLISLLGVVLIVRPSFLFGTPELTDSSSQIVESSDPKS

RLIATLVGLWGVLGMSCVYIIIRYIGKRAHAIMSVSYFSLITAIVSFIGINTIPSMKFQI

PHSKKQWILFGNLGVSGFIFQLLLTMGIQRERAGRGSLMTYTQLLYAVFWDVALYKHWPN

IWSWIGMIIIISATLWVIRIRAANNETTAKDLTPIIDDEENSIPLTEFDLSDSK

YNL065W
>sp|P53943|AQR1_YEAST Probable transporter AQR1 OS = Saccharomyces
cerevisiae (strain ATCC 204508/S288c) GN = AQR1 PE = 1 SV = 1
SEQ ID NO: 59

MSRSNSIYTEDIEMYPTHNEQHLTREYTKPDGQTKSEKLNFEGAYINSHGTLSKTITREI

EGDLDSETSSHSSDDKVDPTQQITAETKAPYTLLSYGQKWGMVAILTMCGFWSSLGSPIY

YPALRQLEKQFNVDENMVNVIVVVYLLFQGISPIVSGGLADCFGRRPIILAGMLIYVIAS

IGLACAPSYGVIIFLRCIQSIGISPTIAISSGVVGDFTLKHERGTFVGATSGFVLLGQCF

GSLIGAVLTARWDWRAIFWFLTIGCGSCFLIAFLILPETKRTIAGNLSIKPKRFINRAPI

FLLGPVRRRFKYDNETYETLDPTIPKLDLSSAGKILVLPEIILSLFPSGLLFAMWTLMLS

SISSGLSVARYNYHLVIIGVCYLPGGIGGLMGSFFTGRIIDMYFKRKIKKFEQDKANGLI

PQDAEINMFKVRLVCLLPQNFLAVVAYLLFGWSIDKGWRIESILITSFVCSYCAMSTLST

STTLLVDLYPTKSSTASSCFNFVRCSLSTIFMGCFAKMKAAMTVGGTFTFLCALVFFFNF

LMFIPMKYGMKWREDRLLKQQRQSWLNTLAVKAKKGTKRDQNDNHN

YNL070W
>sp|P53507|TOM7_YEAST Mitochondrial import receptor subunit TOM7
OS = Saccharomyces cerevisiae (strain ATCC 204508/S288c) GN = TOM7
PE = 1 SV = 2
SEQ ID NO: 60

MSFLPSFILSDESKERISKILTLTHNVAHYGWIPFVLYLGWAHTSNRPNFLNLLSPLPSV

TABLE 14-continued

Sequences disclosed herein.

YNL083W
>sp|D6W196|CMC1_YEAST Truncated non-functional calcium-binding
mitochondrial carrier SAL1-1 OS = Saccharomyces cerevisiae (strain
ATCC 204508/S288c) GN = SAL1 PE = 1 SV = 2

SEQ ID NO: 61

MLLKNCETDKQRDIRYACLFKELDVKGNGQVILDNLISAFEKNDHPLKGNDEAIKMLFTA

MDVNKDSVVDLSDFKKYASNAESQIWNGFQRIDLDHDGKIGINEINRYLSDLDNQSICNN

ELNHELSNEKVNKFSRFFEWAFPKRKANIALRGQASHKKNIDNDRSKKTTDSDLYVTYDQ

WRDFLLLVPRKQGSRLHTAYSYFYLFNEDVDLSSEGDVTLINDFIRGFGFFIAGGISGVI

SRICTAPFDRLKVFLIARTDLSSILLNSKTDLLAKNPNADINKISSPLAKAVKSLYRQGG

IKAFYVGNLNVIKVFPESSIKFGSFEVTKKIMTKLEGCRDTKDLSKFSTYIAGGLAGMA

AQFSVYPIDTLKFRVQCAPLDTKLKGNNLLFQTAKDMFREGGGQIILQRCHSRYSGHISL

CCIRFGDFFCLKKMVYCQTGKDPEPTIRSGHSKQPGCTSNGCIQWNCRSFCCLSNQSFKN

KTTSPRNICTSLCV

YNL095C
>sp|P53932|YNJ5_YEAST Uncharacterized transporter YNL0950
OS = Saccharomyces cerevisiae (strain ATCC 204508/S288c) GN = YNL095C
PE = 1 SV = 1

SEQ ID NO: 62

MVHITLGQAIWVSVKPIIKIYLIIGVGFLMAKMGILTVEATRIISDIVLTVLLPSLSFNK

IVANIEDKDIKSVGIICLSALLIFGSGFFFAYVVRLFLPVPKQWYGGILAGGMFPNISDL

PIAYLQSMDQGLVFSEEEGNKGVANVIIFLTMFLICIFNLGGFRLIESDFEYNDDESAVR

VSETTKTQPAVSANTTNTDTSERFFSNEQQLFNNKYTARDSLTEAIGTKGENADVPPISR

RSTNSIAPLSLETTSSNSKITKPVQVKARNTIACTQSEESQATRGSNPLDSQSSASTIHS

YNTSESYESSIDTMRARRTASQPRAYNTTTLLEENCLDEKCPKNMSMAALEPIRSIDMRA

LPSQNIHHLIREYSNVDQYGHQRRNSSLRGADMNDVHSISSNSTLQTIKTANLTRILTSD

ATVSKKDIETSGESLPQWMRKFSLTPLLVFFLKNCLRPCSMAVIIALTVAFIPWVKALFV

TTANTPHISQAPDNAPPLSFFMDFTGYVGAACVPFGLILLGATLGRLKIGNLYPGFWKAA

VTLVILRQCVMPIFGVLWCDRLVKAGWVNWQDDRMLLFVIAISWNLPTMTTLIYFTASFT

PPETTAPIQMECVSFFLMLQYPLMVVSLPFLVSYFLKVQMNL

YNL121C
>sp|P07213|TOM70_YEAST Mitochondrial import receptor subunit TOM70
OS = Saccharomyces cerevisiae (strain ATCC 204508/S288c) GN = TOM70
PE = 1 SV = 2

SEQ ID NO: 63

MKSFITRNKTAILATVAATGTAIGAYYTYNQLQQQQQRGKKNTINKDEKKDTKDSQKETE

GAKKSTAPSNPPIYPVSSNGEPDFSNKANFTAEEKDKYALALKDKGNQFFRNKKYDDAIK

YYNWALELKEDPVFYSNLSACYVSVGDLKKVVEMSTKALELKPDYSKVLLRRASANEGLG

KFADAMFDLSVLSLNGDFNDASIEPMLERNLNKQAMSKLKEKFGDIDTATATPTELSTQP

AKERKDKQENLPSVTSMASFFGIFKPELTFANYDESNEADKELMNGLSNLYKRSPESYDK

ADESFTKAARLFEEQLDKNNEDEKLKEKLAISLEHTGIFKFLKNDPLGAREDIKKAIELF

PRVNSYIYMALIMADRNDSTEYYNYFDKALKLDSNNSSVYYHRGQMNFILQNYDQAGKDF

DKAKELDPENIFPYIQLACLAYRENKFDDCETLFSEAKRKFPEAPEVPNFFAEILTDKND

FDKALKQYDLAIELENKLDGIYVGIAPLVGKATLLTRNPTVENFIEATNLLEKASKLDPR

SEQAKIGLAQMKLQQEDIDEAITLFEESADLARTMEEKLQAITFAEAAKVQQRIRSDPVL

AKKIQETLAKLREQGLM

YNL142W

TABLE 14-continued

Sequences disclosed herein.

>sp|P41948|MEP2_YEAST Ammonium transporter MEP2 OS = *Saccharomyces cerevisiae* (strain ATCC 204508/S288c) GN = MEP2 PE = 1 SV = 1

SEQ ID NO: 64

MSYNFTGTPTGEGTGGNSLTTDLNTQFDLANMGWIGVASAGVWIMVPGIGLLYSGLSRKK

HALSLLWASMMASAVCIFQWFFWGYSLAFSHNTRGNGFIGTLEFFGFRNVLGAPSSVSSL

PDILFAVYQGMFAAVTGALMLGGACERARLFPMMVFLFLWMTIVYCPIACWVWNAEGWLV

KLGSLDYAGGLCVHLTSGHGGLVYALILGKRNDPVTRKGMPKYKPHSVTSVVLGTVFLWF

GWMFFNGGSAGNATIRAWYSIMSTNLAAACGGLTWMVIDYFRCGRKWTTVGLCSGIIAGL

VGITPAAGFVPIWSAVVIGVVTGAGCNLAVDLKSLLRIDDGLDCYSIHGVGGCIGSVLTG

IFAADYVNATAGSYISPIDGGWINHWYKQVGYQLAGICAALAWTVTVTSILLLTMNAIPF

LKLRLSADEEELGTDAAQIGEFTYEESTAYIPEPIRSKTSAQMPPPHENIDDKIVGNTDA

EKNSTPSDASSTKNTDHIV

YOL020W
>sp|P38967|TAT2_YEAST Tryptophan permease OS = *Saccharomyces cerevisiae* (strain ATCC 204508/S288c) GN = TAT2 PE = 1 SV = 1

SEQ ID NO: 65

MTEDFISSVKRSNEELKERKSNFGFVEITSKQLTSSSSHNSNSSHHDDDNQHGKRNIFQR

CVDSFKSPLOGSFDTSNLKRTLKPRHLIMIAIGGSIGTGLFVGSGKAIAEGGPLGVVIGW

AIAGSQIIGTIHGLGEITVRETVVGAFANYGTRFLDPSISFVVSTIYVLQWFFVLPLEII

AAAMTVQYWNSSIDPVIWVAIFYAVIVSINLFGVRGFGEAEFAFSTIKAITVCGFIILCV

VLICGGGPDHEFIGAKYWHDPGCLANGFPGVLSVLVVASYSLGGIEMTCLASGETDPKGL

PSAIKQVFWRILFFFLISLTLVGFLVPYTNQNLLGGSSVDNSPFVIAIKLHHIKALPSIV

NAVILISVLSVGNSCIFASSRTLCSMAHQGLIPWWFGYIDRAGRPLVGIMANSLFGLLAF

LVKSGSMSEVFNWLMAIAGLATCIVWLSINLSHIRFRLAMKAQGKSLDELEFVSAVGIWG

SAYSALINCLILIAQFYCSLWPIGGWTSGKERAKIFFQNYLCALIMLFIFIVHKIYYKCQ

TGKWWGVKALKDIDLETDRKDIDIEIVKQEIAEKKMYLDSRPWYVRQFHFWC

YOL075C
>sp|Q08234|YO075_YEAST Uncharacterized ABC transporter ATP-binding protein/permease YOL075C OS = *Saccharomyces cerevisiae* (strain ATCC 204508/S288c) GN = YOL075C PE = 1 SV = 3

SEQ ID NO: 66

MSQQENGDVATELIENRLSFSRIPRISLHVRDLSIVASKTNTTLVNTFSMDLPSGSVMAV

MGGSGSGKTTLLNVLASKISGGLTHNGSIRYVLEDTGSEPNETEPKRAHLDGQDHPIQKH

VIMAYLPQQDVLSPRLTCRETLKFAADLKLNSSERTKKLMVEQLIEELGLKDCADTLVGD

NSHRGLSGGEKRRLSIGTQMISNPSIMFLDEPTTGLDAYSAFLVIKTLKKLAKEDGRTFI

MSIHQPRSDILFLLDQVCILSKGNVVYCDKMDNTIPYFESIGYHVPQLVNPADYFIDLSS

VDSRSDKEEAATQSRLNSLIDHWHDYERTHLQLQAESYISNATEIQIQNMTTRLPFWKQV

TVLTRRNFKLNFSDYVTLISTFAEPLIIGTVCGWIYYKPDKSSIGGLRTTTACLYASTIL

QCYLYLLFDTYRLCEQDIALYDRERAEGSVTPLAFIVARKISLFLSDDFAMTMIFVSITY

FMFGLEADARKFFYQFAVVFLCQLSCSGLSMLSVAVSRDFSKASLVGNMTFTVLSMGCGF

FVNAKVMPVYVRWIKYIAFTWYSFGTLMSSTFTNSYCTTDNLDECLGNQILEVYGFPRNW

ITVPAVVLLCWSVGYTVVGAIILYLHKIDITLQNEVKSKQKKIKKKSPTGMKPEIQLLDD

VYHQKDLEAEKGKNIHITIKLEDIDLRVIFSAPFSNWKEGNPHHETKEILQSVNAIFKPG

MINAIMGPSGSGKSSLLNLISGRLKSSVFAKFDTSGSIMFNDIQVSELMFKNVCSYVSQD

DDHLLAALTVKETLKYAAALRLHHLTEAERMERTDNLIRSLGLKHCENNIIGNEFVKGIS

TABLE 14-continued

Sequences disclosed herein.

GGEKRRVTMGVQLLNDPPILLLDEPTSGLDSFTSATILEILEKLCREQGKTIIITIHQPR

SELFKRFGNVLLLAKSGRTAFNGSPDEMIAYFTELGYNCPSFTNVADFFLDLISVNTQNE

QNEISSRARVEKILSAWKANMDNESLSPTPISEKQQYSQESFFTEYSEFVRKPANLVLAY

IVNVKRQFTTTRRSFDSLMARIAQIPGLGVIFALFFAPVKHNYTSISNRLGLAQESTALY

FVGMLGNLACYPTERDYFYEEYNDNVYGIAPFFLAYMTLELPLSALASVLYAVFTVLACG

LPRTAGNFFATVYCSFIVTCCGEALGIMTNTFFERPGFVVNCISIILSIGTQMSGLMSLG

MSRVLKGFNYLNPVGYTSMIIINFAFPGNLKLTCEDGGKNSDGTCEFANGHDVLVSYGLV

RNTQKYLGIIVCVAIIYRLIAFFILKAKLEWIKW

YOL077W-A
>sp|P81451|ATP19_YEAST ATP synthase subunit K, mitochondrial
OS = Saccharomyces cerevisiae (strain ATCC 204508/S288c) GN = ATP19
PE = 1 SV = 1
SEQ ID NO: 67

MGAAYHFMGKAIPPHQLAIGTLGLLGLLVVPNPFKSAKPKTVDIKTDNKDEEKFIENYLK

KHSEKQDA

YOL122C
>sp|P38925|SMF1_YEAST Manganese transporter SMF1 OS = Saccharomyces
cerevisiae (strain ATCC 204508/S288c) GN = SMF1 PE = 1 SV = 2
SEQ ID NO: 68

MVNVGPSHAAVAVDASEARKRNISEEVFELRDKKDSTVVIEGEAPVRTFTSSSSNHERED

TYVSKRQVMRDIFAKYLKFIGPGLMVSVAYIDPGNYSTAVDAGASNQFSLLCIILLSNFI

AIFLQCLCIKLGSVTGLDLSRACREYLPRWLNWTLYFFAECAVIATDIAEVIGTAIALNI

LIKVPLPAGVAITVVDVFLIMFTYKPGASSIRFIRIFECFVAVLVVGVCICFAIELAYIP

KSTSVKQVFRGFVPSAQMFDHNGIYTAISILGATVMPHSLFLGSALVQPRLLDYDVKHGN

YTVSEEQDKVKKSKSTEEIMEEKYFNYRPTNAAIKYCMKYSMVELSITLFTLALFVNCAI

LVVAGSTLYNSPEADGADLFTIHELLSRNLAPAAGTIFMLALLLSGQSAGVVCTMSGQIV

SEGHINWKLQPWQRRLATRCISIIPCLVISICIGREALSKALNASQVVLSIVLPFLVAPL

IFFTCKKSIMKTEITVDHTEEDSHNHQNNNDRSAGSVIEQDGSSGMEIENGKDVKIVYMA

NNWIITVIAIIVWLFLSLLNTLAIVQLGMSHGDIS

YOR079C
>sp|Q12067|ATX2_YEAST Metal homeostasis factor ATX2 OS = Saccharomyces
cerevisiae (strain ATCC 204508/S288c) GN = ATX2 PE = 1 SV = 1
SEQ ID NO: 69

MKFLGVILLASELLIATFLIGLIPLYYIDKQKSSIVTNQEGADSISDFTTNADTQTINDD

VSSYRVKIAVLSQFGIGMLLGTSFMLVIPEGIKACVEHDGNVGVNLLIGFLGVYVLDRLV

TLWVSRKQTVYTHDAVKFQSWKDIINHPRQIWMNLIQNNVVFALFIHGLSDGIALGTTTN

NDSLLIVVLIAIVIHKIPAVLSLTSLMVSRQNLMKWEVICNVELFASSTPIGYIVLSLLN

LSHSPTMDWISGNLLLMSGGSLLYASETAFVGGDSHDHDLSVEQEVVLPHDESVYVLIGV

CIPLVISYCISEE

YOR087W
>sp|Q12324|YVC1_YEAST Calcium channel YVC1 OS = Saccharomyces
cerevisiae (strain ATCC 204508/S288c) GN = YVC1 PE = 1 SV = 2
SEQ ID NO: 70

MVSANGDLHLPISNEQCMPENNGSLGFEAPTPRQILRVTNLKYLIDKVVPIVYDPNDIV

CDHSEILSPKVVKLAYEACGGNPKDKANKRKYQSVIIFSLLKVCEWYSILATMEVHNAKL

YETRNLASQQLCKLLIEREETRDLQFLEMQLLIRRYVINENDEDQEPLNALELATDMHCT

TVIGSSGFQRCLKWIWRGWIVQNGLDPTTFIKDDSLAEVSLISHENPVRLKAPVYQNYLQ

MIFSFLFLGLYTLVVNGKDSERVQSFDLLESIFYVENTGFILDELTKLYYIGYAHLSEWN

TABLE 14-continued

Sequences disclosed herein.

LENDTTYLIITFAMGFRAMSVTPLNAKYSSEDWDKISYRVLSCAAPFVWSRLLLYLESQR

FIGIMLVILKHMMKESIVEFFLLFLIMIGFTQGFLGLDSADGKRDITGPILGNLTITVLG

LGSFDVFEEFAPPYAAILYYGYYFIVSVILLNILIALYSTAYQKVIDNADDEYMALMSQK

TLRYIRAPDEDVYVSPLNLIEVFMTPIFRILPPKRAKDLSYTVMTIVYSPFLLLISVKET

REARRIKYNRMKRLNDDANEYDTPWDLTDGYLDDDDGLFSDNRNSGMRATQLKNSRSLKL

QRTAEQEDVHFKVPKKWYKNVKKCSPSFEQYDNDDTEDDAGEDKDEVKELTKKVENLTAV

ITDLLEKLDIKDKKE

YOR092W
>sp|Q99252|ECM3_YEAST Protein ECM3 OS = Saccharomyces cerevisiae
(strain ATCC 204508/S288c) GN = ECM3 PE = 1 SV = 1

SEQ ID NO: 71

MTHITLGQAIWASVRPIIKIYLIIGVGFGLCKMNILTVQATRSISDIVLTILLPCLSENK

IVANIEDNDIKDVGIICLTSVILFATGLGFAFIVRSVLPVPKRWRGGILAGGMFPNISDL

PIAYLQSMDQGFIFTEAEGEKGVANVIIFLAMFLICVFNLGGFRLIENDFHYKGDDDEEN

TLTNDDSAQQPIQPIEGNSSSSSNQDILKEPNESTVPNSSQASYISEKNKKEKTELSVPK

PTHTAPPAIDDRSSNSSAVVSIDSITHSLRTNHVDAQSVSELNDPTYRTRSQPIAYTTES

RTSHVHNNRRNSITGSLRSIDMRELPAEGMSDLIREYSNVDQYGRRRKSSISSQGAPSVL

QADGTISPNLTRTSTLQRVKTSNLTRIITSDATVSKKDIETSGSSLPKWLQKFPLTKFFV

FFLKNCLRPCSMAVILALIIAFIPWVKALFVTTSNTPKIKQAPDNAPALTFIMDFTSYVG

AASVPFGLILLGATLGRLKIGKLYPGFWKSAVVLVFLRQCIMPIEGVLWCDRLVKAGWLN

WENDKMLLEVTAITWNLPTMTTLIYFTASYTPEDETEPVQMECTSFELMLQYPLMVVSLP

FLVSYFIKVQMKL

YOR130C
>sp|Q12375|ORT1_YEAST Mitochondrial ornithine transporter 1
OS = Saccharomyces cerevisiae (strain ATCC 204508/S288c) GN = ORT1
PE = 1 SV = 2

SEQ ID NO: 72

MEDSKKKGLIEGAILDIINGSIAGACGKVIEFPFDTVKVRLQTQASNVFPITWSCIKFTY

QNEGIARGFFQGIASPLVGACLENATLFVSYNQCSKFLEKHINVSPLGQILISGGVAGSC

ASLVLTPVELVKCKLQVANLQVASAKTKHTKVLPTIKAIITERGLAGLWQGQSGTFIRES

FGGVAWFATYEIVKKSLKDRHSLDDPKRDESKIWELLISGGSAGLAFNASIFPADTVKSV

MQTEHISLTNAVKKIFGKFGLKGFYRGLGITLFRAVPANAAVFYIFETLSAL

YOR222W
>sp|Q99297|ODC2_YEAST Mitochondrial 2-oxodicarboxylate carrier 2
OS = Saccharomyces cerevisiae (strain ATCC 204508/S288c) GN = ODC2
PE = 1 SV = 1

SEQ ID NO: 73

MSSDSNAKPLPFIYQFISGAVAGISELTVMYPLDVVKTRFQLEVITPTAAAVGKQVERYN

GVIDCLKKIVKKEGFSRLYRGISSPMLMEAPKRATKFACNDQYQKIFKNLFNINETTQKI

SIAAGASAGMTEAAVIVETELIKIRMQDVKSSYLGPMDCLKKTIKNEGIMGLYKGIESTM

WRNALWNGGYFGVIYQVRNSMPVAKTKGQKTRNDLIAGAIGGTVGTMLNTPFDVVKSRIQ

SVDAVSSAVKKYNWCLPSLLVIYREEGFRALYKGFVPKVCRLAPGGSLMLVVFTGMMNFF

RDLKYGH

YOR291W

TABLE 14-continued

Sequences disclosed herein.

>sp|Q12697|YPK9_YEAST Vacuolar cation-transporting ATPase YPK9
OS = Saccharomyces cerevisiae (strain ATCC 204508/S288c) GN = YPK9
PE = 1 SV = 1

SEQ ID NO: 74

MDIPSSNQIQHGQRSERNRRMPRASFSSTATTSTAATLTSAMVLDQNNSEPYAGATFEAV

PSSIVSFHHPHSFQSSNLPSPHSSGNLEQRGRRLTESEPLVLSSAEQSRSSSRNPSHFRF

FTQEQISNAEGASTLENTDYDMAWDATPAYEQDRIYGTGLSSRRSSIRSFSRASSLSNAK

SYGSFSKRGRSGSRAPQRLGENSDIGFVYHSATHSSSSLSRYTTRERIPIELESQTDEIL

EDESSTHSLESSDSRRSASENNRGSFSGHDDVHNQHSEYLKPDYHEKFYPQYAPNLHYQR

FYIAEEDLVIGIAAYQTSKFWYIIYNLCCFLTFGLVYLLTRWLPHLKVKLYGVKVPLAKA

EWVVIENEFGEFVIQPIDRQWYNRPLSTVLETENYPNPSYEPNDINLSHHHANEINPNVP

ILITFEYRYIKFIYSPLDDLFKTNNNWIDETWVDLSTVSNGLTKGVQEDRELAFGKNQIN

LRMKTTSEILFNEVLHPFYVFQVFSIILWGIDEYYYYAACIFLISVLSIFDSLNEQKKVS

RNLAEMSHFHCDVRVLRDKFWTTISSSELVPGDIYEVSDPNITILPCDSILLSSDCIVNE

SMLTGESVPVSKFPATEETMYQLCDDFQSTQISSFVSKSFLYNGTNIIRARIAPGQTAAL

AMVVRTGFSITKGSLVRSMVFPKPIGFKFYRDSFKYIGFMSLIAIFGFCVSCVQFIKLGL

DKKTMILRALDIITIVVPPALPATLTIGINFALSRLKEKGIFCISPTRLNISGKIDVMCF

DKTGTLTEDGLDVLGVQISEPNGVRGQKFGELLSDIRQVFPKFSLNDCSSPLDFKSRNFF

MSLLTCHSLRSVDGNLLGDPLDFKMFQFTGWSFEEDFQKRAFHSLYEGRHEDDVFPENSE

IIPAVVHPDSNNRENTFTDNDPHNFLGVVRSFEFLSELRRMSVIVKTNNDDVYWSFIKGA

PEVISEICNKSTLPADFEEVLRCYTHNGYRVIACAGKTLPKRTWLYSQKVSREEVESNLE

FLGFIIFQNKLKKETSETLKSLQDANIRTIMCTGDNILTAISVGREAGLIQCSRVYVPSI

NDTPLHGEPVIVWRDVNEPDKILDTKTLKPVKLGNNSVESLRECNYTLAVSGDVFRLLFR

DENEIPEEYLNEILLNSSIYARMSPDEKHELMIQLQKLDYTVGFCGDGANDCGALKAADV

GISLSEAEASVAAPFTSKIFNISCVLDVIREGRAALVTSFACFQYMSLYSAIQFITITIL

YSRGSNLGDFQFLYIDLLLIVPIAICMSWSKSYEKIDKKRPSANLVSPKILVPLLISVFL

VFLFQFIPWIIVQKMSWYIKPIVGGDDAVQSSDNIVLFFVSNFQYILTAIVLSVGPPYRE

PMSKNFEFIVDITVSIGASLLLMTLDTESYLGKMLQLTPISNSFTMFIIVWVILNYYAQL

YIPPSIKGWLKKKKSSKKYKLLIQEEMKLKEV

YOR306C
>sp|Q08777|MCH5_YEAST Riboflavin transporter MCH5 OS = Saccharomyces
cerevisiae (strain ATCC 204508/S288c) GN = MCH5 PE = 1 SV = 2

SEQ ID NO: 75

MSSDSLTPKDTIVPEEQTNQLRQPDLDEDSIHYDPEADDLESLETTASYASTSVSAKVYT

KKEVNKGTDIESQPHWGENTSSTHDSDKEEDSNEEIESFPEGGFKAWVVTFGCFLGLIAC

FGLLNSTGVIESHLQDNQLSSESVSTIGWLFSLFLFVCSASCIISGTYFDRNGFRTIMIV

GTVFHVAGLFATANSTKYWHFILSFAIVCGFGNGIVLSPLVSVPAHYFFKRRGTALAMAT

IGGSVGGVVFPIMLRSFFSMKSDTDPTYGFVWGIRTLGFLDLALLTLSIILVKERLPHVI

ENSKDGESRWRYILRVYILQCFDAKAFLDMKYLFCVLGTVFSELSINSALTYYGSYATSH

GISANDAYTLIMIINVCGIPGRWVPGYLSDKFGRFNVAIATLLTLFIVMFVGWLPFGTNL

TNMYVISALYGFCSGSVFSLLPVCCGQISKTEEFGKRYSTMYFVVGFGTLVGIPITGAII

SIKTTADYQHYIIFCGLATFVSAVCYIISRAYCVGFKWVRF

YOR316C

TABLE 14-continued

Sequences disclosed herein.

>sp|P32798|COT1_YEAST Cobalt uptake protein COT1 OS = *Saccharomyces cerevisiae* (strain ATCC 204508/S288c) GN = COT1 PE = 1 SV = 2

SEQ ID NO: 76

MKLGSKQVKIISLLLLDTVFFGIEITTGYLSHSLALIADSFHMLNDIISLVVALWAVNVA

KNRNPDSTYTYGWKRAEILGALINAVFLIALCVSILIEALQRIIAPPVIENPKFVLYVGV

AGLISNTVGLFLFHDNDQEHGHGHGHSHGGIFADHEMHMPSSHTHTHAHVDGIENTTPMD

STDNISEIMPNAIVDSFMNENTRLLTPENASKTPSYSTSSHTIASGGNYTEHNKRKRSLN

MHGVFLHVLGDALGNIGVMLSAFFIWKTDYSWKYYTDPLVSLIITGIIFSSALPLSCKAS

KILLQATPSTLSGDQVEGDLLKIPGIIAIHDFHIWNLTESIFIASLHIQLDISPEQFTDL

AKIVRSKLHRYGIHSATLQPEFITREVTSTERAGDSQGDHLQNDPLSRPKTYGTGISGS

TCLIDDAANCNTADCLEDH

YOR334W
>sp|Q01926|MRS2_YEAST Magnesium transporter MRS2, mitochondrial
OS = *Saccharomyces cerevisiae* (strain ATCC 204508/S288c) GN = MRS2
PE = 1 SV = 2

SEQ ID NO: 77

MNRRLLVRSISCFQPLSRITFGRPNTPFLRKYADTSTAANTNSTILRKQLLSLKPISASD

SLFISCTVFNSKGNIISMSEKFPKWSFLTEHSLFPRDLRKIDNSSIDIIPTIMCKPNCIV

INLLHIKALIERDKVYVFDTTNPSAAAKLSVLMYDLESKLSSTKNNSQFYEHRALESIFI

NVMSALETDFKLHSQICIQILNDLENEVNRLKLRHLLIKSKDLTLFYQKTLLIRDLLDEL

LENDDDLANMYLTVKKSPKDNFSDLEMLIETYYTQCDEYVQQSESLIQDIKSTEEIVNII

LDANRNSLMLLELKVTIYTLGFTVASVLPAFYGMNLKNFIEESEWGFTSVAVFSIVSALY

ITKKNFNSLRSVIKMTMYPNSPANSSVYTKTSASIALTNKLKRRRKWWKSTKQRLGVLLY

GSSYTNKANLSNNKINKGFSKVKKFNMENDIKNKQNRDMIWKWLIEDKKN

YPL078C
>sp|P05626|ATPF_YEAST ATP synthase subunit 4, mitochondrial
OS = *Saccharomyces cerevisiae* (strain ATCC 204508/S288c) GN = ATP4
PE = 1 SV = 2

SEQ ID NO: 78

MSMSMGVRGLALRSVSKTLFSQGVRCPSMVIGARYMSSTETKQTDPKAKANSIINAIPGN

NILTKTGVLGTSAAAVIYAISNELYVINDESILLLTFLGFTGLVAKYLAPAYKDFADARM

KKVSDVLNASRNKHVEAVKDRIDSVSQLQNVAETTKVLFDVSKETVELESEAFELKQKVE

LAHEAKAVLDSWVRYEASLRQLEQRQLAKSVISRVQSELGNPKFQEKVLQQSISEIEQLL

SKLK

YPL270W
>sp|P33311|MDL2_YEAST ATP-dependent permease MDL2, mitochondrial
OS = *Saccharomyces cerevisiae* (strain ATCC 204508/S288c) GN = MDL2
PE = 1 SV = 3

SEQ ID NO: 79

MLNGRLPLLRLGICRNMLSRPRLAKLPSIRFRSLVTPSSSQLIPLSRLCLRSPAVGKSLI

LQSFRCNSSKTVPETSLPSASPISKGSARSAHAKEQSKTDDYKDIIRLFMLAKRDWKLLL

TAILLLTISCSIGMSIPKVIGIVLDTLKTSSGSDFFDLKIPIFSLPLYEFLSFFTVALLI

GCAANFGRFILLRILSERVVARLRANVIKKTLHQDAEFFDNHKVGDLISRLGSDAYVVSR

SMTQKVSDGVKALICGVVGVGMMCSLSPQLSILLLFFTPPVLFSASVEGKQIRNTSKDLQ

EATGQLTRVAEEQLSGIKTVQSEVAEGNELSRYNVAIRDIFQVGKTAAFTNAKFFTTTSL

LGDLSFLTVLAYGSYLVLQSQLSIGDLTAFMLYTEYTGNAVEGLSTFYSEIMQGAGAASR

LFELTDRKPSISPTVGHKYKPDRGVIEFKDVSFSYPTRPSVQIFKNLNFKIAPGSSVCIV

GPSGRGKSTIALLLLRYYNPTTGTITIDNQDISKLNCKSLRRHIGIVQQEPVLMSGTIRD

| Sequences disclosed herein. |
|---|

NITYGLTYTPTKEEIRSVAKQCFCHNFITKFPNTYDTVIGPHGTLLSGGQKQRIAIARAL

IKKPTILILDEATSALDVESEGAINYTEGQLMKSKSMTIVSIAHRLSTIRRSENVIVLGH

DGSVVEMGKEKELYANPTSALSQLLNEKAAPGPSDQQLQIEKVIEKEDLNESKEHDDQKK

DDNDDNDNNHDNDSNNQSPETKDNNSDDIEKSVEHLLKDAAKEANPIKITPQP

YPL274W
>sp|Q08986|SAM3_YEAST S-adenosylmethionine permease SAM3
OS = Saccharomyces cerevisiae (strain ATCC 204508/S288c) GN = SAM3
PE = 1 SV = 1
SEQ ID NO: 80
MDILKRGNESDKFTKIETESTTIPNDSDRSGSLIRRMKDSFKQSNLHVIPEDLENSEQTE

QEKIQWKLASQPYQKVLSQRHLTMIAIGGTLGTGLFIGLGYSLASGPAALLIGFLLVGTS

MFCVVQSAAELSCQFPVSGSYATHVSRFIDESVGFTVATNYALAWLISFPSELIGCALTI

SYWNQTVNPAVWVAIFYVFIMVLNLFGVRGFAETEFALSIIKVIAIFIFIIIGIVLIAGG

GPNSTGYIGAKYWHDPGAFAKPVFKNLCNTEVSAAFSFGGSELVLLTSTESKNISAISRA

ARGTFWRIAIFYITTVVIIGCLVPYNDPRLLSGSNSEDVSASPFVIALSNTGSMGAKVSN

FMNVVILVAVVSVCNSCVYASSRLIQALGASGQLPSVCSYMDRKGRPLVGIGISGAFGLL

GFLVASKKEDEVETWLFALCSISSFFTWECICMSQIRFRMALKAQGRSNDEIAYKSILGV

YGGILGCVLNALLIAGEIYVSAAPVGSPSSAEAFFEYCLSIPIMIVVYFAHRFYRRDWKH

FYIKRSEIDLDTGCSVENLELFKAQKEAEEQLIASKPFYYKIYRFWC

YPR003C
>sp|P53394|SULX_YEAST Putative sulfate transporter YPR003C
OS = Saccharomyces cerevisiae (strain ATCC 204508/S288c) GN = YPR003C
PE = 1 SV = 1
SEQ ID NO: 81
MTSNNSLLGRGRMSYSSTAPPRFKRSVDQRDTFSDNFDYDKDSSNRGRTYIAASNSTTGV

PPPNNSRSGCTNNTNNTNNTSNTSNTNNNDSVDENTVFETLPYYLPCFSWLPEYTFNKLW

GDVIAGISVASFQIPLALSYTTSIAHVPPLCGLYSLAISPFVYGILGSVPQMIVGPESAI

SLVVGQAVESITLHKENVSLIDISTVITEVSGTILLFSGISRFGFLGNVLSKALLRGFIS

SVGLVMIINSLISELKLDKFLVSLPQHYHTPFEKILFLIDYAPAQYHIPTAIFSGCCLIV

LFLTRLLKRKLMKYHKSAIFFPDILLVVIVTILISMKENLKHRYGISIIGDFSMDNEDEL

KNPLTRPRRKLIFTLFSASLIVAMLGFFESTTASKSLGTTYNLTVSSNRELVALGFMNIV

ISLFGALPAFGGYGRSKINALSGAQSVMSGVFMGVITLITMNLLLQFVHYIPNCVLSVIT

TIIGISLLEEVPGDIKEHLRCGGESELFVFAVTFCTTIFYSIEAGICIGCVYSIINIIKH

SAKSRIQILARVAGTSNFTNLDDYMMNMKRNSLDVEGTEEIEGCMIVRIPEPLTFTNSED

LKQRLDRIERYGSSKIHPGRKSLRSKDSIKYVIFDLGGMTSIDSSAAQVLEEIITSYKRR

NVFIYLVNVSINDKVRRRLFKAGVAASVERAQANNNENNTSNTESDAGETYSPYFDSIDA

ALYEIEKMKIKGNNVITNDSESFMSNTLENSSLV

YPR011C
>sp|Q12251|YP011_YEAST Uncharacterized mitochondrial carrier YPR011C
OS = Saccharomyces cerevisiae (strain ATCC 204508/S288c) GN = YPR011C
PE = 1 SV = 1
SEQ ID NO: 82
MAEVLIVLEQPNSIKDFLKQDSNIAFLAGGVAGAVSRIVVSPFERVKILLQVQSSTTSYN

RGIFSSIRQVYHEEGTKGLERGNGLNCIRIFPYSAVQFVVYEACKKKLFHVNGNNGQEQL

TNIQRLFSGALCGGCSVVATYPLDLIKTRLSIQTANLSSLNRSKAKSISKPPGIWQLLSE

TYRLEGGLRGLYRGVWPTSLGVVPYVALNFAVYEQLREFGVNSSDAQPSWKSNLYKLTIG

AISGGVAQTITYPFDLLRRREQVLAMGGNELGFRYTSVWDALVTIGRAEGVSGYYKGLAA

TABLE 14-continued

Sequences disclosed herein.

NLFKVVPSTAVSWLVYEVVCDSVRNW

YPR058W
>sp|P32331|YMC1_YEAST Carrier protein YMC1, mitochondrial
OS = Saccharomyces cerevisiae (strain ATCC 204508/S288c) GN = YMC1
PE = 1 SV = 2

SEQ ID NO: 83

MSEEFFSPQLIDDLEEHPQHDNARVVKDLLAGTAGGIAQVLVGQPFDTTKVRLQTSSTPT

TAMEVVRKLLANEGFRGFYKGILTPLIGVGACVSLQFGVNEAMKRFFHHRNADMSSILSL

PQYYACGVIGGIVNSFLASPIEHVRIRLQTQTGSGINAEFKGPLECIKKLRHNKALLRGL

TPTILREGHGCGTYFLVYEALIANQMNKRRGLERKDIPAWKLCIFGALSGTALWLMVYPL

DVIKSVMQTDNLQKPKFGNSISSVAKTLYANGGIGAFFKGFGPTMLRAAPANGATFATFE

LAMRLLG

YPR128C
>sp|Q06497|ANT1_YEAST Peroxisomal adenine nucleotide transporter 1
OS = Saccharomyces cerevisiae (strain ATCC 204508/S288c) GN = ANT1
PE = 1 SV = 1

SEQ ID NO: 84

MLTLESALTGAVASAMANIAVYPLDLSKTIIQSQVSPSSSEDSNEGKVLPNRRYKNVVDC

MINIFKEKGILGLYQGMTVTTVATFVQNFVYFFWYTFIRKSYMKHKLLGLQSLKNRDGPI

TPSTIEELVLGVAAASISQLFTSPMAVVATRQQTVHSAESAKFINVIKDIYRENNGDITA

FWKGLRTGLALTINPSITYASFQRLKEVFFHDHSNDAGSLSAVQNFILGVLSKMISTLVT

QPLIVAKAMLQSAGSKFTTFQEALLYLYKNEGLKSLWKGVLPQLTKGVIVQGLLFAFRGE

LTKSLKRLIFLYSSFELKHNGQRKLAST

YPR201W
>sp|Q06598|ARR3_YEAST Arsenical-resistance protein 3
OS = Saccharomyces cerevisiae (strain ATCC 204508/S288c) GN = ARR3
PE = 1 SV = 1

SEQ ID NO: 85

MSEDQKSENSVPSKVNMVNRIDILITIKSLSWLDLMLPFTIILSIIIAVIISVYVPSSRH

TFDAEGHPNLMGVSIPLTVGMIVMMIPPICKVSWESIHKYFYRSYIRKQLALSLFLNWVI

GPLLMTALAWMALFDYKEYRQGIIMIGVARCIAMVLIWNQIAGGDNDLCVVLVITNSLLQ

MVLYAPLQIFYCYVISHDHLNTSNRVLFEEVAKSVGVFLGIPLGIGIIIRLGSLTIAGKS

NYEKYILRFISPWAMIGFHYTLEVIFISRGYQFIHEIGSAILCFVPLVLYFFIAWFLTFA

LMRYLSISRSDTQRECSCDQELLLKRVWGRKSCEASFSITMTQCFTMASNNFELSLAIAI

SLYGNNSKQAIAATFGPLLEVPILLILAIVARILKPYYIWNNRN

YBR008C
>sp|P38124|FLR1_YEAST Fluconazole resistance protein 1
OS = Saccharomyces cerevisiae (strain ATCC 204508/S288c) GN = FLR1
PE = 1 SV = 1

SEQ ID NO: 86

MVYTSTYRHTIVVDLLEYLGIVSNLETLQSAREDETRKPENTDKKECKPDYDIECGPNRS

CSESSTDSDSSGSQIEKNDPFRVDWNGPSDPENPQNWPLLKKSLVVFQIMLLTCVTYMGS

SIYTPGQEYIQEEFHVGHVVATLNLSLYVLGYGLGPIIFSPLSETARYGRLNLYMVTLFF

FMIFQVGCATVHNIGGLIVMRFISGILCSPSLATGGGTVADIISPEMVPLVLGMWSAGAV

AAPVLAPLLGAAMVDAKNWRFIFWLLMWLSAATFILLAFFFPETQHHNILYRRALKLRKE

TGDDRYYTEQDKLDREVDARTFLINTLYRPLKMIIKEPAILAFDLYIAVAYGCFYLFFEA

FPIVFVGIYHFSLVEVGLAYMGFCVGCVLAYGLFGILNMRIIVPRFRNGTFTPEAFLIVA

MCVCWCLPLSLFLFGWTARVHWILPVISEVFFVLAVFNIFQATFAYLATCYPKYVASVFA

GNGFCRASFACAFPLFGRAKYDNLATKNYPVAWGSSLVGFLTLGLAIIPFILYKYGPSLR

TABLE 14-continued

Sequences disclosed herein.

TRSSYTEE

YBR021W
>sp|P05316|FUR4_YEAST Uracil permease OS = Saccharomyces cerevisiae
(strain ATCC 204508/S288c) GN = FUR4 PE = 3 SV = 2
SEQ ID NO: 87

MPDNLSLHLSGSSKRLNSRQLMESSNETFAPNNVDLEKEYKSSQSNITTEVYEASSFEEK

VSSEKPQYSSFWKKIYYEYVVVDKSILGVSILDSFMYNQDLKPVEKERRVWSWYNYCYFW

LAECFNINTWQIAATGLQLGLNWWQCWITIWIGYGFVGAFVVLASRVGSAYHLSFPISSR

ASFGIFFSLWETINRVVMAIVWYSVQAYIAATPVSLMLKSIFGKDLQDKIPDHFGSPNAT

TYEFMCFFIFWAASLPFLLVITHKIRHLFTVKAVLVPFASFGFLIWAIRRAHGRIALGSL

TDVQPHGSAFSWAFLRSLMGCMANFSTMVINAPDFSRFSKNPNSALWSQLVCIPFLFSIT

CLIGILVTAAGYEIYGINYWSPLDVLEKFLQTTYNKGTRAGVFLISFVFAVAQLGTNISA

NSLSCGTDMSAIETKFINIKRGSLFCAAMALCICPWNLMATSSKFTMALSAYAIFLSSIA

GVVCSDYFVVRRGYIKLTHIYSHQKGSFYMYGNRFGINWRALAAYLCGVAPCLPGFIAEV

GAPAIKVSDGAMKLTYLSYWVGYGLSFSSYTALCYFFPVPGCPVNNIIKDKGWFQRWANV

DDFEEEWKDTIERDDLVDDNISVYEHEHEKTFI

YBR043C
>sp|P38227|QDR3_YEAST Quinidine resistance protein 3
OS = Saccharomyces cerevisiae (strain ATCC 204508/S288c) GN = QDR3
PE = 1 SV = 2
SEQ ID NO: 88

MQAQGSQSNVGSLRSNCSDNSLPNNHVMMHCDESSGSPHSEHNDYSYEKTNLESTASNSR

EHRDNQLSRLKSEEYVVPKNQRRGLLPQLAIIPEFKDARDYPPMMKKMIVFLIAFSSMMG

PMGTSIIFPAINSITTEFKTSVIMVNVSIGVYLLSLGVFPLWWSSLSELEGARTTYITSF

ALLFAFNIGSALAPDINSFIALRMLCGAASASVQSVGAGTVADLYISEDRGKNLSYYYLG

PLLAPLLSPIFGSLLVNRWPWRSTQWFMVILSGCNVILLTVLLPETLRKQDSKGAIAQIL

AERRIQVDNNERGEIQEDYQRGEDETDRIENQVAILSTEKHNYVGEVRDQDSLDLESHSS

PNTYDGRAGETQLQRIYTEASRSLYEYQLDDSGIDATTAQVTRIRSTDPKLARSIRENSL

RKLQTNLEEQVKKVLSSNGGEIAPKQVSAVRKVWDTFFVYFIKPLKSLHFLEYPPVALAI

TFSAISFSTVYFVNMTVEYKYSRPPYNFKPLYIGLLYIPNSVTYFFASIYGGRWVDMLLK

RYKEKYGILAPEARISWNVVTSVISFPIALLIFGWCLDKKCHWVTPLIGTALFGYAAMMT

IGATLSYLVDSL2GKGATGVALNNLIRQILAATAVFVTTPMLNGMGTGWAFTMLAFIVLG

ASSVLIILKKHGDYWRENYDLQKLYDKID

YBR287W
>sp|P38355|YB8B_YEAST Uncharacterized transporter YBR287W
OS = Saccharomyces cerevisiae (strain ATCC 204508/S288c) GN = YBR287W
PE = 1 SV = 1
SEQ ID NO: 89

MVETFSFAHLAYLVFESVLQVVIIALAGFWSASSGLLPKQSQKIISLLNVDLFTPCLIFS

KLAKSLSMAKIFEIAIIPIFFGLITGISFISGKIMSRILDLDKDEINFVVANSVFGNSNS

LPVSLILSLAYTLPNLTWDQIPNDNRDNVASRGILYLLIFQQIGQMLRWSWGYNKLMKWS

GENTQHMPPSQVQSLLERIPNIDNEELVNEEQEEQELLEEENNRMNSSFLSSSSIGDKIW

QKSCIVFERIRANLNPPLYSMIFAVVVAAIGPLQRELFMEDGFINNTFAEAVTQLGSVSI

PLILVVLGSNLYPSAEVFPKTVHHSKLLIGSIIGRMILPSCFLLPIIAIAVKYINVSILD

DPIFLVVGFLLIVSPFAIQLTQITQLNEFFEAEMADILFWGYAVLSLPVSIIVVSGAIYV

LQWANPT

TABLE 14-continued

Sequences disclosed herein.

YBR295W
>sp|P38360|ATU1_YEAST P-type cation-transporting ATPase
OS = Saccharomyces cerevisiae (strain ATCC 204508/S288c) GN = PCA1
PE = 1 SV = 2

SEQ ID NO: 90

MKPEKLFSGLGISDGEYGVVNSENISIDAMQDNRGECHRRSIEMHANDNLGLVSQRDCIN

RPKITPQECLSETEQICHHGENRIKAGLDVDDAETGGDHINESRVDECCAEKVNDTEIGL

DVDSCCGDAQTGGDHINESCVDGCCVRDSSVMVEEVIGSCEAVSSKEQLLTSFEVVPSKS

EGLQSIHDIRETTRCNINSNQHIGKGRLCIESSDSTLKKRSCKVSRQKIEVSSKPECCNI

SCVERIASRSCEKRIFKGSTNVGISGSSSTDSLSEKFFSEQYSRMYNRYSSILKNLGCIC

NYLRILGKESCCLPKVRFCSGEGASKKIKYSYRNSSGCLIKKKTHGDKERLSNDNGHADF

VCSKSCCIKMKDCAVTSTISGHSSSEISRIVSMEPIENHLNLEAGSTGTEHIVLSVSGMS

CTGCESKLKKSFGALKCVHGLKTSLILSQAEFNLDLAQGSVKDVIKHLSKTTEFKYEQIS

NHGSTIDVVVPYAAKDFINEEWPQGVIELKIVERNIIRIYFDPKVIGARDLVNEGWSVPV

SIAPFSCHPTIEVGRKHLVRVGCTIALSIILTIPILVMAWAPQLREKISTISASMVLATI

IQFVIAGPFYLNALKSLIFSRLIEMDLLIVLSTSAAYIFSIVSFGYFVVGRPLSTEQFFE

ISSLLVTLIMVGRFVSELARHRAVKSISVRSLQASSAILVDKTGKETEINIRLLQYGDIF

KVLPDSRIPIDGIVISGSSEVDEALITGESMPVPKKCQSIVVAGSVNGIGTLFVKLSKLP

GNNTISTIATMVDEAKLIKPKIQNIADKIASYFVPTIIGITVVTFCVWIAVGIRVEKQSR

SDAVIQAIIYAITVLIVSCPCVIGLAVPIVFVIASGVAAKRGVIEKSAESIEVAHNTSHV

VFDKIGTLTEGKLIVVHETVRGDRHNSQSLLLGLTEGIKHPVSMAIASYLKEKGVSAQNV

SNIKAVIGKRVEGTSYSGLKLQGGNCRWLGHNNDPDVRKALEQGYSVFCFSVNGSVTAVY

ALEDSLRADAVSTINLLRQRGISLHILSGDDDGAVRSMAARLGIESSNIRSHATPAEKSE

YIKDIVEGRNCDSSSQSKRPVVVFCGDGINDAIGLTQATIGVHINEGSEVAKLAADVVML

KPKLNNILTMITVSQKAMFRVKLNFLWSFTYNLFAILLAAGAFVDFHIPPEYAGLGELVS

ILPVIFVAILLRYAKI

YBR296C
>sp|P38361|PHO89_YEAST Phosphate permease PHO89 OS = Saccharomyces
cerevisiae (strain ATCC 204508/S288c) GN = PHO89 PE = 1 SV = 1

SEQ ID NO: 91

MALHQFDYIFAIAMLFAFLDAFNIGANDVANSFASSISSRSLKYWQAMVLAGLCEFLGAV

LAGARVSGTIKNNIIDSSIFINDPAVLMLTMTSALIGSSCWLIFATAIGMPVSITHSIVG

GTIGAGIAAGGANGVVWGWSGVSQIIASWFIAPILAGAIAAIVFSISRFSVLEVKSLERS

IKNALLLVGVLVFATFSILTMLIVWKGSPNLHLDDLSETETAVSIVLIGAIASIVYFIFF

YPFYRRKVLDQDWILKLIDIFRGPSFYFKSIDDIPPMPEGHQLTIDYYEGRRNLGTIVSV

EDEENKAASNSNDSVKNKEDIQEVDLVRTETEPETKLSTKQYWWSLLKQGPKKWPLLFWL

VISHGWTQDVIHAQVNDRDMLSGDLKGMYERSKFYDNRVEYIYSVLQAITAATMSFAHGA

NDVANATGPLSAVYVIWKTNTIGAKSEVPVWVLAYGGVALVIGCWTYGYNIIKNLGNKMI

LQSPSRGFSIELAVAITTVMATQLGIPTSTIQIAVGGIVAVGLCNKDLKSVNWRMVAWCY

SGWFLTLPIAGLIAGIINGIILNAPRFGVEYQMT

TABLE 14-continued

Sequences disclosed herein.

YCL038C
>sp|P25568|ATG22_YEAST Autophagy-related protein 22 OS = *Saccharomyces cerevisiae* (strain ATCC 204508/S288c) GN = ATG22 PE = 1 SV = 1
SEQ ID NO: 92

MSYGTINDMNESVTNYRIKKAQNNIKGWYAYSFSSEPPFVVSAVSTYIPLLLQQFASINGV

KVHDHSIPCLSETGSDSDKCVLGLFNNRIFVDTSSFALYVFSLSVLFQTIIVISVSGIVD

LWGSVKFKGRILVWFGIVGALSTVAISKLNDTQIYSLAGLYIVANGCFGVINVVGNSLLP

IFVKDSLKCQSQGAYEPDKVDSLITVISGRGASLGYSSALIVQIVSMFLVASKKGSKQDV

QVAVLFVGIWWFVWQLPMIWLIDDVTIPIRVDDSTLASARSPYPGEQDALGQLNWKNYLS

YGWVSLFESFKHARLLKDVMIFLIAWFIISDSITTINSTAVLFSKAELHMSTLNLIMISV

LIVVNAMLGAFMIPQFLATKFRWTSSQTLMYIIIWASFIPFYGILGFFFNAFGLKHKFEM

FLLAIWYGLSLGGLSAVSRSVFSLIVPPGKESTFFSMFSITDKGSSILGPFLVGLLTDKT

HNIRYSFYFFLLLMLSLPVLNCLDVKRGRREAEELSQVLPESERRLD

YCR011C
>sp|P25371|ADP1_YEAST Probable ATP-dependent permease OS = *Saccharomyces cerevisiae* (strain ATCC 204508/S288c) GN = ADP1 PE = 1 SV = 2
SEQ ID NO: 93

MGSHRRYLYYSILSFLLLSCSVVLAKQDKIPFFEGTSSKNSRLTAQDKGNDTCPPCFNCM

LPIFECKQFSECNSYTGRCECIEGFAGDDCSLPLCGGLSPDESGNKDRPIRAQNDTCHCD

NGWGGINCDVCQEDFVCDAFMPDPSIKGTCYKNGMIVDKVFSGCNVTNEKILQILNGKIP

QITFACDKPNQECNFQFWIDQLESFYCGLSDCAFEYDLEQNTSHYKCNDVQCKCVPDTVL

CGAKGSIDISDFLTETIKGPGDFSCDLETRQCKFSEPSMNDLILTVFGDPYITLKCESGE

CVHYSEIPGYKSPSKOPTVSWQGKLVLALTAVMVLALFTFATFYISKSPLFRNGLGSSKS

PIRLPDEDAVNNFLQNEDDTLATLSFENITYSVPSINSDGVEETVLNEISGIVKPGQILA

IMGGSGAGKTTLLDILAMKRKTGHVSGSIKVNGISMDRKSFSKIIGFVDQDDFLLPTLIV

FETVLNSALLRLPKALSFEAKKARVYKVLEELRIIDIKDRIIGNEFDRGISGGEKRAVSI

ACELVTSPLVLFLDEPTSGLDASNANNVIECLVRLSSDYNRTLVLSIHQPRSNIFYLFDK

LVLLSKGEMVYSGNAKKVSEFLRNEGYICPDNYNIADYLIDITFEAGPQGKRRRIRNISD

LEAGTDTNDIDNTIHQTTFTSSDGTTQREWAHLAAHRDEIRSLLRDEEDVEGTDGRRGAT

EIDLNTKLLHDKYKDSVYYAELSQEIEEVLSEGDEESNVLNGDLPTGQQSAGFLQQLSIL

NSRSFKNMYRNPKLLLGNYLLTILLSLFLGTLYYNVSNDISGFQNRMGLFFFILTYFGFV

TFTGLSSFALERIIFIKERSNNYYSPLAYYISKIMSEVVPLRVVPPILLSLIVYPMTGLN

MKDNAFFKCIGILILFNLGISLEILTIGIIFEDLNNSIILSVLVLLGSLLFSGLFINTKN

ITNVAFKYLKNFSVFYYKYESLLINEVKTLMLKERKYGLNIEVPGATILSTFGFVVQNLV

FDIKILALFNVVFLIMGYLALKWIVVEQK

YDL054C
>sp|Q07376|MCH1_YEAST Probable transporter MCH1 OS = *Saccharomyces cerevisiae* (strain ATCC 204508/S288c) GN = MCH1 PE = 1 SV = 1
SEQ ID NO: 94

MPLSKVEHYLSYHTRLLLPHVSLQSSHRVAYIFSLLSAVSTGFITLISLYSQPWQKHLN

YSSWQINTIASMINLGMYLTPPILGMIADSHGPITLSLLAIIGFIPSYSYLAYVFNHPEL

SLGGNGDSSFNLSIICFVFIGISTSALYFSALLTCTKLYPHTKLLSISLPITCYGISSVV

GSQLLRIKWFWSSNASSSSSNSDLNLGRVFQTFALVYVVIGLLAWIATSVVSLLHFNEEQ

DNQKRLDDQTDVEQSPLLERSNHVQEKFTQTMLRIFSDPVTYILAVSILLSLGPLEMFIA

NMGSLTNLLVQLDAPTLSTKLLSTYALSSTFTRLLTGIVADFFAKKKISIKWILLTFLSL

TABLE 14-continued

Sequences disclosed herein.

GVCAQLFLLKMTSSASPMGLVPTGSLVGIVYGGLFTVYPTLVLLVWGERSFGTVYGSLLI

APAIGSMIFCMLYAKFYDSRCMSGGGDLRNPSCISAVYKYSSIAFVVSAVLSAVVFWKLK

SRKLRI

YDL100C
>sp|Q12154|GET3_YEAST ATPase GET3 OS = *Saccharomyces cerevisiae* (strain ATCC 204508/S288c) GN = GET3 PE = 1 SV = 1
SEQ ID NO: 95

MDLTVEPNLHSLITSTTHKWIFVGGKGGVGKTTSSCSIAIQMALSQPNKQFLLISTDPAH

NLSDAFGEKFGKDARKVTGMNNLSCMEIDPSAALKDMNDMAVSRANNNGSDGQGDDLGSL

LQGGALADLTGSIPGIDEALSFMEVMKHIKRQEQGEGETFDTVIFDTAPTGHTLRFLQLP

NTLSKLLEKFGEITNKLGPMLNSFMGAGNVDISGKLNELKANVETIRQQFTDPDLTTFVC

VCISEFLSLYETERLIQELISYDMDVNSIIVNQLLFAENDQEHNCKRCQARWKMQKKYLD

QIDELYEDFHVVKMPLCAGEIRGLNNLTKFSQFLNKEYNPITDGKVIYELEDKE

YDL245C
>sp|P54854|HXT15_YEAST Hexose transporter HXT15 OS = *Saccharomyces cerevisiae* (strain ATCC 204508/S288c) GN = HXT15 PE = 1 SV = 1
SEQ ID NO: 96

MASEQSSPEINADNLNSSAADVHVQPPGEKEWSDGFYDKEVINGNTPDAPKRGFLGYLII

YLLCYPVSFGGFLPGWDSGITAGFINMDNFKMNFGSYKHSTGEYYLSNVRMGLLVAMFSV

GCSIGGVAFARLADTLGRRLAIVIVVLVYMVGAIIQISSNHKWYQYFVGKIIYGLGAGGC

SVLCPMLLSEIAPTDLRGGLVSLYQLNMTFGIFLGYCSVYGTRKYSNTAQWRIPVGLCFL

WALIIIVGMLLVPESPRYLIECERHEEACVSIAKINKVSPEDPWVLKQADEINAGVLAQR

ELGEASWKELFSVKTKVLQRLITGILVQTFLQLTGENYFFFYGTTIFKSVGLTDGFETSI

VLGTVNFFSTIIAVMVVDKIGRRKCLLFGAASMMACMVIFASIGVKCLYPHGQDGPSSKG

AGNAMIVFTCFYIFCFATTWAPVAXIVVAESFPSKVKSKAMSISTAFNWLWQFLIGFFTP

FITGSIHFYYGYVFVGCLVAMFINVFFFLRETIGLSLEEIQLLYEEGIKPWKSASWVPPS

RRGASSRETEAKKKSWKEVLKFPKSFN

YDL247W
>sp|P0CD99|MPH2_YEAST Alpha-glucosides permease MPH2 OS = *Saccharomyces cerevisiae* (strain ATCC 204508/S288c) GN = MPH2 PE = 2 SV = 1
SEQ ID NO: 97

MKNLSFLINRRKENTSDSNVYPGKAKSHEPSWIEMDDQTKKDGLDIVHVEFSPDTRAPSD

SNKVITEIFDATEDAKEADESERGMPLATALNTYPKAAAWSLLVSTTLIMEGYDTAILGA

FYALPIFQRKFGSQNDKTGEWEISASWQIGLTLCYMAGEIVGLQLTGPSVDLVGNRYTLI

IALFFLAAFTFILYFCNSLGMIAVGQALCGMPWGCFQCLTVSYASEICPLALRYYLTTYS

NLCWLFGQLFAAGIMKNSQKKYADSELGYKLETALQWILPVPLALGIFFAPESPWWLVKK

GRFDEARRSLRRTLSGKGPEKEILVTLEVDKIKVTIDKEKRLTSKEGSYSDCFEDKINRR

RTRITCLCWAGQATCGSILIGYSTYTYEKAGVSTEMSFTFSIIQYCLGICATFLSWWASK

YFGRYDLYAFGLAFQTIVFFIIGGLGCSSTHGSKMGSGSLLMAVAFFYNLGIAPVVFCLV

SEMPSSRLRTKTIILARNTYNVVSIICSVLILYQLNSKKWNWGAKSGFFWGVLCFCTLIW

AVVDLPETAGKTFVEINELFKLGVSARKFKSTKVDPFVVKTPLKTSLITTPREISKLPLQ

RNSNVSHHL

TABLE 14-continued

Sequences disclosed herein.

YDR011W
>sp|P32568|SNQ2_YEAST Protein SNQ2 OS = Saccharomyces cerevisiae
(strain ATCC 204508/S288c) GN = SNQ2 PE = 1 SV = 2

SEQ ID NO: 98

MSNIKSTQDSSHNAVARSSSASFAASEESFTGITHDKDEQSDTPADKLTKMLTGPARDTA

SQISATVSEMAPDVVSKVESFADALSRHTTRSGAFNMDSDSDDGFDAHAIFESPIRDADE

QGIHIRKAGVTIEDVSAKGVDASALEGATFGNILCLPLTIFKGIKAKRHQKMRQIISNVN

ALAEAGEMILVLGRPGAGCSSFLKVTAGEIDQFAGGVSGEVAYDGIPQEEMMKRYKADVI

YNGELDVHFPYLTVKQTLDFAIACKTPALRVNNVSKKEYIASRRDLYATIFGLRHTYNTK

VGNDFVRGVSGGERKRVSIAEALAAKGSIYCWDNATRGLDASTALEYAKAIRIMTNLLKS

TAFVTIYQASENIYETFDKVTVLYSGKQIYFGLIHEAKPYFAKMGYLCPPRQATAEFLTA

LTDPNGFHLIKPGYENKVPRTAEEFETYWLNSPEFAQMKKDIAAYKEKVNTEKTKEVYDE

SMAQEKSKYTRKKSYYTVSYWEQVKLCTQRGFQRIYGNKSYTVINVCSAIIQSFITGSLF

YNTPSSTSGAFSRGGVLYFALLYYSLMGLANISFEHRPILQKHKGYSLYHPSAEAIGSTL

ASFPFRMIGLTCFFIILFFLSGLHRTAGSFFTIYLFLTMCSEAINGLFEMVSSVCDTLSQ

ANSISGILMMSISMYSTYMIQLPSMHPWFKWISYVLPIRYAFESMLNAEFHGRHMDCANT

LVPSGGDYDNLSDDYKVCAFVGSKPGQSYVLGDDYLKNQFQYVYKHTWRNFGILWCFLLG

YVVLKVIFTEYKRPVKGGGDALIFKKGSKRFIAHADEESPDNVNDIDAKEQFSSESSGAN

DEVFDDLEAKGVFIWKDVCFTIPYEGGKRMLLDNVSGYCIPGTMTALMGESGAGKTTLLN

TLAQRNVGIITGDMLVNGRPIDASFERRTGYVQQQDIHIAELTVRESLQFSARMRRPQHL

PDSEKMDYVEKIIRVLGMEEYAEALVGEVGCGLNVEQRKKLSIGVELVAKPDLLLFLDEP

TSGLDSQSSWAIIQLLRKLSKAGQSILCTIHQPSATLFEEFDRLLLLRKGGQTVYFGDIG

KNSATILNYFERNGARKCDSSENPAEYILEAIGAGATASVKEDWHEKWLNSVEFEQTKEK

VQDLINDLSKQETKSEVGDKPSKYATSYAYQFRYVLIRTSTSFWRSLNYIMSKMMLMLVG

GLYIGFTFFNVGKSYVGLQNAMFAAFISIILSAPAMNQIQGRAIASRELFEVRESQSNMF

HWSLVLITQYLSELPYHLFFSTIFFVSSYFPLRIFFEASRSAVYFLNYCIMFQLYYVGLG

LMILYMSPNLPSANVILGLCLSFMLSFCGVTQPVSLMPGFWTFMWKASPYTYFVQNLVGI

MLHKKPVVCKKKELNYFNPPNGSTCGEYMKPFLEKATGYIENPDATSDCAYCIYEVGDNY

LTHISSKYSYLWRNFGIFWIYIFFNIIAMVCVYYLFHVRQSSFLSPVSILNKIKNIRKKK

Q

YDR292C
>sp|P32916|SRPR_YEAST Signal recognition particle receptor subunit
alpha homolog OS = Saccharomyces cerevisiae (strain ATCC 204508/
S288c) GN = SRP101 PE = 1 SV = 2

SEQ ID NO: 99

MFDQLAVFTPQGQVLYQYNCLGKKFSEIQINSFISQLITSPVTRKESVANANTDGFDFNL

LTINSEHKNSPSFNALFYLNKQPELYFVVTFAEQTLELNQETQQTLALVLKLWNSLHLSE

SILKNRQGQNEKNKHNYVDILQGIEDDLKKFEQYFRIKYEESIKQDHINPDNFTKNGSVP

QSHNKNTKKKLRDTKGKKQSTGNVGSGRKWGRDGGMLDEMNHEDAAKLDFSSSNSHNSSQ

VALDSTINKDSFGDRTEGGDFLIKEIDDLLSSHKDEITSGNEAKNSGYVSTAFGFLQKHV

LGNKTINESDLKSVLEKLTQQLITKNVAPEAADYLTQQVSHDLVGSKTANWTSVENTARE

SLTKALTQILTPGVSVDLLREIQSKRSKKDEEGKCDPYVFSIVGVNGVGKSTNLSKLAFW

LLQNNFKVLIVACDTFRSGAVEQLRVHVENLAQLMDDSHVRGSKNKRGKTGNDYVELFEA

GYGGSDLVTKIAKQAIKYSRDQNFDIVLMDTAGRRHNDPTLMSPLKSFADQAKPDKIIMV

TABLE 14-continued

Sequences disclosed herein.

GEALVGTDSVQQAKNFNDAFGKGRNLDFFIISKCDTVGEMLGTMVNMVYATGIPILFVGV

GQTYTDLRTLSVKWAVNTLMS

YDR497C
>sp|P30605|ITR1_YEAST Myo-inositol transporter 1 OS = Saccharomyces
cerevisiae (strain ATCC 204508/S288c) GN = ITR1 PE = 1 SV = 2
SEQ ID NO: 100

MGIHIPYLTSKTSQSNVGDAVGNADSVEFNSEHDSPSKRGKITLESHEIQRAPASDDEDR

IQIKPVNDEDDTSVMITFNQSLSPFIITLTFVASISGFMFGYDTGYISSALISIGTDLDH

KVLTYGEKEIVTAATSLGALITSIFAGTAADIFGRKRCLMGSNLMFVIGAILQVSAHTFW

QMAVGRLIMGFGVGIGSLIAPLFISEIAPKMIRGRLTVINSLWLTGGQLVAYGCGAGLNY

VNNGWRILVGLSLIPTAVQFTCLCFLPDTPRYYVMKGDLARATEVLKRSYTDTSEEIIER

KVEELVTLNQSIPGKNVPEKVWNTIKELHTVPSNLRALIIGCGLQAIQQFTGWNSLMYFS

GTIFETVGFKNSSAVSIIVSGINFIFTLVAFFSIDKIGARTILLIGLPGMTMALVVCSIA

FHFLGIKFDGAVAVVVSSGFSSWGIVIIVFIIVFAAFYALGIGTVPWQQSELFPQNVRGI

GTSYATATNWAGSLVIASTFLTMLQNITPAGTFAFFAGLSCLSTIFCYFCYPELSGLELE

EVQTILKDGFNIKASKALAKKRKQQVARVHELKYEPTQEIIEDI

YEL006W
>sp|P39953|YEA6_YEAST Mitochondrial nicotinamide adenine
dinucleotide transporter 2 OS = Saccharomyces cerevisiae (strain ATCC
204508/S288c) GN = YEA6 PE = 1 SV = 1
SEQ ID NO: 101

MNNGDNKTTLENSKNASLANGNYAIFTKLNRLKKNADPRVAAISGALSGALSAMLVCPFD

VAKTRLQAQGLQNMTHQSQHYKGFEGTFATIFKDEGAAGLYKGLQPTVLGYIPTLMIYFS

VYDFCRKYSVDIFPHSETISNASSAITAGAISTVATNPIWVVKTRLMLQTGIGKYSTHYK

GTIDTFRKIIQQEGAKALYAGLVPALLGMLNVAIQFPLYENLKIRFGYSESTDVSTDVIS

SNFQKLILASMLSKMVASTVTYPHEILRTRMQLKSDLPNTVQRHLLPLIKITYRQEGFAG

FYSGFATNLVRTVPAAVVTLVSFEYSKKYLTTFFQ

YEL027W
>sp|P25515|VATL1_YEAST V-type proton ATPase subunit c
OS = Saccharomyces cerevisiae (strain ATCC 204508/S288c) GN = VMA3
PE = 1 SV = 1
SEQ ID NO: 102

MTELCPVYAPFFGAIGCASAIIFTSLGAAYGTAKSGVGICATCVLRPDLLFKNIVPVIMA

GIIAIYGLVVSVLVCYSLGQKQALYTGFIQLGAGLSVGLSGLAAGFAIGIVGDAGVRGSS

QQPRLFVGMILILIFAEVLGLYGLIVALLLNSRATQDVVC

YEL065W
>sp|P39980|SIT1_YEAST Siderophore iron transporter 1
OS = Saccharomyces cerevisiae (strain ATCC 204508/S288c) GN = SIT1
PE = 3 SV = 1
SEQ ID NO: 103

MDPGIANHTLPEEFEEVVVPEMLEKEVGAKVDVKPTLTTSSPAPSYIELIDPGVHNIEIY

AEMYNRPIYRVALFFSLFLIAYAYGLDGNIRYTFQAYATSSYSQHSLLSTVNCIKTVIAA

VGQIFFARLSDIFGRFSIMIVSIIFYSMGTIIESQAVNITRFAVGGCFYQLGLTGIILIL

EVIASDFSNLNWRLLALFIPALETIINTWISGNVTSAIDANWKWGIGMWAFILPLACIPL

GICMLHMRYLARKHAKDRLKPEFEALNKLKWKSECIDIAFWKLDIIGMLLITVFFGCVLV

PFTLAGGLKEEWKTAHIIVPEVIGWVVVLPLYMLWEIKYSRHPLTPWDLIQDRGIFFALL

IAFFINFNWYMQGDYMYTVLVVAVHESIKSATRITSLYSFVSVIVGTILGFILIKVRRTK

PFIIFGISCWIVSFGLLVHYRGDSGAHSGIIGSLCLLGFGAGSFTYVTQASIQASAKTHA

TABLE 14-continued

Sequences disclosed herein.

RMAVVTSLYLATYNIGSAFGSSVSGAVWTNILPKEISKRISDPILAAQAYGSPFTFITTY

TWGTPERIALVMSYRYVQKILCIIGLVFCFPLLGCAFMLRNHKLTDSIALEGNDHLESKN

TFEIEEKEESFLKNKFFTHFTSSKDRKD

YER019C-A
>sp|P52871|SC6B2_YEAST Protein transport protein SBH2
OS = Saccharomyces cerevisiae (strain ATCC 204508/S288c) GN = SBH2
PE = 1 SV = 1
SEQ ID NO: 104

MAASVPPGGQRILQKRRQAQSIKEKQAKTPTSTRQAGYGGSSSSILKLYTDEANGFRVD

SLVVLFLSVGFIFSVIALHLLTKFTHII

YER053C
>sp|P40035|PIC2_YEAST Mitochondrial phosphate carrier protein 2
OS = Saccharomyces cerevisiae (strain ATCC 204508/S288c) GN = PIC2
PE = 1 SV = 1
SEQ ID NO: 105

MESNKQPRKIQLYTKEFYATCTLGGIIACGPTHSSITPLDLVKCRLQVNPKLYTSNLQGF

RKIIANEGWKKVYTGFGATFVGYSLQGAGKYGGYEYFKHLYSSWLSPGVTVYLMASATAE

FLADIMLCITEAIKVKQQTTMPPFCNNVVDGWKKMYAESGGMKAFYKGIVPLWCRQIPYT

MCKFTSFEKIVQKIYSVLPKKKEEMNALQQISVSFVGGYLAGILCAAVSHPADVMVSKIN

SERKANESMSVASKRIYQKIGFTGLWNGLMVRIVMIGTLTSFQWLIYDSFKAYVGLPTTG

YER119C
>sp|P40074|AVT6_YEAST Vacuolar amino acid transporter 6
OS = Saccharomyces cerevisiae (strain ATCC 204508/S288c) GN = AVT6
PE = 1 SV = 1
SEQ ID NO: 106

MVASIRSGVLTLLHTACGAGILAMPYAFKPFGLIPGVIMIVLCGACAMQSLFIQARVAKY

VPQGRASFSALTRLINPNLGIVFDLAIAIKCFGVGVSYMIVVGDLMPQIMSVWTRNAWLL

NRNVQISLIMLFFVAPLSFLKKLNSLRYASMVAISSVAYLCVLVLLHYVAPSDEILRLKG

RISYLLETQSHDLNVLNTLPIFVFAYTCHHNMFSIINEQRSSRFEHVMKIPLIAISLALI

LYIAIGCAGYLTFGDNITGNIIMLYPQAVSSTIGRIAIVLLVMLAFPLQCHPARASIHQI

LQHFAEENVSISATSADEPTVATESSPLIRDSSLDLNEVIEEESIYQPKETPLRGKSFIV

ITCSILVASYLVAISVSSLARVLAIVGATGSTSISFILPGLFGYKLIGTEHKTAVPLTTK

IFKYTGLLLFIWGLIIMITCLTAALKLN

YFL028C
>sp|P43569|CAF16_YEAST CCR4-associated factor 16 OS = Saccharomyces
cerevisiae (strain ATCC 204508/S288c) GN = CAF16 PE = 1 SV = 1
SEQ ID NO: 107

MVSQFAIEVRNLTYKFKESSDPSVVDINLQIPWNTRSLVVGANGAGKSTLLKLLSGKHLC

LDGKILVNGLDPFSPLSMNQVDDDESVEDSTNYQTTTYLGTEWCHMSIINRDIGVLELLK

SIGFDHFRERGERLVRILDIDVRWRMHRLSDGQKRRVQLAMGLLKPWRVLLLDEVTVDLD

VIARARLLEFLKWETETRRCSVVYATHIFDGLAKWPNQVYHMKSGKIVDNLDYQKDVEFS

EVVNAKVNGQVAFENDNNKVVISKVNSLHPLALEWLKRDNQIPDKEIGI

YFR045W
>sp|P43617|YFL5_YEAST Uncharacterized mitochondrial carrier YFR045W
OS = Saccharomyces cerevisiae (strain ATCC 204508/S288c) GN = YFR045W
PE = 1 SV = 3
SEQ ID NO: 108

MANQNSDLYKQITAGSVAAVFQTTMTYPFEYLKTGLQLQPKGTAFEIILPQIKSYFVGCS

ALNVAAFGKTILRFVTFDKLCHSLNNNIDNNDNFQRLTGYNLLIAGTLTGIVESLFIIPF

ENIKTTLIQSAMIDHKKLEKNQPVVNAKATPHKVATKSTPVARIEKLLPAVKHMYQTRGP

AAFVQGTTATIFRQIANTSIQFTAYTAFKRLLQARNDKASSVITGLATSFTLVAMTQPID

TABLE 14-continued

Sequences disclosed herein.

VVKIRMMSQNAKTEYKNTLNCMYRIFVQEGMATFWKGSIFRFMKVGISGGLIFTVYEQVS

LLLGFSSRS

YGL084C
>sp|P53154|GUP1_YEAST Glycerol uptake protein 1 OS = Saccharomyces
cerevisiae (strain ATCC 204508/S288c) GN = GUP1 PE = 1 SV = 1
SEQ ID NO: 109

MSLISILSPLITSEGLDSRIKPSPKKDASTITKPSLWKITEFKFYYIAFLVVVPLMFYAG

LQASSPENPNYARYERLLSQGWLFGRKVDNSDSQYRFFRDNFALLSVLMLVHTSIKRIVL

YSTNITKLRFDLIFGLIFLVAAHGVNSIRILAHMLILYAIAHVLKNERRIATISIWIYGI

STLFINDNFRAYPFGNICSFLSPLDHWYRGIIPRWDVFFNFTLLRVLSYNLDFLERWENL

QKKKSPSYESKEAKSAILLNERARLTAAHPIQDYSLMNYIAYVTYTPLFIAGPIITENDY

VYQSKHTLPSINFKFIFYYAVREVIALLSMEFILHFLHVVAISKTKAWENDTPFQISMIG

LENLNIIWLKLLIPWRLFRLWALLDGIDTPENMIRCVDNNYSSLAFWRAWHRSYNKWVVR

YIYIPLGGSKNRVLTSLAVFSEVAIWHDIELKLLLWGWLIVLEILPEIFATQIFSHYTDA

VWYRHVCAVGAVFNIWVMMIANLEGFCLGSDGTKKLLSDMECTVSGFKEVILASVSLFIA

VQIMFEIREEEKRHGIYLKC

YGL104C
>sp|P53142|VPS73_YEAST Vacuolar protein sorting-associated protein
73 OS = Saccharomyces cerevisiae (strain ATCC 204508/S288c) GN = VPS73
PE = 1 SV = 1
SEQ ID NO: 110

MNRILSSASLLSNVSMPRQNKHKITKALCYAIIVASIGSIQFGYHLSELNAPQQVLSCSE

FDIPMEGYPYDRTWLGKRGYEQCIPLNDEQIGIVISVFCIGGILGSYFATSLANIYGRKF

SSLINCTLNIVGSLIIFNSNSYRGLIIGRILVGISCGSLIVIIPLFIKEVAPSGWEGLLG

SMIQICIRLGVLLTQGIALPLTDSYRWRWILFGSFLIAVLNFFMWFIVDESPKWLLAHGR

VTDAKLSLCKLRGVIFDEAAQEIQDWQLQIESGDPLIEPTITNSISGSNSLWKYLRDRTN

VKSRHVITVLLFGQQFCGINSIVLYGTKIISQLYPQBAIRINFFISMVNVLVTILVSLLI

HSLPRKPLLMTSTVLVSVTAFIMGIAMNHNKMNLLIVESFIYMGVETMGLNPLPFIIMRE

VSKPQDMVLAQRYGTICNWVGIFIIAYTFPIIHDVLSGYVFIIFAIIACSISAFIWKKVP

ETKRSG

YGL114W
>sp|P53134|YGL4_YEAST Putative oligopeptide transporter YGL114W
OS = Saccharomyces cerevisiae (strain ATCC 204508/S288c) GN = YGL114W
PE = 1 SV = 1
SEQ ID NO: 111

MPQSTPSQEVQRVPWDNKPALKQITLRATIAGIAIGSLVLISNFQFGLQTGWVSMMSLPS

ALLACAFFKNIWPLIFPNDRITSDVENVYVQSMAVAVGTGPLAFGFVGVIPAIEKFLIND

ESGGLREQGQSFTFRELLTWSTALAFFGIFFAVPLRKQVIVREKLPFPSGSATATLISVL

NGTEILQEVSKSELLEMRQRRLNECPEVLQPNRDPEEADYLMNSSHSELGDYTATSQDGS

SILSTGSENYRANIIILLKTFVVSSLYTMVSYFVPVIRSIPVEGKYLSNNYLWNFQPSPA

YIGQGIIMGLPTVSYMLIGCFLGWGVLAPLARYKRWVPPDADVHDWEEGVQGWILWSSLS

IMVADSVVAFIVVTVKSIVKFILIDDKAALLNNIIDDTFQSMLLEEERAINSSRRNTYVD

GRQDTVRLVSRDNEIEVDSKHLVRYTTVISGCLVSSIICIVSIIYLEGIQVIPLYAIITA

LILALFLSILGIRALGETDLNPVSGIGKISQLIFAFIIPRDRPGSVLMNVVSGGIAEASA

QQAGDLMQDLKIGHLLGASPRAQFCAQLIGACWSIILSSEMYLCYNKVYSIPSEQFRIPT

AVVWIDCARLVTGKGLPDKALECSMILGVIFAVLSLIRNTYRDYGYGWILYIPSGVAVGV

GIFNSPSFTIARFIGGWASHEWLKNHRGDLNAKTKMIVESSGLVLGEGIFSVINMLFICL

NVPHY

YGL167C
>sp|P13586|ATC1_YEAST Calcium-transporting ATPase 1 OS = Saccharomyces
cerevisiae (strain ATCC 204508/S288c) GN = PMR1 PE = 1 SV = 1

SEQ ID NO: 112

MSDNPFNASLLDEDSNREREILDATAEALSKPSPSLEYCTLSVDEALEKLDTDKNGGLRS

SNEANNRRSLYGPNEITVEDDESLFKKFLSNFIEDRMILLLIGSAVVSLFMGNIDDAVSI

TLAIFIVVTVGFVQEYRSEKSLEALNKLVPAECHLMRCGQESHVLASTLVPGDLVHFRIG

DRIPADIRIIEAIDLSIDESNLIGENEPVHKTSQTIEKSSFNDQPNSIVPISERSCIAYM

GTLVKEGHGKGIVVGTGTNTSFGAVFEMMNNIEKPKTPLQLTMDKLGKDLSLVSFIVIGM

ICLVGIIQGRSWLEMFQISVSLAVAAIPEGLPIIVIVTLALGVLRMAKRKAIVRRLPSVE

TLGSVNVICSDKTGTLTSNHMTVSKLWCLDSMSNKLNVLSLDKNKKTKNSNGNLKNYLTE

DVRETLTIGNLCNNASFSQEHAIFLGNPTDVALLEQLANFEMPDIRNTVQKVQELPFNSK

RKLMATKILNPVDNKCTVYVKGAFERILEYSTSYLKSKGKKTEKLTEAQKATINECANSM

ASEGLRVFGFAKLTLSDSSTPLTEDLIKDLTFTGLIGMNDPPRPNVKFAIEQLLQGGVHI

IMITGDSENTAVNIAKQIGIPVIDPKLSVLSGDKLDEMSDDQLANVIDHVNIFARATPER

KLNIVRALRKRGDVVAMTGDGVNDAPALKLSDIGVSMGRIGTDVAKEASDMVLTDDDFST

ILTAIEEGKGIFNNIQNFLTFQLSTSVAALSLVALSTAFKLPNPLNAMQILWINILMDGP

PAQSLGVEPTDHEVMKKETRKRTDKILTHDVMKRLLITAACIIVGTVYIFVKEMAEDGKV

TARDTIMIFTCFVFFDMENALACRHNTKSIFEIGFFTNKMFNYAVGLSLLGQMCAIYIPF

FQSIFKTEKLGISDILLLLLISSSVFIVDELRKLWTRKKNEEDSTYFSNV

YGR257C
>sp|P53320|MTM1_YEAST Mitochondrial carrier protein MTM1
OS = Saccharomyces cerevisiae (strain ATCC 204508/S288c) GN = MTM1
PE = 1 SV = 1

SEQ ID NO: 113

MSDRNTSNSLTLKERMLSAGAGSVLTSLILIPMDVVRIRLQQQQMIPDCSCDGAAEVPNA

VSSGSKMKTFTNVGGQNLNNAKIFWESACFQELHCKNSSLKFNGTLEAFTKIASVEGITS

LWRGISLTLLMAIPANMVYFSGYEYIRDVSPIASTYPTLNPLFCGAIARVFAATSIAPLE

LVKTKLQSIPRSSKSTKTWMMVKDLLNETRQEMKMVGPSRALFKGLEITLWRDVPFSAIY

WSSYELCKERLWLDSTRFASKDANWVHFINSFASGCISGMIAAICTHPFDVGKTRWQISM

MNNSDPKGGNRSRNMFKFLETIWRTEGLAALYTGLAARVIKIRPSCAIMISSYEISKKVF

GNKLHQ

YHL035C
>sp|P38735|VMR1_YEAST ABC transporter ATP-binding protein/permease
VMR1 OS = Saccharomyces cerevisiae (strain ATCC 204508/S288c)
GN = VMR1 PE = 2 SV = 1

SEQ ID NO: 114

MGTDPLIIRNNGSFWEVDDFTRLGRTQLLSYYLPLAIIASIGIFALCRSGLSRYVRSAEC

DLVNEYLFGAQEERKEDNSIERLLRNSNTQANYVNVKKQGRILKLRHFDITTIDVKQIDA

KNHGGLTFSRPSTSDHLRKSSEIVLMSLQIIGLSFLRVTKINIELTNRDVTTLLLFWLIL

LSLSILRVYKRSTNLWAICFTAHTTIWISTWIPIRSVYIGNIDDVPSQIFYIFEFVITST

LQPIKLTSPIKDNSSIIYVRDDHTSPSREHISSILSCITWSWITNFIWEAQKNTIKLKDI

WGLSMEDYSIFILKGPTRRNKHINNLTLALFESFKTYLLIGMLWVLVNSIVNLLPTILMK

RFLEIVDNPNRSSSCMNLAWLYIIGMFICRLTLAICNSQGQFVSDKICLRIRAILIGEIY

TABLE 14-continued

Sequences disclosed herein.

AKGLRRRLFTSPKTSSDSDSISANLGTIINLISIDSFKVSELANYLYVIVQAVIMIIVVV

GLLFNFLGVSAFAGISIILVMFPLNFLLANLLGKFQKQTLKCTDQRISKLNECLQNIRIV

KYFAWERNIINEIKSIRQKELRSLLKKSLVWSVTSFLWFVTPTLVTGVTFAICTFVQHED

LNAPLAFTTLSLFTLLKTPLDQLSNMLSFINQSKVSLKRISDFLRMDDTEKYNQLTISPD

KNKIEFKNATLTWNENDSDMNAFKLCGLNIKFQIGKLNLILGSTGSGKSALLLGLLGELN

LISGSIIVPSLEPKHDLIPDCEGLTNSFAYCSQSAWLLNDTVKNNIIFDNFYNEDRYNKV

IDACGLKRDLEILPAGDLTEIGEKGITLSGGQKQRISLARAVYSSAKHVLLDDCLSAVDS

HTAVWIYENCITGPLMKNRICILVTHNVSLTLRNAHFAIVLENGKVKNQGTITELOSKGL

FKEKYVQLSSRDSINEKNANRLKAPRKNDSQKIEPVTENINFDANFVNDGQLIEEEEKSN

GAISPDVYKWYLKFFGGFKALTALFALYITAQILFISQSWWIRHWVNDTNVRINAPGFAM

DTLPLKGMTDSSKNKHNAFYYLTVYFLIGIIQAMLGGFKTMMTFLSGMRASRKIFNNLLD

LVLHAQIRFFDVTPVGRIMNRFSKDIEGVDQELIPYLEVTIFCLIQCASIIFLITVITPR

FLTVAVIVFVLYFFVGKWYLTASRELKRLDSITKSPIFQHFSETLVGVCTIRAFGDERRF

ILENMNKIDQNNRAFFYLSVTVKWFSFRVDMIGAFIVLASGSFILLNIANIDSGLAGISL

TYAILFTDGALWLVRLYSTFEMNMNSVERLKEYSSIEQENYLGHDEGRILLLNEPSWPKD

GEIEIENLSLRYAPNLPPVIRNVSFKVDPOSKIGIVGRTGAGKSTIITALFRLLEPITGC

IKIDGQDISKIDLVTLRRSITIIPQDPILFAGTIKSNVDPYDEYDEKKIFKALSQVNLIS

SHEFEEVLNSEERFNSTHNKFLNLHTEIAEGGLNLSQGERQLLFIARSLLREPKIILLDE

ATSSIDYDSDHLIQGIIRSEFNKSTILTIAHRLRSVIDYDRIIVMDAGEVKEYDRPSELL

KDERGIFYSMCRDSGGLELLKQIAKQSSKMMK

YHL036W
>sp|P38734|MUP3_YEAST Low-affinity methionine permease
OS = Saccharomyces cerevisiae (strain ATCC 204508/S288c) GN = MUP3
PE = 1 SV = 1
SEQ ID NO: 115

MEPLLFNSGKANFSQDVFIDVEVGDITTKYGSTNTGSFSSMDTVEAQAIKAETARFMEVP

QGRHLGVFSTVVLFVSRIMGSGIFAVPSVILLNTGGNKLIYFAIWVFSAAIAFAGLYLFL

EFGSWIPKSGGRKNFLERSFERPRLLISVVFSCYSVLTGYALTGSIVFGKYVLSAFGVTD

DSWSKYVSISFIIFAVLIHGVSVRHGVFIQNALGGLKLIMIVLMCFAGLYTLFFYKSTGQ

VAWDLPVTQVEKDSLLSVSSIATAFISSFFCFSGWDTVHTVISEIKNPVKTLKVSGPLSL

IICFVCYTMMNVAYLKVLTYEEIVSAGPLVGSVLFTKLFGPRVGGKFIAFSIAISAASNI

LVVIYSISRVNQEIFKEGYLPFSIHMSKNWPFDAPLPSISLCGFITIAWILILPKEGESF

NYLVSMDGYGNQFFLLLVAIGLFIWRFKHKNEVPEIRASTFGVLAIITLSLYMLMAPFFA

DPSLNRVGFLPPYQIMSLLVIVACFFFWLVKFVLLPKFFHYKLLPKITYLHDGLIVTEWV

KKPCLC

YHR002W
>sp|P38702|LEU5_YEAST Mitochondrial carrier protein LEU5
OS = Saccharomyces cerevisiae (strain ATCC 204508/S288c) GN = LEU5
PE = 3 SV = 1
SEQ ID NO: 116

MTRDSPDSNDSYKHINKNTTQKTSFDRNSFDYIVRSGLAGGISGSCAKTLIAPLDRIKIL

FQTSNPHYTKYTGSLIGLVEAAKHIWINDGVRGFFQGHSAILLRIFPYAAVKFVAYEQIR

NTLIPSKEFESHWRRLVSGSLAGLCSVFITYPLDLVRVRLAYETEHKRVKLGRIIKKIYK

EPASATLIKNDYIPNWFCHWCNFYRGYVPTVLGMIPYAGVSFFAHDLLHDVLKSPFFAPY

TABLE 14-continued

Sequences disclosed herein.

SVLELSEDDELERVQKKQRRPLRTWAELISGGLAGMASQTAAYPFEIIRRRLQVSALSPK

TMYDRKFQSISEIAHIIFKERGVRGFFVGLSIGYIKVTPMVACSFFVYERMKWNFGI

YHR096C
>sp|P38695|HXT5_YEAST Probable glucose transporter HXT5
OS = Saccharomyces cerevisiae (strain ATCC 204508/S288c) GN = HXT5
PE = 1 SV = 1

SEQ ID NO: 117

MSELENAHQGPLEGSATVSTNSNSYNEKSGNSTAPGTAGYNDNLAQAKPVSSYISHEGPP

KDELEELQKEVDKQLEKKSKSDLLFVSVCCLMVAFGGFVFGWDTGTISGFVRQTDFIRRF

GSTRANGTTYLSDVRTGLMVSIFNIGCAIGGIVLSKLGDMYGRKIGLMTVVVIYSIGIII

QIASIDKWYQYFIGRIISGLGVGGITVLAPMLISEVSPKQLRGTLVSCYQLMITFGIFLG

YCTNFGTKNYSNSVQWRVPLGLCFAWSIFMIVGMTFVPESPRYLVEVGKIEEAKRSLARA

NKTTEDSPLVTLEMENYQSSIEAERLAGSASWGELVTGKPQMFRRTLMGMMIQSLQQLTG

DNYFFYYGTTIFQAVGLEDSFETAIVLGVVNFVSTFFSLYTVDRFGRRNCLLWGCVGMIC

CYVVYASVGVTRLWPNGQDQPSSKGAGNCMIVFACFYIFCFATTWAPVAYVLISESYPLR

VRGKAMSIASACNWIWGFLISFFTPFITSAINFYYGYVFMGCMVFAYFYVFFFVPETKGL

TLEEVNEMYEENVLPWKSTKWIPPSRRTITYDLDATRNDPRPFYKRMFTKEK

SEQ ID NO: 118

YIL006W
>sp|P40556|YIA6_YEAST Mitochondrial nicotinamide adenine
dinucleotide transporter 1 OS = Saccharomyces cerevisiae (strain ATCC
204508/S288c) GN = YIA6 PE = 1 SV = 1
MTQTDNPVPNCGLLPEQQYCSADHEEPLLLHEEQLIFPDHSSQLSSADIIEPIKMNSSTE

SIIGTTLRKKWVPLSSTQITALSGAFAGFLSGVAVCPLDVAKTRLQAQGLQTRFENPYYR

GIMGTLSTIVRDEGPRGLYKGLVPIVLGYFPTWMIYFSVYEFSKKFFHGIFPQFDFVAQS

CAAITAGAASTTLTNPIWVVKTRLMLQSNLGEHPTHYKGTFDAFRKLFYQEGFKALYAGL

VPSLLGLFHVAIHFPIYEDLKVRFHCYSRENNTNSINLQRLIMASSVSKMIASAVTYPHE

ILRTRMQLKSDIPDSIQRRLFPLIKATYAQEGLKGFYSGFTTNLVRTIPASAITLVSFEY

FRNRLENISTMVI

YIL120W
>sp|P40475|QDR1_YEAST Quinidine resistance protein 1
OS = Saccharomyces cerevisiae (strain ATCC 204508/S288c) GN = QDR1
PE = 1 SV = 1

SEQ ID NO: 119

MTKQQTSVMRNASIAKEEREGSDNNNVDRSSSDAISDNDAERSNSHSEIDNESNFDMVPY

SRFSHKQKMLLVVQCAFTGFFSTVAGSIYYPVLTIIERKFNITEELANVTIVVYFIFQGV

APSIMGGLADTFGRRPIVLWAILAYFCACIGLACAHNYAQILALRCLQAAGISPVIAINS

GIMGDVTTKVERGGYVGLVAGFQVVGTAFGALIGAGLSSKWGWRAIFWFLAIGSGICLVF

STLLMPETKRTLVGNGSVTPRSFLNRSLILHVGSVKKTLHLDDPDPETLEPRTSVDFLAP

LKILHIREIDILLSIAGLQFSTWTTHQTALTIVLSKKYNLSVAKIGLCFLPAGISTLTSI

ISAGRYLNWSYRTRKVKYNRWIKEQELQLMEKYKGDKNKVAELIHSNSHYAFNLVEARLH

PAFVTLLLSSIGFTAFGWCISVKTPLAAVLCTSAFASLFSNCILTFSTTLIVDLFPSKAS

TATGCLNLFRCLLSAIFIAALTKMVEKMRYGGVFTFLSAITSSSSLLLFYLLKNGKQLSF

DRIRANDKSAGRSVGKNSEKVST

TABLE 14-continued

Sequences disclosed herein.

YIL121W
>sp|P40474|QDR2_YEAST Quinidine resistance protein 2
OS = Saccharomyces cerevisiae (strain ATCC 204508/S288c) GN = QDR2
PE = 1 SV = 1

SEQ ID NO: 120

MAGATSSIIRENDFEDELAESMQSYNRETADKLALTRTESVKPEPEITAPPHSRFSRSFK

TVLIAQCAFTGFFSTIAGAIYYPVLSVIERKFDIDEELVNVTVVVYFVFQGLAPTFMGGF

ADSLGRRPVVLVAIVIYFGACIGLACAQTYAQIIVLRCLQAAGISPVIAINSGIMGDVTT

RAERGGYVGYVAGFQVLGSAFGALIGAGLSSRWGWRAIFWFLAIGSGICFLASFLILPET

KRNISGNGSVTPKSYLNRAPILVLPTVRKSLHLDNPDYETLELPTQLNLLAPFKILKAYE

ICILMLVAGLQFAMYTTHLTALSTALSKQYHLTVAKVGLCYLPSGICTLCSIVIAGRYLN

WNYRRRLKYYQNWLGKKRSKLLEEHDNDLNLVQRIIENDPKYTFNIFKARLQPAFVTLLL

SSSGFCAYGWCITVKAPLAAVLCMSGFASLFSNCILTFSTTLIVDLFPTKTSTATGCLNL

FRCILSAVFIAALSKMVEKMKFGGVFTFLGALTSSSSILLFILLRKGKELAFKRKKQELG

VN

YIL166C
>sp|P40445|YIQ6_YEAST Uncharacterized transporter YIL166C
OS = Saccharomyces cerevisiae (strain ATCC 204508/S288c) GN = YIL166C
PE = 1 SV = 1

SEQ ID NO: 121

MSVQKEEYDIVEKAQLSVSAESLTSDSESISHNPFDDFHKAERWRKVYESSGYEGLSKFD

PEFTWTKDEEKKLVRKMDLKIFLWVFIMFAFLDLIRKNIARAVSDNFIVDLKMNTNDYNL

GQTVYLVIFLASELPGNLLSKRFGPERVIPVQIVLWSVICITQAGLKNRGQFIATRCLLG

MVQGGFIPDNILYISYYYTGAELTFRLSFFWCAIPLFQILGSLLASGIIEMRGIHNLAGW

QYLFIIEGFLSLSVGVASFYLMRRGPTQTGESAFHKGKSLFTEYEEKIMVNRILRDDPSK

GDMSNRQPVTFKEILYTLTEFDLWALFIQGITAFISLQTVGSYLSLILKSLNYSTFLSNI

LAIPGQALLLINLPLAALLSRKLKEKSLCVGIANVWVLPFIVSLVALPIDTNPWIKYILL

TGILGLPYTHSILAGWVSEISNSVRSRTVGTALYNMSAQVGAIIASNMYRNDDKPYYTRG

NKILLGFTCFNICMAVATKFYYISRNKYKDRKWNSMTKEEQINYLDTTKDKGMKRLDYRF

IH

YJL133W
>sp|P10566|MRS3_YEAST Mitochondrial RNA-splicing protein MRS3
OS = Saccharomyces cerevisiae (strain ATCC 204508/S288c) GN = MRS3
PE = 1 SV = 4

SEQ ID NO: 122

MVENSSSNNSTRPIPAIPMDLPDYEALPTHAPLYHQLIAGAFAGIMEHSVMFPIDALKTR

IQSANAKSLSAKNMLSQISHISTSEGTLALWKGVQSVILGAGPAHAVYFGTYEFCKKNLI

DSSDTQTHHPFKTAISGACATTASDALMNPFDTIKQRIQLNTSASVWQTTKQIYQSEGLA

AFYYSYPTTLVMNIPFAAFNFVIYESSTKFLNPSNEYNPLIHCLCGSISGSTCAAITTPL

DCIKTVLQIRGSQTVSLEIMRKADTFSKAASAIYQVYGWKGFWRGWKPRIVANMPATAIS

WTAYECAKHFLMTY

YJL219W
>sp|P40885|HXT9_YEAST Hexose transporter HXT9 OS = Saccharomyces
cerevisiae (strain ATCC 204508/S288c) GN = HXT9 PE = 1 SV = 1

SEQ ID NO: 123

MSGVNNTSANDLSTTESNSNSVANAPSVKTEHNDSKNSLNLDATEPPIDLPQKPLSAYTT

VAILCLMIAFGGFIFGWDTGTISGFVNLSDFIRRFGQKNDKGTYYLSKVRMGLIVSIFNI

GCAIGGIVLSKVGDIYGRRIGLITVTAIYVVGILIQITSINKWYQYFIGRIISGLGVGGI

AVLSPMLISEVAPKQIRGTLVQLYQLMCTMGIFLGYCTNYGTKNYHNATQWRVGLGLCFA

TABLE 14-continued

Sequences disclosed herein.

WTTFMVSGMMFVPESPRYLIEVGKDEEAKRSLSKSNKVSVDDPALLAEYDTIKAGIELEK

LAGNASWSELLSTKTKVFQRVLMGVMIQSLQQLTGDNYFFYYGTTIFKSVGLKDSFQTSI

IIGVVNFFSSFIAVYTIERFGRRTCLLWGAASMLCCFAVFASVGVTKLWPQGSSHQDITS

QGAGNCMIVFTMFFIFSFATTWAGGCYVIVSETFPLRVKSRGMAIATAANWMWGFLISFF

TPFITGAINFYYGYVFLGCLVFAYFYVFFFVPETKGLTLEEVNTMWLEGVPAWKSASWVP

PERRTADYDADAIDHDDRPIYKRFFSS

YKL016C
>sp|P30902|ATP7_YEAST ATP synthase subunit d, mitochondrial
OS = Saccharomyces cerevisiae (strain ATCC 204508/S288c) GN = ATP7
PE = 1 SV = 2
SEQ ID NO: 124

MSLAKSAANKLDWAKVISSLRITGSTATQLSSFKKRNDEARRQLLELQSQPTEVDFSHYR

SVLKNTSVIDKIESYVKQYKPVKIDASKQLQVIESFEKHAMTNAKETESLVSKELKDLQS

TLDNIQSARPFDELTVDDLTKIKPEIDAKVEEMVKKGKWDVPGYKDREGNLNVM

YKL050C
>sp|P35736|YKF0_YEAST Uncharacterized protein YKL050C
OS = Saccharomyces cerevisiae (strain ATCC 204508/S288c) GN = YKL050C
PE = 1 SV = 1
SEQ ID NO: 125

MSLISALQTTDVESVQTSPEQITERKAVRVSTLQESLHSSEMHRAAPETPRSISNSVHKL

KTIYSTYQQSGQPLSKEAIFRAKQKYGILNTPANYKTLGLGDSKSESVDLAARLASKRTK

VSPDDCVETAIEQKARGEAFKVTFSKIPLTPPEDVPITVNLGLKGRRDFLTRLAAQKALA

FSPSLDNSMKGTSDSSSVKKKRFSGAPIGNEFDANLVNPQHFAGFKSLDLSKVLDGAERR

AISRVNDRLYPQKVNEKNGLQSSDQSGVSKANKEVEKKGTLEKLEHSAEQFLESHAGNER

QRLSDQQYMCAKGAADAVKDLDPKTLEDPDFAAREAQKKINIKQVASPVVLNEAQKLANR

KLQDIDSRDTYMLLFGNQAYNKLAVNIALQHYSVKQEEKKKIYLGGGLWMTPEEVNAVAK

ELISPVVNEIDERASRQRDVDKDIERRSRVLDQEYEDGNSMERAKEQNDGQLLLAMASKQ

QQEKEAKKAEEGQRYDQFVQKMNIKLQQKEKELENARENRENLRNELQERLSKNLSGEND

ELNDWNDACERDLKNSSIEHYYAVRSHFDNLGNSERGYDELLEERSKIQVEIERLVASIA

EHKTAIHGFGETADAGGAIPAVQKQKIPTRKDLLDATVNDPLVISAEMAKEEAEMATEEC

MLKELQVDEMIIRNIMLRECEKKLEEEKETAKRSRRGTEESKNNSNFSRDVIMSTPDNN

EKVTPIGKSASPKDVVKSRELSTYNTGKDIDSSASARSITGVSGVLDDGPKTPTSNKENE

LIDDEVKSYKVHQAVDGTGEDSIANKRDKSSRPAANSGGSITIEQFLFNKNADKQGLSKT

ESVTMKREPVVDQMDSKKGHDFTHCNDNGRRSFSGFSQGSIENDYSNEVTDDQDDQEGSE

IRVRDSNDSNTSPKESFFKEVI

YKL120W
>sp|P32332|OAC1_YEAST Mitochondrial oxaloacetate transport protein
OS = Saccharomyces cerevisiae (strain ATCC 204508/S288c) GN = OAC1
PE = 1 SV = 1
SEQ ID NO: 126

MSSDNSKQDKQIEKTAAQKISKFGSFVAGGLAACIAVTVTNPIELIKIRMQLQGEMSASA

AKVYKNPIQGMAVIFKNEGIKGLQKGLNAAYIYQIGLNGSRLGFYEPIRSSLNQLFFPDQ

EPHKVQSVGVNVFSGAASGIIGAVIGSPLFLVKTRLQSYSEFIKIGEQTHYTGVWNGLVT

IFKTEGVKGLFRGIDAAILRTGAGSSVQLPIYNTAKNILVKNDLMKDGPALHLTASTISG

LGVAVVMNPWDVILTRIYNQKGDLYKGPIDCLVKTVRIEGVTALYKGFAAQVFRIAPHTI

MCLTFMEQTMKLVYSIESRVLGHN

TABLE 14-continued

Sequences disclosed herein.

YKL146W
>sp|P36062|AVT3_YEAST Vacuolar amino acid transporter 3
OS = *Saccharomyces cerevisiae* (strain ATCC 204508/S288c) GN = AVT3
PE = 1 SV = 1

SEQ ID NO: 127

MNGKEVSSGSGRTQSNNNKKNNNGGSTGISHASGSPLTDGNGGNSNGNSRSRSRSRKSSG

TTGGLLKKPPLLVNNEAVHASVPDASHTSCNNGTLEVSINNPEPHVVDAVARHLIRNPSN

SLQLQGGDITRDLYKWTNDHPSSPSQYQYPSQPALSTSIPSQAPSFSNRKRSMSFSAASI

ASSSHLNNNSEANGNPLAAIGLAPAPMTHEEIRAPGGFRRSFIIQKRRKHNVDAPIPNEF

TRNFIEFLTLYGHFAGEDLSEEEEEEEETEEEPEEEALETESTQLVSREHGRHPHKSSTV

KAVLLLLKSFVGTGVLFLPKAFHNGGWGFSALCLLSCALISYGCFVSLITTKDKVGVDGY

GDMGRILYGPKMKFAILSSIALSQIGFSAAYTVFTATNLQVFSENFFHLKPGSISLATYI

FAQVLIFVPLSLTRNIAKLSGTALIADLFILLGLVYVYVYSIYYIAVNGVASDTMLMFNK

ADWSLFIGTAIFTFEGIGLLIPIQESMKHPKHFRPSLSAVMCIVAVIFISCGLLCYAAFG

SDVKTVVLLNFPQDTSYTLTVQLLYALAILLSTPLQLFPAIRILENWTFPSNASGKYNPK

VKWLKNYFRCAIVVLTSILAWVGANDLDKFVSLVGSFACIPLIYIYPPLLHYKASILSGT

SRARLLLDLIVIVFGVAVMAYTSWQTIKMWSQ

YKL209C
>sp|P12866|STE6_YEAST Alpha-factor-transporting ATPase
OS = *Saccharomyces cerevisiae* (strain ATCC 204508/S288c) GN = STE6
PE = 1 SV = 1

SEQ ID NO: 128

MNFLSFKTTKHYHIFRYVNIRNDYRLLMIMIIGTVATGLVPAITSILTGRVFDLLSVFVA

NGSHQGLYSQLVQRSMAVMALGAASVPVMWLSLTSWMHIGERQGFRIRSQILEAYLEEKP

MEWYDNNEKLLGDFTQINRCVEELRSSSAEASAITFQNLVAICALLGTSFYYSWSLTLII

LCSSPIITFFAVVFSRMIHVYSEKENSETSKAAQLLTWSMNAAQLVRLYCTQRLERKKFK

EIILNCNTFFIKSCFFVAANAGILRFLTLTMFVQGFWFGSAMIKKGKLNINDVITCFHSC

IMLGSTLNNTLHQIVVLQKGGVAMEKIMTLLKDGSKRNPLNKTVAHQFPLDYATSDLTFA

NVSFSYPSRPSEAVLKNVSLNFSAGQFTFIVGKSGSGKSTLSNLLLRFYDGYNGSISING

HNIQTIDQKLLIENITVVEQRCTLFNDTLRKNILLGSTDSVRNADCSTNENRHLIKDACQ

MALLDRFILDLPDGLETLIGTGGVTLSGGQQQRVAIARAFIRDTPILFLDEAVSALDIVH

RNLLMKAIRHWRKGKTTIILTHELSQIESDDYLYLMKEGEVVESGTQSELLADPTTTFST

WYHLQNDYSDAKTIVDTETEEKSIHTVESFNSQLETPKLGSCLSNLGYDETDQLSFYEAI

YQKRSNVRTRRVKVEEENIGYALKQQKNTESSTGPQLLSIIQIIKRMIKSIRYKKILILG

LLCSLIAGATNPVFSYTFSFLLEGIVPSTDGKTGSSHYLAKWSLLVLGVAAADGIFNFAK

GFLLDCCSEYWVMDLRNEVMEKLTRKNMDWFSGENNKASEISALVLNDLRDLRSLVSEFL

SAMTSFVTVSTIGLIWALVSGWKLSLVCISMFPLIIIFSAIYGGILQKCETDYKTSVAQL

ENCLYQIVTNIKTIKCLQAEFHFQLTYHDLKIKMQQIASKRAIATGFGISMTNMIVMCIQ

AIIYYYGLKLVMIHEYTSKEMFTTFTLLLFTIMSCTSLVSQIPDISRGQRAASWIYRILD

EKHNTLEVENNNARTVGIAGHTYHGKEKKPIVSIQNLTFAYPSAPTAFVYKNMNFDMFCG

QTLGIIGESGTGKSTLVLLLTKLYNCEVGKIKIDGTDVNDWNLTSLRKEISVVEQKPLLF

NGTIRDNLTYGLQDEILEIEMYDALKYVGIHDFVISSPQGLDTRIDTTLLSGGQAQRLCI

ARALLRKSKILILDECTSALDSVSSSIINEIVKKGPPALLTMVITHSEQMMRSCNSIAVL

KDGKVVERGNFDTLYNNRGELFQIVSNQSS

TABLE 14-continued

Sequences disclosed herein.

YKR039W
>sp|P19145|GAP1_YEAST General amino-acid permease GAP1
OS = *Saccharomyces cerevisiae* (strain ATCC 204508/S288c) GN = GAP1
PE = 1 SV = 2

SEQ ID NO: 129

MSNTSSYEKNNPDNLKHNGITIDSEFLTQEPITIPSNGSAVSIDETGSGSKWQDFKDSFK

RVKPIEVDPNLSEAEKVAIITAQTPLKHHLKNRHLQMIAIGGAIGTGLLVGSGTALRTGG

PASLLIGWGSTGTMIYAMVMALGELAVIFPISGGFTTYATRFIDESFGYANNFNYMLQWL

VVLPLEIVSASITVNFWGTDPKYRDGFVALFWLAIVIINMFGVKGYGEAEFVFSFIKVIT

VVGFIILGIILNCGGGPTGGYIGGKYWHDPGAFAGDTPGAKFKGVCSVFVTAAFSFAGSE

LVGLAASESVEPRKSVPKAAKQVFWRITLFYILSLLMIGLLVPYNDKSLIGASSVDAAAS

PFVIAIKTHGIKGLPSVVNVVILIAVLSVGNSAIYACSRTMVALAEQRFLPEIFSYVDRK

GRPLVGIAVTSAFGLIAFVAASKKEGEVFNWLLALSGLSSLFTWGGICICHIRFRKALAA

QGRGLDELSFKSPTGVWGSYWGLFMVIIMFIAQFYVAVFPVGDSPSAEGFFEAYLSFPLV

MVMYIGHKIYKRNWKLFIPAEKMDIDTGRREVDLDLLKQEIAEEKAIMATKPRWYRIWNF

WC

YLR411W
>sp|Q06686|CTR3_YEAST Copper transport protein CTR3 OS = *Saccharomyces
cerevisiae* (strain ATCC 204508/S288c) GN = CTR3 PE = 1 SV = 1

SEQ ID NO: 130

MNMGGSSSTAAKKATCKISMLWNWYTIDTCFIARSWRNDTKGKFAGSCIGCFALVVVAQW

LTRFSRQFDVELLKRQKIKHLASYSPEEYVVKCGEEDAKSDIEELQGFYNEPSWKITLIS

LQKSFIYSFYVWGFRRLNEPEDDLLKKVLSCCTLITPVDLYPTFLDHMIRVTIFVLQWGL

SYIIMLLFMYYNGYIIISCLIGAIVGRFIFCYEPLGSLGANGSAQGTVSYDKESDDRKCC

L

YML038C
>sp|Q03697|YMD8_YEAST Putative nucleotide-sugar transporter YMD8
OS = *Saccharomyces cerevisiae* (strain ATCC 204508/S288c) GN = YMD8
PE = 1 SV = 1

SEQ ID NO: 131

MNRTVFLAFVFGWYFCSIALSIYNRWMFDPKDGLGIGYPVLVTIFHQATLWLLSGIYIKL

RHKPVKNVLRKNNGFNWSFFLKFLLPTAVASAGDIGLSNVSFQYVPLTIYTIIKSSSIAF

VLLFGCIFKLEKFHWKLALSVIIMFVGVALMVFKPSDSTSTKNDQALVIFGSFLVLASSC

LSGLRWVYTQLMLRNNPIQTNTAAAVEESDGALFTENEDNVDNEPVVNLANNKMLENFGE

SKPHPIHTIHQLAPIMGITLLLTSLLVEKPFPGIFSSSIFRLDTSNGGVGTETTVLSIVR

GIVLLILPGFAVFLLTICEFSILEQTPVLTVSIVGIVKELLTVIFGIIILSERLSGFYNW

LGMLIIMADVCYYNYFRYKQDLLQKYHSVSTQDNRNELKGFQDFEQLGSKKIAPYSISVD

LTNQEYELDMIAQNVSRSSQQV

YMR166C
>sp|Q03829|Y1439_YEAST Uncharacterized mitochondrial carrier YMR166C
OS = *Saccharomyces cerevisiae* (strain ATCC 204508/S288c) GN = YMR166C
PE = 1 SV = 1

SEQ ID NO: 132

MNSWNLSSSIPIIHTPHDHETTSEGTPDQPNNNRKDDKLHKKRGDSDEDLSPIWHCVVSG

GIGGKIGDSAMHSLDTVKTRQQGAPNVKKYRNMISAYRTIWLEEGVRRGLYGGYMAAMLG

SFPSAAIFFGTYEYTKRTMIEDWQINDTITHLSAGFLGDFISSFVYVPSEVLKTRLQLQG

RFNNPFFQSGYNYSNLRNAIKTVIKEEGFRSLFFGYKATLARDLPFSALQFAFYEKFRQL

TABLE 14-continued

Sequences disclosed herein.

AFKIEQKDGRDGELSIPNEILTGACAGGLAGIITTPMDVVKTRVQTQQPPSQSNKSYSVT

HPHVTNGRPAALSNSISLSLRTVYQSEGVLGFFSGVGPRFVWTSVQSSIMLLLYQMTLRG

LSNAFPTD

YMR279C
>sp|Q03263|YM8M_YEAST Uncharacterized transporter YMR279C
OS = Saccharomyces cerevisiae (strain ATCC 204508/S288c) GN = YMR279C
PE = 1 SV = 1
SEQ ID NO: 133

MFSIFKKKTSVQGTDSEIDEKITVKAKDKVVVSTEDEEVTTIVSSTKSTQVTNDSPWQDP

TYFSSFGKELMFIATCMLAQLLNQAGQTHALCIMNVLSKSFNSEANNQAWLMASFPLAAG

SFILISGRLGDIYGLKKMLIVGYVIVIVWSIISGLSKYSNSDAFFITSRAFQGVGIAFIL

PNIMGLVGHVYKVGSFRKNIVISFIGACAPTGGMFGGLFGGLIVTEDPNQWPWVFYAFGI

ATFLSLLMAWYSIPNNVPTNIHGLSMDWTGSALAIIGLILFNFVWNQAPIVGWDKPYIIV

LLIISVIFLVAFFVYESKYAEVPLLPRAMTKNRHMIMILLAVFLGWGSFGIWTFYYVSFQ

LNLRHYSPVWTGGTYFVFVIFGSMAAFFVAFSIKRLGPALLLCFSLMAFDAGSIMFSVLP

VEQSYWKLNFAMQAILCFGMDLSFPASSIILSDGLPMQYQGMAGSLVNTVINYSASLCLG

MGGTVEHQINKSGNDLLKGYRAAVYLGVGLASLGVVISVTYMLENLWNRHRKSEDRSLEA

YNL003C
>sp|P38921|PET8_YEAST Putative mitochondrial carrier protein PET8
OS = Saccharomyces cerevisiae (strain ATCC 204508/S288c) GN = PET8
PE = 1 SV = 1
SEQ ID NO: 134

MNTFFLSLLSGAAAGTSTDLVFFPIDTIKTRLQAKGGFFANGGYKGIYRGLGSAVVASAP

GASLFFISYDYMKVKSRPYISKLYSQGSEQLIDTTTHMLSSSIGEICACLVRVPAEVVKQ

RTQVHSTNSSWQTLQSILRNDNKEGLRKNLYRGWSTTIMREIPFTCIQFPLYEYLKKTWA

KANGQSQVEPWKGAICGSIAGGIAAATTTPLDFLKTRLMLNKTTASLGSVIIRIYREEGP

AVFFSGVGPRTMWISAGGAIFLGMYETVHSLLSKSFPTAGEMRA

YNL268W
>sp|P32487|LYP1_YEAST Lysine-specific permease OS = Saccharomyces
cerevisiae (strain ATCC 204508/S288c) GN = LYP1 PE = 1 SV = 2
SEQ ID NO: 135

MGRFSNIITSNKWDEKQNNIGEQSMQELPEDQIEHEMEAIDPSNKTTPYSIDEKQYNTKK

KHGSLQGGAIADVNSITNSLTRLQVVSHETDINEDEEEAHYEDKHVKRALKQRHIGMIAL

GGTIGTGLFVGISTPLSNAGPVGSLIAYIFMGTIVYFVTQSLGEMATFIPVTSSITVFSK

RFLSPAFGVSNGYMYWFNWAITYAVEVSVIGQVIEYWTDKVPLAAWIAIFWVIITLMNFF

PVKVYGEFEFWVASVKVLAIMGYLIYALIIVCGGSHQGPIGFRYWRNPGAWGPGIISSDK

SEGRFLGWVSSLINAAFTYQGTELVGITAGEAANPRKTVPRAINKVVFRIVLFYIMSLFF

IGLLVPYNDSRLSASSAVIASSPFVISIQNAGTYALPDIFNAVVLITVVSAANSNVYVGS

RVLYSLARTGNAPKQFGYVTRQGVPYLGVVCTAALGLLAFLVVNNNANTAFNWLINISTL

AGLCAWLFISLAHIRFMQALKHRGISRDDLPFKAKLMPYGAYYAAFFVTVIIFIQGFQAF

CPFKVSEFFTSYTSLILLAVVFIGCQIYYKCRFIWKLEDIDIDSDRREIEAIIWEDDEPK

NLWEKFWAAVA

YNR055C
>sp|P53389|HOL1_YEAST Protein HOL1 OS = Saccharomyces cerevisiae
(strain ATCC 204508/S288c) GN = HOL1 PE = 1 SV = 1
SEQ ID NO: 136

MDKYTNRDHITYIPGTFNIYSSQNLENGIIYESKLKKTSSGVVLIPQPSYSPNDPLNWSS

WRKLAHFGLMAFITAFTAATSNDAGAAQDSLNEIYGISYDSMNTGAGVLFLGIGWSTLFL

TABLE 14-continued

Sequences disclosed herein.

APFANLYGRKITYIVCTTLGLFGALWFALAKRTSDTIWSQLFVGISESCAEAQVQLSLSD

IFFQHQLGSVLTVYIMCTSIGTFLGPLIAGYISAFTNFRWVGWVAVIISGGLLITIIFGC

EETYFDRGQYMTPLTSCQSGYEDGTTLQNSDNTAVSRRKRHLDAKLSTPGAMGEKGVDLS

ETAEFEVNNEEEVTIPETRELIDGSKEHLKPYPKRVAILTKATNLKGYGFKQYFKYLKIN

LRMFLFPPVWLSGMFWGIQDVFLTFYLTTQESAYYEPPWNYSDFGVAIMNVPTLIGAVIG

CICAGIVSDYFVLWMARHNRGILEAEFRLYFSIATAIIGPAGLLMFGIGTARQWPWQAIY

VGLGFVGFAWGCSGDIAMAYLMDCYPDMVLEGMVCTAIINNTISCIFTFTCSDWLAASGT

ENTYIALAVINFGITAFALPMYYYGKRIRLWTKRWYLQSVNLRDGV

YOL158C
>sp|Q08299|ENB1_YEAST Siderophore iron transporter ENB1
OS = Saccharomyces cerevisiae (strain ATCC 204508/S288c) GN = ENB1
PE = 1 SV = 1
SEQ ID NO: 137

MLETDHSRNDNLDDKSTVCYSEKTDSNVEKSTTSGLRRIDAVNKVLSDYSSFTAFGVTFS

SLKTALLVALFLQGITTGLGGQISQSIQTYAANSFGKHSQVGSINTVKSIVASVVAVPYA

RISDRFGRIECWIFALVLYTIGEIISAATPTFSGLFAGIVIQQFGYSGFRLLATALTGDL

SGLRDRTFAMNIFLIPVIINTWVSGNIVSSVAGNVAPYKWRWGYGIFCIIVPISTLILVL

PYVYAQYISWRSGKLPPLKLKEKGQTLRQTLWKFADDINLIGVILFTAFLVLVLLPLTIA

GGATSKWREGHIIAMIVVGGCLGFIFLIWELKFAKNPFIPRVYLGDPTIYVALLMEFVWR

LGLQIELEYLVTVLMVAFGESTLSAQRIAQLYNFLQSCTNIVVGIMLHFYPHPKVFVVAG

SLLGVIGMGLLYKYRVVYDGISGLIGAEIVVGIAGGMIRFPMWTLVHASITHNEMATVIG

LLMSVYQIGDAVGASIAGAIWTQRLAKELIQRLGSSLGMAIYKSPLNYLKKYPIGSEVRV

QMIESYSKIQRLLIIVSISFAAFNAVLCFFLRGFTVNKKQSLSAEEREKEKLKIKQQSWL

RRVIGY

YOR100C
>sp|Q12289|CRC1_YEAST Mitochondrial carnitine carrier
OS = Saccharomyces cerevisiae (strain ATCC 204508/S288c) GN = CRC1
PE = 1 SV = 1
SEQ ID NO: 138

MSSDTSLSESSLLKEESGSLTKSRPPIKSNPVRENIKSFVAGGVGGVCAVFTGHPFDLIK

VRCQNGQANSTVHAITNIIKEAKTQVKGILFINSVKGFYKGVIPPLLGVTPIFAVSFWGY

DVGKKLVTFNNKQGGSNELTMGQMAAAGFISAIPTTLVTAPTERVKVVLQTSSKGSFIQA

AKTIVKEGGIASLFKGSLATLARDGPGSALYFASYEISKNYLNSRQPRQDAGKDEPVNIL

NVCLAGGIAGMSMWLAVFPIDTIKTKLQASSTRQNMLSATKEIYLQRGGIKGFFPGLGPA

LLRSFPANAATFLGVEMTHSLFKKYGI

YOR153W
>sp|P33302|PDR5_YEAST Pleiotropic ABC efflux transporter of multiple
drugs OS = Saccharomyces cerevisiae (strain ATCC 204508/S288c)
GN = PDR5 PE = 1 SV = 1
SEQ ID NO: 139

MPEAKLNNNVNDVTSYSSASSSTENAADLHNYNGFDEHTEARIQKLARTLTAQSMQNSTQ

SAPNKSDAQSIFSSGVEGVNPIFSDPEAPGYDPKLDPNSENFSSAAWVKNMAHLSAADPD

FYKPYSLGCAWKNLSASGASADVAYQSTVVNIPYKILKSGLRKFQRSKETNTFQILKPMD

GCLNPGELLVVLGRPGSGCTTLLKSISSNTHGFDLGADTKISYSGYSGDDIKKHFRGEVV

YNAEADVHLPHLTVFETLVTVARLKTPQNRIKGVDRESYANHLAEVAMATYGLSHTRNTK

VGNDIVRGVSGGERKRVSIAEVSICGSKFQCWDNATRGLDSATALEFIRALKTQADISNT

SATVAIYQCSQDAYDLFNKVCVLDDGYQIYYGPADKAKKYFEDMGYVCPSRQTTADFLTS

TABLE 14-continued

Sequences disclosed herein.

VTSPSERTLNKDMLKKGIHIPQTPKEMNDYWVKSPNYKELMKEVDQRLLNDDEASREAIK

EAHIAKQSKRARPSSPYTVSYMMQVKYLLIRNMWRLRNNIGFTLFMILGNCSMALILGSM

FFKIMKKGDTSTFYFRGSAMFFAILFNAFSSLLEIFSLYEARPITEKHRTYSLYHPSADA

FASVLSEIPSKLIIAVCFNIIFYFLVDFRRNGGVFFFYLLINIVAVFSMSHLFRCVGSLT

KTLSEAMVPASMLLLALSMYTGFAIPKKKILRWSKWIWYINPLAYLFESLLINEFHGIKF

PCAEYVPRGPAYANISSTESVCTVVGAVPGQDYVLGDDFIRGIYQYYHKDKWRGFGIGMA

YVVFFFFVYLFLCEYNEGAKQKGEILVFPRSIVKRMKKRGVLTEKNANDPENVGERSDLS

SDRKMLQESSEEESDTYGEIGLSKSEAIFHWRNLCYEVQIKAETRRILNNVDGWVKPGTL

TALMGASGAGKTTLLDCLAERVTMGVITGDILVNGIPRDKSFPRSIGYCQQQDLHLKTAT

VRESLRFSAYLRQPAEVSIEEKNRYVEEVIKILEMEKYADAVVGVAGEGLNVEQRKRLTI

GVELTAKPKLLVFLDEPTSGLDSQTAWSICQLMKKLANHGQAILCTIHQPSAILMQEFDR

LLFMQRGGKTVYFGDLGEGCKTMIDYFESHGAHKCPADANPAEWMLEVVGAAPGSHANQD

YYEVWRNSEEYRAVQSELDWMERELPKKGSITAAEDKHEFSQSIIYQTKLVSIRLFQQYW

RSPDYLWSKFILTIFNQLFIGFTFFKAGTSLQGLQNQMLAVFMFTVIFNPILQQYLPSFV

QQRDLYEARERPSRTFSWISFIFAQIFVEVPWNILAGTIAYFIYYYPIGFYSNASAAGQL

HERGALFWLFSCAFYVYVGSMGLLVISFNQVAESAANLASLLFTMSLSFCGVMTTPSAMP

RFWIFMYRVSPLTYFIQALLAVGVANVDVKCADYELLEFTPPSGMTCGQYMEPYLQLAKT

GYLTDENATDTCSFCQISTTNDYLANVNSFYSERWRNYGIFICYIAFNYIAGVFFYWLAR

VPKKNGKLSKK

YOR271C
>sp|Q12029|FSF1_YEAST Probable mitochondrial transport protein FSF1
OS = *Saccharomyces cerevisiae* (strain ATCC 204508/S288c) GN = FSF1
PE = 1 SV = 1

SEQ ID NO: 140

MASSVPGPIDLPESRITLSTYWGRIRHCAEISDPTMLLTTEKDLAHAREIISAYRHGELK

ETTPEFWRAKKQLDSTVHETTGKTVLLETRMSSNVLSNLVVTVGMLTPGLGTAGTVFWQW

ANQSLNVAVNSANANKSHPMSTSQLLTNYAAAVTASCGVALGLNNLVPRLKNISPHSKLI

LGRLVPFAAVVSAGIVNVFLMRGNEIRKGISVFDSNGDEVGKSKKAAFMAVGETALSRVI

NATPTMVIPPLILVRLQRGVLKGKSLGVQTLANLGLISVTMFSALPFALGIFPQRQAIHL

NKLEPELHGKKDKDGKPIEKVYFNRGI

YOR273C
>sp|Q12256|TPO4_YEAST Polyamine transporter 4 OS = *Saccharomyces cerevisiae* (strain ATCC 204508/S288c) GN = TPO4 PE = 1 SV = 1

SEQ ID NO: 141

MPSSLTKTESNSDPRTNIQQVPKALDKNVTNSGNLDSTSSSTGSITEDEKRSEPNADSNN

MTGGEPIDPRDLDWDGPDDPDNPHNWSSLKKWYTTMTSAFLCLVVTMGSSLYVSSVPELV

ERYHVSQTLALAGLTFYLLGLSTVIGAPLSEVFGRKENYLFSLPVSMLFTMGVGLSNGHM

RIILPLRFLSGVFASPALSVGSGTILDIFDVDQVSVAMTYFVLSPFLGPVLSPIMAGFAT

EAKGWRWSEWIQLIAGGLILPFIALMPETHKGIILRKRAKKRNIALKKFSREAQKEFLKT

TVTITILRPLKMLVVEPIVFVFSVYVAFIFAILFGFFEAYAVIYRGVYHMSMGISGLPFI

GIGVGLWIGAFFYLYIDRKYLFPKPPAGTQPLTEKERTSKRTTPYRGARDAETGELLPVV

PEKFLIACKFGSVALPIGLFWQAWTARSDVHWMAPVAAGVPFGFGLILIFFSVLMYFSTC

YPPLTVASCLAANNLLRYVMSSVETLFTIQKYTKMKIKWASTLFALVCVVMIPIPWVFEK

TABLE 14-continued

Sequences disclosed herein.

WGSKLRHKSQFGYAAMEKEAETEGGIDDVNAVDGELNLTRMTTLRTMETDPSTREKPGER

LSLRRTHTQPVPASFDREDGQHAQNRNEPISNSLYSAIKDNEDGYSYTEMATDASARMV

YOR307C
>sp|P22215|SLY41_YEAST Uncharacterized transporter SLY41
OS = Saccharomyces cerevisiae (strain ATCC 204508/S288c) GN = SLY41
PE = 1 SV = 2
SEQ ID NO: 142

MIQTQSTAIKRRNSVHKNLFDPSLYQIPEPPRGGFQHQKKEYSKETFSNQVEGYDITSLK

KRFTQLFPSNIQGYLPEVDLRITIICSIWYVTSSISSNLSKAILRTFNHPIALTELQFLV

SAVLCVGFASIVNLFRLFRLKHTKFSKALNSFPDGILPEYIDGNFRSSILHKFLVPSKLV

LMTTFPMGIFQFIGHITSHKAVSMIPVSLVHSVKALSPIITVGYYKFFEHRYYNSMTYYT

LLLLIFGVMTTCWSTHGSKRASDNKSGSSLIGLLFAFISMIIFVAQNIFAKNILTIRRKV

GILPSSSTDDVTSKEGQPSLDKTRFSPLQVDKITILFYCSCIGFSLTLLPFLTGELMHGG

SVINDLTLETVALVAIHGIAHFFQAMLAFQLIGLLSSINYSVANIMKRIVVISVALFWET

KLNFFQVFGVILTIAGLYGYDKWGLSKKDGRQA

YOR332W
>sp|P22203|VATE_YEAST V-type proton ATPase subunit E
OS = Saccharomyces cerevisiae (strain ATCC 204508/S288c) GN = VMA4
PE = 1 SV = 4
SEQ ID NO: 143

MSSAITALTPNQVNDELNKMQAFIRKEAEEKAKEIQLKADQEYEIEKTNIVRNETNNIDG

NFKSKLKKAMLSQQITKSTIANKMRLKVLSAREQSLDGIFEETKEKLSGIANNRDEYKPI

LQSLIVEALLKLLEPKAIVKALERDVDLIESMKDDIMREYGEKAQRAPLEEIVISNDYLN

KDLVSGGVVVSNASDKIEINNTLEERLKLLSEEALPAIRLELYGPSKTRKFFD

YOR348C
>sp|P15380|PDT4_YEAST Proline-specific permease OS = Saccharomyces
cerevisiae (strain ATCC 204508/S288c) GN = PUT4 PE = 1 SV = 2
SEQ ID NO: 144

MVNILPFHKNNRHSAGVVTCADDVSGDGSGGDTKKEEDVVQVTESPSSGSRNNHRSDNEK

DDAIRMEKISKNQSASSNGTIREDLIMDVDLEKSPSVDGDSEPHKLKQGLQSRHVQLIAL

GGAIGTGLLVGTSSTLHTCGPAGLFISYIIISAVIYPIMCALGEMVCFLPGDGSDSAGST

ANLVTRYVDPSLGFATGWNYFYCYVILVAAECTAASGVVEYWTTAVPKGVWITIFLCVVV

ILNESAVKVYGESEFWFASIKILCIVGLIILSFILFWGGGPNHDRLGFRYWQHPGAFAHH

LTGGSLGNFTDIYTGIIKGAFAFILGPELVCMTSAECADQRRNIAKASRRFVWRLIFFYV

LGTLAISVIVPYNDPTLVNALAQGKPGAGSSPFVIGIQNAGIKVLPHIINGCILTSAWSA

ANAFMFASTRSLLTMAQTGQAPKCLGRINKWGVPYVAVGVSFLCSCLAYLNVSSSTADVF

NWFSNISTISGFLGWMCGCIAYLRFRKAIFYNGLYDRLPFKTWGQPYTVWFSLIVIGIIT

ITNGYAIFIPKYWRVADFIAAYITLPIFLVLWFGHKLYTRTWRQWWLPVSEIDVTTGLVE

IEEKSREIEEMRLPPTGFKDKFLDALL

YPL036W
>sp|P19657|PMA2_YEAST Plasma membrane ATPase 2 OS = Saccharomyces
cerevisiae (strain ATCC 204508/S288c) GN = PMA2 PE = 1 SV = 3
SEQ ID NO: 145

MSSTEAKQYKEMDSKEYLHASDGDDPANNSAASSSSSSTSTSASSSAAAVPRKAAAASA

ADDSDSDEDIDQLIDELQSNYGEGDESGEEEVRTDGVHAGQRVVPEKDLSTDPAYGLTSD

EVARRRKKYGLNQMAEENESLIVKFLMFFVGPIQFVMEAAAILAAGLSDWVDVGVICALL

LLNASVGFIQEFQAGSIVDELKKTLANTATVIRDGQLIEIPANEVVPGEILQLESGTIAP

ADGRIVTEDCFLQIDQSAITGESLAAEKHYGDEVESSSTVKTGEAFMVVTATGDNTFVGR

TABLE 14-continued

Sequences disclosed herein.

AAALVGQASGVEGHFTEVLNGIGIILLVLVIATLLLVWTACFYRTVGIVSILRYTLGITI

IGVPVGLPAVVTTTMAVGANYLAKKQAIVQKLSAIESLAGVEILCSDKTGTLTKNKLSLH

EPYTVEGVSPDDLMLTACLAASRKKKGLDAIDKAFLKSLIEYPKAKDALTKYKVLEFHPF

DPVSKKVTAVVESPEGERIVCVKGAPLEVLKTVEEDHPIPEDVHENYENKVAELASRGER

ALGVARKRGEGHWEILGVMPCMDPPRDDTAQTINEARNLGLRIKMLTGDAVGIAKETCRQ

LGLGTNIYNAERLGLGGGGDMPGSELADFVENADGFAEVFPQHKYRVVEILQNRGYLVAM

TGDGVNDAPSLKKADTGIAVEGATDAARSAADIVFLAPGLSAIIDALKTSRQIEHRMYSY

VVYRIALSLHLEIFLGLWIAILNNSLDINLIVFIAIFADVATLTIAYDNAPYAPEPVKWN

LPRLWGMSIILGIVLAIGSWITLTTMELPNGGIIQNFGAMNGVMFLQISLTENWLIFVTR

AAGPFWSSIPSWQLAGAVFAVDIIATMFTLFGWWSENWTDIVSVVRVWIWSIGIFCVLGG

FYYIMSTSQAFDRLMNGKSLKEKKSTRSVEDFMAAMQRVSTQHEKSS

YDL198C
SEQ ID NO: 146
MPHTDKKQSG LARLLGSASA GIMEIAVFHP VDTISKRLMS NHTKITSGQE LNRVIFRDHF

SEPLGKRLFT LFPGLGYAAS YKVLQRVYKY GGQPFANEFL NKHYKKDFDN LFGEKTGKAM

RSAAAGSLIG IGEIVLLPLD VLKIKRQTNP ESFKGRGFIK ILRDEGLFNL YRGWGWTAAR

NAPGSFALFG GNAFAKEYIL GLKDYSQATW SQNFISSIVG ACSSLIVSAP LDVIKTRIQN

RNFDNPESGL RIVKNTLKNE GVTAFFKGLT PKLLTTGPKL VFSFALAQSL IPRFDNLLSK

YFL054C
SEQ ID NO: 147
MSYESGRSSS SSESTRPPTL KEEPNGKIAW EESVKKSREN NENDSTLLRR KLGETRKAIE

TGGSSRNKLS ALTPLKKVVD ERKDSVQPQV PSMGFTYSLP NLKTLNSFSD AEQARIMQDY

LSRGVNQGNS NNYVDPLYRQ LNPTMGSSRN RPVWSLNQPL PHVLDRGLAA KMIQKNMDAR

SRASSRRGST DISRGGSTTS VKDWKRLLRG AAPGKKLGDI EAQTQRDNTV GADVKPTKLE

PENPQKPSNT HIENVSRKKK RTSHNVNFSL GDESYASSIA DAESRKLKNM QTLDGSTPVY

TKLPEELIEE ENKSTSALDG NEIGASEDED ADIMTFPNFW AKIRYHMREP FAEFLGTLVL

VIFGVGGNLQ ATVTKGSGGS YESLSFAWGF GCMLGVYVAG GISGGHINPA VTISMAIFRK

FPWKKVPVYI VAQIIGAYFG GAMAYGYFWS SITEFEGGPH IRTTATGACL FTDPKSYVTW

RNAFFDEFIG ASILVGCLMA LLDDSNAPPG NGMTALIIGF LVAAIGMALG YQTSFTINPA

RDLGPRIFAS MIGYGPHAFH LTHWWWTWGA WGGPIAGGIA GALIYDIFIF TGCESPVNYP

DNGYIENRVG KLLHAEFHQN DGTVSDESGV NSNSNTGSKK SVPTSS

*Oryza sativa* sequence encoding EUGT11
SEQ ID NO: 148
MDSGYSSSYA AAAGMHVVIC PWLAFGHLLP CLDLAQRLAS RGHRVSFVST PRNISRLPPV

RPALAPLVAF VALPLPRVEG LPDGAESTND VPHDRPDMVE LHRRAFDGLA APFSEFLGTA

CADWVIVDVF HHWAAAAALE HKVPCAMMLL GSAHMIASIA DRRLERAETE SPAAAGQGRP

AAAPTFEVAR MKLIRTKGSS GMSLAERFSL TLSRSSLVVG RSCVEFEPET VPLLSTLRGK

PITFLGLMPP LHEGRREDGE DATVRWLDAQ PAKSVVYVAL GSEVPLGVEK VHELALGLEL

AGTRFLWALR KPTGVSDADL LPAGFEERTR GRGVVATRWV PQMSILAHAA VGAFLTHCGW

NSTIEGLMFG HPLIMLPIFG DQGPNARLIE AKNAGLQVAR NDGDGSFDRE GVAAAIRAVA

VEEESSKVFQ AKAKKLQEIV ADMACHERYI DGFIQQLRSY KD

TABLE 14-continued

Sequences disclosed herein.

*Synechococcus* sp. GGPPS

SEQ ID NO: 149

MVAQTFNLDT YLSQRQQQVE EALSAALVPA YPERIYEAMR YSLLAGGKRL RPILCLAACE

LAGGSVEQAM PTACALEMIH TMSLIHDDLP AMDNDDFRRG KPTNHKVFGE DIAILAGDAL

LAYAFEHIAS QTRGVPPQLV LQVIARIGHA VAATGLVGGQ VVDLESEGKA ISLETLEYIH

SHKTGALLEA SVVSGGILAG ADEELLARLS HYARDIGLAF QIVDDILDVT ATSEQLGKTA

GKDQAAAKAT YPSLLGLEAS RQKAEELIQS AKEALRPYGS QAEPLLALAD FITRRQH

*Zea mays* truncated CDPS

SEQ ID NO: 150

MAQHTSESAA VAKGSSLTPI VRTDAESRRT RWPTDDDDAE PLVDEIRAML TSMSDGDISV

SAYDTAWVGL VPRLDGGEGP QFPAAVRWIR NNQLPDGSWG DAALFSAYDR LINTLACVVT

LTRWSLEPEM RGRGLSFLGR NMWKLATEDE ESMPIGFELA FPSLIELAKS LGVHDFPYDH

QALQGIYSSR EIKMKRIPKE VMHTVPTSIL HSLEGMPGLD WAKLLKLQSS DGSFLFSPAA

TAYALMNTGD DRCFSYIDRT VKKFNGGVPN VYPVDLFEHI WAVDRLERLG ISRYFQKEIE

QCMDYVNRHW TEDGICWARN SDVKEVDDTA MAFRLLRLHG YSVSPDVFKN FEKDGEFFAF

VGQSNQAVTG MYNLNRASQI SFPGEDVLHR AGAFSYEFLR RKEAEGALRD KWIISKDLPG

EVVYTLDFPW YGNLPRVEAR DYLEQYGGGD DVWIGKTLYR MPLVNNDVYL ELARMDFNHC

QALHQLEWQG LKRWYTENRL MDFGVAQEDA LRAYFLAAAS VYEPCRAAER LAWARAAILA

NAVSTHLRNS PSFRERLEHS LRCRPSEETD GSWFNSSSGS DAVLVKAVLR LTDSLAREAQ

PIHGGDPEDI IHKLLRSAWA EWVREKADAA DSVCNGSSAV EQEGSRMVHD KQTCLLLARM

IEISAGRAAG EAASEDGDRR IIQLTGSICD SLKQKMLVSQ DPEKNEEMMS HVDDELKLRI

REFVQYLLRL GEKKTGSSET RQTFLSIVKS CYYAAHCPPH VVDRHISRVI FEPVSAAK

*Arabidopsis thaliana* KS (similar to GenBank AEE36246.1)

SEQ ID NO: 151

MSINLRSSGC SSPISATLER GLDSEVQTRA NNVSFEQTKE KIRKMLEKVE LSVSAYDTSW

VAMVPSPSSQ NAPLFPQCVK WLLDNQHEDG SWGLDNHDHQ SLKKDVLSST LASILALKKW

GIGERQINKG LQFIELNSAL VTDETIQKPT GFDIIFPGMI KYARDLNLTI PLGSEVVDDM

IRKRDLDLKC DSEKFSKGRE AYLAYVLEGT RNLKDWDLIV KYQRKNGSLF DSPATTAAAF

TQFGNDGCLR YLCSLLQKFE AAVPSVYPFD QYARLSIIVT LESLGIDRDF KTEIKSILDE

TYRYWLRGDE EICLDLATCA LAFRLLLAHG YDVSYDPLKP FAEESGFSDT LEGYVKNTFS

VLELFKAAQS YPHESALKKQ CCWTKQYLEM ELSSWVKTSV RDKYLKKEVE DALAFPSYAS

LERSDHRRKI LNGSAVENTR VTKTSYRLHN ICTSDILKLA VDDFNFCQSI HREEMERLDR

WIVENRLQEL KFARQKLAYC YFSGAATLFS PELSDARISW AKGGVLTTVV DDFFDVGGSK

EELENLIHLV EKWDLNGVPE YSSEHVEIIF SVLRDTILET GDKAFTYQGR NVTHHIVKIW

LDLLKSMLRE AEWSSDKSTP SLEDYMENAY ISFALGPIVL PATYLIGPPL PEKTVDSHQY

NQLYKLVSTM GRLLNDIQGF KRESAEGKLN AVSLHMKHER DNRSKEVIIE SMKGLAERKR

EELHKLVLEE KGSVVPRECK EAFLKMSKVL NLFYRKDDGF TSNDLMSLVK SVIYEPVSLQ

KESLT

*S. rebaudiana* KO1

SEQ ID NO: 152

MDAVTGLLTV PATAITIGGT AVALAVALIF WYLKSYTSAR RSQSNHLPRV PEVPGVPLLG

NLLQLKEKKP YMTFTRWAAT YGPIYSIKTG ATSMVVVSSN EIAKEALVTR FQSISTRNLS

KALKVLTADK TMVAMSDYDD YHKTVKRHIL TAVLGPNAQK KHRIHRDIMM DNISTQLHEF

TABLE 14-continued

Sequences disclosed herein.

```
VKNNPEQEEV DLRKIFQSEL FGLAMRQALG KDVESLYVED LKITMNRDEI FQVLVVDPMM
GAIDVDWRDF FPYLKWVPNK KFENTIQQMY IRREAVMKSL IKEHKKRIAS GEKLNSYIDY
LLSEAQTLTD QQLLMSLWEP IIESSDTTMV TTEWAMYELA KNPKLQDRLY RDIKSVCGSE
KITEEHLSQL PYITAIFHET LRRHSPVPII PLRHVHEDTV LGGYHVPAGT ELAVNIYGCN
MDKNVWENPE EWNPERFMKE NETIDFQKTM AFGGGKRVCA GSLQALLTAS IGIGRMVQEF
EWKLKDMTQE EVNTIGLTTQ MLRPLRAIIK PRI
```

A. thaliana ATR2

SEQ ID NO: 153

```
MSSSSSSSTS MIDLMAAIIK GEPVIVSDPA NASAYESVAA ELSSMLIENR QFAMIVTTSI
AVLIGCIVML VWRRSGSGNS KRVEPLKPLV IKPREEEIDD GRKKVTIFFG TQTGTAEGFA
KALGEEAKAR YEKTRFKIVD LDDYAADDDE YEEKLKKEDV AFFFLATYGD GEPTDNAARF
YKWFTEGNDR GEWLKNLKYG VFGLGNRQYE HFNKVAKVVD DILVEQGAQR LVQVGLGDDD
QCIEDDFTAW REALWPELDT ILREEGDTAV ATPYTAAVLE YRVSIHDSED AKFNDITLAN
GNGYTVFDAQ HPYKANVAVK RELHTPESDR SCIHLEFDIA GSGLTMKLGD HVGVLCDNLS
ETVDEALRLL DMSPDTYFSL HAEKEDGTPI SSSLPPPFPP CNLRTALTRY ACLLSSPKKS
ALVALAAHAS DPTEAERLKH LASPAGKDEY SKWVVESQRS LLEVMAEFPS AKPPLGVFFA
GVAPRLQPRF YSISSSPKIA ETRIHVTCAL VYEKMPTGRI HKGVCSTWMK NAVPYEKSEK
LFLGRPIFVR QSNFKLPSDS KVPIIMIGPG TGLAPFRGFL QERLALVESG VELGPSVLFF
GCRNRRMDFI YEEELQRFVE SGALAELSVA FSREGPTKEY VQHKMMDKAS DIWNMISQGA
YLYVCGDAKG MARDVHRSLH TIAQEQGSMD STKAEGFVKN LQTSGRYLRD VW
```

Stevia rebaudiana KAHe1

SEQ ID NO: 154

```
MEASYLYISI LLLLASYLFT TQLRRKSANL PPTVFPSIPI IGHLYLLKKP LYRTLAKIAA
KYGPILQLQL GYRRVLVISS PSAAEECFTN NDVIFANRPK TLFGKIVGGT SLGSLSYGDQ
WRNLRRVASI EILSVHRLNE FHDIRVDENR LLIRKLRSSS SPVTLITVFY ALTLNVIMRM
ISGKRYFDSG DRELEEEGKR FREILDETLL LAGASNVGDY LPILNWLGVK SLEKKLIALQ
KKRDDFFQGL IEQVRKSRGA KVGKGRKTMI ELLLSLQESE PEYYTDAMIR SFVLGLLAAG
SDTSAGTMEW AMSLLVNHPH VLKKAQAEID RVIGNNRLID ESDIGNIPYI GCIINETLRL
YPAGPLLFPH ESSADCVISG YNIPRGTMLI VNQWAIHHDP KVWDDPETFK PERFQGLEGT
RDGFKLMPFG SGRRGCPGEG LAIRLLGMTL GSVIQCFDWE RVGDEMVDMT EGLGVTLPKA
VPLVAKCKPR SEMTNLLSEL
```

Stevia rebaudiana CPR8

SEQ ID NO: 155

```
MQSNSVKISP LDLVTALFSG KVLDTSNASE SGESAMLPTI AMIMENRELL MILTTSVAVL
IGCVVVLVWR RSSTKKSALE PPVIVVPKRV QEEEVDDGKK KVTVFEGTQT GTAEGFAKAL
VEEEAKARYEK AVFKVIDLDD YAADDDEYEE KLKKESLAFF FLATYGDGEP TDNAARFYKW
FTEGDAKGEW LNKLQYGVFG LGNRQYEHFN KIAKVVDDGL VEQGAKRLVP VGLGDDDQCI
EDDFTAWKEL VWPELDQLLR DEDDTTVATP YTAAVAEYRV VFHEKPDALS EDYSYTNGHA
VHDAQHPCRS NVAVKKELHS PESDRSCTHL EFDISNTGLS YETGDHVGVY CENLSEVVND
AERLVGLPPD TYSSIHTDSE DGSPLGGASL PPPFPPCTLR KALTCYADVL SSPKKSALLA
LAAHATDPSE ADRLKFLASP AGKDEYSQWI VASQRSLLEV MEAFPSAKPS LGVFFASVAP
RLQPRYYSIS SSPKMAPDRI HVTCALVYEK TPAGRIHKGV CSTWMKNAVP MTESQDCSWA
```

TABLE 14-continued

Sequences disclosed herein.

PIYVRTSNFR LPSDPKVPVI MIGPGTGLAP FRGFLQERLA LKEAGTDLGL SILFFGCRNR

KVDFIYENEL NNFVETGALS ELIVAFSREG PTKEYVQHKM SEKASDIWNL LSEGAYLYVC

GDAKGMAKDV HRTLHTIVQE QGSLDSSKAE LYVKNLQMSG RYLRDVW

*Stevia rebaudiana* UGT85C2
SEQ ID NO: 156
MDAMATTEKK PHVIFIPFPA QSHIKAMLKL AQLLHHKGLQ ITFVNTDFIH NQFLESSGPH

CLDGAPGFRF ETIPDGVSHS PEASIPIRES LLRSIETNFL DRFIDLVTKL PDPPTCIISD

GFLSVFTIDA AKKLGIPVMM YWTLAACGFM GFYHIHSLIE KGFAPLKDAS YLTNGYLDTV

IDWVPGMEGI RLKDFPLDWS TDLNDKVLMF TTEAPQRSHK VSHHIFHTFD ELEPSIIKTL

SLRYNHIYTI GPLQLLLDQI PEEKKQTGIT SLHGYSLVKE EPECFQWLQS KEPNSVVYVN

FGSTTVMSLE DMTEFGWGLA NSNHYFLWII RSNLVIGENA VLPPELEEHI KKRGFIASWC

SQEKVLKHPS VGGFLTHCGW GSTIESLSAG VPMICWPYSW DQLTNCRYIC KEWEVGLEMG

TKVKRDEVKR LVQELMGEGG HKMRNKAKDW KEKARIAIAP NGSSSLNIDK MVKEITVLAR

N

*S. rebaudiana* UGT74G1 (GenBank AAR06920.1)
SEQ ID NO: 157
MAEQQKIKKS PHVLLIPFPL QGHINPFIQF GKRLISKGVK TTLVTTIHTL NSTLNHSNTT

TTSIEIQAIS DGCDEGGFMS AGESYLETFK QVGSKSLADL IKKLQSEGTT IDAIIYDSMT

EWVLDVAIEF GIDGGSFFTQ ACVVNSLYYH VHKGLISLPL GETVSVPGFP VLQRWETPLI

LQNHEQIQSP WSQMLFGQFA NIDQARWVFT NSFYKLEEEV IEWTRKIWNL KVIGPTLPSM

YLDKRLDDDK DNGFNLYKAN HHECMNWLDD KPKESVVYVA FGSLVKHGPE QVEEITRALI

DSDVNFLWVI KHKEEGKLPE NLSEVIKTGK GLIVAWCKQL DVLAHESVGC FVTHCGFNST

LEAISLGVPV VAMPQFSDQT TNAKLLDEIL GVGVRVKADE NGIVRRGNLA SCIKMIMEEE

RGVIIRKNAV KWKDLAKVAV HEGGSSDNDI VEFVSELIKA

*S. rebaudiana* UGT76G1
SEQ ID NO: 158
MENKTETTVR RRRRIILFPV PFQGHINPIL QLANVLYSKG FSITIFHTNF NKPKTSNYPH

FTFRFILDND PQDERISNLP THGPLAGMRI PIINEHGADE LRRELELLML ASEEDEEVSC

LITDALWYFA QSVADSLNLR RLVLMTSSLF NFHAHVSLPQ FDELGYLDPD DKTRLEEQAS

GFPMLKVKDI KSAYSNWQIL KEILGKMIKQ TKASSGVIWN SFKELEESEL ETVIREIPAP

SFLIPLPKHL TASSSSLLDH DRTVFQWLDQ QPPSSVLYVS FGSTSEVDEK DFLEIARGLV

DSKQSFLWVV RPGFVKGSTW VEPLPDGFLG ERGRIVKWVP QQEVLAHGAI GAFWTHSGWN

STLESVCEGV PMIFSDFGLD QPLNARYMSD VLKVGVYLEN GWERGEIANA IRRVMVDEEG

EYIRQNARVL KQKADVSLMK GGSSYESLES LVSYISSL

*S. rebaudiana* UGT91D2e-b
SEQ ID NO: 159
MATSDSIVDD RKQLHVATFP WLAFGHILPY LQLSKLIAEK GHKVSFLSTT RNIQRLSSHI

SPLINVVQLT LPRVQELPED AEATTDVHPE DIPYLKKASD GLQPEVTRFL EQHSPDWIIY

DYTHYWLPSI AASLGISRAH FSVTTPWAIA YMGPSADAMI NGSDGRTTVE DLTTPPKWFP

FPTKVCWRKH DLARLVPYKA PGISDGYRMG MVLKGSDCLL SKCYHEFGTQ WLPLLETLHQ

VPVVPVGLLP PEIPGDEKDE TWVSIKKWLD GKQKGSVVYV ALGSEALVSQ TEVVELALGL

TABLE 14-continued

Sequences disclosed herein.

ELSGLPFVWA YRKPKGPAKS DSVELPDGFV ERTRDRGLVW TSWAPQLRIL SHESVCGFLT

HCGSGSIVEG LMFGHPLIML PIFGDQPLNA RLLEDKQVGI EIPRNEEDGC LTKESVARSL

RSVVVEKEGE IYKANARELS KIYNDTKVEK EYVSQFVDYL EKNARAVAID HES

SEQ ID NO: 160
atggctacct tgttggaaca ttttcaagct atgccattcg ctattccaat tgctttggct gctttgtctt ggttgttttt gttctacatc aaggtttctt tcttctccaa caaatccgct caagctaaat tgccaccagt tccagttgtt ccaggtttgc cagttattgg taatttgttg caattgaaag aaaagaagcc ataccaaacc ttcactagat gggctgaaga atatggtcca atctactcta ttagaactgg tgcttctact atggttgtct tgaacactac tcaagttgcc aaagaagcta tggttaccag atacttgtct atctctacca gaaagttgtc caacgccttg aaaattttga ccgctgataa gtgcatggtt gccatttctg attacaacga tttccacaag atgatcaaga gatatatctt gtctaacgtt tgggtccat ctgcccaaaa agacatcga tctaacagag ataccttgag agccaacgtt tgttctagat tgcattccca agttaagaac tctccaagag aagctgtcaa ctttagaaga gttttcgaat gggaattatt cggtatcgct ttgaaacaag ccttcggtaa ggatattgaa aagccaatct acgtcgaaga attgggtact actttgtcca gagatgaaat cttcaaggtt ttggtcttgg acattatgga aggtgccatt gaagttgatt ggagagattt tttcccatac ttgcgttgga ttccaaacac cagaatggaa actaagatcc aaagattata ctttagaaga aaggccgtta tgaccgcctt gattaacgaa caaaagaaaa gaattgcctc cggtgaagaa atcaactgct acatcgattt cttgttgaaa gaaggtaaga ccttgaccat ggaccaaatc tctatgttgt tgtgggaaac cgttattgaa actgctgata ccacaatggt tactactgaa tgggctatgt acgaagttgc taaggattct aaaagacaag acagattata ccaagaaatc caaaaggtct gcggttctga atggttaca gaagaatact tgtcccaatt gccatacttg aatgctgttt tccacgaaac tttgagaaaa cattctccag ctgctttggt tccattgaga tatgctcatg aagatactca attgggtggt tattacattc cagccggtac tgaaattgcc attaacatct acggttgcaa catggacaaa caccaatggg aatctccaga agaatggaag ccagaaagat ttttggatcc taagtttgac ccaatggact tgtacaaaac tatggctttt ggtgctggta aaagagtttg cgctggttct ttacaagcta tgttgattgc ttgtccaacc atcggtagat tggttcaaga atttgaatgg aagttgagag atggtgaaga agaaaacgtt gatactgttg gtttgaccac ccataagaga tatccaatgc atgctatttt gaagccaaga tcttaa

SEQ ID NO: 161
MATLLEHFQA MPFAIPIALA ALSWLFLFYI KVSFFSNKSA QAKLPPVPVV PGLPVIGNLL

QLKEKKPYQT FTRWAEEYGP IYSIRTGAST MVVLNTTQVA KEAMVTRYLS ISTRKLSNAL

KILTADKCMV AISDYNDFHK MIKRYILSNV LGPSAQKRHR SNRDTLRANV CSRLHSQVKN

SPREAVNFRR VFEWELFGIA LKQAFGKDIE KPIYVEELGT TLSRDEIFKV LVLDIMEGAI

EVDWRDFFPY LRWIPNTRME TKIQRLYFRR KAVMTALINE QKKRIASGEE INCYIDFLLK

EGKTLTMDQI SMLLWETVIE TADTTMVTTE WAMYEVAKDS KRQDRLYQEI QKVCGSEMVT

EEYLSQLPYL NAVFHETLRK HSPAALVPLR YAHEDTQLGG YYIPAGTEIA INIYGCNMDK

HQWESPEEWK PERFLDPKFD PMDLYKTMAF GAGKRVCAGS LQAMLIACPT IGRLVQEFEW

KLRDGEEENV DTVGLTTHKR YPMHAILKPR S

Having described the invention in detail and by reference to specific embodiments thereof, it will be apparent that modifications and variations are possible without departing from the scope of the invention defined in the appended claims. More specifically, although some aspects of the present invention are identified herein as particularly advantageous, it is contemplated that the present invention Is not necessarily limited to these particular aspects of the invention.

SEQUENCE LISTING

The patent contains a lengthy "Sequence Listing" section. A copy of the "Sequence Listing" is available in electronic form from the USPTO web site (https://seqdata.uspto.gov/?pageRequest=docDetail&DocID=US11168343B2). An electronic copy of the "Sequence Listing" will also be available from the USPTO upon request and payment of the fee set forth in 37 CFR 1.19(b)(3).

The invention claimed is:

1. A recombinant host cell producing a steviol glycoside in a cell culture, wherein the recombinant host cell has a modified expression of an endogenous transporter gene encoding a transporter polypeptide, wherein the modified expression comprises increasing expression or activity of the endogenous transporter gene encoding the transporter polypeptide having at least 95% sequence identity to the amino acid sequence set forth in SEQ ID NO:38 above the level of expression or activity observed in a corresponding unmodified recombinant host cell;
wherein at least a portion of the steviol glycoside is transported from the recombinant host into the cell culture medium; and
wherein the host cell is a plant cell, a fungal cell, or a bacterial cell.

2. The recombinant host cell of claim 1, further comprising:
(a) one or more genes encoding a sucrose transporter (SUC1) polypeptide and a sucrose synthase (SUS1) polypeptide;
(b) a gene encoding a polypeptide capable of synthesizing geranylgeranyl pyrophosphate (GGPP) from farnesyl diphosphate (FPP) and isopentenyl diphosphate (IPP);
wherein the polypeptide comprises a polypeptide having at least 95% sequence identity to the amino acid sequence set forth in SEQ ID NO:149;
(c) a gene encoding a polypeptide capable of synthesizing ent-copalyl diphosphate from GGPP;
wherein the polypeptide comprises a polypeptide having at least 95% sequence identity to the amino acid sequence set forth in SEQ ID NO:150;
(d) a gene encoding a polypeptide capable of synthesizing ent-kaurene from ent-copalyl pyrophosphate;
wherein the polypeptide comprises a polypeptide having at least 95% sequence identity to the amino acid sequence set forth in SEQ ID NO:152;
(e) a gene encoding a polypeptide capable of synthesizing ent-kaurenoic acid from ent-kaurene;
wherein the polypeptide comprises a polypeptide having at least 95% sequence identity to the amino acid sequence set forth in SEQ ID NO:151;
(f) a gene encoding a polypeptide capable of synthesizing steviol from ent-kaurenoic acid;
wherein the polypeptide comprises a polypeptide having at least 95% sequence identity to the amino acid sequence set forth in SEQ ID NO:154;
(g) a gene encoding a polypeptide capable of reducing cytochrome P450 complex;
wherein the polypeptide comprises a polypeptide having at least 95% sequence identity to the amino acid sequence set forth in SEQ ID NO:153 or 155;
(h) a gene encoding a polypeptide capable of glycosylating steviol or a steviol glycoside at its C-13 hydroxyl group;
wherein the polypeptide comprises a polypeptide having at least 95% sequence identity to the amino acid sequence set forth in SEQ ID NO:156;
(i) a gene encoding a polypeptide capable of beta 1,3 glycosylation of the C3' of the 13-O-glucose, 19-O-glucose, or both 13-O-glucose and 19-O-glucose of a steviol glycoside;
wherein the polypeptide comprises a polypeptide having at least 95% sequence identity to the amino acid sequence set forth in SEQ ID NO:158;
(j) a gene encoding a polypeptide capable of glycosylating steviol or a steviol glycoside at its C-19 carboxyl group;
wherein the polypeptide comprises a polypeptide having at least 95% sequence identity to the amino acid sequence set forth in SEQ ID NO:157; and/or
(k) a gene encoding a polypeptide capable of beta 1,2 glycosylation of the C2' of the 13-O-glucose, 19-O-glucose, or both 13-O-glucose and 19-O-glucose of a steviol glycoside;
wherein the polypeptide comprises a polypeptide having at least 95% sequence identity to the amino acid sequence set forth in SEQ ID NO:159 or 148;
wherein at least one of the genes in items (a)-(k) is a recombinant gene; and
wherein the steviol glycoside is Rebaudioside A, Rebaudioside B, Rebaudioside D and/or Rebaudioside M or an isomer thereof.

3. The recombinant host cell of claim 2, wherein at least one of the genes in items (a)-(k) is codon optimized for expression in the recombinant host cell.

4. The recombinant host cell of claim 3, wherein at least one of the genes in items (a)-(k) is codon optimized for expression in *Saccharomyces cerevisiae*.

5. The recombinant host cell of claim 1, wherein the bacterial cell comprises *Escherichia* bacteria cells, *Lactobacillus* bacteria cells, *Lactococcus* bacteria cells, *Cornebacterium* bacteria cells, *Acetobacter* bacteria cells, *Acinetobacter* bacteria cells, or *Pseudomonas* bacterial cells.

6. The recombinant host cell of claim 1, wherein the fungal cell is a yeast cell.

7. The recombinant host cell of claim 6, wherein the yeast cell is a cell from *Saccharomyces cerevisiae, Schizosaccharomyces pombe, Yarrowia lipolytica, Candida glabrata, Ashbya gossypii, Cyberlindnera jadinii, Pichia pastoris, Kluyveromyces lactis, Hansenula polymorpha, Candida boidinii, Arxula adeninivorans, Xanthophyllomyces dendrorhous*, or *Candida albicans* species.

8. The recombinant host cell of claim 1, wherein the recombinant host cell is a *Yarrowia lipolytica* cell.

9. The recombinant host cell of claim 1, wherein:
   (a) RebD and RebM transport into the culture medium is increased by at least 2-fold relative to the corresponding unmodified recombinant host cell;
   (b) the amount of RebA, RebB, RebD, and/or RebM in the supernatant is increased by at least 2-fold relative to the corresponding unmodified recombinant host cell;
   (c) the ratio of RebD transported into the culture medium is increased by at least 2-fold compared to the total RebD produced by the recombinant host cell; and/or
   (d) the ratio of RebM transported into the culture medium is increased by at least 2-fold compared to the total RebD produced by the recombinant host cell.

10. A method of producing a steviol glycoside in a cell culture, comprising culturing the recombinant host cell of claim 1 in a culture medium, under conditions in which one or more of the genes are expressed;
   wherein the at least one endogenous transporter gene is expressed;
   wherein culturing includes inducing expression of one or more of the genes or constitutively expressing one or more of the genes; and
   wherein the steviol glycoside is produced by the recombinant host cell.

11. The method of claim 10, wherein:
   (a) Rebaudioside A is produced in the recombinant host cell expressing the polypeptide capable of glycosylating steviol or a steviol glycoside at its C-13 hydroxyl group; the polypeptide capable of beta 1,3 glycosylation of the C3' of the 13-O-glucose, 19-O-glucose, or both 13-O-glucose and 19-O-glucose of a steviol glycoside; the polypeptide capable of glycosylating steviol or a steviol glycoside at its C-19 carboxyl group; and the polypeptide capable of beta 1,2 glycosylation of the C2' of the 13-O-glucose, 19-O-glucose, or both 13-O-glucose and 19-O-glucose of a steviol glycoside;
   (b) Rebaudioside B is produced in the recombinant host cell expressing the polypeptide capable of glycosylating steviol or a steviol glycoside at its C-13 hydroxyl group; the polypeptide capable of beta 1,3 glycosylation of the C3' of the 13-O-glucose, 19-O-glucose, or both 13-O-glucose and 19-O-glucose of a steviol glycoside; and the polypeptide capable of beta 1,2 glycosylation of the C2' of the 13-O-glucose, 19-O-glucose, or both 13-O-glucose and 19-O-glucose of a steviol glycoside;
   (c) Rebaudioside D is produced in the recombinant host cell expressing the polypeptide capable of glycosylating steviol or the steviol glycoside at its C-13 hydroxyl group; the polypeptide capable of beta 1,3 glycosylation of the C3' of the 13-O-glucose, 19-O-glucose, or both 13-O-glucose and 19-O-glucose of a steviol glycoside; the polypeptide capable of glycosylating steviol or a steviol glycoside at its C-19 carboxyl group; and the polypeptide capable of beta 1,2 glycosylation of the C2' of the 13-O-glucose, 19-O-glucose, or both 13-O-glucose and 19-O-glucose of a steviol glycoside; and/or
   (d) Rebaudioside M is produced in the recombinant host cell expressing the polypeptide capable of glycosylation of the 13-OH of steviol; the polypeptide capable of beta 1,3 glycosylation of the C3' of the 13-O-glucose, 19-O-glucose, or both 13-O-glucose and 19-O-glucose of a steviol glycoside; the polypeptide capable of glycosylating steviol or a steviol glycoside at its C-19 carboxyl group; and the polypeptide capable of beta 1,2 glycosylation of the C2' of the 13-O-glucose, 19-O-glucose, or both 13-O-glucose and 19-O-glucose of a steviol glycoside.

12. The method of claim 10, wherein the steviol glycoside is produced at a concentration of at least 500 mg/L of the cell culture.

13. The method of claim 10, that further comprises isolating the Rebaudioside M, alone or together with at least one other steviol glycoside from the cell culture.

14. The method of claim 10, wherein the isolating step comprises separating a liquid phase of the cell culture from a solid phase of the cell culture to obtain a supernatant comprising Rebaudioside M, alone or together with at least one other steviol glycoside, and:
   (a) contacting the supernatant with one or more adsorbent resins in order to obtain at least a portion of Rebaudioside M, alone or together with at least one other steviol glycoside; or
   (b) contacting the supernatant with one or more ion exchange or reversed-phase chromatography columns in order to obtain at least a portion of Rebaudioside M, alone or together with at least one other steviol glycoside; or
   (c) crystallizing or extracting Rebaudioside M, alone or together with at least one other steviol glycoside;
   thereby isolating Rebaudioside M, alone or together with at least one other steviol glycoside.

15. The method of claim 10, that further comprises recovering a steviol glycoside composition comprising Rebaudioside M, alone or together with at least one other steviol glycoside from the cell culture.

16. The method of claim 15, wherein the recovered steviol glycoside composition is enriched for Rebaudioside M relative to a steviol glycoside composition of *Stevia* plant and has a reduced level of *Stevia* plant-derived components relative to a steviol glycoside composition obtained from a plant-derived *Stevia* extract.

17. The method of claim 10, wherein the cell culture comprises:
   (a) the steviol glycoside produced by the recombinant host cell;
   (b) glucose, fructose, sucrose, xylose, rhamnose, uridine diphosphate (UDP)-glucose, UDP-rhamnose, UDP-xylose, and/or N-acetyl-glucosamine; and/or
   (c) supplemental nutrients comprising trace metals, vitamins, salts, yeast nitrogen base (YNB) and/or amino acids.

18. The method of claim 10, wherein the recombinant host cell is grown in a fermentor at a temperature for a period of time, wherein the temperature and the period of time facilitate the production of the steviol glycoside composition.

19. The method of claim 10, wherein the recombinant host cell is a *Yarrowia lipolytica* cell.

20. The method of claim 10, wherein Rebaudioside A is produced in the recombinant host cell expressing the polypeptide capable of glycosylating steviol or a steviol glycoside at its C-13 hydroxyl group; the polypeptide capable of beta 1,3 glycosylation of the C3' of the 13-O-glucose, 19-O-glucose, or both 13-O-glucose and 19-O-glucose of a steviol glycoside; the polypeptide capable of glycosylating steviol or a steviol glycoside at its C-19 carboxyl group; and the polypeptide capable of beta 1,2 glycosylation of the C2' of the 13-O-glucose, 19-O-glucose, or both 13-O-glucose and 19-O-glucose of a steviol glycoside.

21. The method of claim 10, wherein Rebaudioside D is produced in the recombinant host cell expressing the polypeptide capable of glycosylating steviol or the steviol glycoside at its C-13 hydroxyl group; the polypeptide capable of beta 1,3 glycosylation of the C3' of the 13-O-glucose, 19-O-glucose, or both 13-O-glucose and 19-O-glucose of a steviol glycoside; the polypeptide capable of glycosylating steviol or a steviol glycoside at its C-19 carboxyl group; and the polypeptide capable of beta 1,2 glycosylation of the C2' of the 13-O-glucose, 19-O-glucose, or both 13-O-glucose and 19-O-glucose of a steviol glycoside.

22. The method of claim 10, wherein Rebaudioside M is produced in the recombinant host cell expressing the polypeptide capable of glycosylation of the 13-OH of steviol; the polypeptide capable of beta 1,3 glycosylation of the C3' of the 13-O-glucose, 19-O-glucose, or both 13-O-glucose and 19-O-glucose of a steviol glycoside; the polypeptide capable of glycosylating steviol or a steviol glycoside at its C-19 carboxyl group; and the polypeptide capable of beta 1,2 glycosylation of the C2' of the 13-O-glucose, 19-O-glucose, or both 13-O-glucose and 19-O-glucose of a steviol glycoside.

23. A method of increasing production or transport of a steviol glycoside into a culture medium, comprising culturing the recombinant host cell of claim 1 in a culture medium, under conditions in which one or more of the genes are expressed;
wherein at the least one endogenous transporter gene encoding the transporter polypeptide, the at least one endogenous transcription factor gene encoding the transcription factor polypeptide that regulates expression of the at least one endogenous transporter gene, or both are expressed;
wherein culturing includes inducing expression of one or more of the genes or constitutively expressing one or more of the genes wherein the steviol glycoside is produced by the recombinant host cell; and
wherein the steviol glycoside is RebA, RebB, RebD or RebM or an isomer thereof.

24. The method of claim 23, wherein the steviol glycoside is Rebaudioside A (Reb A), Rebaudioside B (Reb B), Rebaudioside D (Reb D), and/or Rebaudioside M (Reb M) or an isomer thereof.

25. A cell culture, comprising the recombinant host cell of claim 1, the cell culture further comprising:
(a) the steviol glycoside produced by the recombinant host cell;
(b) glucose, fructose, sucrose, xylose, rhamnose, uridine diphosphate (UDP)-glucose, UDP-rhamnose, UDP-xylose, and/or N-acetyl-glucosamine; and
(c) supplemental nutrients comprising trace metals, vitamins, salts, YNB, and/or amino acids;
wherein the steviol glycoside is present at a concentration of at least 1 mg/liter of the cell culture.

26. An in vitro method for producing a steviol glycoside, comprising:
(a) adding at least one endogenous transporter gene encoding a transporter polypeptide having at least 95% sequence identity to the amino acid sequence set forth in SEQ ID NO:38;
and plant-derived- or synthetic steviol or steviol glycosides to a reaction mixture;
wherein at least one of the polypeptides is a recombinant polypeptide; and
(b) synthesizing steviol glycoside, glycosylated ent-kaurenol compound, and/or the glycosylated ent-kaurenoic acid compound in the reaction mixture.

27. The method of claim 1, further comprising:
(c) recovering the steviol glycoside, glycosylated ent-kaurenol compound, and/or a glycosylated ent-kaurenoic acid compound alone or a composition comprising the steviol glycoside, glycosylated ent-kaurenol compound, and/or the glycosylated ent-kaurenoic acid compound from the reaction mixture.

28. The method of claim 1, wherein the reaction mixture comprises:
(a) one or more steviol glycosides, glycosylated ent-kaurenol compounds, and/or a glycosylated ent-kaurenoic acid compounds produced in the reaction mixture;
(b) a UGT polypeptide;
(c) UDP-glucose, UDP-rhamnose, UDP-xylose, and/or N-acetyl-glucosamine; and/or
(d) reaction buffer and/or salts.

29. The method of claim 26, wherein the reaction mixture comprises:
(a) one or more steviol glycosides, glycosylated ent-kaurenol compounds, and/or a glycosylated ent-kaurenoic acid compounds produced in the reaction mixture;
(b) a UGT polypeptide;
(c) UDP-glucose, UDP-rhamnose, UDP-xylose, and/or N-acetyl-glucosamine; and
(d) reaction buffer and/or salts.

* * * * *